US012577287B2

(12) United States Patent
Hirano et al.

(10) Patent No.: US 12,577,287 B2
(45) Date of Patent: Mar. 17, 2026

(54) T CELL RECEPTORS AND METHODS OF USE THEREOF

(71) Applicant: University Health Network, Toronto (CA)

(72) Inventors: Naoto Hirano, Toronto (CA); Kenji Murata, Toronto (CA); Kayoko Saso, Toronto (CA)

(73) Assignee: University Health Network, Toronto (CA)

( * ) Notice: Subject to any disclaimer, the term of this patent is extended or adjusted under 35 U.S.C. 154(b) by 982 days.

(21) Appl. No.: 17/598,763

(22) PCT Filed: Mar. 24, 2020

(86) PCT No.: PCT/IB2020/052776
§ 371 (c)(1),
(2) Date: Sep. 27, 2021

(87) PCT Pub. No.: WO2020/194195
PCT Pub. Date: Oct. 1, 2020

(65) Prior Publication Data
US 2022/0324938 A1     Oct. 13, 2022

Related U.S. Application Data

(60) Provisional application No. 62/823,487, filed on Mar. 25, 2019.

(51) Int. Cl.

| | |
|---|---|
| *C07K 14/725* | (2006.01) |
| *A61K 39/00* | (2006.01) |
| *A61K 40/11* | (2025.01) |
| *A61K 40/32* | (2025.01) |
| *A61K 40/42* | (2025.01) |
| *A61P 35/00* | (2006.01) |
| *C07K 14/47* | (2006.01) |
| *C07K 14/74* | (2006.01) |
| *C07K 16/40* | (2006.01) |
| *C12N 5/0783* | (2010.01) |
| *C12N 15/63* | (2006.01) |

(52) U.S. Cl.
CPC .. *C07K 14/7051* (2013.01); *A61K 39/001156* (2018.08); *A61K 40/11* (2025.01); *A61K 40/32* (2025.01); *A61K 40/4245* (2025.01); *A61P 35/00* (2018.01); *C07K 14/4748* (2013.01); *C07K 14/70539* (2013.01); *C07K 16/40* (2013.01); *C12N 5/0636* (2013.01); *A61K 2239/57* (2023.05); *C12N 15/63* (2013.01); *C12N 2310/14* (2013.01); *C12N 2510/00* (2013.01); *C12N 2800/00* (2013.01)

(58) Field of Classification Search
CPC .......... C07K 14/7051; C07K 14/70539; C07K 16/40; A61K 40/11; A61K 40/32; A61K 40/4245; A61K 2239/57; A61K 48/00; A61K 31/713; A61P 35/00; C12N 5/0636
See application file for complete search history.

(56) References Cited

U.S. PATENT DOCUMENTS

| | | | | |
|---|---|---|---|---|
| 8,785,601 | B2 * | 7/2014 | Rosenberg ....... | C07K 14/70503 |
| | | | | 530/387.3 |
| 2010/0273213 | A1 | 10/2010 | Mineno et al. | |
| 2012/0015888 | A1 | 1/2012 | Rosenberg et al. | |
| 2013/0287748 | A1 | 10/2013 | June et al. | |
| 2014/0206620 | A1 | 7/2014 | Rosenberg et al. | |
| 2016/0317633 | A1 | 11/2016 | Yee et al. | |
| 2022/0152104 | A1 | 5/2022 | Hirano et al. | |
| 2022/0152105 | A1 | 5/2022 | Hirano et al. | |
| 2022/0168345 | A1 | 6/2022 | Hirano et al. | |
| 2022/0168346 | A1 | 6/2022 | Hirano et al. | |

(Continued)

FOREIGN PATENT DOCUMENTS

| | | | |
|---|---|---|---|
| EP | 3118322 | A1 | 1/2017 |
| JP | 2018070540 | A | 5/2018 |

(Continued)

OTHER PUBLICATIONS

Springer I, Besser H, Tickotsky-Moskovitz N, Dvorkin S, Louzoun Y. Prediction of Specific TCR-Peptide Binding From Large Dictionaries of TCR-Peptide Pairs. Front Immunol. Aug. 25, 2020;11:1803. doi: 10.3389/fimmu.2020.01803. PMID: 32983088; PMCID: PMC7477042. (Year: 2020).*
Sewell AK. Why must T cells be cross-reactive? Nat Rev Immunol. Sep. 2012;12(9):669-77. doi: 10.1038/nri3279. PMID: 22918468; PMCID: PMC7097784. (Year: 2012).*
Huang, S., and Kamihira, M., et al., "Development of hybrid viral vectors for gene therapy," Biotechnol Adv. 31(2):208-223, Elsevier, Netherlands (Mar. 2013).

(Continued)

*Primary Examiner* — Janet L Andres
*Assistant Examiner* — Carol Ann Chase
(74) *Attorney, Agent, or Firm* — Sterne, Kessler, Goldstein & Fox P.L.L.C.

(57) ABSTRACT

The present disclosure is directed recombinant T cell receptors capable of binding a tyrosinase epitope, a MAGA-A1 epitope, a MART1 epitope, a MAGE-A3 epitope, or an SSX2 epitope and nucleic acid molecules encoding the same. In some embodiments, the nucleic acid molecules further comprise a second nucleotide sequence, wherein the second nucleotide sequence or the polypeptide encoded by the second nucleotide sequence inhibits the expression of an endogenous TCR. Other aspects of the disclosure are directed to vectors comprising the nucleic acid molecule and cells comprising the recombinant TCR, the nucleic acid molecule, or the vector. Still other aspects of the disclosure are directed to methods of using the same. In some embodiments, the methods comprise treating a cancer in a subject in need thereof.

19 Claims, 41 Drawing Sheets

Specification includes a Sequence Listing.

(56) References Cited

U.S. PATENT DOCUMENTS

| | | | |
|---|---|---|---|
| 2022/0168347 A1 | 6/2022 | Hirano et al. | |
| 2022/0169695 A1 | 6/2022 | Hirano et al. | |
| 2022/0169696 A1 | 6/2022 | Hirano et al. | |
| 2022/0324938 A1 | 10/2022 | Hirano et al. | |

FOREIGN PATENT DOCUMENTS

| | | | | |
|---|---|---|---|---|
| WO | WO-1999045954 A1 | 9/1999 | | |
| WO | WO-2001030382 A1 | 5/2001 | | |
| WO | WO-0226778 A2 | 4/2002 | | |
| WO | WO-2008120202 A2 | 10/2008 | | |
| WO | WO-2010037395 A2 | 4/2010 | | |
| WO | WO-2010058023 A1 | 5/2010 | | |
| WO | WO-2010112962 A1 * | 10/2010 | .............. | C07K 7/06 |
| WO | WO-2011140284 A2 | 11/2011 | | |
| WO | WO-2012038055 A1 | 3/2012 | | |
| WO | WO-2014207708 A2 | 12/2014 | | |
| WO | WO-2016073755 A2 | 5/2016 | | |
| WO | WO-2016199140 A1 | 12/2016 | | |
| WO | WO-2017120428 A2 | 7/2017 | | |
| WO | WO-2020194195 A1 | 10/2020 | | |

OTHER PUBLICATIONS

Hirano, N., et al., "Efficient presentation of naturally processed HLA class I peptides by artificial antigen-presenting cells for the generation of effective antitumor responses," Clin. Cancer Res. 12:2967-75, American Association for Cancer Research, United States (May 2006).

Butler, M., and Hirano, N., et al., "Human cell-based artificial antigen-presenting cells for cancer immunotherapy," Immunol. Rev. 257:191-209, Wiley, United States (Jan. 2014).

Kagoya, Y., et al., "DOTIL inhibition attenuates graft-versus-host disease by allogeneic T cells in adoptive immunotherapy models," Nat. Commun. 9:1915, Springer Nature, Germany (May 2018).

Anczurowski, M., et al., "Mechanisms underlying the lack of endogenous processing and CLIP-mediated binding of the invariant chain by HLA-DP 84Gly," Sci. Rep. 8:4804, Springer Nature, Germany (Mar. 2018).

Yamashita, Y., et al., "HLA-DP 84Gly constitutively presents endogenous peptides generated by the class I antigen processing pathway," Nat Commun. 8:15244, Springer Nature, Germany (May 2017).

International Search Report and Written Opinion for International Application No. PCT/IB2020/052776, Canadian Intellectual Property Office, Quebec, mailed on Jul. 17, 2020, 15 pages.

Ikeda, H., "T-cell adoptive immunotherapy using tumor-infiltrating T cells and genetically engineered TCR-T cells," Int. Immunol. 28(7):349-353, Oxford University Press, United Kingdom (Jul. 2016).

Lowe, K.L., et al., "Novel TCR-based biologics: mobilising T cells to warm 'cold' tumours," Cancer Treat Rev. 77:35-43, Elsevier, Netherlands (Jul. 2019).

Johnson, L.A., et al., "Gene therapy with human and mouse T-ce;; receptors mediates cancer regression and targets normal tissues expressing cognate antigen," Blood 114(3):535-546, American Society of Hematology, United States (Jul. 2009).

Met, O., et al., "Principles of adoptive T cell therapy in cancer," Seminars in Immunopathology 41:49-58 (Sep. 2018).

Eisenberg, G., et al., "Transcutaneous immunization with hydrophilic recombinant gp100 protein induces antigen-specific cellular immune response," Cell Immunol 266(1):98-103, Elsevier, Netherlands (Sep. 2010).

Genbank, "Homo sapiens premelanosome protein (PMEL), transcript variant 3, mRNA," Accession No. NM_006928, accessed at https://www.ncbi.nlm.nih.gov/nuccore/NM_006928.5/, accessed on Jul. 21, 2022, 6 pages.

Thomas, R., et al., "NY-ESO-1 Based Immunotherapy of Cancer: Current Perspectives," Front Immunol 9:947, Frontiers Media S.A., Switzerland (May 2018).

UniProtKB, "TYRO_HUMAN," Accession No. P14679, accessed at https://www.uniprot.org/uniprot/P14679, accessed on Jan. 23, 2025, 18 pages.

UniProtKB, "MAGA1_HUMAN," Accession No. P43355, accessed at https://www.uniprot.org/uniprot/P43355, accessed on Jan. 23, 2025, 9 pages.

UniProtKB, "MAGA3_HUMAN," Accession No. P43357, accessed at https://www.uniprot.org/uniprot/P43357, accessed on Jan. 23, 2025, 13 pages.

UniProtKB, "SSX2_HUMAN," Accession No. Q16385, accessed at https://www.uniprot.org/uniprot/Q16385, accessed on Jan. 23, 2025, 8 pages.

UniProtKB, "MAR1_HUMAN," Accession No. Q16655, accessed at https://www.uniprot.org/uniprot/Q16655, accessed on Jan. 23, 2025, 9 pages.

* cited by examiner

Jurkat 76/CD8 transduced with

None

C*05:01/ tyrosinase$_{460-468}$ TCR

C*07:02/ MAGE-A1$_{289-297}$ TCR (CL2)

C*05:01/ tyrosinase$_{460-468}$ multimer

C*05:01/ HIV rev$_{67-75}$ multimer

C*05:01/ unexchanged multimer

Multimer

| | | C*05:01 | Tyrosinase |
|---|---|---|---|
| ⬜ | Malme-3M | - | + |
| ▨ | Malme-3M/C*05:01 | + | + |
| ▤ | Me275 | - | + |
| ⬛ | Me275/C*05:01 | + | + |
| ▩ | MCF7 | + | - |
| ▧ | MCF7/tyrosinase | + | + |

Malme-3M    Me275    MCF7    MCF7/tyrosinase

Tyrosinase

Malme-3M    Malme-3M/C*05:01    Me275    Me275/C*05:01

ΔNGFR

B*07:02/
MAGE-A1$_{289-297}$
multimer

B*07:02/
EBV EBNA3A$_{379-387}$
multimer

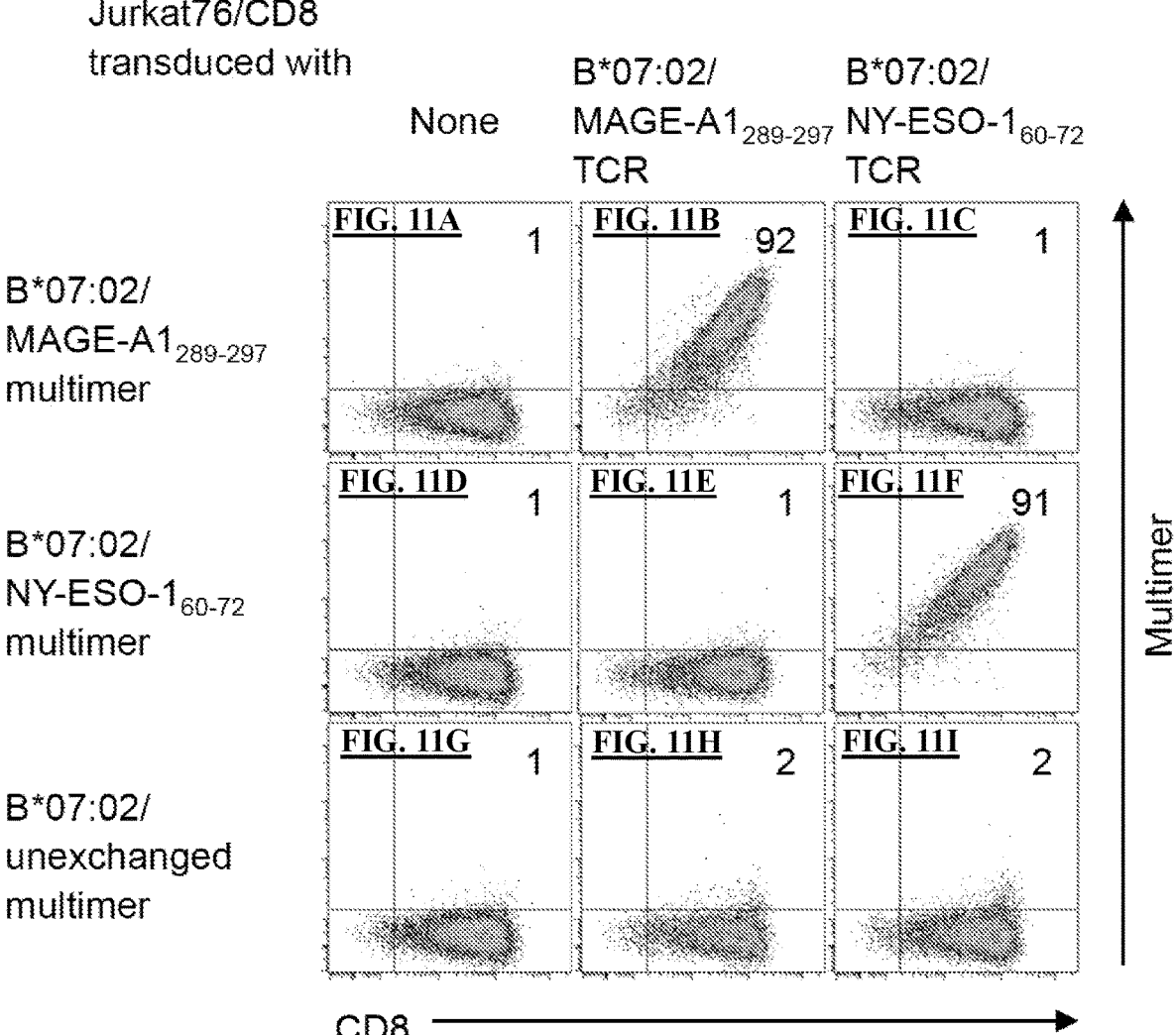

Transduced with

None

B*07:02/
MAGE-A1$_{289-297}$
TCR

B*07:02/
MAGE-A1$_{289-297}$
multimer

0%

13.9%

B*07:02/
HIV nef$_{128-137}$
multimer 0.1%

0.1%

Multimer

CD8

|  |  | B*07:02 | MAGE-A1 |
|---|---|---|---|
| □ | Me275 | - | + |
| ▦ | Me275/B*07:02 | + | + |
| ▤ | SK-MEL-37 | - | + |
| ■ | SK-MEL-37/B*07:02 | + | + |
| ▨ | SK-MEL-21 | + | - |
| ▨ | SK-MEL-21/MAGE-A1 | + | + |

MAGE-A1

B*18:01/
unexchanged
multimer

B*18:01/
MART1$_{25-33}$
multimer

B*18:01/
HIV gag$_{161-170}$
multimer

Multimer

CD8

| | | B*18:01 | MART1 |
|---|---|---|---|
| ☐ | Malem-3M | - | + |
| | Malme-3M/B*18:01 | + | + |
| | SK-MEL-28 | - | + |
| ■ | SK-MEL-28/B*18:01 | + | + |
| | A375 | - | - |
| | A375/B*18:01 | + | - |
| | A375/MART1 | - | + |
| | A375/B*18:01/MART1 | + | + |

FIG. 24A
Malme-3M
FIG. 24B
SK-MEL-28
FIG. 24C
A375
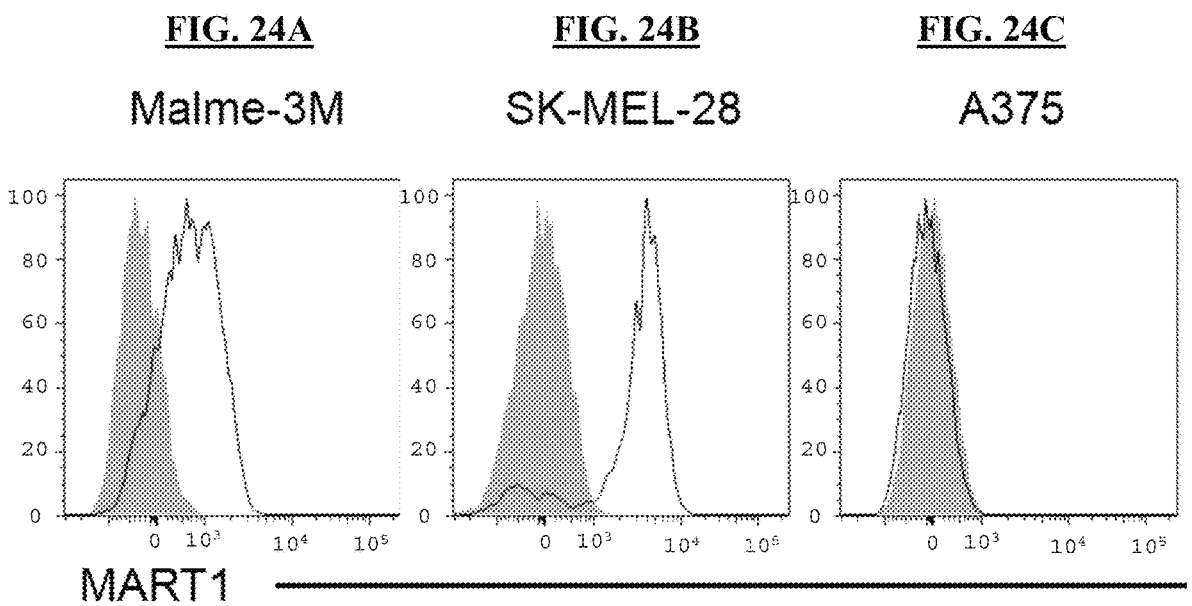
MART1
FIG. 24D
A375/
MART1
FIG. 24E
A375/B*18:01/
MART1
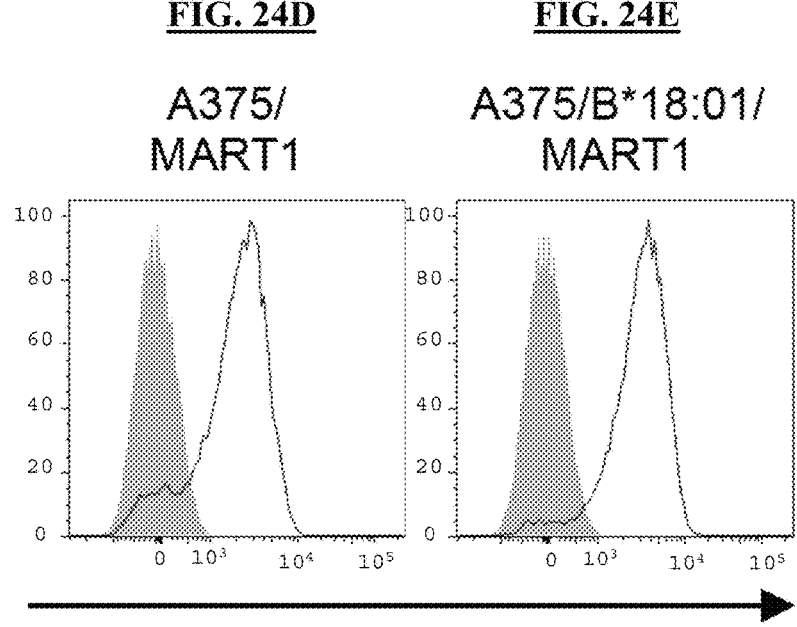

FIG. 25A
Malme-3M
FIG. 25B
Malme-3M/B*18:01
FIG. 25C
SK-MEL-28
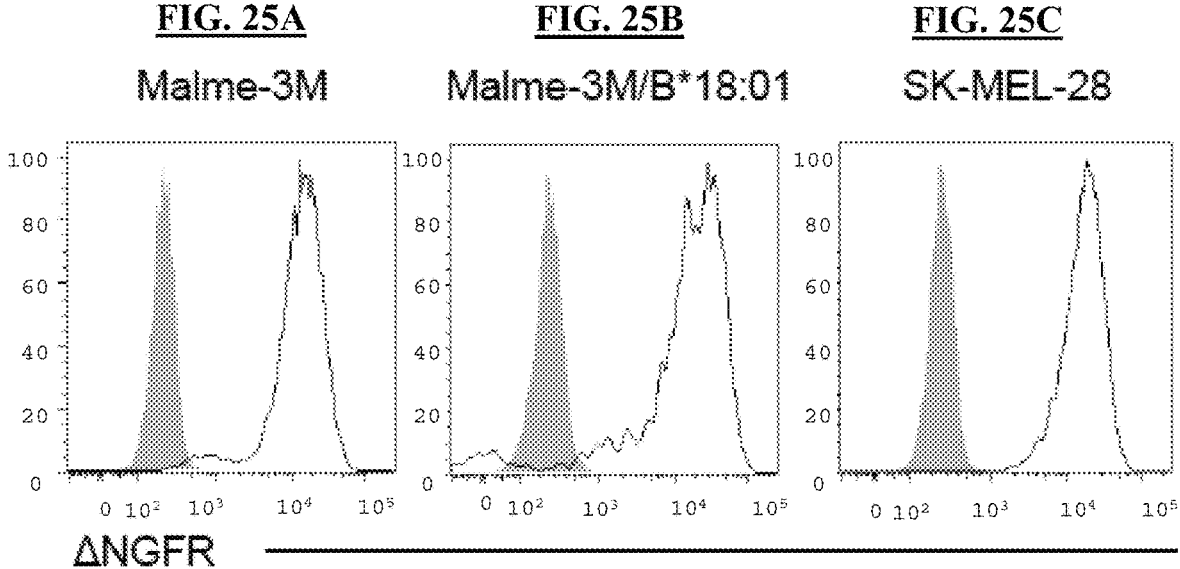
ΔNGFR
FIG. 25D
SK-MEL-28/B*18:01
FIG. 25E
A375
FIG. 25F
A375/B*18:01
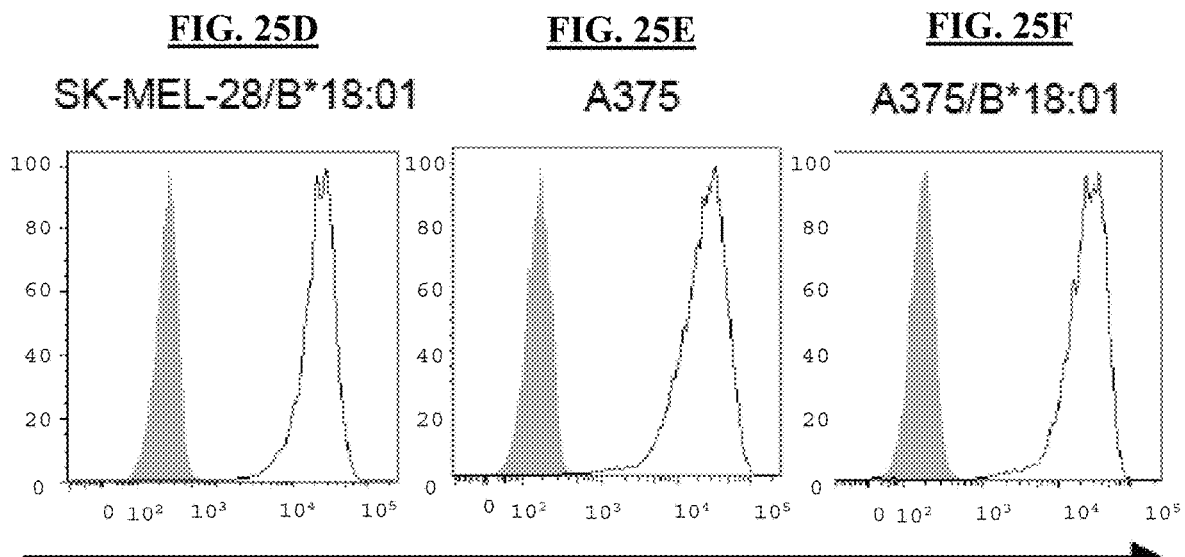

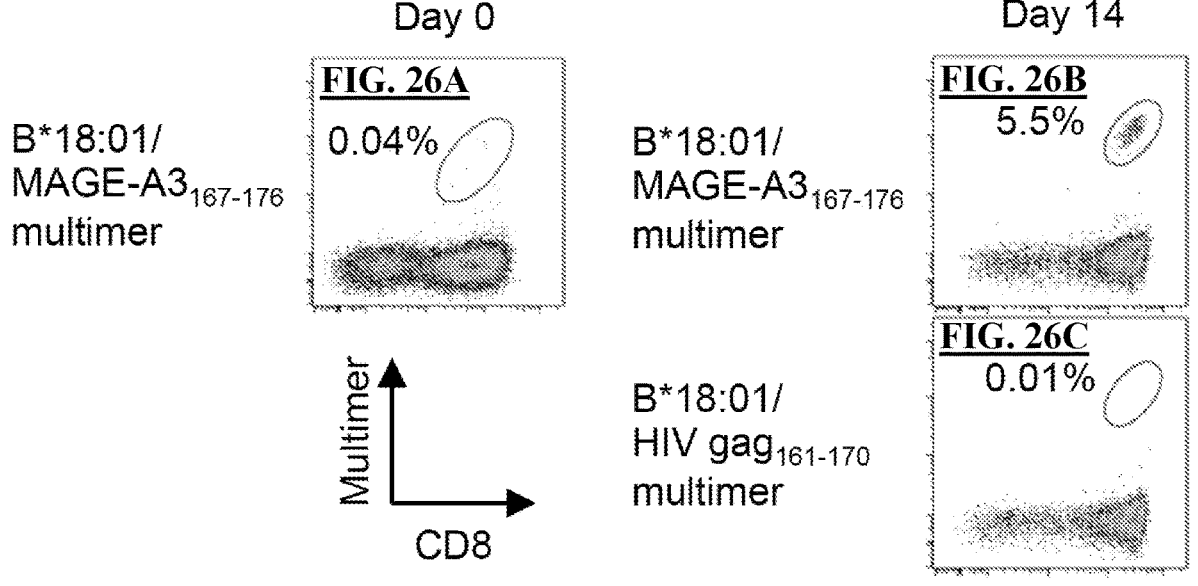

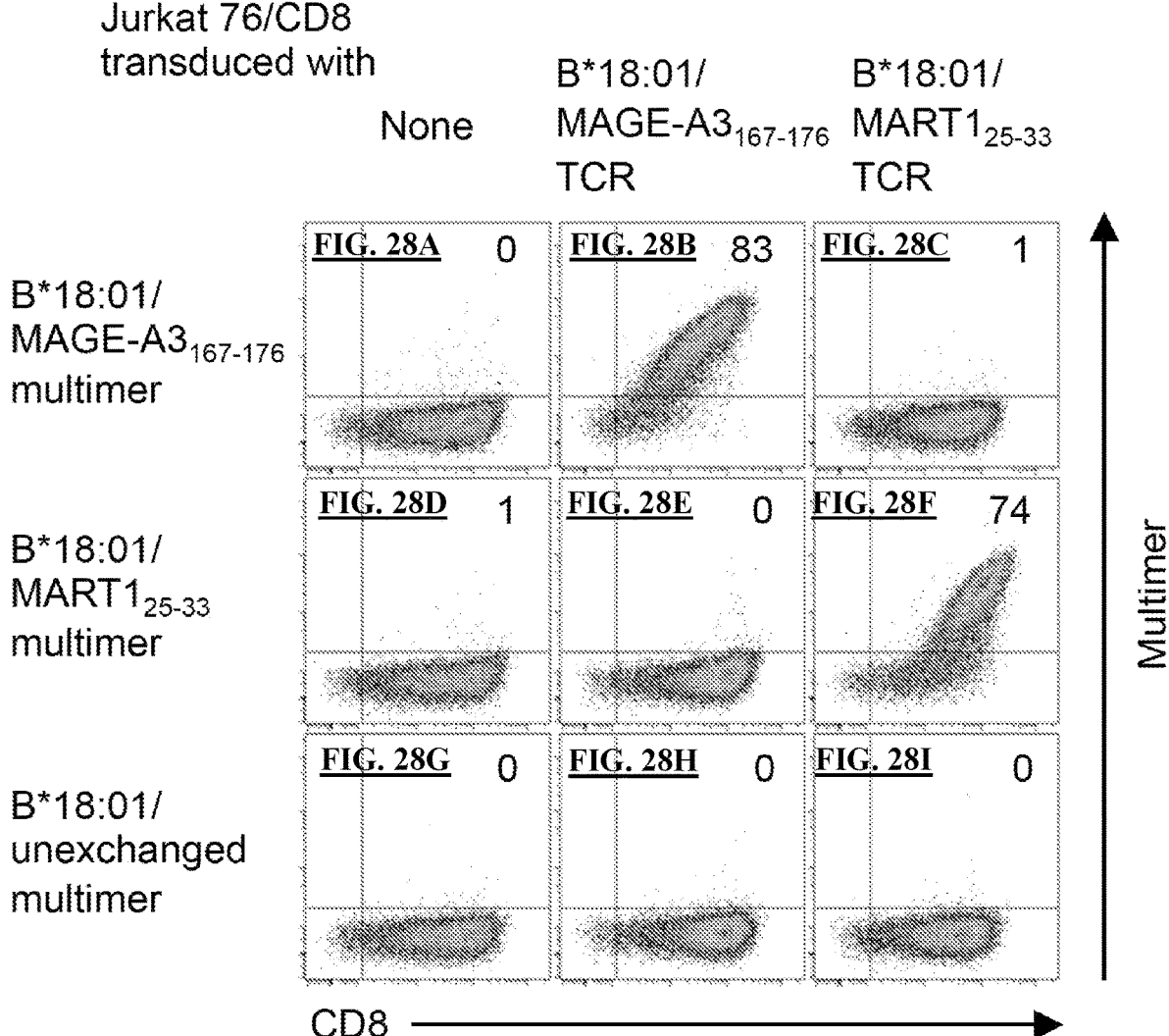

Transduced with

None

B18*:01/
MAGE-A3$_{167-176}$
multimer

0%

35.2%

B*18:01/
HIV gag$_{161-170}$
multimer

0%

0.1%

Multimer

CD8

|  |  | B*18:01 | MAGE-A3 |
|---|---|---|---|
| ☐ | SK-MEL-28 | - | + |
| ▦ | SK-MEL-28/B*18:01 | + | + |
| ▤ | HEK293T | - | - |
| ■ | HEK293T/B*18:01 | + | - |
| ▨ | HEK293T/MAGE-A3 | - | + |
| ▧ | HEK293T/B*18:01/MAGE-A3 | + | + |

A*02:01/
SSX2$_{41-49}$
multimer

A*02:01/
HTLV-1 tax$_{11-19}$
multimer 9.9%

0%

Multimer

CD8

|  |  | A*02:01 | SSX2 |
|---|---|:---:|:---:|
| ☐ | SK-MEL-21 | + | − |
| ▦ | SK-MEL-21/SSX2 | + | + |
| ▤ | SK-MEL-37 | + | + |
| ■ | SK-MEL-28 | − | − |
| ▨ | SK-MEL-28/A*02:01 | + | − |
| ▧ | SK-MEL-28/SSX2 | − | + |
| ▧ | SK-MEL-28/A*02:01/SSX2 | + | + |

SEQUENCE LISTING

```
<160> NUMBER OF SEQ ID NOS: 93

<210> SEQ ID NO 1
<211> LENGTH: 271
<212> TYPE: PRT
<213> ORGANISM: Artificial Sequence
<220> FEATURE:
<223> OTHER INFORMATION: Tyr-alpha chain amino acid sequence

<400> SEQUENCE: 1

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Val Glu Gly
                100                 105                 110

Ser Gln Gly Asn Leu Ile Phe Gly Lys Gly Thr Lys Leu Ser Val Lys
            115                 120                 125

Pro Asn Ile Gln Asn Pro Asp Pro Ala Val Tyr Gln Leu Arg Asp Ser
        130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240
```

-continued

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser Glx
        260                 265                 270

<210> SEQ ID NO 2
<211> LENGTH: 314
<212> TYPE: PRT
<213> ORGANISM: Artificial Sequence
<220> FEATURE:
<223> OTHER INFORMATION: Tyr-beta chain amino acid sequence

<400> SEQUENCE: 2

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser His His Ser Gly Gly Ile Tyr Asn Glu Gln Phe Phe Gly Pro Gly
            115                 120                 125

Thr Arg Leu Thr Val Leu Glu Asp Leu Lys Asn Val Phe Pro Pro Glu
            130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
        210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
                260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
    290                 295                 300

Met Val Lys Arg Lys Asp Ser Arg Gly Glx
305                 310

<210> SEQ ID NO 3
<211> LENGTH: 813

<212> TYPE: DNA
<213> ORGANISM: Artificial Sequence
<220> FEATURE:
<223> OTHER INFORMATION: Tyr-alpha chain nucleotide sequence

<400> SEQUENCE: 3
atgaggcaag tggcgagagt gatcgtgttc ctgaccctga gtactttgag ccttgctaag        60
accacccagc ccatctccat ggactcatat gaaggacaag aagtgaacat aacctgtagc       120
cacaacaaca ttgctacaaa tgattatatc acgtggtacc aacagtttcc cagccaagga       180
ccacgattta ttattcaagg atacaagaca aaagttacaa acgaagtggc ctccctgttt       240
atccctgccg acagaaagtc cagcactctg agcctgcccc gggtttccct gagcgacact       300
gctgtgtact actgcctcgt gggtgacgta gaaggaagcc aaggaaatct catctttgga       360
aaaggcacta aactctctgt taaaccaaat atccagaacc ctgaccctgc cgtgtaccag       420
ctgagagact ctaaatccag tgacaagtct gtctgcctat tcaccgattt tgattctcaa       480
acaaatgtgt cacaaagtaa ggattctgat gtgtatatca cagacaaaac tgtgctagac       540
atgaggtcta tggacttcaa gagcaacagt gctgtggcct ggagcaacaa atctgacttt       600
gcatgtgcaa acgccttcaa caacagcatt attccagaag acaccttctt ccccagccca       660
gaaagttcct gtgatgtcaa gctggtcgag aaaagctttg aaacagatac gaacctaaac       720
tttcaaaacc tgtcagtgat tgggttccga atcctcctcc tgaaagtggc cgggtttaat       780
ctgctcatga cgctgcggct gtggtccagc tga                                    813

<210> SEQ ID NO 4
<211> LENGTH: 942
<212> TYPE: DNA
<213> ORGANISM: Artificial Sequence
<220> FEATURE:
<223> OTHER INFORMATION: Tyr-beta chain nucleotide sequence

<400> SEQUENCE: 4
atgagcatcg gcctcctgtg ctgtgcagcc ttgtctctcc tgtgggcagg tccagtgaat        60
gctggtgtca ctcagacccc aaaaattccag gtcctgaaga caggacagag catgacactg       120
cagtgtgccc aggatatgaa ccatgaatac atgtcctggt atcgacaaga cccaggcatg       180
gggctgaggc tgattcatta ctcagttggt gctggtatca ctgaccaagg agaagtcccc       240
aatggctaca atgtctccag atcaaccaca gaggatttcc cgctcaggct gctgtcggct       300
gctccctccc agacatctgt gtacttctgt gccagcagtc accattcggg ggggatctac       360
aatgagcagt tcttcgggcc agggacacgg ctcaccgtgc tagaggacct gaaaaacgtg       420
ttcccacccg aggtcgctgt gtttgagcca tcagaagcag agatctccca cacccaaaag       480
gccacactgg tatgcctggc cacaggcttc tacccccgacc acgtggagct gagctggtgg       540
gtgaatggga aggaggtgca cagtggggtc agcacagacc cgcagcccct caaggagcag       600
cccgccctca atgactccag atactgcctg agcagccgcc tgagggtctc ggccaccttc       660
tggcagaacc ccgcaacca cttccgctgt caagtccagt tctacgggct ctcggagaat       720
gacgagtgga cccaggatag ggccaaacct gtcacccaga tcgtcagcgc cgaggcctgg       780
ggtagagcag actgtggctt cacctccgag tcttaccagc aaggggtcct gtctgccacc       840
atcctctatg agatcttgct agggaaggcc accttgtatg ccgtgctggt cagtgccctc       900
gtgctgatgg ccatggtcaa gagaaaggat tccagaggct ag                         942

<210> SEQ ID NO 5

<211> LENGTH: 7
<212> TYPE: PRT
<213> ORGANISM: Artificial Sequence
<220> FEATURE:
<223> OTHER INFORMATION: Tyr-alpha CDR1

<400> SEQUENCE: 5

Asn Ile Ala Thr Asn Asp Tyr
1               5

<210> SEQ ID NO 6
<211> LENGTH: 5
<212> TYPE: PRT
<213> ORGANISM: Artificial Sequence
<220> FEATURE:
<223> OTHER INFORMATION: Tyr-alpha CDR2

<400> SEQUENCE: 6

Gly Tyr Lys Thr Lys
1               5

<210> SEQ ID NO 7
<211> LENGTH: 15
<212> TYPE: PRT
<213> ORGANISM: Artificial Sequence
<220> FEATURE:
<223> OTHER INFORMATION: Tyr-alpha CDR3

<400> SEQUENCE: 7

Cys Leu Val Gly Asp Val Glu Gly Ser Gln Gly Asn Leu Ile Phe
1               5                   10                  15

<210> SEQ ID NO 8
<211> LENGTH: 5
<212> TYPE: PRT
<213> ORGANISM: Artificial Sequence
<220> FEATURE:
<223> OTHER INFORMATION: Tyr-beta CDR1

<400> SEQUENCE: 8

Met Asn His Glu Tyr
1               5

<210> SEQ ID NO 9
<211> LENGTH: 6
<212> TYPE: PRT
<213> ORGANISM: Artificial Sequence
<220> FEATURE:
<223> OTHER INFORMATION: Tyr-beta CDR2

<400> SEQUENCE: 9

Ser Val Gly Ala Gly Ile
1               5

<210> SEQ ID NO 10
<211> LENGTH: 16
<212> TYPE: PRT
<213> ORGANISM: Artificial Sequence
<220> FEATURE:
<223> OTHER INFORMATION: Tyr-beta CDR3

<400> SEQUENCE: 10

Cys Ala Ser Ser His His Ser Gly Gly Ile Tyr Asn Glu Gln Phe Phe
1               5                   10                  15

<210> SEQ ID NO 11
<211> LENGTH: 280

-continued

```
<212> TYPE: PRT
<213> ORGANISM: Artificial Sequence
<220> FEATURE:
<223> OTHER INFORMATION: MAGE-A1-alpha chain amino acid sequence

<400> SEQUENCE: 11

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
                20                  25                  30

Val Val Glu Lys Glu Asp Val Thr Leu Asp Cys Val Tyr Glu Thr Arg
            35                  40                  45

Asp Thr Thr Tyr Tyr Leu Phe Trp Tyr Lys Gln Pro Pro Ser Gly Glu
        50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Glu Ser Tyr Ser Gly Ala Gly Ser Tyr Gln Leu Thr Phe
            115                 120                 125

Gly Lys Gly Thr Lys Leu Ser Val Ile Pro Asn Ile Gln Asn Pro Asp
    130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
            180                 185                 190

Met Asp Phe Lys Ser Asn Ser Ala Val Ala Trp Ser Asn Lys Ser Asp
            195                 200                 205

Phe Ala Cys Ala Asn Ala Phe Asn Asn Ser Ile Ile Pro Glu Asp Thr
    210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
                260                 265                 270

Thr Leu Arg Leu Trp Ser Ser Glx
        275                 280

<210> SEQ ID NO 12
<211> LENGTH: 312
<212> TYPE: PRT
<213> ORGANISM: Artificial Sequence
<220> FEATURE:
<223> OTHER INFORMATION: MAGE-A1-beta chain amino acid sequence

<400> SEQUENCE: 12

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
                20                  25                  30

Lys Arg Gly Gln Asn Val Thr Phe Arg Cys Asp Pro Ile Ser Glu His
            35                  40                  45
```

```
Asn Arg Leu Tyr Trp Tyr Arg Gln Thr Leu Gly Gln Gly Pro Glu Phe
    50              55              60

Leu Thr Tyr Phe Gln Asn Glu Ala Gln Leu Glu Lys Ser Arg Leu Leu
65                  70              75                  80

Ser Asp Arg Phe Ser Ala Glu Arg Pro Lys Gly Ser Phe Ser Thr Leu
                85              90                  95

Glu Ile Gln Arg Thr Glu Gln Gly Asp Ser Ala Met Tyr Leu Cys Ala
                100             105             110

Ser Ser Leu Ala Ser Gly Ser Asn Gln Pro Gln His Phe Gly Asp Gly
            115             120             125

Thr Arg Leu Ser Ile Leu Glu Asp Leu Asn Lys Val Phe Pro Pro Glu
    130             135             140

Val Ala Val Phe Glu Pro Ser Glu Ala Glu Ile Ser His Thr Gln Lys
145             150             155             160

Ala Thr Leu Val Cys Leu Ala Thr Gly Phe Phe Pro Asp His Val Glu
                165             170             175

Leu Ser Trp Trp Val Asn Gly Lys Glu Val His Ser Gly Val Ser Thr
                180             185             190

Asp Pro Gln Pro Leu Lys Glu Gln Pro Ala Leu Asn Asp Ser Arg Tyr
            195             200             205

Cys Leu Ser Ser Arg Leu Arg Val Ser Ala Thr Phe Trp Gln Asn Pro
    210             215             220

Arg Asn His Phe Arg Cys Gln Val Gln Phe Tyr Gly Leu Ser Glu Asn
225             230             235             240

Asp Glu Trp Thr Gln Asp Arg Ala Lys Pro Val Thr Gln Ile Val Ser
                245             250             255

Ala Glu Ala Trp Gly Arg Ala Asp Cys Gly Phe Thr Ser Val Ser Tyr
                260             265             270

Gln Gln Gly Val Leu Ser Ala Thr Ile Leu Tyr Glu Ile Leu Leu Gly
            275             280             285

Lys Ala Thr Leu Tyr Ala Val Leu Val Ser Ala Leu Val Leu Met Ala
    290             295             300

Met Val Lys Arg Lys Asp Phe Glx
305                 310

<210> SEQ ID NO 13
<211> LENGTH: 840
<212> TYPE: DNA
<213> ORGANISM: Artificial Sequence
<220> FEATURE:
<223> OTHER INFORMATION: MAGE-A1-alpha chain nucleotide sequence

<400> SEQUENCE: 13
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctggta caagcaacca     180
ccaagtggag aattggtttt ccttattcgt cggaactctt ttgatgagca aaatgaaata     240
agtggtcggt attcttggaa cttccagaaa tccaccagtt ccttcaactt caccatcaca     300
gcctcacaag tcgtggactc agcagtatac ttctgtgctc tgagtgagtc atactctggg     360
gctgggagtt accaactcac tttcgggaag gggaccaaac tctcggtcat accaaatatc     420
cagaaccctg accctgccgt gtaccagctg agagactcta atccagtga caagtctgtc     480 tgcctattca ccgatttga ttctcaaaca aatgtgtcac aaagtaagga ttctgatgtg     540
```

-continued

```
tatatcacag acaaaactgt gctagacatg aggtctatgg acttcaagag caacagtgct      600
gtggcctgga gcaacaaatc tgactttgca tgtgcaaacg ccttcaacaa cagcattatt      660
ccagaagaca ccttcttccc cagcccagaa agttcctgtg atgtcaagct ggtcgagaaa      720
agctttgaaa cagatacgaa cctaaacttt caaaacctgt cagtgattgg gttccgaatc      780
ctcctcctga aagtggccgg gtttaatctg ctcatgacgc tgcggctgtg gtccagctga      840
```

<210> SEQ ID NO 14
<211> LENGTH: 936
<212> TYPE: DNA
<213> ORGANISM: Artificial Sequence
<220> FEATURE:
<223> OTHER INFORMATION: MAGE-A1-beta chain nucleotide sequence

<400> SEQUENCE: 14

```
atgggcacca gcctcctctg ctggatggcc ctgtgtctcc tgggggcaga tcacgcagat       60
actggagtct cccagaaccc cagacacaag atcacaaaga ggggacagaa tgtaactttc      120
aggtgtgatc caatttctga acacaaccgc ctttattggt accgacagac cctggggcag      180
ggcccagagt ttctgactta cttccagaat gaagctcaac tagaaaaatc aaggctgctc      240
agtgatcggt tctctgcaga gaggcctaag ggatctttct ccaccttgga gatccagcgc      300
acagagcagg gggactcggc catgtatctc tgtgccagca gcttagcttc gggcagcaat      360
cagccccagc attttggtga tgggactcga ctctccatcc tagaggacct gaacaaggtg      420 ttcccaccccg aggtcgctgt gtttgagcca tcagaagcag agatctccca cacccaaaag      480
gccacactgg tgtgcctggc cacaggcttc ttccccgacc acgtggagct gagctggtgg      540
gtgaatggga aggaggtgca cagtggggtc agcacggacc cgcagcccct caaggagcag      600
cccgccctca tgactccag atactgcctg agcagccgcc tgagggtctc ggccaccttc      660
tggcagaacc cccgcaacca cttccgctgt caagtccagt ctacgggct ctcggagaat      720 gacgagtgga cccaggatag ggccaaaccc gtcacccaga tcgtcagcgc cgaggcctgg      780
ggtagagcag actgtggctt tacctcggtg tcctaccagc aagggtcct gtctgccacc      840 atcctctatg agatcctgct agggaaggcc accctgtatg ctgtgctggt cagcgccctt      900
gtgttgatgg ccatggtcaa gagaaaggat ttctga                             936
```

<210> SEQ ID NO 15
<211> LENGTH: 8
<212> TYPE: PRT
<213> ORGANISM: Artificial Sequence
<220> FEATURE:
<223> OTHER INFORMATION: MAGE-A1-alpha CDR1

<400> SEQUENCE: 15

```
Thr Arg Asp Thr Thr Tyr Tyr Leu
1               5
```

<210> SEQ ID NO 16
<211> LENGTH: 8
<212> TYPE: PRT
<213> ORGANISM: Artificial Sequence
<220> FEATURE:
<223> OTHER INFORMATION: MAGE-A1-alpha CDR2

<400> SEQUENCE: 16

```
Arg Asn Ser Phe Asp Glu Gln Asn
1               5
```

-continued

```
<210> SEQ ID NO 17
<211> LENGTH: 17
<212> TYPE: PRT
<213> ORGANISM: Artificial Sequence
<220> FEATURE:
<223> OTHER INFORMATION: MAGE-A1-alpha CDR3

<400> SEQUENCE: 17

Cys Ala Leu Ser Glu Ser Tyr Ser Gly Ala Gly Ser Tyr Gln Leu Thr
1               5                   10                  15

Phe

<210> SEQ ID NO 18
<211> LENGTH: 5
<212> TYPE: PRT
<213> ORGANISM: Artificial Sequence
<220> FEATURE:
<223> OTHER INFORMATION: MAGE-A1-beta CDR1

<400> SEQUENCE: 18

Ser Glu His Asn Arg
1               5

<210> SEQ ID NO 19
<211> LENGTH: 6
<212> TYPE: PRT
<213> ORGANISM: Artificial Sequence
<220> FEATURE:
<223> OTHER INFORMATION: MAGE-A1-beta CDR2

<400> SEQUENCE: 19

Phe Gln Asn Glu Ala Gln
1               5

<210> SEQ ID NO 20
<211> LENGTH: 15
<212> TYPE: PRT
<213> ORGANISM: Artificial Sequence
<220> FEATURE:
<223> OTHER INFORMATION: MAGE-A1-beta CDR3

<400> SEQUENCE: 20

Cys Ala Ser Ser Leu Ala Ser Gly Ser Asn Gln Pro Gln His Phe
1               5                   10                  15

<210> SEQ ID NO 21
<211> LENGTH: 269
<212> TYPE: PRT
<213> ORGANISM: Artificial Sequence
<220> FEATURE:
<223> OTHER INFORMATION: MART1-alpha chain amino acid sequence

<400> SEQUENCE: 21

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
                20                  25                  30

Ala Ile Val Gln Ile Asn Cys Thr Tyr Gln Thr Ser Gly Phe Asn Gly
            35                  40                  45

Leu Phe Trp Tyr Gln Gln His Ala Gly Glu Ala Pro Thr Phe Leu Ser
        50                  55                  60

Tyr Asn Val Leu Asp Gly Leu Glu Glu Lys Gly Arg Phe Ser Ser Phe
65                  70                  75                  80
```

-continued

```
Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Tyr Gly Gly Ala Thr
                100                 105                 110

Asn Lys Leu Ile Phe Gly Thr Gly Thr Leu Leu Ala Val Gln Pro Asn
                115                 120                 125

Ile Gln Asn Pro Asp Pro Ala Val Tyr Gln Leu Arg Asp Ser Lys Ser
        130                 135                 140

Ser Asp Lys Ser Val Cys Leu Phe Thr Asp Phe Asp Ser Gln Thr Asn
145                 150                 155                 160

Val Ser Gln Ser Lys Asp Ser Asp Val Tyr Ile Thr Asp Lys Thr Val
                165                 170                 175

Leu Asp Met Arg Ser Met Asp Phe Lys Ser Asn Ser Ala Val Ala Trp
                180                 185                 190

Ser Asn Lys Ser Asp Phe Ala Cys Ala Asn Ala Phe Asn Asn Ser Ile
                195                 200                 205

Ile Pro Glu Asp Thr Phe Phe Pro Ser Pro Glu Ser Ser Cys Asp Val
        210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Leu Lys Val Ala Gly
                245                 250                 255

Phe Asn Leu Leu Met Thr Leu Arg Leu Trp Ser Ser Glx
                260                 265
```

```
<210> SEQ ID NO 22
<211> LENGTH: 313
<212> TYPE: PRT
<213> ORGANISM: Artificial Sequence
<220> FEATURE:
<223> OTHER INFORMATION: MART1-beta chain amino acid sequence

<400> SEQUENCE: 22
```

```
Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
                20                  25                  30

Arg Arg Gly Gln Glu Ala Arg Leu Arg Cys Ser Pro Met Lys Gly His
                35                  40                  45

Ser His Val Tyr Trp Tyr Arg Gln Leu Pro Glu Glu Gly Leu Lys Phe
        50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
                100                 105                 110

Ser Ser Pro His Ala Gly Gly Val Asp Glu Lys Leu Phe Phe Gly Ser
                115                 120                 125

Gly Thr Gln Leu Ser Val Leu Glu Asp Leu Asn Lys Val Phe Pro Pro
        130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175
```

-continued

```
Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Phe Glx
305                 310
```

```
<210> SEQ ID NO 23
<211> LENGTH: 807
<212> TYPE: DNA
<213> ORGANISM: Artificial Sequence
<220> FEATURE:
<223> OTHER INFORMATION: MART1-alpha chain nucleotide sequence

<400> SEQUENCE: 23
atgtggggag ttttccttct ttatgtttcc atgaagatgg gaggcactac aggacaaaac      60
attgaccagc ccactgagat gacagctacg gaaggtgcca ttgtccagat caactgcacg     120
taccagacat ctgggttcaa cgggctgttc tggtaccagc aacatgctgg cgaagcaccc     180
acatttctgt cttacaatgt tctggatggt ttggaggaga aagtcgtttt ttcttcattc     240
cttagtcggt ctaaagggta cagttacctc cttttgaagg agctccagat gaaagactct     300
gcctcttacc tctgtgctgt gtatggtggt gctacaaaca agctcatctt tggaactggc     360
actctgcttg ctgtccagcc aaatatccag aaccctgacc ctgccgtgta ccagctgaga     420
gactctaaat ccagtgacaa gtctgtctgc ctattcaccg attttgattc tcaaacaaat     480
gtgtcacaaa gtaaggattc tgatgtgtat atcacagaca aaactgtgct agacatgagg     540
tctatggact tcaagagcaa cagtgctgtg gcctggagca caaatctga ctttgcatgt      600 gcaaacgcct tcaacaacag cattattcca gaagacacct cttcccag cccagaaagt       660 tcctgtgatg tcaagctggt cgagaaaagc tttgaaacag atacgaacct aaactttcaa     720
aacctgtcag tgattgggtt ccgaatcctc ctcctgaaag tggccgggtt taatctgctc     780
atgacgctgc ggctgtggtc cagctga                                         807
```

```
<210> SEQ ID NO 24
<211> LENGTH: 939
<212> TYPE: DNA
<213> ORGANISM: Artificial Sequence
<220> FEATURE:
<223> OTHER INFORMATION: MART1-beta chain nucleotide sequence

<400> SEQUENCE: 24
atggacacca gagtactctg ctgtgcggtc atctgtcttc tggggcagg tctctcaaat      60 gccggcgtca tgcagaaccc aagacacctg gtcaggagga ggggacagga ggcaagactg    120
```

```
agatgcagcc caatgaaagg acacagtcat gtttactggt atcggcagct cccagaggaa    180
ggtctgaaat tcatggttta tctccagaaa gaaaatatca tagatgagtc aggaatgcca    240
aaggaacgat tttctgctga atttcccaaa gagggcccca gcatcctgag gatccagcag    300
gtagtgcgag gagattcggc agcttatttc tgtgccagct caccacacgc ggggggagtt    360
gatgaaaaac tgtttttttgg cagtggaacc cagctctctg tcttggagga cctgaacaag    420
gtgttcccac ccgaggtcgc tgtgtttgag ccatcagaag cagagatctc ccacacccaa    480
aaggccacac tggtgtgcct ggccacaggc ttcttccctg accacgtgga gctgagctgg    540
tgggtgaatg ggaaggaggt gcacagtggg gtcagcacgg accccgcagcc cctcaaggag    600 cagcccgccc tcaatgactc cagatactgc ctgagcagcc gcctgagggt ctcggccacc    660
ttctggcaga accccgcaa ccacttccgc tgtcaagtcc agttctacgg gctctcggag    720
aatgacgagt ggacccagga tagggccaaa cccgtcaccc agatcgtcag cgccgaggcc    780
tggggtagag cagactgtgg ctttacctcg gtgtcctacc agcaaggggt cctgtctgcc    840
accatcctct atgagatcct gctagggaag gccaccctgt atgctgtgct ggtcagcgcc    900
cttgtgttga tggccatggt caagagaaag gatttctga                            939
```

<210> SEQ ID NO 25
<211> LENGTH: 6
<212> TYPE: PRT
<213> ORGANISM: Artificial Sequence
<220> FEATURE:
<223> OTHER INFORMATION: MART1-alpha CDR1

<400> SEQUENCE: 25

Thr Ser Gly Phe Asn Gly
1               5

<210> SEQ ID NO 26
<211> LENGTH: 6
<212> TYPE: PRT
<213> ORGANISM: Artificial Sequence
<220> FEATURE:
<223> OTHER INFORMATION: MART1-alpha CDR2

<400> SEQUENCE: 26

Asn Val Leu Asp Gly Leu
1               5

<210> SEQ ID NO 27
<211> LENGTH: 13
<212> TYPE: PRT
<213> ORGANISM: Artificial Sequence
<220> FEATURE:
<223> OTHER INFORMATION: MART1-alpha CDR3

<400> SEQUENCE: 27

Cys Ala Val Tyr Gly Gly Ala Thr Asn Lys Leu Ile Phe
1               5                   10

<210> SEQ ID NO 28
<211> LENGTH: 5
<212> TYPE: PRT
<213> ORGANISM: Artificial Sequence
<220> FEATURE:
<223> OTHER INFORMATION: MART1-beta CDR1

<400> SEQUENCE: 28

Lys Gly His Ser His
1               5

```
<210> SEQ ID NO 29
<211> LENGTH: 6
<212> TYPE: PRT
<213> ORGANISM: Artificial Sequence
<220> FEATURE:
<223> OTHER INFORMATION: MART1-beta CDR2

<400> SEQUENCE: 29

Leu Gln Lys Glu Asn Ile
1               5

<210> SEQ ID NO 30
<211> LENGTH: 16
<212> TYPE: PRT
<213> ORGANISM: Artificial Sequence
<220> FEATURE:
<223> OTHER INFORMATION: MART1-beta CDR3

<400> SEQUENCE: 30

Cys Ala Ser Ser Pro His Ala Gly Gly Val Asp Glu Lys Leu Phe Phe
1               5                   10                  15

<210> SEQ ID NO 31
<211> LENGTH: 277
<212> TYPE: PRT
<213> ORGANISM: Artificial Sequence
<220> FEATURE:
<223> OTHER INFORMATION: MAGE-A3-alpha chain amino acid sequence

<400> SEQUENCE: 31

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Glu Val Arg Ser Ser Ala Ser Lys Ile Ile Phe Gly Ser Gly
        115                 120                 125

Thr Arg Leu Ser Ile Arg Pro Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220
```

```
Ser Pro Glu Ser Ser Cys Asp Val Lys Leu Val Glu Lys Ser Phe Glu
225             230             235             240

Thr Asp Thr Asn Leu Asn Phe Gln Asn Leu Ser Val Ile Gly Phe Arg
            245             250             255

Ile Leu Leu Leu Lys Val Ala Gly Phe Asn Leu Leu Met Thr Leu Arg
            260             265             270

Leu Trp Ser Ser Glx
        275
```

```
<210> SEQ ID NO 32
<211> LENGTH: 310
<212> TYPE: PRT
<213> ORGANISM: Artificial Sequence
<220> FEATURE:
<223> OTHER INFORMATION: MAGE-A3-beta chain amino acid sequence

<400> SEQUENCE: 32

Met Leu Leu Leu Leu Leu Leu Leu Gly Pro Gly Ser Gly Leu Gly Ala
1               5               10              15

Val Val Ser Gln His Pro Ser Trp Val Ile Cys Lys Ser Gly Thr Ser
            20              25              30

Val Lys Ile Glu Cys Arg Ser Leu Asp Phe Gln Ala Thr Thr Met Phe
            35              40              45

Trp Tyr Arg Gln Phe Pro Lys Gln Ser Leu Met Leu Met Ala Thr Ser
        50              55              60

Asn Glu Gly Ser Lys Ala Thr Tyr Glu Gln Gly Val Glu Lys Asp Lys
65              70              75              80

Phe Leu Ile Asn His Ala Ser Leu Thr Leu Ser Thr Leu Thr Val Thr
            85              90              95

Ser Ala His Pro Glu Asp Ser Ser Phe Tyr Ile Cys Ser Ala Asn Pro
            100             105             110

Arg Thr Thr Leu Tyr Glu Gln Tyr Phe Gly Pro Gly Thr Arg Leu Thr
            115             120             125

Val Thr Glu Asp Leu Lys Asn Val Phe Pro Pro Glu Val Ala Val Phe
            130             135             140

Glu Pro Ser Glu Ala Glu Ile Ser His Thr Gln Lys Ala Thr Leu Val
145             150             155             160

Cys Leu Ala Thr Gly Phe Tyr Pro Asp His Val Glu Leu Ser Trp Trp
            165             170             175

Val Asn Gly Lys Glu Val His Ser Gly Val Ser Thr Asp Pro Gln Pro
            180             185             190

Leu Lys Glu Gln Pro Ala Leu Asn Asp Ser Arg Tyr Cys Leu Ser Ser
            195             200             205

Arg Leu Arg Val Ser Ala Thr Phe Trp Gln Asn Pro Arg Asn His Phe
        210             215             220

Arg Cys Gln Val Gln Phe Tyr Gly Leu Ser Glu Asn Asp Glu Trp Thr
225             230             235             240

Gln Asp Arg Ala Lys Pro Val Thr Gln Ile Val Ser Ala Glu Ala Trp
            245             250             255

Gly Arg Ala Asp Cys Gly Phe Thr Ser Glu Ser Tyr Gln Gln Gly Val
            260             265             270

Leu Ser Ala Thr Ile Leu Tyr Glu Ile Leu Leu Gly Lys Ala Thr Leu
        275             280             285

Tyr Ala Val Leu Val Ser Ala Leu Val Leu Met Ala Met Val Lys Arg
        290             295             300
```

-continued

Lys Asp Ser Arg Gly Glx
305                     310

<210> SEQ ID NO 33
<211> LENGTH: 831
<212> TYPE: DNA
<213> ORGANISM: Artificial Sequence
<220> FEATURE:
<223> OTHER INFORMATION: MAGE-A3-alpha chain nucleotide sequence

<400> SEQUENCE: 33
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctggta caagcaacca     180
ccaagtggag aattggtttt ccttattcgt cggaactctt ttgatgagca aaatgaaata     240
agtggtcggt attcttggaa cttccagaaa tccaccagtt ccttcaactt caccatcaca     300
gcctcacaag tcgtggactc agcagtatac ttctgtgctc tggaagtgag aagcagtgct     360
tccaagataa tctttggatc agggaccaga ctcagcatcc ggccaaatat ccagaaccct     420
gaccctgccg tgtaccagct gagagactct aaatccagtg acaagtctgt ctgcctattc     480
accgattttg attctcaaac aaatgtgtca caaagtaagg attctgatgt gtatatcaca     540
gacaaaactg tgctagacat gaggtctatg gacttcaaga gcaacagtgc tgtggcctgg     600
agcaacaaat ctgactttgc atgtgcaaac gccttcaaca cagcattat ccagaagac     660 accttcttcc ccagcccaga aagttcctgt gatgtcaagc tggtcgagaa aagctttgaa     720
acagatacga acctaaactt tcaaaacctg tcagtgattg ggttccgaat cctcctcctg     780
aaagtggccg ggtttaatct gctcatgacg ctgcggctgt ggtccagctg a             831

<210> SEQ ID NO 34
<211> LENGTH: 930
<212> TYPE: DNA
<213> ORGANISM: Artificial Sequence
<220> FEATURE:
<223> OTHER INFORMATION: MAGE-A3-beta chain nucleotide sequence

<400> SEQUENCE: 34
atgctgctgc ttctgctgct tctggggcca ggctccgggc ttggtgctgt cgtctctcaa      60
catccgagct gggttatctg taagagtgga acctctgtga agatcgagtg ccgttccctg     120
gactttcagg ccacaactat gttttggtat cgtcagttcc cgaaacagag tctcatgctg     180
atggcaactt ccaatgaggg ctccaaggcc acatacgagc aaggcgtcga gaaggacaag     240
tttctcatca accatgcaag cctgaccttg tccactctga cagtgaccag tgcccatcct     300
gaagacagca gcttctacat ctgcagtgca accccggga ctaccctcta cgagcagtac     360
ttcgggccgg gcaccaggct cacggtcaca gaggacctga aaacgtgtt cccacccgag     420 gtcgctgtgt ttgagccatc agaagcagag atctcccaca cccaaaaggc cacactggtg     480
tgcctggcca caggcttcta ccccgaccac gtggagctga ctggtgggt gaatgggaag     540 gaggtgcaca gtggggtcag cacagacccg cagcccctca aggagcagcc cgccctcaat     600
gactccagat actgcctgag cagccgcctg agggtctcgg ccaccttctg cagaacccc     660 cgcaaccact tccgctgtca gtccagttc tacgggctct cggagaatga cgagtggacc     720
caggataggg ccaaacctgt cacccagatc gtcagcgccg aggcctgggg tagagcagac     780
tgtggcttca cctccgagtc ttaccagcaa ggggtcctgt ctgccaccat cctctatgag     840

-continued

```
atcttgctag ggaaggccac cttgtatgcc gtgctggtca gtgcccttgt gctgatggcc       900
atggtcaaga gaaaggattc cagaggctag                                         930
```

```
<210> SEQ ID NO 35
<211> LENGTH: 7
<212> TYPE: PRT
<213> ORGANISM: Artificial Sequence
<220> FEATURE:
<223> OTHER INFORMATION: MAGE-A3-alpha CDR1

<400> SEQUENCE: 35

Thr Arg Asp Thr Thr Tyr Tyr
1               5

<210> SEQ ID NO 36
<211> LENGTH: 8
<212> TYPE: PRT
<213> ORGANISM: Artificial Sequence
<220> FEATURE:
<223> OTHER INFORMATION: MAGE-A3-alpha CDR2

<400> SEQUENCE: 36

Arg Asn Ser Phe Asp Glu Gln Asn
1               5

<210> SEQ ID NO 37
<211> LENGTH: 14
<212> TYPE: PRT
<213> ORGANISM: Artificial Sequence
<220> FEATURE:
<223> OTHER INFORMATION: MAGE-A3-alpha CDR3

<400> SEQUENCE: 37

Cys Ala Leu Glu Val Arg Ser Ser Ala Ser Lys Ile Ile Phe
1               5                   10

<210> SEQ ID NO 38
<211> LENGTH: 6
<212> TYPE: PRT
<213> ORGANISM: Artificial Sequence
<220> FEATURE:
<223> OTHER INFORMATION: MAGE-A3-beta CDR1

<400> SEQUENCE: 38

Asp Phe Gln Ala Thr Thr
1               5

<210> SEQ ID NO 39
<211> LENGTH: 7
<212> TYPE: PRT
<213> ORGANISM: Artificial Sequence
<220> FEATURE:
<223> OTHER INFORMATION: MAGE-A3-beta CDR2

<400> SEQUENCE: 39

Ser Asn Glu Gly Ser Lys Ala
1               5

<210> SEQ ID NO 40
<211> LENGTH: 14
<212> TYPE: PRT
<213> ORGANISM: Artificial Sequence
<220> FEATURE:
<223> OTHER INFORMATION: MAGE-A3-beta CDR3
```

-continued

```
<400> SEQUENCE: 40

Cys Ser Ala Asn Pro Arg Thr Thr Leu Tyr Glu Gln Tyr Phe
1               5                   10

<210> SEQ ID NO 41
<211> LENGTH: 274
<212> TYPE: PRT
<213> ORGANISM: Artificial Sequence
<220> FEATURE:
<223> OTHER INFORMATION: SSX2-alpha chain amino acid sequence

<400> SEQUENCE: 41

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Glu
                100                 105                 110

Pro Met Glu Tyr Gly Asn Lys Leu Val Phe Gly Ala Gly Thr Ile Leu
            115                 120                 125

Arg Val Lys Ser Tyr Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
                180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
            260                 265                 270

Ser Glx

<210> SEQ ID NO 42
<211> LENGTH: 313
<212> TYPE: PRT
<213> ORGANISM: Artificial Sequence
<220> FEATURE:
<223> OTHER INFORMATION: SSX2-beta chain amino acid sequence
```

<400> SEQUENCE: 42

```
Met Ser Asn Gln Val Leu Cys Cys Val Val Leu Cys Leu Leu Gly Ala
1               5                   10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
        50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
                100                 105                 110

Ser Ala Leu Phe Ser Gly Ala Asn Val Leu Thr Phe Gly Ala Gly Ser
            115                 120                 125

Arg Leu Thr Val Leu Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
        210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
        290                 295                 300

Val Lys Arg Lys Asp Ser Arg Gly Glx
305                 310
```

<210> SEQ ID NO 43
<211> LENGTH: 822
<212> TYPE: DNA
<213> ORGANISM: Artificial Sequence
<220> FEATURE:
<223> OTHER INFORMATION: SSX2-alpha chain nucleotide sequence

<400> SEQUENCE: 43

```
atggagaccc tcttgggcct gcttatcctt tggctgcagc tgcaatgggt gagcagcaaa        60
caggaggtga cacagattcc tgcagctctg agtgtcccag aaggagaaaa cttggttctc       120
aactgcagtt tcactgatag cgctatttac aacctccagt ggtttaggca ggaccctggg       180
```

```
aaaggtctca catctctgtt gcttattcag tcaagtcaga gagagcaaac aagtggaaga    240
cttaatgcct cgctggataa atcatcagga cgtagtactt tatacattgc agcttctcag    300
cctggtgact cagccaccta cctctgtgct gtggaaccca tggaatatgg aaacaaactg    360
gtctttggcg caggaaccat tctgagagtc aagtcctata tccagaaccc tgaccctgcc    420
gtgtaccagc tgagagactc taaatccagt gacaagtctg tctgcctatt caccgatttt    480
gattctcaaa caaatgtgtc acaaagtaag gattctgatg tgtatatcac agacaaaact    540
gtgctagaca tgaggtctat ggacttcaag agcaacagtg ctgtggcctg gagcaacaaa    600
tctgactttg catgtgcaaa cgccttcaac aacagcatta ttccagaaga caccttcttc    660
cccagcccag aaagttcctg tgatgtcaag ctggtcgaga aaagctttga aacagatacg    720
aacctaaact ttcaaaacct gtcagtgatt gggttccgaa tcctcctcct gaaagtggcc    780
gggtttaatc tgctcatgac gctgcggctg tggtccagct ga                      822
```

```
<210> SEQ ID NO 44
<211> LENGTH: 939
<212> TYPE: DNA
<213> ORGANISM: Artificial Sequence
<220> FEATURE:
<223> OTHER INFORMATION: SSX2-beta chain nucleotide sequence

<400> SEQUENCE: 44
atgagcaacc aggtgctctg ctgtgtggtc ctttgtctcc tgggagcaaa caccgtggat     60
ggtggaatca ctcagtcccc aaagtacctg ttcagaaagg aaggacagaa tgtgaccctg    120
agttgtgaac agaatttgaa ccacgatgcc atgtactggt accgacagga cccagggcaa    180
gggctgagat tgatctacta ctcacagata gtaaatgact ttcagaaagg agatatagct    240
gaagggtaca gcgtctctcg ggagaagaag gaatcctttc ctctcactgt gacatcggcc    300
caaaagaacc cgacagcttt ctatctctgt gccagtagtg cgttattctc tggggccaac    360
gtcctgactt cggggccggg cagcaggctg accgtgctgg aggacctgaa aaacgtgttc    420
ccacccgagg tcgctgtgtt tgagccatca gaagcagaga tctcccacac ccaaaaggcc    480
acactggtgt gcctggccac aggcttctac cccgaccacg tggagctgag ctggtgggtg    540
aatgggaagg aggtgcacag tggggtcagc acagacccgc agcccctcaa ggagcagccc    600
gccctcaatg actccagata ctgcctgagc agccgcctga gggtctcggc caccttctgg    660 cagaacccc gcaaccactt ccgctgtcaa gtccagttct acgggctctc ggagaatgac    720
gagtggaccc aggatagggc caaacctgtc acccagatcg tcagcgccga ggcctggggt    780
agagcagact gtggcttcac ctccgagtct taccagcaag gggtcctgtc tgccaccatc    840
ctctatgaga tcttgctagg gaaggccacc ttgtatgccg tgctggtcag tgccctcgtg    900
ctgatggcca tggtcaagag aaaggattcc agaggctga                          939
```

```
<210> SEQ ID NO 45
<211> LENGTH: 6
<212> TYPE: PRT
<213> ORGANISM: Artificial Sequence
<220> FEATURE:
<223> OTHER INFORMATION: SSX2-alpha CDR1

<400> SEQUENCE: 45

Asp Ser Ala Ile Tyr Asn
1               5

<210> SEQ ID NO 46
```

-continued

```
<211> LENGTH: 7
<212> TYPE: PRT
<213> ORGANISM: Artificial Sequence
<220> FEATURE:
<223> OTHER INFORMATION: SSX2-alpha CDR2

<400> SEQUENCE: 46

Ile Gln Ser Ser Gln Arg Glu
1               5

<210> SEQ ID NO 47
<211> LENGTH: 14
<212> TYPE: PRT
<213> ORGANISM: Artificial Sequence
<220> FEATURE:
<223> OTHER INFORMATION: SSX2-alpha CDR3

<400> SEQUENCE: 47

Cys Ala Val Glu Pro Met Glu Tyr Gly Asn Lys Leu Val Phe
1               5                   10

<210> SEQ ID NO 48
<211> LENGTH: 5
<212> TYPE: PRT
<213> ORGANISM: Artificial Sequence
<220> FEATURE:
<223> OTHER INFORMATION: SSX2-beta CDR1

<400> SEQUENCE: 48

Leu Asn His Asp Ala
1               5

<210> SEQ ID NO 49
<211> LENGTH: 6
<212> TYPE: PRT
<213> ORGANISM: Artificial Sequence
<220> FEATURE:
<223> OTHER INFORMATION: SSX2-beta CDR2

<400> SEQUENCE: 49

Ser Gln Ile Val Asn Asp
1               5

<210> SEQ ID NO 50
<211> LENGTH: 15
<212> TYPE: PRT
<213> ORGANISM: Artificial Sequence
<220> FEATURE:
<223> OTHER INFORMATION: SSX2-beta CDR3

<400> SEQUENCE: 50

Cys Ala Ser Ser Ala Leu Phe Ser Gly Ala Asn Val Leu Thr Phe
1               5                   10                  15

<210> SEQ ID NO 51
<211> LENGTH: 9
<212> TYPE: PRT
<213> ORGANISM: Artificial Sequence
<220> FEATURE:
<223> OTHER INFORMATION: Tyr-epitope (460-468)

<400> SEQUENCE: 51

Phe Gln Asp Tyr Ile Lys Ser Tyr Leu
1               5

<210> SEQ ID NO 52
<211> LENGTH: 9
```

```
<212> TYPE: PRT
<213> ORGANISM: Artificial Sequence
<220> FEATURE:
<223> OTHER INFORMATION: MAGE-A1-epitope (289-297)

<400> SEQUENCE: 52

Arg Val Arg Phe Phe Phe Pro Ser Leu
1               5

<210> SEQ ID NO 53
<211> LENGTH: 9
<212> TYPE: PRT
<213> ORGANISM: Artificial Sequence
<220> FEATURE:
<223> OTHER INFORMATION: MART1-epitope (25-33)

<400> SEQUENCE: 53

Glu Glu Ala Ala Gly Ile Gly Ile Leu
1               5

<210> SEQ ID NO 54
<211> LENGTH: 10
<212> TYPE: PRT
<213> ORGANISM: Artificial Sequence
<220> FEATURE:
<223> OTHER INFORMATION: MAGE-A3-epitope (167-176)

<400> SEQUENCE: 54

Met Glu Val Asp Pro Ile Gly His Leu Tyr
1               5                   10

<210> SEQ ID NO 55
<211> LENGTH: 9
<212> TYPE: PRT
<213> ORGANISM: Artificial Sequence
<220> FEATURE:
<223> OTHER INFORMATION: SSX2-epitope (41-49)

<400> SEQUENCE: 55

Lys Ala Ser Glu Lys Ile Phe Tyr Val
1               5

<210> SEQ ID NO 56
<211> LENGTH: 119
<212> TYPE: PRT
<213> ORGANISM: Artificial Sequence
<220> FEATURE:
<223> OTHER INFORMATION: B2m amino acid sequence

<400> SEQUENCE: 56

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110
```

-continued

```
Val Lys Trp Asp Arg Asp Met
        115

<210> SEQ ID NO 57
<211> LENGTH: 21
<212> TYPE: DNA
<213> ORGANISM: Artificial Sequence
<220> FEATURE:
<223> OTHER INFORMATION: siRNA-TCRa-1 Nucleotides 1 to 19 are
      ribonucleotides-other nucleotides are deoxyribonucleotides

<400> SEQUENCE: 57
guaaggauuc ugauguguat t                                              21

<210> SEQ ID NO 58
<211> LENGTH: 21
<212> TYPE: DNA
<213> ORGANISM: Artificial Sequence
<220> FEATURE:
<223> OTHER INFORMATION: siRNA-TCRa-2 Nucleotides 1 to 19 are
      ribonucleotides-other nucleotides are deoxyribonucleotides

<400> SEQUENCE: 58
uacacaucag aauccuuact t                                              21

<210> SEQ ID NO 59
<211> LENGTH: 21
<212> TYPE: DNA
<213> ORGANISM: Artificial Sequence
<220> FEATURE:
<223> OTHER INFORMATION: siRNA-TCRb-1 Nucleotides 1 to 19 are
      ribonucleotides-other nucleotides are deoxyribonucleotides

<400> SEQUENCE: 59
ccaccauccu cuaugagaut t                                              21

<210> SEQ ID NO 60
<211> LENGTH: 21
<212> TYPE: DNA
<213> ORGANISM: Artificial Sequence
<220> FEATURE:
<223> OTHER INFORMATION: siRNA-TCRb-2 Nucleotides 1 to 19 are
      ribonucleotides-other nucleotides are deoxyribonucleotides

<400> SEQUENCE: 60
aucucauaga ggaugguggt t                                              21

<210> SEQ ID NO 61
<211> LENGTH: 20
<212> TYPE: PRT
<213> ORGANISM: Artificial Sequence
<220> FEATURE:
<223> OTHER INFORMATION: MART1-derived overlapping peptide position 1

<400> SEQUENCE: 61

Met Pro Arg Glu Asp Ala His Phe Ile Tyr Gly Tyr Pro Lys Lys Gly
1               5                   10                  15

His Gly His Ser
            20

<210> SEQ ID NO 62
<211> LENGTH: 20
<212> TYPE: PRT
<213> ORGANISM: Artificial Sequence
<220> FEATURE:
<223> OTHER INFORMATION: MART1-derived overlapping peptide position 6
```

```
<400> SEQUENCE: 62

Ala His Phe Ile Tyr Gly Tyr Pro Lys Lys Gly His Gly His Ser Tyr
1               5                   10                  15

Thr Thr Ala Glu
            20

<210> SEQ ID NO 63
<211> LENGTH: 20
<212> TYPE: PRT
<213> ORGANISM: Artificial Sequence
<220> FEATURE:
<223> OTHER INFORMATION: MART1-derived overlapping peptide position 11

<400> SEQUENCE: 63

Gly Tyr Pro Lys Lys Gly His Gly His Ser Tyr Thr Thr Ala Glu Glu
1               5                   10                  15

Ala Ala Gly Ile
            20

<210> SEQ ID NO 64
<211> LENGTH: 20
<212> TYPE: PRT
<213> ORGANISM: Artificial Sequence
<220> FEATURE:
<223> OTHER INFORMATION: MART1-derived overlapping peptide position 16

<400> SEQUENCE: 64

Gly His Gly His Ser Tyr Thr Thr Ala Glu Glu Ala Ala Gly Ile Gly
1               5                   10                  15

Ile Leu Thr Val
            20

<210> SEQ ID NO 65
<211> LENGTH: 20
<212> TYPE: PRT
<213> ORGANISM: Artificial Sequence
<220> FEATURE:
<223> OTHER INFORMATION: MART1-derived overlapping peptide position 21

<400> SEQUENCE: 65

Tyr Thr Thr Ala Glu Glu Ala Ala Gly Ile Gly Ile Leu Thr Val Ile
1               5                   10                  15

Leu Gly Val Leu
            20

<210> SEQ ID NO 66
<211> LENGTH: 20
<212> TYPE: PRT
<213> ORGANISM: Artificial Sequence
<220> FEATURE:
<223> OTHER INFORMATION: MART1-derived overlapping peptide position 26

<400> SEQUENCE: 66

Glu Ala Ala Gly Ile Gly Ile Leu Thr Val Ile Leu Gly Val Leu Leu
1               5                   10                  15

Leu Ile Gly Cys
            20

<210> SEQ ID NO 67
<211> LENGTH: 20
<212> TYPE: PRT
<213> ORGANISM: Artificial Sequence
<220> FEATURE:
```

<223> OTHER INFORMATION: MART1-derived overlapping peptide position 31

<400> SEQUENCE: 67

Gly Ile Leu Thr Val Ile Leu Gly Val Leu Leu Leu Ile Gly Cys Trp
1               5                   10                  15

Tyr Cys Arg Arg
            20

<210> SEQ ID NO 68
<211> LENGTH: 20
<212> TYPE: PRT
<213> ORGANISM: Artificial Sequence
<220> FEATURE:
<223> OTHER INFORMATION: MART1-derived overlapping peptide position 36

<400> SEQUENCE: 68

Ile Leu Gly Val Leu Leu Leu Ile Gly Cys Trp Tyr Cys Arg Arg Arg
1               5                   10                  15

Asn Gly Tyr Arg
            20

<210> SEQ ID NO 69
<211> LENGTH: 20
<212> TYPE: PRT
<213> ORGANISM: Artificial Sequence
<220> FEATURE:
<223> OTHER INFORMATION: MART1-derived overlapping peptide position 41

<400> SEQUENCE: 69

Leu Leu Ile Gly Cys Trp Tyr Cys Arg Arg Arg Asn Gly Tyr Arg Ala
1               5                   10                  15

Leu Met Asp Lys
            20

<210> SEQ ID NO 70
<211> LENGTH: 20
<212> TYPE: PRT
<213> ORGANISM: Artificial Sequence
<220> FEATURE:
<223> OTHER INFORMATION: MART1-derived overlapping peptide position 46

<400> SEQUENCE: 70

Trp Tyr Cys Arg Arg Arg Asn Gly Tyr Arg Ala Leu Met Asp Lys Ser
1               5                   10                  15

Leu His Val Gly
            20

<210> SEQ ID NO 71
<211> LENGTH: 20
<212> TYPE: PRT
<213> ORGANISM: Artificial Sequence
<220> FEATURE:
<223> OTHER INFORMATION: MART1-derived overlapping peptide position 51

<400> SEQUENCE: 71

Arg Asn Gly Tyr Arg Ala Leu Met Asp Lys Ser Leu His Val Gly Thr
1               5                   10                  15

Gln Cys Ala Leu
            20

<210> SEQ ID NO 72
<211> LENGTH: 20
<212> TYPE: PRT
<213> ORGANISM: Artificial Sequence

```
<220> FEATURE:
<223> OTHER INFORMATION: MART1-derived overlapping peptide position 56

<400> SEQUENCE: 72

Ala Leu Met Asp Lys Ser Leu His Val Gly Thr Gln Cys Ala Leu Thr
1               5                   10                  15

Arg Arg Cys Pro
            20

<210> SEQ ID NO 73
<211> LENGTH: 20
<212> TYPE: PRT
<213> ORGANISM: Artificial Sequence
<220> FEATURE:
<223> OTHER INFORMATION: MART1-derived overlapping peptide position 61

<400> SEQUENCE: 73

Ser Leu His Val Gly Thr Gln Cys Ala Leu Thr Arg Arg Cys Pro Gln
1               5                   10                  15

Glu Gly Phe Asp
            20

<210> SEQ ID NO 74
<211> LENGTH: 20
<212> TYPE: PRT
<213> ORGANISM: Artificial Sequence
<220> FEATURE:
<223> OTHER INFORMATION: MART1-derived overlapping peptide position 66

<400> SEQUENCE: 74

Thr Gln Cys Ala Leu Thr Arg Arg Cys Pro Gln Glu Gly Phe Asp His
1               5                   10                  15

Arg Asp Ser Lys
            20

<210> SEQ ID NO 75
<211> LENGTH: 20
<212> TYPE: PRT
<213> ORGANISM: Artificial Sequence
<220> FEATURE:
<223> OTHER INFORMATION: MART1-derived overlapping peptide position 71

<400> SEQUENCE: 75

Thr Arg Arg Cys Pro Gln Glu Gly Phe Asp His Arg Asp Ser Lys Val
1               5                   10                  15

Ser Leu Gln Glu
            20

<210> SEQ ID NO 76
<211> LENGTH: 20
<212> TYPE: PRT
<213> ORGANISM: Artificial Sequence
<220> FEATURE:
<223> OTHER INFORMATION: MART1-derived overlapping peptide position 76

<400> SEQUENCE: 76

Gln Glu Gly Phe Asp His Arg Asp Ser Lys Val Ser Leu Gln Glu Lys
1               5                   10                  15

Asn Cys Glu Pro
            20

<210> SEQ ID NO 77
<211> LENGTH: 20
<212> TYPE: PRT
```

```
<213> ORGANISM: Artificial Sequence
<220> FEATURE:
<223> OTHER INFORMATION: MART1-derived overlapping peptide position 81

<400> SEQUENCE: 77

His Arg Asp Ser Lys Val Ser Leu Gln Glu Lys Asn Cys Glu Pro Val
1               5                   10                  15

Val Pro Asn Ala
            20

<210> SEQ ID NO 78
<211> LENGTH: 20
<212> TYPE: PRT
<213> ORGANISM: Artificial Sequence
<220> FEATURE:
<223> OTHER INFORMATION: MART1-derived overlapping peptide position 86

<400> SEQUENCE: 78

Val Ser Leu Gln Glu Lys Asn Cys Glu Pro Val Val Pro Asn Ala Pro
1               5                   10                  15

Pro Ala Tyr Glu
            20

<210> SEQ ID NO 79
<211> LENGTH: 20
<212> TYPE: PRT
<213> ORGANISM: Artificial Sequence
<220> FEATURE:
<223> OTHER INFORMATION: MART1-derived overlapping peptide position 91

<400> SEQUENCE: 79

Lys Asn Cys Glu Pro Val Val Pro Asn Ala Pro Pro Ala Tyr Glu Lys
1               5                   10                  15

Leu Ser Ala Glu
            20

<210> SEQ ID NO 80
<211> LENGTH: 20
<212> TYPE: PRT
<213> ORGANISM: Artificial Sequence
<220> FEATURE:
<223> OTHER INFORMATION: MART1-derived overlapping peptide position 96

<400> SEQUENCE: 80

Val Val Pro Asn Ala Pro Pro Ala Tyr Glu Lys Leu Ser Ala Glu Gln
1               5                   10                  15

Ser Pro Pro Pro
            20

<210> SEQ ID NO 81
<211> LENGTH: 20
<212> TYPE: PRT
<213> ORGANISM: Artificial Sequence
<220> FEATURE:
<223> OTHER INFORMATION: MART1-derived overlapping peptide position 99

<400> SEQUENCE: 81

Asn Ala Pro Pro Ala Tyr Glu Lys Leu Ser Ala Glu Gln Ser Pro Pro
1               5                   10                  15

Pro Tyr Ser Pro
            20

<210> SEQ ID NO 82
<211> LENGTH: 9
```

-continued

```
<212> TYPE: PRT
<213> ORGANISM: Artificial Sequence
<220> FEATURE:
<223> OTHER INFORMATION: HIV rev67-75

<400> SEQUENCE: 82

Ser Ala Glu Pro Val Pro Leu Gln Leu
1               5

<210> SEQ ID NO 83
<211> LENGTH: 13
<212> TYPE: PRT
<213> ORGANISM: Artificial Sequence
<220> FEATURE:
<223> OTHER INFORMATION: NY-ESO-1 60-72

<400> SEQUENCE: 83

Ala Pro Arg Gly Pro His Gly Gly Ala Ala Ser Gly Leu
1               5                   10

<210> SEQ ID NO 84
<211> LENGTH: 9
<212> TYPE: PRT
<213> ORGANISM: Artificial Sequence
<220> FEATURE:
<223> OTHER INFORMATION: EBV EBNA3A379-387

<400> SEQUENCE: 84

Arg Pro Pro Ile Phe Ile Arg Arg Leu
1               5

<210> SEQ ID NO 85
<211> LENGTH: 10
<212> TYPE: PRT
<213> ORGANISM: Artificial Sequence
<220> FEATURE:
<223> OTHER INFORMATION: HIV nef128-137

<400> SEQUENCE: 85

Thr Pro Gly Pro Gly Val Arg Tyr Pro Leu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: HIV gag161-170

<400> SEQUENCE: 86

Phe Arg Asp Tyr Val Asp Arg Phe Tyr Lys
1               5                   10

<210> SEQ ID NO 87
<211> LENGTH: 9
<212> TYPE: PRT
<213> ORGANISM: Artificial Sequence
<220> FEATURE:
<223> OTHER INFORMATION: NY-ESO-1 157-165

<400> SEQUENCE: 87

Ser Leu Leu Met Trp Ile Thr Gln Val
1               5

<210> SEQ ID NO 88
<211> LENGTH: 9
<212> TYPE: PRT
```

```
<213> ORGANISM: Artificial Sequence
<220> FEATURE:
<223> OTHER INFORMATION: HTLV-1 tax11-19

<400> SEQUENCE: 88

Leu Leu Phe Gly Tyr Pro Val Tyr Val
1               5

<210> SEQ ID NO 89
<211> LENGTH: 529
<212> TYPE: PRT
<213> ORGANISM: Artificial Sequence
<220> FEATURE:
<223> OTHER INFORMATION: Tyr - Full Length Amino Acid Sequence

<400> SEQUENCE: 89

Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
                20                  25                  30

Lys Glu Cys Cys Pro Pro Trp Ser Gly Asp Arg Ser Pro Cys Gly Gln
            35                  40                  45

Leu Ser Gly Arg Gly Ser Cys Gln Asn Ile Leu Leu Ser Asn Ala Pro
        50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
                100                 105                 110

Thr Glu Arg Arg Leu Leu Val Arg Arg Asn Ile Phe Asp Leu Ser Ala
            115                 120                 125

Pro Glu Lys Asp Lys Phe Phe Ala Tyr Leu Thr Leu Ala Lys His Thr
        130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
                180                 185                 190

Glu Ile Trp Arg Asp Ile Asp Phe Ala His Glu Ala Pro Ala Phe Leu
            195                 200                 205

Pro Trp His Arg Leu Phe Leu Leu Arg Trp Glu Gln Glu Ile Gln Lys
        210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255

Pro Thr Asn Pro Asn Leu Leu Ser Pro Ala Ser Phe Phe Ser Ser Trp
                260                 265                 270

Gln Ile Val Cys Ser Arg Leu Glu Glu Tyr Asn Ser His Gln Ser Leu
            275                 280                 285

Cys Asn Gly Thr Pro Glu Gly Pro Leu Arg Arg Asn Pro Gly Asn His
        290                 295                 300

Asp Lys Ser Arg Thr Pro Arg Leu Pro Ser Ser Ala Asp Val Glu Phe
305                 310                 315                 320
```

```
Cys Leu Ser Leu Thr Gln Tyr Glu Ser Gly Ser Met Asp Lys Ala Ala
            325                 330                 335

Asn Phe Ser Phe Arg Asn Thr Leu Glu Gly Phe Ala Ser Pro Leu Thr
            340                 345                 350

Gly Ile Ala Asp Ala Ser Gln Ser Ser Met His Asn Ala Leu His Ile
            355                 360                 365

Tyr Met Asn Gly Thr Met Ser Gln Val Gln Gly Ser Ala Asn Asp Pro
        370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                405                 410                 415

Pro Ile Gly His Asn Arg Glu Ser Tyr Met Val Pro Phe Ile Pro Leu
            420                 425                 430

Tyr Arg Asn Gly Asp Phe Phe Ile Ser Ser Lys Asp Leu Gly Tyr Asp
            435                 440                 445

Tyr Ser Tyr Leu Gln Asp Ser Asp Pro Asp Ser Phe Gln Asp Tyr Ile
        450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
            500                 505                 510

Pro Leu Leu Met Glu Lys Glu Asp Tyr His Ser Leu Tyr Gln Ser His
            515                 520                 525

Leu

<210> SEQ ID NO 90
<211> LENGTH: 309
<212> TYPE: PRT
<213> ORGANISM: Artificial Sequence
<220> FEATURE:
<223> OTHER INFORMATION: MAGE-A1 - Full Length Amino Acid Sequence

<400> SEQUENCE: 90

Met Ser Leu Glu Gln Arg Ser Leu His Cys Lys Pro Glu Glu Ala Leu
1               5                   10                  15

Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
        50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Pro Glu Ile Phe
        130                 135                 140
```

-continued

```
Gly Lys Ala Ser Glu Ser Leu Gln Leu Val Phe Gly Ile Asp Val Lys
145             150             155             160

Glu Ala Asp Pro Thr Gly His Ser Tyr Val Leu Val Thr Cys Leu Gly
                165             170             175

Leu Ser Tyr Asp Gly Leu Leu Gly Asp Asn Gln Ile Met Pro Lys Thr
            180             185             190

Gly Phe Leu Ile Ile Val Leu Val Met Ile Ala Met Glu Gly Gly His
            195             200             205

Ala Pro Glu Glu Glu Ile Trp Glu Glu Leu Ser Val Met Glu Val Tyr
    210             215             220

Asp Gly Arg Glu His Ser Ala Tyr Gly Glu Pro Arg Lys Leu Leu Thr
225             230             235             240

Gln Asp Leu Val Gln Glu Lys Tyr Leu Glu Tyr Arg Gln Val Pro Asp
            245             250             255

Ser Asp Pro Ala Arg Tyr Glu Phe Leu Trp Gly Pro Arg Ala Leu Ala
            260             265             270

Glu Thr Ser Tyr Val Lys Val Leu Glu Tyr Val Ile Lys Val Ser Ala
            275             280             285

Arg Val Arg Phe Phe Phe Pro Ser Leu Arg Glu Ala Ala Leu Arg Glu
    290             295             300

Glu Glu Glu Gly Val
305
```

```
<210> SEQ ID NO 91
<211> LENGTH: 118
<212> TYPE: PRT
<213> ORGANISM: Artificial Sequence
<220> FEATURE:
<223> OTHER INFORMATION: MART1 - Full Length Amino Acid Sequence

<400> SEQUENCE: 91

Met Pro Arg Glu Asp Ala His Phe Ile Tyr Gly Tyr Pro Lys Lys Gly
1               5               10              15

His Gly His Ser Tyr Thr Thr Ala Glu Glu Ala Ala Gly Ile Gly Ile
            20              25              30

Leu Thr Val Ile Leu Gly Val Leu Leu Leu Ile Gly Cys Trp Tyr Cys
        35              40              45

Arg Arg Arg Asn Gly Tyr Arg Ala Leu Met Asp Lys Ser Leu His Val
    50              55              60

Gly Thr Gln Cys Ala Leu Thr Arg Arg Cys Pro Gln Glu Gly Phe Asp
65              70              75              80

His Arg Asp Ser Lys Val Ser Leu Gln Glu Lys Asn Cys Glu Pro Val
            85              90              95

Val Pro Asn Ala Pro Pro Ala Tyr Glu Lys Leu Ser Ala Glu Gln Ser
            100             105             110

Pro Pro Pro Tyr Ser Pro
        115
```

```
<210> SEQ ID NO 92
<211> LENGTH: 314
<212> TYPE: PRT
<213> ORGANISM: Artificial Sequence
<220> FEATURE:
<223> OTHER INFORMATION: MAGE-A3 - Full Length Amino Acid Sequence
```

-continued

<400> SEQUENCE: 92

```
Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
            35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
            195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
            245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
            275                 280                 285

His Met Val Lys Ile Ser Gly Gly Pro His Ile Ser Tyr Pro Pro Leu
            290                 295                 300

His Glu Trp Val Leu Arg Glu Gly Glu Glu
305                 310
```

```
<210> SEQ ID NO 93
<211> LENGTH: 188
<212> TYPE: PRT
<213> ORGANISM: Artificial Sequence
<220> FEATURE:
<223> OTHER INFORMATION: SSX2 - Full Length Amino Acid Sequence
```

<400> SEQUENCE: 93

```
Met Asn Gly Asp Asp Ala Phe Ala Arg Arg Pro Thr Val Gly Ala Gln
1               5                   10                  15
```

-continued

```
Ile Pro Glu Lys Ile Gln Lys Ala Phe Asp Asp Ile Ala Lys Tyr Phe
            20              25              30

Ser Lys Glu Glu Trp Glu Lys Met Lys Ala Ser Glu Lys Ile Phe Tyr
        35              40              45

Val Tyr Met Lys Arg Lys Tyr Glu Ala Met Thr Lys Leu Gly Phe Lys
    50              55              60

Ala Thr Leu Pro Pro Phe Met Cys Asn Lys Arg Ala Glu Asp Phe Gln
65              70              75              80

Gly Asn Asp Leu Asp Asn Asp Pro Asn Arg Gly Asn Gln Val Glu Arg
            85              90              95

Pro Gln Met Thr Phe Gly Arg Leu Gln Gly Ile Ser Pro Lys Ile Met
            100             105             110

Pro Lys Lys Pro Ala Glu Glu Gly Asn Asp Ser Glu Glu Val Pro Glu
        115             120             125

Ala Ser Gly Pro Gln Asn Asp Gly Lys Glu Leu Cys Pro Pro Gly Lys
    130             135             140

Pro Thr Thr Ser Glu Lys Ile His Glu Arg Ser Gly Pro Lys Arg Gly
145             150             155             160

Glu His Ala Trp Thr His Arg Leu Arg Glu Arg Lys Gln Leu Val Ile
            165             170             175

Tyr Glu Glu Ile Ser Asp Pro Glu Glu Asp Asp Glu
            180             185
```

1

T CELL RECEPTORS AND METHODS OF USE THEREOF

CROSS REFERENCE TO RELATED APPLICATIONS

This PCT application claims the priority benefit of U.S. Provisional Application No. 62/823,487, filed Mar. 25, 2019, which is incorporated herein by reference in its entirety.

REFERENCE TO SEQUENCE LISTING SUBMITTED ELECTRONICALLY VIA EFS-WEB

The content of the electronically submitted sequence listing (Name: 4285_008PC01_SeqListing_ST25.txt, Size: 69,638 bytes; and Date of Creation: Mar. 23, 2020) is incorporated herein by reference in its entirety.

FIELD OF THE DISCLOSURE

The present disclosure provides recombinant T cell receptors ("TCRs") that specifically bind a target human protein selected from the group consisting of tyrosinase, MAGE-A1, MART1, MAGE-A3, and SSX2 and uses thereof.

BACKGROUND OF THE DISCLOSURE

Immunotherapy has immerged as a critical tool in the battle against a variety of diseases, including cancer. T cell therapies are at the forefront of immunotherapeutic development, and adoptive transfer of antitumor T cells has been shown induce clinical responses in cancer patients. Though many T cell therapies target mutated tumor antigens, the vast majority of neoantigens are not shared and are unique to each patient.

Potential non-mutated antigens out number mutated antigens by multiple orders of magnitude. The elucidation of T cell epitopes derived from shared antigens may facilitate the robust development of efficacious and safe adoptive T cell therapies that are readily available to a larger cohort of cancer patients. However, the sheer number of non-mutated antigens and the high polymorphism of HLA genes may have hampered comprehensive analyses of the specificity of antitumor T cell responses toward non-mutated antigens.

The present disclosure provides novel epitopes for the non-mutated antigens tyrosinase, MAGE-A1, MART1, MAGE-A3, and SSX2 and TCRs capable of specifically binding the epitopes. These novel epitopes are associated with associated with particular HLA alleles. The use of these tumor-reactive HLA-restricted TCRs stand to widen the applicability of TCR gene therapy, particularly in immuno-oncology.

SUMMARY OF THE DISCLOSURE

Certain aspects of the present disclosure are directed to a nucleic acid molecule comprising (i) a first nucleotide sequence encoding a recombinant T cell receptor (TCR) or an antigen binding portion thereof that specifically binds a target human protein; and (ii) a second nucleotide sequence, wherein the second nucleotide sequence or the polypeptide encoded by the second nucleotide sequence inhibits the expression of an endogenous TCR; wherein: (a) the target human protein is tyrosinase ("anti-tyrosinase TCR"), wherein the anti-tyrosinase TCR cross competes for binding to human tyrosinase with a reference anti-tyrosinase TCR, wherein the reference anti-tyrosinase TCR comprises an alpha chain and a beta chain, and wherein the alpha chain comprises an amino acid sequence as set forth in SEQ ID NO: 1, and the beta chain comprises an amino acid sequence as set forth in SEQ ID NO: 2; (b) the target human protein is MAGE-A1 ("anti-MAGE-A1 TCR"), wherein the anti-MAGE-A1 TCR cross competes for binding to human MAGE-A1 with a reference anti-MAGE-A1 TCR, wherein the reference anti-MAGE-A1 TCR comprises an alpha chain and a beta chain, and wherein the alpha chain comprises an amino acid sequence as set forth in SEQ ID NO: 11, and the beta chain comprises an amino acid sequence as set forth in SEQ ID NO: 12; (c) the target human protein is MART1 ("anti-MAGE-A1 TCR"), wherein the anti-MAGE-A1 TCR cross competes for binding to human MART1 with a reference anti-MART1 TCR, wherein the reference anti-MAGE-A1 TCR comprises an alpha chain and a beta chain, and wherein the alpha chain comprises an amino acid sequence as set forth in SEQ ID NO: 21, and the beta chain comprises an amino acid sequence as set forth in SEQ ID NO: 22; (d) the target human protein is MAGE-A3 ("anti-MAGE-A3 TCR"), wherein the anti-MAGE-A3 TCR cross competes for binding to human MAGE-A3 with a reference anti-MAGE-A3 TCR, wherein the reference anti-MAGE-A3 TCR comprises an alpha chain and a beta chain, and wherein the alpha chain comprises an amino acid sequence as set forth in SEQ ID NO: 31, and the beta chain comprises an amino acid sequence as set forth in SEQ ID NO: 32; or (e) the target human protein is SSX2 ("anti-SSX2 TCR"), wherein the anti-SSX2 TCR cross competes for binding to human SSX2 with a reference anti-SSX2 TCR, wherein the reference anti-SSX2 TCR comprises an alpha chain and a beta chain, and wherein the alpha chain comprises an amino acid sequence as set forth in SEQ ID NO: 41, and the beta chain comprises an amino acid sequence as set forth in SEQ ID NO: 42.

Certain aspects of the present disclosure are directed to a nucleic acid molecule comprising (i) a first nucleotide sequence encoding a recombinant T cell receptor (TCR) or an antigen binding portion thereof that specifically binds a target human protein; and (ii) a second nucleotide sequence, wherein the second nucleotide sequence or the polypeptide encoded by the second nucleotide sequence inhibits the expression of an endogenous TCR; wherein: (a) target human protein is tyrosinase ("anti-tyrosinase TCR"), wherein the anti-tyrosinase TCR binds the same epitope or an overlapping epitope of human tyrosinase as a reference anti-tyrosinase TCR, wherein the reference anti-tyrosinase TCR comprises an alpha chain and a beta chain, wherein the alpha chain comprises an amino acid sequence as set forth in SEQ ID NO: 1 and the beta chain comprises an amino acid sequence as set forth in SEQ ID NO: 2; (b) the target human protein is MAGE-A1 ("anti-MAGE-A1 TCR"), wherein the anti-MAGE-A1 TCR binds the same epitope or an overlapping epitope of human MAGE-A1 as a reference anti-MAGE-A1 TCR, wherein the reference anti-MAGE-A1 TCR comprises an alpha chain and a beta chain, and wherein the alpha chain comprises an amino acid sequence as set forth in SEQ ID NO: 11, and the beta chain comprises an amino acid sequence as set forth in SEQ ID NO: 12; (c) the target human protein is MART1 ("anti-MART1 TCR"), wherein the anti-MART1 TCR binds the same epitope or an overlapping epitope of human MART1 as a reference anti-MART1 TCR, wherein the reference anti-MART1 TCR comprises an alpha chain and a beta chain, and wherein the alpha chain comprises an amino acid sequence as set forth in SEQ ID NO: 21, and the beta chain comprises an amino acid sequence as set forth in SEQ ID NO: 22; (d) the target human protein is MAGE-A3 ("anti-MAGE-A3 TCR"), wherein the anti-MAGE-A3 TCR binds the same epitope or an overlapping epitope of human MAGE-A3 as a reference anti-MAGE-A3 TCR, wherein the reference anti-MAGE-A3 TCR comprises an alpha chain and a beta chain, and wherein the alpha chain comprises an amino acid sequence as set forth in SEQ ID NO: 31, and the beta chain comprises an amino acid sequence as set forth in SEQ ID NO: 32; or (e) the target human protein is SSX2 ("anti-SSX2 TCR"), wherein the anti-SSX2 TCR binds the same epitope or an overlapping epitope of human SSX2 as a reference anti-SSX2 TCR, wherein the reference anti-SSX2 TCR comprises an alpha chain and a beta chain, and wherein the alpha chain comprises an amino acid sequence as set forth in SEQ ID NO: 41, and the beta chain comprises an amino acid sequence as set forth in SEQ ID NO: 42.

In some embodiments, (a) the anti-tyrosinase TCR binds to an epitope of tyrosinase consisting of an amino acid sequence as set forth in SEQ ID NO: 51; (b) the anti-MAGE-A1 TCR binds to an epitope of MAGE-A1 consisting of an amino acid sequence as set forth in SEQ ID NO: 52; (c) the anti-MART1 TCR binds to an epitope of MART1 consisting of an amino acid sequence as set forth in SEQ ID NO: 53; (d) the anti-MAGE-A3 TCR binds to an epitope of MAGE-A3 consisting of an amino acid sequence as set forth in SEQ ID NO: 54; or (e) the anti-SSX2 TCR binds to an epitope of SSX2 consisting of an amino acid sequence as set forth in SEQ ID NO: 55.

In some embodiments, the epitope is complexed with an HLA class I molecule. In some embodiments, the HLA class I molecule is an HLA-A, HLA-B, HLA-C, HLA-E, HLA-F, or HLA-G allele. In some embodiments, (a) the target human protein is tyrosinase, and the HLA class I molecule is an HLA-C*05 allele; (b) the target human protein is MAGE-A1, and the HLA class I molecule is an HLA-B*07 allele; (c) the target human protein is MART1, and the HLA class I molecule is an HLA-B*18 allele; (d) the target human protein is MAGE-A3, and the HLA class I molecule is an HLA-B*18 allele; or (e) the target human protein is SSX2, and the HLA class I molecule is an HLA-A*02 allele.

In some embodiments, (a) the target human protein is tyrosinase, and the HLA class I molecule is selected from an HLA-C*05:01 allele, an HLA-C*05:03 allele, an HLA-C*05:04 allele, an HLA-C*05:05 allele, and an HLA-C*05:06 allele; (b) the target human protein is MAGE-A1, and the HLA class I molecule is selected from an HLA-B*07:02 allele, an HLA-B*07:03 allele, an HLA-B*07:04 allele, an HLA-B*07:05 allele, and an HLA-B*07:06 allele; (c) the target human protein is MART1, and the HLA class I molecule is selected from an HLA-B*18:01 allele, an HLA-B*18:02 allele, an HLA-B*18:03 allele, an HLA-B*18:04 allele, and an HLA-B*18:05 allele; (d) the target human protein is MAGE-A3, and the HLA class I molecule is selected from an HLA-B*18:01 allele, an HLA-B*18:02 allele, an HLA-B*18:03 allele, an HLA-B*18:04 allele, and an HLA-B*18:05 allele; or (e) the target human protein is SSX2, and the HLA class I molecule is selected from an HLA-A*02:01 allele, an HLA-A*02:02 allele, an HLA-A*02:03 allele, an HLA-A*02:04 allele, and an HLA-A*02:05 allele.

In some embodiments, (a) the target human protein is tyrosinase, and the HLA class I molecule is an HLA-C*05:01 allele; (b) the target human protein is MAGE-A1, and the HLA class I molecule is an HLA-B*07:02 allele; (c) the target human protein is MART1, and the HLA class I molecule is an HLA-B*18:01 allele; (d) the target human protein is MAGE-A3, and the HLA class I molecule is an HLA-B*18:01 allele; or (e) the target human protein is SSX2, and the HLA class I molecule is an HLA-A*02:01 allele.

In some embodiments, the recombinant TCR or an antigen binding portion thereof that specifically binds the target human protein comprises an alpha chain and a beta chain; wherein the alpha chain comprises a variable region comprising an alpha chain CDR1, an alpha chain CDR2, and an alpha chain CDR3; wherein the beta chain comprises variable domain comprising a beta chain CDR1, a beta chain CDR2, and a beta chain CDR3; and wherein: (a) the target human protein is tyrosinase, and the alpha chain CDR3 comprises an amino acid sequence as set forth in SEQ ID NO: 7; (b) the target human protein is MAGE-A1, and the alpha chain CDR3 comprises an amino acid sequence as set forth in SEQ ID NO: 17; (c) the target human protein is MART1, and the alpha chain CDR3 comprises an amino acid sequence as set forth in SEQ ID NO: 27; (d) the target human protein is MAGE-A3, and the alpha chain CDR3 comprises an amino acid sequence as set forth in SEQ ID NO: 37; or (e) the target human protein is SSX2, and the alpha chain CDR3 comprises an amino acid sequence as set forth in SEQ ID NO: 47.

In some embodiments, (a) the target human protein is tyrosinase, and the beta chain CDR3 comprises an amino acid sequence as set forth in SEQ ID NO: 10; (b) the target human protein is MAGE-A1, and the beta chain CDR3 comprises an amino acid sequence as set forth in SEQ ID NO: 20; (c) the target human protein is MART1, and the beta chain CDR3 comprises an amino acid sequence as set forth in SEQ ID NO: 30; (d) the target human protein is MAGE-A3, and the beta chain CDR3 comprises an amino acid sequence as set forth in SEQ ID NO: 40; or (e) the target human protein is SSX2, and the alpha beta CDR3 comprises an amino acid sequence as set forth in SEQ ID NO: 50.

In some embodiments, the recombinant TCR or an antigen binding portion thereof that specifically binds the target human protein comprises an alpha chain and a beta chain, wherein the alpha chain comprises a variable region comprising an alpha chain CDR1, an alpha chain CDR2, and an alpha chain CDR3; wherein the beta chain comprises variable domain comprising a beta chain CDR1, a beta chain CDR2, and a beta chain CDR3; and wherein: (a) the target human protein is tyrosinase, and the beta chain CDR3 comprises an amino acid sequence as set forth in SEQ ID NO: 10; (b) the target human protein is MAGE-A1, and the beta chain CDR3 comprises an amino acid sequence as set forth in SEQ ID NO: 20; (c) the target human protein is MART1, and the beta chain CDR3 comprises an amino acid sequence as set forth in SEQ ID NO: 30; (d) the target human protein is MAGE-A3, and the beta chain CDR3 comprises an amino acid sequence as set forth in SEQ ID NO: 40; or (e) the target human protein is SSX2, and the alpha beta CDR3 comprises an amino acid sequence as set forth in SEQ ID NO: 50.

In some embodiments, (a) the target human protein is tyrosinase, and the alpha chain CDR3 comprises an amino acid sequence as set forth in SEQ ID NO: 7; (b) the target human protein is MAGE-A1, and the alpha chain CDR3 comprises an amino acid sequence as set forth in SEQ ID NO: 17; (c) the target human protein is MART1, and the alpha chain CDR3 comprises an amino acid sequence as set forth in SEQ ID NO: 27; (d) the target human protein is MAGE-A3, and the alpha chain CDR3 comprises an amino acid sequence as set forth in SEQ ID NO: 37; or (e) the target human protein is SSX2, and the alpha chain CDR3 comprises an amino acid sequence as set forth in SEQ ID NO: 47.

In some embodiments, (a) the target human protein is tyrosinase, and the alpha chain CDR1 comprises an amino acid sequence as set forth in SEQ ID NO: 5; (b) the target human protein is MAGE-A1, and the alpha chain CDR1 comprises an amino acid sequence as set forth in SEQ ID NO: 15; (c) the target human protein is MART1, and the alpha chain CDR1 comprises an amino acid sequence as set forth in SEQ ID NO: 25; (d) the target human protein is MAGE-A3, and the alpha chain CDR1 comprises an amino acid sequence as set forth in SEQ ID NO: 35; or (e) the target human protein is SSX2, and the alpha chain CDR1 comprises an amino acid sequence as set forth in SEQ ID NO: 45.

In some embodiments, (a) the target human protein is tyrosinase, and the beta chain CDR1 comprises an amino acid sequence as set forth in SEQ ID NO: 8; (b) the target human protein is MAGE-A1, and the beta chain CDR1 comprises an amino acid sequence as set forth in SEQ ID NO: 18; (c) the target human protein is MART1, and the beta chain CDR1 comprises an amino acid sequence as set forth in SEQ ID NO: 28; (d) the target human protein is MAGE-A3, and the beta chain CDR1 comprises an amino acid sequence as set forth in SEQ ID NO: 38; or (e) the target human protein is SSX2, and the beta chain CDR1 comprises an amino acid sequence as set forth in SEQ ID NO: 48.

In some embodiments, (a) the target human protein is tyrosinase, and the alpha chain CDR2 comprises an amino acid sequence as set forth in SEQ ID NO: 6; (b) the target human protein is MAGE-A1, and the alpha chain CDR2 comprises an amino acid sequence as set forth in SEQ ID NO: 16; (c) the target human protein is MART1, and the alpha chain CDR2 comprises an amino acid sequence as set forth in SEQ ID NO: 26; (d) the target human protein is MAGE-A3, and the alpha chain CDR2 comprises an amino acid sequence as set forth in SEQ ID NO: 36; or (e) the target human protein is SSX2, and the alpha chain CDR2 comprises an amino acid sequence as set forth in SEQ ID NO: 46.

In some embodiments, (a) the target human protein is tyrosinase, and the beta chain CDR2 comprises an amino acid sequence as set forth in SEQ ID NO: 9; (b) the target human protein is MAGE-A1, and the beta chain CDR2 comprises an amino acid sequence as set forth in SEQ ID NO: 19; (c) the target human protein is MART1, and the beta chain CDR2 comprises an amino acid sequence as set forth in SEQ ID NO: 29; (d) the target human protein is MAGE-A3, and the beta chain CDR2 comprises an amino acid sequence as set forth in SEQ ID NO: 39; or (e) the target human protein is SSX2, and the beta chain CDR2 comprises an amino acid sequence as set forth in SEQ ID NO: 49.

In some embodiments, (a) the target human protein is tyrosinase, and the alpha chain variable domain comprises an amino acid sequence of a variable domain present in the amino acid sequence set forth SEQ ID NO: 1; (b) the target human protein is MAGE-A1, and the alpha chain variable domain comprises an amino acid sequence of a variable domain present in the amino acid sequence set forth SEQ ID NO: 11; (c) the target human protein is MART1, and the alpha chain variable domain comprises an amino acid sequence of a variable domain present in the amino acid sequence set forth SEQ ID NO: 21; (d) the target human protein is MAGE-A3, and the alpha chain variable domain comprises an amino acid sequence of a variable domain present in the amino acid sequence set forth SEQ ID NO: 31;

or (e) the target human protein is SSX2, and the alpha chain variable domain comprises an amino acid sequence of a variable domain present in the amino acid sequence set forth SEQ ID NO: 41.

In some embodiments, (a) the target human protein is tyrosinase, and the beta chain variable domain comprises an amino acid sequence of a variable domain present in the amino acid sequence set forth SEQ ID NO: 2; (b) the target human protein is MAGE-A1, and the beta chain variable domain comprises an amino acid sequence of a variable domain present in the amino acid sequence set forth SEQ ID NO: 12; (c) the target human protein is MART1, and the beta chain variable domain comprises an amino acid sequence of a variable domain present in the amino acid sequence set forth SEQ ID NO: 22; (d) the target human protein is MAGE-A3, and the beta chain variable domain comprises an amino acid sequence of a variable domain present in the amino acid sequence set forth SEQ ID NO: 32; or (e) the target human protein is SSX2, and the beta chain variable domain comprises an amino acid sequence of a variable domain present in the amino acid sequence set forth SEQ ID NO: 42. In some embodiments, the alpha chain further comprises a constant region, wherein the constant region is different from endogenous constant region of the alpha chain.

In some embodiments, the alpha chain further comprises a constant region, wherein: (a) the target human protein is tyrosinase, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 1; (b) the target human protein is MAGE-A1, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 11; (c) the target human protein is MART1, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 21; (d) the target human protein is MAGE-A3, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 31; or (e) the target human protein is SSX2, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 41.

In some embodiments, (a) the target human protein is tyrosinase, and the alpha chain constant region comprises an amino acid sequence comprising at least 1, at least 2, at least 3, at least 4, or at least 5 amino acid substitutions relative to a constant region present in the amino acid sequence set forth SEQ ID NO: 1; (b) the target human protein is MAGE-A1, and the alpha chain constant region comprises an amino acid sequence comprising at least 1, at least 2, at least 3, at least 4, or at least 5 amino acid substitutions relative to a constant region present in the amino acid sequence set forth SEQ ID NO: 11; (c) the target human protein is MART1, and the alpha chain constant region comprises an amino acid sequence comprising at least 1, at least 2, at least 3, at least 4, or at least 5 amino acid substitutions relative to a constant region present in the amino acid sequence set forth SEQ ID NO: 21; (d) the target human protein is MAGE-A3, and the alpha chain constant region comprises an amino acid sequence comprising at least 1, at least 2, at least 3, at least 4, or at least 5 amino acid substitutions relative to a constant region present in the amino acid sequence set forth SEQ ID NO: 31; or (e) the target human protein is SSX2, and the alpha chain constant region comprises an amino acid sequence comprising at least 1, at least 2, at least 3, at least 4, or at least 5 amino acid substitutions relative to a constant region present in the amino acid sequence set forth SEQ ID NO: 41. In some embodiments, the beta chain further comprises a constant region, wherein the constant region is different from endogenous constant regions of the beta chain.

In some embodiments, the beta chain further comprises a constant region, wherein: (a) the target human protein is tyrosinase, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 2; (b) the target human protein is MAGE-A1, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 12; (c) the target human protein is MART1, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 22; (d) the target human protein is MAGE-A3, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 32; or (e) the target human protein is SSX2, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 42.

In some embodiments, (a) the target human protein is tyrosinase, and the beta chain constant region comprises an amino acid sequence comprising at least 1, at least 2, at least 3, at least 4, or at least 5 amino acid substitutions relative to a constant region present in the amino acid sequence set forth SEQ ID NO: 2; (b) the target human protein is MAGE-A1, and the beta chain constant region comprises an amino acid sequence comprising at least 1, at least 2, at least 3, at least 4, or at least 5 amino acid substitutions relative to a constant region present in the amino acid sequence set forth SEQ ID NO: 12; (c) the target human protein is MART1, and the beta chain constant region comprises an amino acid sequence comprising at least 1, at least 2, at least 3, at least 4, or at least 5 amino acid substitutions relative to a constant region present in the amino acid sequence set forth SEQ ID NO: 22; (d) the target human protein is MAGE-A3, and the beta chain constant region comprises an amino acid sequence comprising at least 1, at least 2, at least 3, at least 4, or at least 5 amino acid substitutions relative to a constant region present in the amino acid sequence set forth SEQ ID NO: 32; or (e) the target human protein is SSX2, and the beta chain constant region comprises an amino acid sequence comprising at least 1, at least 2, at least 3, at least 4, or at least 5 amino acid substitutions relative to a constant region present in the amino acid sequence set forth SEQ ID NO: 42.

In some embodiments, (a) the target human protein is tyrosinase, and the alpha chain comprises an amino acid sequence as set forth in SEQ ID NO: 1; (b) the target human protein is MAGE-A1, and the alpha chain comprises an amino acid sequence as set forth in SEQ ID NO: 11; (c) the target human protein is MART1, and the alpha chain comprises an amino acid sequence as set forth in SEQ ID NO: 21; (d) the target human protein is MAGE-A3, and the alpha chain comprises an amino acid sequence as set forth in SEQ ID NO: 31; or (e) the target human protein is SSX2, and the alpha chain comprises an amino acid sequence as set forth in SEQ ID NO: 41.

In some embodiments, (a) the target human protein is tyrosinase, and the beta chain comprises an amino acid sequence as set forth in SEQ ID NO: 2; (b) the target human protein is MAGE-A1, and the beta chain comprises an amino acid sequence as set forth in SEQ ID NO: 12; (c) the target human protein is MART1, and the beta chain comprises an amino acid sequence as set forth in SEQ ID NO: 22; (d) the target human protein is MAGE-A3, and the beta chain comprises an amino acid sequence as set forth in SEQ ID NO: 32; or (e) the target human protein is SSX2, and the beta chain comprises an amino acid sequence as set forth in SEQ ID NO: 42.

In some embodiments, the second nucleotide sequence is one or more siRNAs that reduce the expression of endogenous TCRs. In some embodiments, the one or more siRNAs are complementary to a target sequence within a nucleotide sequence encoding a constant region of the endogenous TCRs. In some embodiments, the one or more siRNAs comprise one or more nucleotide sequences selected from the group consisting of SEQ ID NOs: 57-60. In some embodiments, the second nucleotide sequence encodes Cas9.

In some embodiments, the recombinant TCR or an antigen binding portion thereof comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

Certain aspects of the present disclosure are directed to a vector comprising a nucleic acid molecule disclosed herein. In some embodiments, the vector is a viral vector, a mammalian vector, or bacterial vector. In some embodiments, the vector is a retroviral vector. In some embodiments, the vector is selected from the group consisting of an adenoviral vector, a lentivirus, a Sendai virus vector, a baculoviral vector, an Epstein Barr viral vector, a papovaviral vector, a vaccinia viral vector, a herpes simplex viral vector, a hybrid vector, and an adeno associated virus (AAV) vector. In some embodiments, the vector is a lentivirus.

Certain aspects of the present disclosure are directed to a T cell receptor (TCR) or an antigen binding portion thereof comprising the alpha chain variable domain of the recombinant TCR or an antigen binding portion thereof disclosed herein and the beta chain variable domain of the recombinant TCR or an antigen binding portion thereof disclosed herein.

Certain aspects of the present disclosure are directed to a recombinant T cell receptor (TCR) or an antigen binding portion thereof ("recombinant TCR") that specifically binds a target human protein, wherein: (a) the target human protein is tyrosinase ("anti-tyrosinase TCR"), wherein the anti-tyrosinase TCR cross competes for binding to human tyrosinase with a reference anti-tyrosinase TCR, wherein the reference anti-tyrosinase TCR comprises an alpha chain and a beta chain, and wherein the alpha chain comprises an amino acid sequence as set forth in SEQ ID NO: 1, and the beta chain comprises an amino acid sequence as set forth in SEQ ID NO: 2; (b) the target human protein is MAGE-A1 ("anti-MAGE-A1 TCR"), wherein the anti-MAGE-A1 TCR cross competes for binding to human MAGE-A1 with a reference anti-MAGE-A1 TCR, wherein the reference anti-MAGE-A1 TCR comprises an alpha chain and a beta chain, and wherein the alpha chain comprises an amino acid sequence as set forth in SEQ ID NO: 11, and the beta chain comprises an amino acid sequence as set forth in SEQ ID NO: 12; (c) the target human protein is MART1 ("anti-MART1 TCR"), wherein the anti-MART1 TCR cross competes for binding to human MART1 with a reference anti-MART1 TCR, wherein the reference anti-MART1 TCR comprises an alpha chain and a beta chain, and wherein the alpha chain comprises an amino acid sequence as set forth in SEQ ID NO: 21, and the beta chain comprises an amino acid sequence as set forth in SEQ ID NO: 22; (d) the target human protein is MAGE-A3 ("anti-MAGE-A3 TCR"), wherein the anti-MAGE-A3 TCR cross competes for binding to human MAGE-A3 with a reference anti-MAGE-A3 TCR, wherein the reference anti-MAGE-A3 TCR comprises an alpha chain and a beta chain, and wherein the alpha chain comprises an amino acid sequence as set forth in SEQ ID NO: 31, and the beta chain comprises an amino acid sequence as set forth in SEQ ID NO: 32; or (e) the target human protein is SSX2 ("anti-SSX2 TCR"), wherein the anti-SSX2 TCR cross competes for binding to human SSX2 with a reference anti-SSX2 TCR, wherein the reference anti-SSX2 TCR comprises an alpha chain and a beta chain, and wherein the alpha chain comprises an amino acid sequence as set forth in SEQ ID NO: 41, and the beta chain comprises an amino acid sequence as set forth in SEQ ID NO: 42.

Certain aspects of the present disclosure are directed to a recombinant T cell receptor (TCR) or an antigen binding portion thereof ("recombinant TCR") that specifically binds a target human protein, wherein: (a) target human protein is tyrosinase ("anti-tyrosinase TCR"), wherein the anti-tyrosinase TCR binds the same epitope or an overlapping epitope of human tyrosinase as a reference anti-tyrosinase TCR, wherein the reference anti-tyrosinase TCR comprises an alpha chain and a beta chain, wherein the alpha chain comprises an amino acid sequence as set forth in SEQ ID NO: 1 and the beta chain comprises an amino acid sequence as set forth in SEQ ID NO: 2; (b) the target human protein is MAGE-A1 ("anti-MAGE-A1 TCR"), wherein the anti-MAGE-A1 TCR binds the same epitope or an overlapping epitope of human MAGE-A1 as a reference anti-MAGE-A1 TCR, wherein the reference anti-MAGE-A1 TCR comprises an alpha chain and a beta chain, and wherein the alpha chain comprises an amino acid sequence as set forth in SEQ ID NO: 11, and the beta chain comprises an amino acid sequence as set forth in SEQ ID NO: 12; (c) the target human protein is MART1 ("anti-MART1 TCR"), wherein the anti- MART1 TCR binds the same epitope or an overlapping epitope of human MART1 as a reference anti-MART1 TCR, wherein the reference anti-MART1 TCR comprises an alpha chain and a beta chain, and wherein the alpha chain comprises an amino acid sequence as set forth in SEQ ID NO: 21, and the beta chain comprises an amino acid sequence as set forth in SEQ ID NO: 22; (d) the target human protein is MAGE-A3 ("anti-MAGE-A3 TCR"), wherein the anti-MAGE-A3 TCR binds the same epitope or an overlapping epitope of human MAGE-A3 as a reference anti-MAGE-A3 TCR, wherein the reference anti-MAGE-A3 TCR comprises an alpha chain and a beta chain, and wherein the alpha chain comprises an amino acid sequence as set forth in SEQ ID NO: 31, and the beta chain comprises an amino acid sequence as set forth in SEQ ID NO: 32; or (e) the target human protein is SSX2 ("anti-SSX2 TCR"), wherein the anti-SSX2 TCR binds the same epitope or an overlapping epitope of human SSX2 as a reference anti-SSX2 TCR, wherein the reference anti-SSX2 TCR comprises an alpha chain and a beta chain, and wherein the alpha chain comprises an amino acid sequence as set forth in SEQ ID NO: 41, and the beta chain comprises an amino acid sequence as set forth in SEQ ID NO: 42.

In some embodiments, (a) the anti-tyrosinase TCR binds to an epitope of tyrosinase consisting of an amino acid sequence as set forth in SEQ ID NO: 51; (b) the anti-MAGE-A1 TCR binds to an epitope of MAGE-A1 consisting of an amino acid sequence as set forth in SEQ ID NO: 52; (c) the anti-MART1 TCR binds to an epitope of MART1 consisting of an amino acid sequence as set forth in SEQ ID NO: 53; (d) the anti-MAGE-A3 TCR binds to an epitope of MAGE-A3 consisting of an amino acid sequence as set forth in SEQ ID NO: 54; or (e) the anti-SSX2 TCR binds to an epitope of SSX2 consisting of an amino acid sequence as set forth in SEQ ID NO: 55.

In some embodiments, the epitope is complexed with an HLA class I molecule. In some embodiments, the HLA class I molecule is an HLA-A, HLA-B, HLA-C, HLA-E, HLA-F, or HLA-G allele. In some embodiments: (a) the target human protein is tyrosinase, and the HLA class I molecule is an HLA-C*05 allele; (b) the target human protein is MAGE-A1, and the HLA class I molecule is an HLA-B*07 allele; (c) the target human protein is MART1, and the HLA class I molecule is an HLA-B*18 allele; (d) the target human protein is MAGE-A3, and the HLA class I molecule is an HLA-B*18 allele; or (e) the target human protein is SSX2, and the HLA class I molecule is an HLA-A*02 allele.

In some embodiments, (a) the target human protein is tyrosinase, and the HLA class I molecule is selected from an HLA-C*05:01 allele, an HLA-C*05:03 allele, an HLA-C*05:04 allele, an HLA-C*05:05 allele, and an HLA-C*05:06 allele; (b) the target human protein is MAGE-A1, and the HLA class I molecule is selected from an HLA-B*07:02 allele, an HLA-B*07:03 allele, an HLA-B*07:04 allele, an HLA-B*07:05 allele, and an HLA-B*07:06 allele; (c) the target human protein is MART1, and the HLA class I molecule is selected from an HLA-B*18:01 allele, an HLA-B*18:02 allele, an HLA-B*18:03 allele, an HLA-B*18:04 allele, and an HLA-B*18:05 allele; (d) the target human protein is MAGE-A3, and the HLA class I molecule is selected from an HLA-B*18:01 allele, an HLA-B*18:02 allele, an HLA-B*18:03 allele, an HLA-B*18:04 allele, and an HLA-B*18:05 allele; or (e) the target human protein is SSX2, and the HLA class I molecule is selected from an HLA-A*02:01 allele, an HLA-A*02:02 allele, an HLA-A*02:03 allele, an HLA-A*02:04 allele, and an HLA-A*02:05 allele.

In some embodiments, (a) the target human protein is tyrosinase, and the HLA class I molecule is an HLA-C*05: 01 allele; (b) the target human protein is MAGE-A1, and the HLA class I molecule is an HLA-B*07:02 allele; (c) the target human protein is MART1, and the HLA class I molecule is an HLA-B*18:01 allele; (d) the target human protein is MAGE-A3, and the HLA class I molecule is an HLA-B*18:01 allele; or (e) the target human protein is SSX2, and the HLA class I molecule is an HLA-A*02:01 allele.

In some embodiments, the recombinant TCR or an antigen binding portion thereof that specifically binds the target human protein comprises an alpha chain and a beta chain; wherein the alpha chain comprises a variable region comprising an alpha chain CDR1, an alpha chain CDR2, and an alpha chain CDR3; wherein the beta chain comprises variable domain comprising a beta chain CDR1, a beta chain CDR2, and a beta chain CDR3; and wherein: (a) the target human protein is tyrosinase, and the alpha chain CDR3 comprises an amino acid sequence as set forth in SEQ ID NO: 7; (b) the target human protein is MAGE-A1, and the alpha chain CDR3 comprises an amino acid sequence as set forth in SEQ ID NO: 17; (c) the target human protein is MART1, and the alpha chain CDR3 comprises an amino acid sequence as set forth in SEQ ID NO: 27; (d) the target human protein is MAGE-A3, and the alpha chain CDR3 comprises an amino acid sequence as set forth in SEQ ID NO: 37; or (e) the target human protein is SSX2, and the alpha chain CDR3 comprises an amino acid sequence as set forth in SEQ ID NO: 47.

In some embodiments, (a) the target human protein is tyrosinase, and the beta chain CDR3 comprises an amino acid sequence as set forth in SEQ ID NO: 10; (b) the target human protein is MAGE-A1, and the beta chain CDR3 comprises an amino acid sequence as set forth in SEQ ID NO: 20; (c) the target human protein is MART1, and the beta chain CDR3 comprises an amino acid sequence as set forth in SEQ ID NO: 30; (d) the target human protein is MAGE-A3, and the beta chain CDR3 comprises an amino acid sequence as set forth in SEQ ID NO: 40; or (e) the target human protein is SSX2, and the alpha beta CDR3 comprises an amino acid sequence as set forth in SEQ ID NO: 50.

In some embodiments, the recombinant TCR or an antigen binding portion comprises an alpha chain and a beta chain, wherein the alpha chain comprises a variable region comprising an alpha chain CDR1, an alpha chain CDR2, and an alpha chain CDR3; wherein the beta chain comprises variable domain comprising a beta chain CDR1, a beta chain CDR2, and a beta chain CDR3; and wherein: (a) the target human protein is tyrosinase, and the beta chain CDR3 comprises an amino acid sequence as set forth in SEQ ID NO: 10; (b) the target human protein is MAGE-A1, and the beta chain CDR3 comprises an amino acid sequence as set forth in SEQ ID NO: 20; (c) the target human protein is MART1, and the beta chain CDR3 comprises an amino acid sequence as set forth in SEQ ID NO: 30; (d) the target human protein is MAGE-A3, and the beta chain CDR3 comprises an amino acid sequence as set forth in SEQ ID NO: 40; or (e) the target human protein is SSX2, and the alpha beta CDR3 comprises an amino acid sequence as set forth in SEQ ID NO: 50.

In some embodiments, (a) the target human protein is tyrosinase, and the alpha chain CDR3 comprises an amino acid sequence as set forth in SEQ ID NO: 7; (b) the target human protein is MAGE-A1, and the alpha chain CDR3 comprises an amino acid sequence as set forth in SEQ ID NO: 17; (c) the target human protein is MART1, and the alpha chain CDR3 comprises an amino acid sequence as set forth in SEQ ID NO: 27; (d) the target human protein is MAGE-A3, and the alpha chain CDR3 comprises an amino acid sequence as set forth in SEQ ID NO: 37; or (e) the target human protein is SSX2, and the alpha chain CDR3 comprises an amino acid sequence as set forth in SEQ ID NO: 47.

In some embodiments, (a) the target human protein is tyrosinase, and the alpha chain CDR1 comprises an amino acid sequence as set forth in SEQ ID NO: 5; (b) the target human protein is MAGE-A1, and the alpha chain CDR1 comprises an amino acid sequence as set forth in SEQ ID NO: 15; (c) the target human protein is MART1, and the alpha chain CDR1 comprises an amino acid sequence as set forth in SEQ ID NO: 25; (d) the target human protein is MAGE-A3, and the alpha chain CDR1 comprises an amino acid sequence as set forth in SEQ ID NO: 35; or (e) the target human protein is SSX2, and the alpha chain CDR1 comprises an amino acid sequence as set forth in SEQ ID NO: 45.

In some embodiments, (a) the target human protein is tyrosinase, and the beta chain CDR1 comprises an amino acid sequence as set forth in SEQ ID NO: 8; (b) the target human protein is MAGE-A1, and the beta chain CDR1 comprises an amino acid sequence as set forth in SEQ ID NO: 18; (c) the target human protein is MART1, and the beta chain CDR1 comprises an amino acid sequence as set forth in SEQ ID NO: 28; (d) the target human protein is MAGE-A3, and the beta chain CDR1 comprises an amino acid sequence as set forth in SEQ ID NO: 38; or (e) the target human protein is SSX2, and the beta chain CDR1 comprises an amino acid sequence as set forth in SEQ ID NO: 48.

In some embodiments, (a) the target human protein is tyrosinase, and the alpha chain CDR2 comprises an amino acid sequence as set forth in SEQ ID NO: 6; (b) the target human protein is MAGE-A1, and the alpha chain CDR2 comprises an amino acid sequence as set forth in SEQ ID NO: 16; (c) the target human protein is MART1, and the alpha chain CDR2 comprises an amino acid sequence as set forth in SEQ ID NO: 26; (d) the target human protein is MAGE-A3, and the alpha chain CDR2 comprises an amino acid sequence as set forth in SEQ ID NO: 36; or (e) the target human protein is SSX2, and the alpha chain CDR2 comprises an amino acid sequence as set forth in SEQ ID NO: 46.

In some embodiments, (a) the target human protein is tyrosinase, and the beta chain CDR2 comprises an amino acid sequence as set forth in SEQ ID NO: 9; (b) the target human protein is MAGE-A1, and the beta chain CDR2 comprises an amino acid sequence as set forth in SEQ ID NO: 19; (c) the target human protein is MART1, and the beta chain CDR2 comprises an amino acid sequence as set forth in SEQ ID NO: 29; (d) the target human protein is MAGE-A3, and the beta chain CDR2 comprises an amino acid sequence as set forth in SEQ ID NO: 39; or (e) the target human protein is SSX2, and the beta chain CDR2 comprises an amino acid sequence as set forth in SEQ ID NO: 49.

In some embodiments, (a) the target human protein is tyrosinase, and the alpha chain variable domain comprises an amino acid sequence of a variable domain present in the amino acid sequence set forth SEQ ID NO: 1; (b) the target human protein is MAGE-A1, and the alpha chain variable domain comprises an amino acid sequence of a variable domain present in the amino acid sequence set forth SEQ ID NO: 11; (c) the target human protein is MART1, and the alpha chain variable domain comprises an amino acid sequence of a variable domain present in the amino acid sequence set forth SEQ ID NO: 21; (d) the target human protein is MAGE-A3, and the alpha chain variable domain comprises an amino acid sequence of a variable domain present in the amino acid sequence set forth SEQ ID NO: 31; or (e) the target human protein is SSX2, and the alpha chain variable domain comprises an amino acid sequence of a variable domain present in the amino acid sequence set forth SEQ ID NO: 41.

In some embodiments, (a) the target human protein is tyrosinase, and the beta chain variable domain comprises an amino acid sequence of a variable domain present in the amino acid sequence set forth SEQ ID NO: 2; (b) the target human protein is MAGE-A1, and the beta chain variable domain comprises an amino acid sequence of a variable domain present in the amino acid sequence set forth SEQ ID NO: 12; (c) the target human protein is MART1, and the beta chain variable domain comprises an amino acid sequence of a variable domain present in the amino acid sequence set forth SEQ ID NO: 22; (d) the target human protein is MAGE-A3, and the beta chain variable domain comprises an amino acid sequence of a variable domain present in the amino acid sequence set forth SEQ ID NO: 32; or (e) the target human protein is SSX2, and the beta chain variable domain comprises an amino acid sequence of a variable domain present in the amino acid sequence set forth SEQ ID NO: 42.

In some embodiments, the alpha chain further comprises a constant region, wherein: (a) the target human protein is tyrosinase, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 1; (b) the target human protein is MAGE-A1, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 11; (c) the target human protein is MART1, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 21; (d) the target human protein is MAGE-A3, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 31; or (e) the target human protein is SSX2, and the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 41.

In some embodiments, the beta chain further comprises a constant region, and wherein: (a) the target human protein is tyrosinase, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 2; (b) the target human protein is MAGE-A1, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 12; (c) the target human protein is MART1, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 22; (d) the target human protein is MAGE-A3, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 32; or (e) the target human protein is SSX2, and the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 42.

In some embodiments, (a) the target human protein is tyrosinase, and the alpha chain comprises an amino acid sequence as set forth in SEQ ID NO: 1; (b) the target human protein is MAGE-A1, and the alpha chain comprises an amino acid sequence as set forth in SEQ ID NO: 11; (c) the target human protein is MART1, and the alpha chain comprises an amino acid sequence as set forth in SEQ ID NO: 21; (d) the target human protein is MAGE-A3, and the alpha chain comprises an amino acid sequence as set forth in SEQ ID NO: 31; or (e) the target human protein is SSX2, and the alpha chain comprises an amino acid sequence as set forth in SEQ ID NO: 41.

In some embodiments, (a) the target human protein is tyrosinase, and the beta chain comprises an amino acid sequence as set forth in SEQ ID NO: 2; (b) the target human protein is MAGE-A1, and the beta chain comprises an amino acid sequence as set forth in SEQ ID NO: 12; (c) the target human protein is MART1, and the beta chain comprises an amino acid sequence as set forth in SEQ ID NO: 22; (d) the target human protein is MAGE-A3, and the beta chain comprises an amino acid sequence as set forth in SEQ ID NO: 32; or (e) the target human protein is SSX2, and the beta chain comprises an amino acid sequence as set forth in SEQ ID NO: 42.

Certain aspects of the present disclosure are directed to a bispecific TCR comprising a first antigen-binding domain and a second antigen-binding domain, wherein the first antigen-binding domain comprises a TCR or an antigen-binding portion thereof disclosed herein or a recombinant TCR of disclosed herein. In some embodiments, the first antigen-binding domain comprises a single chain variable fragment ("scFv"). In some embodiments, the second antigen-binding domain binds specifically to a protein expressed on the surface of a T cell. In some embodiments, the second antigen-binding domain binds specifically to CD3. In some embodiments, the second antigen-binding domain comprises an scFv. In some embodiments, the first antigen-binding domain and the second antigen-binding domain are linked or associated by a covalent bond. In some embodiments, the first antigen-binding domain and the second antigen-binding domain are linked by a peptide bond.

Certain aspects of the present disclosure are directed to a cell comprising a nucleic acid molecule disclosed herein, a vector disclosed herein, a TCR disclosed herein, a recombinant TCR disclosed herein, or a bispecific TCR disclosed herein. In some embodiments, the cell further expresses CD3. In some embodiments, the cell is selected from the group consisting of a T cell, a natural killer (NK) cell, an natural killer T (NKT) cell, or an ILC cell.

Certain aspects of the present disclosure are directed to a method of treating a cancer in a subject in need thereof, comprising administering to the subject a cell disclosed herein. In some embodiments, the cancer is selected from the group consisting of melanoma, bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers.

In some embodiments, the cancer is relapsed or refractory. In some embodiments, the cancer is locally advanced. In some embodiments, the cancer is advanced. In some embodiments, the cancer is metastatic.

In some embodiments, the cells are obtained from the subject. In some embodiments, the cells are obtained from a donor other than the subject. In some embodiments, the subject is preconditioned prior to the administering of the cells. In some embodiments, the preconditioning comprises administering to the subject a chemotherapy, a cytokine, a protein, a small molecule, or any combination thereof. In some embodiments, the preconditioning comprises administering an interleukin. In some embodiments, the preconditioning comprises administering IL-2, IL-4, IL-7, IL-9, IL-15, IL-21, or any combination thereof. In some embodiments, the preconditioning comprises administering a preconditioning agent selected from the group consisting of cyclophosphamide, fludarabine, vitamin C, an AKT inhibitor, ATRA, Rapamycin, or any combination thereof. In some embodiments, the preconditioning comprises administering cyclophosphamide, fludarabine, or both.

Certain aspects of the present disclosure are directed to a method of engineering an antigen-targeting cell, comprising transducing a cell collected from a subject in need of a T cell therapy with a nucleic acid molecule disclosed herein or a vector disclosed herein. In some embodiments, the antigen-targeting cell further expresses CD3. In some embodiments, the cell is a T cell or a natural killer (NK) cell.

Certain aspects of the present disclosure are directed to an HLA class I molecule complexed to a peptide, wherein the HLA class I molecule comprises an α1 domain, an α2 domain, an α3 domain and a β2m, and wherein the peptide consists of an amino acid sequence selected from the group consisting of SEQ ID NOs: 51, 52, 53, 54, 55, and any combination thereof. In some embodiments, the HLA class I molecule is an HLA-A, HLA-B, HLA-C, HLA-E, HLA-F, or HLA-G. In some embodiments, (a) the peptide consists of an amino acid sequence set forth in SEQ ID NO: 51, and the HLA class I molecule is an HLA-C; (b) the peptide consists of an amino acid sequence set forth in SEQ ID NO: 52, and the HLA class I molecule is an HLA-B; (c) the peptide consists of an amino acid sequence set forth in SEQ ID NO: 53, and the HLA class I molecule is an HLA-B; (d) the peptide consists of an amino acid sequence set forth in SEQ ID NO: 54, and the HLA class I molecule is an HLA-B; or (e) the peptide consists of an amino acid sequence set forth in SEQ ID NO: 55, and the HLA class I molecule is an HLA-A.

In some embodiments, (a) the peptide consists of an amino acid sequence set forth in SEQ ID NO: 51, and the HLA class I molecule is an HLA-C*05; (b) the peptide consists of an amino acid sequence set forth in SEQ ID NO: 52, and the HLA class I molecule is an HLA-B*07; (c) the peptide consists of an amino acid sequence set forth in SEQ ID NO: 53, and the HLA class I molecule is an HLA-B*18; (d) the peptide consists of an amino acid sequence set forth in SEQ ID NO: 54, and the HLA class I molecule is an HLA-B*18; or (e) the peptide consists of an amino acid sequence set forth in SEQ ID NO: 55, and the HLA class I molecule is an HLA-A*02.

In some embodiments, (a) the peptide consists of an amino acid sequence set forth in SEQ ID NO: 51, and the HLA class I molecule is selected from an HLA-C*05:01 allele, an HLA-C*05:03 allele, an HLA-C*05:04 allele, an HLA-C*05:05 allele, and an HLA-C*05:06 allele; (b) the peptide consists of an amino acid sequence set forth in SEQ ID NO: 52, and the HLA class I molecule is selected from an HLA-B*07:02 allele, an HLA-B*07:03 allele, an HLA-B*07:04 allele, an HLA-B*07:05 allele, and an HLA-B*07:06 allele; (c) the peptide consists of an amino acid sequence set forth in SEQ ID NO: 53, and the HLA class I molecule is selected from an HLA-B*18:01 allele, an HLA-B*18:02 allele, an HLA-B*18:03 allele, an HLA-B*18:04 allele, and an HLA-B*18:05 allele; (d) the peptide consists of an amino acid sequence set forth in SEQ ID NO: 54, and the HLA class I molecule is selected from an HLA-B*18:01 allele, an HLA-B*18:02 allele, an HLA-B*18:03 allele, an HLA-B*18:04 allele, and an HLA-B*18:05 allele; or (e) the peptide consists of an amino acid sequence set forth in SEQ ID NO: 55, and the HLA class I molecule is selected from an HLA-A*02:01 allele, an HLA-A*02:02 allele, an HLA-A*02:03 allele, an HLA-A*02:04 allele, and an HLA-A*02:05 allele.

In some embodiments, (a) the peptide consists of an amino acid sequence set forth in SEQ ID NO: 51, and the HLA class I molecule is an HLA-C*05:01; (b) the peptide consists of an amino acid sequence set forth in SEQ ID NO: 52, and the HLA class I molecule is an HLA-B*07:02; (c) the peptide consists of an amino acid sequence set forth in SEQ ID NO: 53, and the HLA class I molecule is an HLA-B*18:01; (d) the peptide consists of an amino acid sequence set forth in SEQ ID NO: 54, and the HLA class I molecule is an HLA-B*18:01; or (e) the peptide consists of an amino acid sequence set forth in SEQ ID NO: 55, and the HLA class I molecule is an HLA-A*02:01.

In some embodiments, the HLA class I molecule is a monomer. In some embodiments, the HLA class I molecule is a dimer. In some embodiments, the HLA class I molecule is a trimer. In some embodiments, the HLA class I molecule is a tetramer. In some embodiments, the HLA class I molecule is a pentamer.

Certain aspects of the present disclosure are directed to an antigen presenting cell (APC), comprising an HLA class I molecule disclosed herein. In some embodiments, the HLA class I molecule is expressed on the surface of the APC.

Certain aspects of the present disclosure are directed to a method of enriching a target population of T cells obtained from a human subject, comprising contacting the T cells with an HLA class I molecule disclosed herein or an APC disclosed herein, wherein following the contacting, the enriched population of T cells comprises a higher number of T cells capable of binding the HLA class I molecule relative to the number of T cells capable of binding the HLA class I molecule prior to the contacting.

Certain aspects of the present disclosure are directed to a method of enriching a target population of T cells obtained from a human subject, comprising contacting the T cells in vitro with a peptide; wherein the peptide consists of an amino acid sequence selected from the group consisting of SEQ ID NOs: 51, 52, 53, 54, 55, and any combination thereof wherein following the contacting, the enriched population of T cells comprises a higher number of T cells capable of targeting a tumor cell relative to the number of T cells capable of targeting a tumor cell prior to the contacting. In some embodiments, the T cells obtained from the human subject are tumor infiltrating lymphocytes (TIL).

Certain aspects of the present disclosure are directed to a method of treating a tumor in a subject in need thereof, comprising administering to the subject enriched T cells disclosed herein.

Certain aspects of the present disclosure are directed to a method of enhancing cytotoxic T cell-mediated targeting of cancer cells in a subject afflicted with a cancer, comprising administering to the subject a peptide having an amino acid sequence selected from the group consisting of SEQ ID NOs: 51, 52, 53, 54, 55, and any combination thereof.

Certain aspects of the present disclosure are directed to a cancer vaccine comprising a peptide having an amino acid sequence selected from the group consisting of SEQ ID NOs: 51, 52, 53, 54, 55, and any combination thereof.

Certain aspects of the present disclosure are directed to a method of selecting a T cell capable of targeting a tumor cell, comprising contacting a population of isolated T cells in vitro with a peptide, wherein the peptide consists of an amino acid sequence selected from the group consisting of SEQ ID NOs: 51, 52, 53, 54, 55, and any combination thereof. In some embodiments, the T cell is a tumor infiltrating lymphocytes (TIL).

BRIEF DESCRIPTION OF THE DRAWINGS

FIGS. 1A and 1C) and 14 days after stimulation (day 14; FIGS. 1B and 1D) are shown. The percentage of multimer$^{+}$ cells in CD8$^{+}$ T cells is shown.

FIGS. 3C, 3F, and 3I) were used as controls, as well as Jurkat 76/CD8 not transduced with a TCR (FIGS. 3A, 3D, and 3G). The percentage of multimer$^{+}$ CD8$^{+}$ T cells is shown.

FIG. 9A shows staining of the TILs with B*07:02/MAGE-A1$_{289-297}$ multimer. B*07:02/EBV EBNA3A$_{379-387}$ (FIG. 9B) multimer was used as a negative control. The percentage of multimer$^+$ cells in CD8$^+$ T cells is shown.

FIGS. 11A-11I are graphical representations of positive staining of Jurkat 76/CD8 cells transduced with B*07:02/MAGE-A1$_{289-297}$ TCR genes with a cognate multimer. Jurkat 76/CD8 cells transduced with the B*07:02/MAGE-A1$_{289-297}$ TCR (FIGS. 11B, 11E, and 11H) were stained with the B*07:02/MAGE-A1$_{289-297}$ multimer (FIG. 11B). The B*07:02/NY-ESO-1$_{60-72}$ multimer (FIGS. 11D, 11E, and 11F), B*07:02/unexchanged multimer (FIGS. 11G, 11H, and 11I), and B*07:02/NY-ESO-1$_{60-72}$ TCR (FIGS. 11C, 11F, and 11I) were employed as controls, as well as Jurkat 76/CD8 not transduced with a TCR (FIGS. 11A, 11D, and 11G). The percentage of multimer$^+$ CD8$^+$ cells is shown.

FIG. 18B shows staining of the TILs with B*18:01/MART1$_{25-33}$ multimer. B*18:01/HIV gag$_{161-170}$ (FIG. 18C) and B*18:01/unexchanged (FIG. 18A) multimers were used as negative controls. The percentage of multimer$^+$ cells in CD8$^+$ T cells is shown.

FIGS. 24A-24E are graphical representations of the expression of MART1 derived from endogenous or transduced full-length gene. The expression of MART1 derived from endogenous or transduced full-length gene in target cells was analyzed via intracellular flow cytometry following staining with anti-MART1 mAb (open curve) and an isotype control (filled curve).

FIGS. 25A-25F are graphical representations of the expression of ΔNGFR in target cells transduced with the full-length HLA-B*18:01 gene tagged with ΔNGFR (FIGS. 25B, 25D, and 25F). Surface expression of ΔNGFR in target cells transduced with the full-length HLA-B*18:01 gene tagged with ΔNGFR was analyzed by flow cytometry following staining with an anti-NGFR mAb (open curve) and an isotype control (filled curve). ΔNGFR alone was used as a control (FIGS. 25A, 25C, and 25E).

FIGS. 26A-26C are graphical representations of B*18:01/MAGE-A3$_{167-176}$ multimer staining of melanoma TILs. The TILs were stimulated once with B*18:01-artificial APCs pulsed with the MAGE-A3$_{167-176}$ peptide. Data on B*18:01/MAGE-A3$_{167-176}$ (FIGS. 26A-26B) or control B18:01/HIV gag$_{161-170}$ multimer (FIG. 26C) staining before stimulation (day 0; FIG. 26A) and 14 days after stimulation (day 14; FIGS. 26B-26C) are shown. The percentage of multimer$^+$ cells in CD8$^+$ T cells is shown.

FIGS. 28A-28I are graphical representations of positive staining of Jurkat 76/CD8 cells transduced with B*18:01/MAGE-A3$_{167-176}$ TCR genes with a cognate multimer. Jurkat 76/CD8 cells transduced with the B*18:01/MAGE-A3$_{167-176}$ TCR (FIGS. 28B, 28E, and 28H) were stained with the B*18:01/MAGE-A3$_{167-176}$ multimer (FIG. 28B). The B*18:01/MART1$_{25-33}$ multimer (FIGS. 28D, 28E, and 28F), B*18:01/unexchanged multimer (FIGS. 28G, 28H, and 28I), and B*18:01/MART1$_{25-33}$ TCR (FIGS. 28C, 28F, and 28I) were employed as controls, as well as Jurkat 76/CD8 not transduced with a TCR (FIGS. 28A, 28D, and 28G). The percentage of multimer$^+$ CD8$^+$ cells is shown.

FIG. 34A shows staining of the TILs with A*02:01/SSX2$_{41-49}$ multimer. A*02:01/HTLV-1 tax$_{11-19}$ (FIG. 34B) multimer was used as a negative control. The percentage of multimer$^+$ cells in CD8$^+$ T cells is shown.

FIGS. 36C, 36F, and 36I) were employed as controls, as well as Jurkat 76/CD8 not transduced with a TCR (FIGS. 36A, 36D, and 36G). The percentage of multimer$^+$ CD8$^+$ cells is shown.

DETAILED DESCRIPTION OF THE DISCLOSURE

Figure 1:
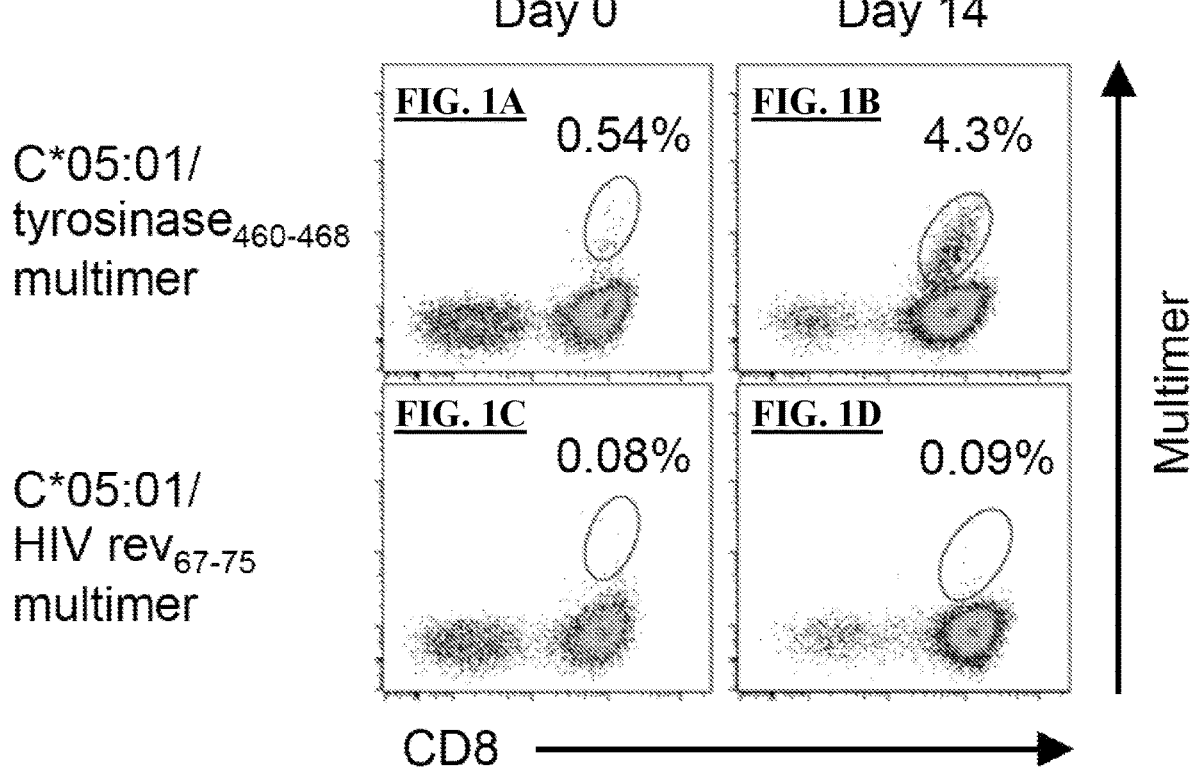
FIGS. 1A-1D are graphical representations of C*05:01/tyrosinase$_{460-468}$ multimer staining of melanoma TILs. The TILs were stimulated once with C*05:01-artificial APCs pulsed with the tyrosinase$_{460-468}$ peptide. Data on C*05:01/tyrosinase$_{460-468}$ (FIGS. 1A-1B) or control C*05:01/HIV rev$_{67-75}$ multimer (FIGS. 1C-1D) staining before stimulation (day 0.

The present disclosure is directed to TCRs or antigen binding portions thereof that specifically bind to an epitope on a target human protein selected from the group consisting of tyrosinase, MAGE-A1, MART1, MAGE-A3, and SSX2, nucleic acid molecules that encode the same, and cells that comprise the TCR or the nucleic acid molecule. Some aspects of the present disclosure are directed to methods of treating a caner in a subject in need thereof, comprising administering to the subject the cell. Other aspects of the present disclosure are directed to HLA class I molecules complexed to a peptide comprising the tyrosinase, MAGE-A1, MART1, MAGE-A3, or SSX2 epitope.

I. Terms

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "T cell receptor" (TCR), as used herein, refers to a heteromeric cell-surface receptor capable of specifically interacting with a target antigen. As used herein, "TCR" includes but is not limited to naturally occurring and non-naturally occurring TCRs; full-length TCRs and antigen binding portions thereof; chimeric TCRs; TCR fusion constructs; and synthetic TCRs. In human, TCRs are expressed on the surface of T cells, and they are responsible for T cell recognition and targeting of antigen presenting cells. Antigen presenting cells (APCs) display fragments of foreign proteins (antigens) complexed with the major histocompatibility complex (WIC; also referred to herein as complexed with an HLA molecule, e.g., an HLA class 1 molecule). A TCR recognizes and binds to the antigen:HLA complex and recruits CD3 (expressed by T cells), activating the TCR. The activated TCR initiates downstream signaling and an immune response, including the destruction of the EPC.

In general, a TCR can comprise two chains, an alpha chain and a beta chain (or less commonly a gamma chain and a delta chain), interconnected by disulfide bonds. Each chain comprises a variable domain (alpha chain variable domain and beta chain variable domain) and a constant region (alpha chain constant region and beta chain constant region). The variable domain is located distal to the cell membrane, and the variable domain interacts with an antigen. The constant region is located proximal to the cell membrane. A TCR can further comprises a transmembrane region and a short cytoplasmic tail. As used herein, the term "constant region" encompasses the transmembrane region and the cytoplasmic tail, when present, as well as the traditional "constant region."

The variable domains can be further subdivided into regions of hypervariability, termed complementarity determining regions (CDRs), interspersed with regions that are more conserved, termed framework regions (FR). Each alpha chain variable domain and beta chain variable domain comprises three CDRs and four FRs: FR1, CDR1, FR2, CDR2, FR3, CDR3, FR4. Each variable domain contains a binding domain that interacts with an antigen. Though all three CDRs on each chain are involved in antigen binding, CDR3 is believed to be the primary antigen binding region. CDR1 is also interacts with the antigen, while CD2 is believed to primarily recognize the HLA complex.

Where not expressly stated, and unless the context indicates otherwise, the term "TCR" also includes an antigen-binding fragment or an antigen-binding portion of any TCR disclosed herein, and includes a monovalent and a divalent fragment or portion, and a single chain TCR. The term "TCR" is not limited to naturally occurring TCRs bound to the surface of a T cell. As used herein, the term "TCR" further refers to a TCR described herein that is expressed on the surface of a cell other than a T cell (e.g., a cell that naturally expresses or that is modified to express CD3, as described herein), or a TCR described herein that is free from a cell membrane (e.g., an isolated TCR or a soluble TCR).

An "antigen binding molecule," "portion of a TCR," or "TCR fragment" refers to any portion of an TCR less than the whole. An antigen binding molecule can include the antigenic complementarity determining regions (CDRs).

An "antigen" refers to any molecule, e.g., a peptide, that provokes an immune response or is capable of being bound by a TCR. An "epitope," as used herein, refers to a portion of a polypeptide that provokes an immune response or is capable of being bound by a TCR. The immune response may involve either antibody production, or the activation of specific immunologically-competent cells, or both. A person of skill in the art would readily understand that any macromolecule, including virtually all proteins or peptides, can serve as an antigen. An antigen and/or an epitope can be endogenously expressed, i.e. expressed by genomic DNA, or can be recombinantly expressed. An antigen and/or an epitope can be specific to a certain tissue, such as a cancer cell, or it can be broadly expressed. In addition, fragments of larger molecules can act as antigens. In one embodiment, antigens are tumor antigens. An epitope can be present in a longer polypeptide (e.g., in a protein), or an epitope can be present as a fragment of a longer polypeptide. In some embodiments, an epitope is complexed with a major histocompatibility complex (MHC; also referred to herein as complexed with an HLA molecule, e.g., an HLA class 1 molecule).

"Tyrosinase" or "TYR" (UniProtKB-P14679), as used herein, refers to a copper-containing oxidase that functions in the formation of pigments such as melanins and other polyphenolic compounds. Tyrosinase catalyzes the initial and rate limiting step in the cascade of reactions leading to melanin production from tyrosine. In addition to hydroxylating tyrosine to DOPA (3,4-dihydroxyphenylalanine), tyrosinase also catalyzes the oxidation of DOPA to DOPA-quinone, and possibly the oxidation of DHI (5,6-dihydroxy-indole) to indole-5,6 quinone. Tyrosinase is expressed in the retina, skin, heart, aorta, mouth, and various other organs in the human body. The canonical tyrosinase amino acid sequence (SEQ ID NO: 89) is shown in Table 1.

"Melanoma-associated antigen 1" or "MAGE-A1" (UniProtKB-P43355), as used herein, refers to a tumor antigen with expression in numerous cancer types, including melanoma, head and neck squamous cell carcinoma, lung carcinoma, and bread carcinoma. MAGE-A1 is not expressed in normal tissues other than the testes. MAGE-A1 is believed to be involved in transcriptional regulation through interaction with SNW1 and recruiting histone deactelyase HDAC1. MAGE-A1 is believed to also inhibit notch intracellular domain (NICD) transactivation and to potentially play a role in embryonal development and tumor transformation or aspects of tumor progression. The MAGE-A1 amino acid sequence (SEQ ID NO: 90) is shown in Table 1.

"MART1," "MART-1," or "Melanoma antigen recognized by T-cells 1" (UniProtKB-Q16655), as used herein, refers to an antigen involved in melanosome biogenesis by ensuring the stability of GPR143. MART1 plays a vital role in the expression, stability, trafficking, and processing of melanocyte protein PMEL, which is critical to the formation of stage II melanosomes. MART1 is expressed in melanoma cells, malanocytes, and in the retina. The MART1 amino acid sequence (SEQ ID NO: 91) is shown in Table 1.

"MAGE-A3" or "Melanoma-associated antigen 3" (UniProtKB-P43357), as used herein, refers to an antigen believed to enhance ubiquitin ligase activity of RING-type zinc finger-containing E3 ubiquitin-protein ligases. MAGE-A3 may also act to enhance ubiquitin ligase activity of TRIM28 and stimulate p53/TP53 ubiquitination by TRIM28. MAGE-A3 is also believed to act through recruitment and/or stabilization of the Ubl-conjugating enzyme (E2) at the E3: substrate complex. MAGE-A3 may also play a role in embryonal development and tumor transformation or aspects of tumor progression. In vitro expression of MAGE-A3 promotes cell viability in melanoma cell lines. MAGE-A3 is expressed in numerous cancer types, including melanoma, head and neck squamous cell carcinoma, lung carcinoma, and bread carcinoma. MAGE-A3 is not expressed in normal tissues other than the testes and the placenta. The MAGE-A3 amino acid sequence (SEQ ID NO: 92) is shown in Table 1.

"SSX2" or "protein SSX2" (UniProtKB-Q16385), as used herein, is an antigen that is expressed in rhabdomyosarcoma and fibrosarcoma cell lines. SSX2 is also expressed at high levels in the testis and at low levels in the thyroid. The function of SSX2 is not clear, though it is speculated that SSX2 may act as a modulator of transcription. The SSX2 amino acid sequence (SEQ ID NO: 93) is shown in Table 1.

TABLE 1

Target Protein Amino Acid Sequences

| Target Protein | Amino Acid Sequence |
|---|---|
| Tyrosinase | MLLAVLYCLLWSFQTSAGHFPRACVSSKNLMEKECCPP<br>WSGDRSPCGQLSGRGSCQNILLSNAPLGPQFPFTGVDD<br>RESWPSVFYNRTCQCSGNFMGFNCGNCKFGFWGPNCTE<br>RRLLVRRNIFDLSAPEKDKFFAYLTLAKHTISSDYVIP<br>IGTYGQMKNGSTPMFNDINIYDLFVWMHYYVSMDALLG<br>GSEIWRDIDFAHEAPAFLPWHRLFLLRWEQEIQKLTGD<br>ENFTIPYWDWRDAEKCDICTDEYMGGQHPTNPNLLSPA<br>SFFSSWQIVCSRLEEYNSHQSLCNGTPEGPLRRNPGNH<br>DKSRTPRLPSSADVEFCLSLTQYESGSMDKAANFSFRN<br>TLEGFASPLTGIADASQSSMHNALHIYMNGTMSQVQGS<br>ANDPIFLLHHAFVDSIFEQWLRRHRPLQEVYPEANAPI<br>GHNRESYMVPFIPLYRNGDFFISSKDLGYDYSYLQDSD<br>PDSFQDYIKSYLEQASRIWSWLLGAAMVGAVLTALLAG<br>LVSLLCRHKRKQLPEEKQPLLMEKEDYHSLYQSHL<br>(SEQ ID NO: 89) |
| MAGE-A1 | MSLEQRSLHCKPEEALEAQQEALGLVCVQAATSSSSPL<br>VLGTLEEVPTAGSTDPPQSPQGASAFPTTINFTRQRQP<br>SEGSSSREEEGPSTSCILESLFRAVITKKVADLVGFLL<br>LKYRAREPVTKAEMLESVIKNYKHCFPEIFGKASESLQ<br>LVFGIDVKEADPTGHSYVLVTCLGLSYDGLLGDNQIMP<br>KTGFLIIVLVMIAMEGGHAPEEEIWEELSVMEVYDGRE<br>HSAYGEPRKLLTQDLVQEKYLEYRQVPDSDPARYEFLW<br>GPRALAETSYVKVLEYVIKVSARVRFFFPSLREAALRE<br>EEEGV (SEQ ID NO: 90) |
| MART1 | MPREDAHFIYGYPKKGHGHSYTTAEEAAGIGILTVILG<br>VLLLIGCWYCRRRNGYRALMDKSLHVGTQCALTRRCPQ<br>EGFDHRDSKVSLQEKNCEPVVPNAPPAYEKLSAEQSPP<br>PYSP (SEQ ID NO: 91) |
| MAGE-A3 | MPLEQRSQHCKPEEGLEARGEALGLVGAQAPATEEQEA<br>ASSSSTLVEVTLGEVPAAESPDPPQSPQGASSLPTTMN<br>YPLWSQSYEDSSNQEEEGPSTFPDLESEFQAALSRKVA<br>ELVHFLLLKYRAREPVTKAEMLGSVVGNWQYFFPVIFS<br>KASSSLQLVFGIELMEVDPIGHLYIFATCLGLSYDGLL<br>GDNQIMPKAGLLIIVLAIIAREGDCAPEEKIWEELSVL<br>EVFEGREDSILGDPKKLLTQHFVQENYLEYRQVPGSDP<br>ACYEFLWGPRALVETSYVKVLHHMVKISGGPHISYPPL<br>HEWVLREGEE (SEQ ID NO: 92) |
| SSX2 | MNGDDAFARRPTVGAQIPEKIQKAFDDIAKYFSKEEWE<br>KMKASEKIFYVYMKRKYEAMTKLGFKATLPPFMCNKRA<br>EDFQGNDLDNDPNRGNQVERPQMTFGRLQGISPKIMPK<br>KPAEEGNDSEEVPEASGPQNDGKELCPPGKPTTSEKIH<br>ERSGPKRGEHAWTHRLRERKQLVIYEEISDPEEDDE<br>(SEQ ID NO: 93) |

The term "HLA," as used herein, refers to the human leukocyte antigen. HLA genes encode the major histocompatibility complex (MHC) proteins in humans. MHC proteins are expressed on the surface of cells, and are involved in activation of the immune response. HLA class I genes encode MHC class I molecules, which are expressed on the surface of cells in complex with peptide fragments (antigens) of self or non-self proteins. T cells expressing TCR and CD3 recognize the antigen:MHC class I complex and initiate an immune response to target and destroy antigen presenting cells displaying non-self proteins.

As used herein, an "HLA class I molecule" or "HLA class I molecule" refers to a protein product of a wild-type or variant HLA class I gene encoding an MHC class I molecule. Accordingly, "HLA class I molecule" and "MHC class I molecule" are used interchangeably herein.

The MHC Class I molecule comprises two protein chains: the alpha chain and the β2-microglobulin ((32m) chain. Human β2m is encoded by the B2M gene. The amino acid sequence of β2m is set forth in SEQ ID NO: 56 (Table 2). The alpha chain of the MHC Class I molecule is encoded by the HLA gene complex. The HLA complex is located within the 6p21.3 region on the short arm of human chromosome 6 and contains more than 220 genes of diverse function. The HLA gene are highly variant, with over 20,000 HLA alleles and related alleles, including over 15,000 HLA Class I alleles, known in the art, encoding thousands of HLA proteins, including over 10,000 HLA Class I proteins (see, e.g., hla.alleles.org, last visited Feb. 27, 2019). There are at least three genes in the HLA complex that encode an MHC Class I alpha chain protein: HLA-A, HLA-B, and HLA-C. In addition, HLA-E, HLA-F, and HLA-G encode proteins that associate with the MHC Class I molecule.

TABLE 2

Amino Acid Sequence of Human β2m

| SEQ ID NO: | Sequence |
|---|---|
| 56 | MSRSVALAVLALLSLSGLEAIQRTPKIQVYSRHPAENGKSN<br>FLNCYVSGFHPSDIEVDLLKNGERIEKVEHSDLSFSKDWSF<br>YLLYYTEFTPTEKDEYACRVNHVTLSQPKIVKWDRDM |

The term "autologous" refers to any material derived from the same individual to which it is later to be re-introduced. For example, an autologous T cell therapy comprises administering to a subject a T cell that was isolated from the same subject. The term "allogeneic" refers to any material derived from one individual which is then introduced to another individual of the same species. For example, an allogeneic T cell transplantation comprises administering to a subject a T cell that was obtained from a donor other than the subject.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, and other leukocyte malignancies. In some embodiments, the methods of the present invention can be used to reduce the tumor size of a tumor derived from, for example, bone cancer, renal cancer, prostate cancer, breast cancer, colon cancer, lung cancer, cutaneous or intraocular malignant melanoma, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. The particular cancer can be responsive to chemo- or radiation therapy or the cancer can be refractory. A refractory cancer refers to a cancer that is not amendable to surgical intervention, and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival," which can be abbreviated as PFS, as used herein refers to the time from the treatment date to the date of disease progression per the revised IWG Response Criteria for Malignant Lymphoma or death from any cause.

"Disease progression" or "progressive disease," which can be abbreviated as PD, as used herein, refers to a worsening of one or more symptom associated with a particular disease. For example, disease progression for a subject afflicted with a cancer can include an increase in the number or size of one or more malignant lesions, tumor metastasis, and death.

The "duration of response," which can be abbreviated as DOR, as used herein refers to the period of time between a subject's first objective response to the date of confirmed disease progression, per the revised IWG Response Criteria for Malignant Lymphoma, or death.

The term "overall survival," which can be abbreviated as OS, is defined as the time from the date of treatment to the date of death.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1a, MIP-1a), MIP-1β (MIP-1b), gamma-induced protein 10 (IP-10), and thymus and activation regulated chemokine (TARC or CCL17).

Other examples of analytes and cytokines of the present invention include, but are not limited to chemokine (C-C motif) ligand (CCL) 1, CCL5, monocyte-specific chemokine 3 (MCP3 or CCL7), monocyte chemoattractant protein 2 (MCP-2 or CCL8), CCL13, IL-1, IL-3, IL-9, IL-11, IL-12, IL-14, IL-17, IL-20, IL-21, granulocyte colony-stimulating factor (G-CSF), leukemia inhibitory factor (LIF), oncostatin M (OSM), CD154, lymphotoxin (LT) beta, 4-1BB ligand (4-1BBL), a proliferation-inducing ligand (APRIL), CD70, CD153, CD178, glucocorticoid-induced TNFR-related ligand (GITRL), tumor necrosis factor superfamily member 14 (TNFSF14), OX40L, TNF- and ApoL-related leukocyte-expressed ligand 1 (TALL-1), or TNF-related apoptosis-inducing ligand (TRAIL).

A "therapeutically effective amount," "effective dose," "effective amount," or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). T-cell receptors (TCR) differentiate T cells from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). A B cell makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell or a modified cell that expresses CD3, which can either be obtained from a patient or a donor. The cell can be modified to express an exogenous construct, such as, e.g., a T cell receptor (TCR) disclosed herein, which is incorporated into the cell's genome. In some embodiments, the cell is modified to express CD3.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation.

Cells used in an immunotherapy described herein can come from any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety. An immunotherapy can also comprise administering a modified cell to a subject, wherein the modified cell expresses CD3 and a TCR disclosed herein. In some embodiments, the modified cell is not a T cell.

A "patient" as used herein includes any human who is afflicted with a cancer (e.g., a lymphoma or a leukemia). The terms "subject" and "patient" are used interchangeably herein.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an aAPC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class I molecule loaded with a peptide, an anti-CD3 antibody, a superagonist anti-CD28 antibody, and a superagonist anti-CD2 antibody.

The terms "conditioning" and "pre-conditioning" are used interchangeably herein and indicate preparing a patient in need of a T cell therapy for a suitable condition. Conditioning as used herein includes, but is not limited to, reducing the number of endogenous lymphocytes, removing a cytokine sink, increasing a serum level of one or more homeostatic cytokines or pro-inflammatory factors, enhancing an effector function of T cells administered after the conditioning, enhancing antigen presenting cell activation and/or availability, or any combination thereof prior to a T cell therapy. In one embodiment, "conditioning" comprises increasing a serum level of one or more cytokines, e.g., interleukin 7 (IL-7), interleukin 15 (IL-15), interleukin 10 (IL-10), interleukin 5 (IL-5), gamma-induced protein 10 (IP-10), interleukin 8 (IL-8), monocyte chemotactic protein 1 (MCP-1), placental growth factor (PLGF), C-reactive protein (CRP), soluble intercellular adhesion molecule 1

(sICAM-1), soluble vascular adhesion molecule 1 (sVCAM-1), or any combination thereof. In another embodiment, "conditioning" comprises increasing a serum level of IL-7, IL-15, IP-10, MCP-1, PLGF, CRP, or any combination thereof.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

II. Compositions of the Disclosure

The present disclosure is directed to T Cell Receptors (TCRs) or antigen binding portions thereof that specifically bind to an epitope on a target human protein selected from the group consisting of tyrosinase, MAGE-A1, MART1, MAGE-A3, and SSX2, nucleic acid molecules that encode the same, and cells that comprise the TCR or the nucleic acid molecule. Some aspects of the present disclosure are directed to methods of treating a caner in a subject in need thereof, comprising administering to the subject a cell comprising the TCRs described herein. Other aspects of the present disclosure are directed to an epitope of tyrosinase, MAGE-A1, MART1, MAGE-A3, or SSX2 that the TCRs bind to and HLA class I molecules complexed to a peptide comprising the epitope of tyrosinase, MAGE-A1, MART1, MAGE-A3, or SSX2.

The T-cell receptor, or TCR, is a molecule found on the surface of T cells, or T lymphocytes, that is responsible for recognizing fragments of antigen as peptides bound to major histocompatibility complex (MHC) molecules. The binding between TCR and antigen peptides is of relatively low affinity and is degenerate: that is, many TCRs recognize the same antigen peptide and many antigen peptides are recognized by the same TCR.

The TCR is composed of two different protein chains (that is, it is a heterodimer). In humans, in 95% of T cells the TCR consists of an alpha (α) chain and a beta (β) chain (encoded by TRA and TRB, respectively), whereas in 5% of T cells, the TCR consists of gamma and delta (γ/δ) chains (encoded by TRG and TRD, respectively). This ratio changes during ontogeny and in diseased states (such as leukemia). It also differs between species. Orthologues of the 4 loci have been mapped in various species. Each locus can produce a variety of polypeptides with constant and variable regions.

When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors.

II.A. Nucleic Acid Molecules

Certain aspects of the present disclosure are directed to nucleic acid molecules comprising (i) a first nucleotide sequence encoding a recombinant TCR or an antigen binding portion thereof that specifically binds a target human protein selected from the group consisting of tyrosinase, MAGE-A1, MART1, MAGE-A3, and SSX2 ("epitope-specific TCR"); and (ii) a second nucleotide sequence, wherein the second nucleotide sequence or the polypeptide encoded by the second nucleotide sequence inhibits the expression of an endogenous TCR. In some embodiments, the second nucleotide sequence is a non-naturally occurring sequence. In other embodiments, the second nucleotide sequence is synthetic. In yet other embodiments, the second nucleotide sequence comprises a sequence that targets a nucleotide sequence encoding the endogenous TCR. In some embodiments, the epitope-specific TCR cross competes for binding to the target human protein with a reference TCR. In some embodiments, the TCR binds the same epitope or an overlapping epitope of the target human protein as a reference TCR.

In some embodiments, the reference TCR comprises an alpha chain and a beta chain; wherein the alpha chain comprises a complementarity determining region 1 (CDR1), a CDR2, and a CDR3; wherein the beta chain comprises a CDR1, a CDR2, and a CDR3; and wherein the reference TCR comprises an alpha chain CDR3 amino acid sequence selected from the amino acid sequences set forth in SEQ ID NOs: 7, 17, 27, 37, and 47; and a beta chain CDR3 amino acid sequence selected from the amino acid sequences set forth in SEQ ID NOs: 10, 20, 30, 40, and 50. In some embodiments, the alpha chain CDR3 comprises the amino acid sequence set forth in SEQ ID NO: 7, and the beta chain CDR3 comprises the amino acid sequence set forth in SEQ ID NO: 10. In some embodiments, the alpha chain CDR3 comprises the amino acid sequence set forth in SEQ ID NO: 17, and the beta chain CDR3 comprises the amino acid sequence set forth in SEQ ID NO: 20. In some embodiments, the alpha chain CDR3 comprises the amino acid sequence set forth in SEQ ID NO: 27, and the beta chain CDR3 comprises the amino acid sequence set forth in SEQ ID NO: 30. In some embodiments, the alpha chain CDR3 comprises the amino acid sequence set forth in SEQ ID NO: 37, and the beta chain CDR3 comprises the amino acid sequence set forth in SEQ ID NO: 40. In some embodiments, the alpha chain CDR3 comprises the amino acid sequence set forth in SEQ ID NO: 47, and the beta chain CDR3 comprises the amino acid sequence set forth in SEQ ID NO: 50.

In some embodiments, the reference TCR comprises the alpha chain CDR1, CDR2, and CDR3 sequences present in amino acid sequence selected from the amino acid sequences set forth in SEQ ID NOs: 1, 11, 21, 31, and 41, and the reference TCR comprises the beta chain CDR1, CDR2, and CDR3 sequences present in an amino acid sequence selected from the amino acid sequences set forth in SEQ ID NO: 2, 12, 22, 32, and 42. In some embodiments, the reference TCR comprises an alpha chain and a beta chain, wherein the alpha chain comprises an amino acid sequence as set forth in SEQ ID NO: 1, 11, 21, 31, or 41; and the beta chain comprises an amino acid sequence as set forth in SEQ ID NO: 2, 12, 22, 32, or 42.

TABLE 3A

Tyrosinase Alpha Chain and Beta Chain TCR Sequences

| SEQ ID NO: | TCR Chain | Sequence |
|---|---|---|
| 1 | Alpha Chain (amino acid) | MRQVARVIVFLTLSTLSLAKTTQPISMDSYEGQEV NITCSHNNIATNDYITWYQQFPSQGPRFIIQGYKT KVTNEVASLFIPADRKSSTLSLPRVSLSDTAVYYC LVGDVEGSQGNLIFGKGTKLSVKPNIQNPDPAVYQ LRDSKSSDKSVCLFTDFDSQTNVSQSKDSDVYITD KTVLDMRSMDFKSNSAVAWSNKSDFACANAFNNSI IPEDTFFPSPESSCDVKLVEKSFETDTNLNFQNLS VIGFRILLLKVAGFNLLMTLRLWSSZ |
| 3 | Alpha Chain (nucle- otide) | ATGAGGCAAGTGGCGAGAGTGATCGTGTTCCTGAC CCTGAGTACTTTGAGCCTTGCTAAGACCACCCAGC CCATCTCCATGGACTCATATGAAGGACAAGAAGTG AACATAACCTGTAGCCACAACAACATTGCTACAAA TGATTATATCACGTGGTACCAACAGTTTCCCAGCC AAGGACCACGATTTATTATTCAAGGATACAAGACA AAAGTTACAAACGAAGTGGCCTCCCTGTTTATCCC TGCCGACAGAAAGTCCAGCACTCTGAGCCTGCCCC GGGTTTCCCTGAGCGACACTGCTGTGTACTACTGC CTCGTGGGTGACGTAGAAGGAAGCCAAGGAAATCT CATCTTTGGAAAAGGCACTAAAGTCTCTGTTAAAC CAAATATCCAGAACCCTGACCCTGCCGTGTACCAG CTGAGAGACTCTAAATCCAGTGACAAGTCTGTCTG CCTATTCACCGATTTTGATTCTCAAACAAATGTGT CACAAAGTAAGGATTCTGATGTGTATATCACAGAC AAAACTGTGCTAGACATGAGGTCTATGGACTTCAA GAGCAACAGTGCTGTGGCCTGGAGCAACAAATCTG ACTTTGCATGTGCAAACGCCTTCAACAACAGCATT ATTCCAGAAGACACCTTCTTCCCCAGCCCAGAAAG TTCCTGTGATGTCAAGCTGGTCGAGAAAAGCTTTG AAACAGATACGAACCTAAACTTTCAAAACCTGTCA GTATTGGGTTCCGAATCCTCCTCCTGAAAGTGGCG CGGGTTTAATCTGCTCATGACGCTGCGGCTGTGGT CCAGCTGA |
| 2 | Beta Chain (amino acid) | MSIGLLCCAALSLLWAGPVNAGVTQTPKFQVLKTG QSMTLQCAQDMNHEYMSWYRQDPGMGLRLIHYSVG AGITDQGEVPNGYNVSRSTTEDFPLRLLSAAPSQT SVYFCASSHHSGGIYNEQFFGPGTRLTVLEDLKNV FPPEVAVFEPSEAEISHTQKATLVCLATGFYPDHV ELSWWVNGKEVHSGVSTDPQPLKEQPALNDSRYCL SSRLRVSATFWQNPRNHFRCQVQFYGLSENDEWTQ DRAKPVTQIVSAEAWGRADCGFTSESYQQGVLSAT ILYEILLGKATLYAVLVSALVLMAMVKRKDSRGZ |
| 4 | Beta Chain (nucle- otide) | ATGAGCATCGGCCTCCTGTGCTGTGCAGCCTTGTC TCTCCTGTGGGCAGGTCCAGTGAATGCTGGTGTCA CTCAGACCCCAAAATTCCAGGTCCTGAAGACAGGA CAGAGCATGACACTGCAGTGTGCCCAGGATATGAA CCATGAATACATGTCCTGGTATCGACAAGACCCAG GCATGGGGCTGAGGCTGATTCATTACTCAGTTGGT GCTGGTATCACTGACCAAGGAGAAGTCCCCAATGG CTACAATGTCTCCAGATCAACCACAGAGGATTTCC CGCTCAGGCTGCTGTCGGCTGCTCCCTCCCAGACA |

TABLE 3A-continued

Tyrosinase Alpha Chain and Beta Chain TCR Sequences

| SEQ ID NO: | TCR Chain | Sequence |
|---|---|---|
| | | TCTGTGTACTTCTGTGCCAGCAGTCACCATTCGGG GGGGATCTACAATGAGCAGTTCTTCGGGCCAGGGA CACGGCTCACCGTGCTAGAGGACCTGAAAAACGTG TTCCCACCCGAGGTGCTGCTGTGTGTTTGAGCCATCAGA AGCAGAGATCTCCCACACCCAAAAGGCCACACTGG TATGCCTGGCCACAGGCTTCTACCCCGACCACGTG GAGCTGAGCTGGTGGGTGAATGGGAAGGAGGTGCA CAGTGGGGTCAGCACAGACCCGCAGCCCCTCAAGG AGCAGCCCGCCCTCAATGACTCCAGATACTGCCTG AGCAGCCGCCTGAGGGTCTCGGCCACCTTCTGGCA GAACCCCCGCAACCACTTCCGCTGTCAAGTCCAGT TCTACGGGCTCTCGGAGAATGACGAGTGGACCCAG GATAGGGCCAAACCTGTCACCCAGATCGTCAGCGC CGAGGCCTGGGGTAGAGCAGACTGTGGCTTCACCT CCGAGTCTTACCAGCAAGGGGTCCTGTCTGCCACC ATCCTCTATGAGATCTTGCTAGGGAAGGCCACCTT GTATGCCGTGCTGGTCAGTGCCCTCGTGCTGATGG CCATGGTCAAGAGAAAGGATTCCAGAGGCTAG |

TABLE 3B

MAGE-A1 Alpha Chain and Beta Chain TCR Sequences

| SEQ ID NO: | TCR Chain | Sequence |
|---|---|---|
| 11 | Alpha Chain (amino acid) | MLTASLLRAVIASICVVSSMAQKVTQAQTEISVVE KEDVTLDCVYETRDTTYYLFWYKQPPSGELVFLIR RNSFDEQNEISGRYSWNFQKSTSSFNFTITASQVV DSAVYFCALSESYSGAGSYQLTFGKGTKLSVIPNI QNPDPAVYQLRDSKSSDKSVCLFTDFDSQTNVSQS KDSDVYITDKTVLDMRSMDFKSNSAVAWSNKSDFA CANAFNNSIIPEDTFFPSPESSCDVKLVEKSFETD TNLNFQNLSVIGFRILLLKVAGFNLLMTLRLWSSZ |
| 13 | Alpha Chain (nucle- otide) | ATGCTGACTGCCAGCCTGTTGAGGGCAGTCATAGC CTCCATCTGTGTTGTATCCAGCATGGCTCAGAAGG TAACTCAAGCGCAGACTGAAATTTCTGTGGTGGAG AAGGAGGATGTGACCTTGGACTGTGTGTATGAAAC CCGTGATACTACTTATTACTTATTCTGGTACAAGC AACCACCAAGTGGAGAATTGGTTTTCCTTATTCGT CGGAACTCTTTTGATGAGCAAAATGAAATAAGTGG TCGGTATTCTTGGAACTTCCAGAAATCCACCAGTT CCTTCAACTTCACCATCACAGCCTCACAAGTCGTG GACTCAGCAGTATACTTCTGTGCTCTGAGTGAGTC ATACTCTGGGAGCTGGGAGTTACCAACTCACTTTCG GGAAGGGGACCAAACTCTCGGTCATACCCAAATATC CAGAACCCTGACCCTGCCGTGTACCAGCTGAGAGA CTCTAAATCCAGTGACAAGTCTGTCTGCCTATTCA CCGATTTTGATTCTCAAACAAATGTGTCACAAAGT AAGGATTCTGATGTGTATATCACAGACAAAACTGT GCTAGACATGAGGTCTATGGACTTCAAGAGCAACA GTGCTGTGGCCTGGAGCAACAAATCTGACTTTGCA TGTGCAAACGCCTTCAACAACAGCATTATTCCAGA AGACACCTTCTTCCCCAGCCCAGAAAGTTCCTGTG ATGTCAAGCTGGTCGAGAAAAGCTTTGAAACAGAT ACGAACCTAAACTTTCAAAACCTGTCAGTGATTGG GTTCCGAATCCTCCTCCTGAAAGTGGCCGGGTTTA ATCTGCTCATGACGCTGCGGCTGTGGTCCAGCTGA |
| 12 | Beta Chain (amino acid) | MGTSLLCWMALCLLGADHADTGVSQNPRHKITKRG QNVTFRCDPISEHNRLYWYRQTLGQGPEFLTYFQN EAQLEKSRLLSDRFSAERPKGSFSTLEIQRTEQGD SAMYLCASSLASGSNQPQHFGDGTRLSILEDLKNV FPPEVAVFEPSEAEISHTQKATLVCLATGFFPDHV ELSWWVNGKEVHSGVSTDPQPLKEQPALNDSRYCL SSRLRVSATFWQNPRNHFRCQVQFYGLSENDEWTQ |

TABLE 3B-continued

| SEQ ID NO: | TCR Chain | Sequence |
|---|---|---|
| | | MAGE-A1 Alpha Chain and Beta Chain TCR Sequences |
| | | DRAKPVTQIVSAEAWGRADCGFTSVSYQQGVLSAT ILYEILLGKATLYAVLVSALVLMAMVKRKDFZ |
| 14 | Beta Chain (nucle- otide) | ATGGGCACCAGCCTCCTCTGCTGGATGGCCCTGTG TCTCCTGGGGGCAGATCACGCAGATACTGGAGTCT CCCAGAACCCCAGACACAAGATCACAAAGAGGGGA CAGAATGTAACTTTCAGGTGTGATCCAATTTCTGA ACACAACCGCCTTTATTGGTACCGACAGACCCTGG GGCAGGGCCCAGAGTTTCTGACTTACTTCCAGAAT GAAGCTCAACTAGAAAAATCAAGGCTGCTCAGTGA TCGGTTCTCTGCAGAGAGGCCTAAGGGATCTTTCT CCACCTTGGAGATCCAGCGCACAGAGCAGGGGGAC TCGGCCATGTATCTCTGTGCCAGCAGCTTAGCTTC GGGCAGCAATCAGCCCCAGCATTTTGGTGATGGGA CTCGACTCTCCATCGTAGAGGACCTGAACAAGGTG TTCCCACCCGAGGTCGCTGTGTTTGAGCCATCAGA AGCAGAGATCTCCCACACCCAAAAGGCCACACTGG TGTGCCTGGCCACAGGCTTCTTCCCCGACCACGTG GAGCTGAGCTGGTGGGTGAATGGGAAGGAGGTGCA CAGTGGGGTCAGCACGGACCCGCAGCCCCTCAAGG AGCAGCCCGCCCTCAATGACTCCAGATACTGCCTG AGCAGCCGCCTGAGGGTCTCGGCCACCTTCTGGCA GAACCCCGCAACCACTTCCGCTGTCAAGTCCAGT TCTACGGGCTCTCGGAGAATGACGAGTGGACCCAG GATAGGGCCAAACCCGTCACCCAGATCGTCAGCGC CGAGGCCTGGGGTAGAGCAGACTGTGGCTTTACCT CGGTGTCCTACCAGCAAGGGGTCCTGTCTGCCACC ATCCTCTATGAGATCCTGCTAGGGAAGGCCACCCT GTATGCTGTGCTGGTCAGCGCCCTTGTGTTGATGG CCATGGTCAAGAGAAAGGATTTCTGA |

TABLE 3C

| SEQ ID NO: | TCR Chain | Sequence |
|---|---|---|
| | | MART1 Alpha Chain and Beta Chain TCR Sequences |
| 21 | Alpha Chain (amino acid) | MWGVFLLYVSMKMGGTTGQNIDQPTEMTATEGAIV QINCTYQTSGFNGLFWYQQHAGEAPTFLSYNVLDG LEEKGRFSSFLSRSKGYSYLLLKELQMKDSASYLC AVYGGATNKLIFGTGTLLAVQPNIQNPDPAVYQLR DSKSSDKSVCLFTDFDSQTNVSQSKDSDVYITDKT VLDMRSMDFKSNSAVAWSNKSDFACANAFNNSIIP EDTFFPSPESSCDVKLVEKSFETDTNLNFQNLSVI GFRILLLKVAGFNLLMTLRLWSSZ |
| 23 | Alpha Chain (nucle- otide) | ATGTGGGGAGTTTTCCTTCTTTATGTTTCCATGAA GATGGGAGGCACTACAGGACAAAACATTGACCAGC CCACTGAGATGACAGCTACGGAAGGTGCCATTGTC CAGATCAACTGCACGTACCAGACATCTGGGTTCAA CGGGCTGTTCTGGTACCAGCAACATGCTGGCGAAG CACCCACATTTCTGTCTTACAATGTTCTGGATGGT TTGGAGGAGAAAGGTCGTTTTTCTTCATTCCTTAG TCGGTCTAAAGGGTACAGTTACCTCCTTTTGAAGG AGCTCCAGATGAAAGACTCTGCCTCTTACCTCTGT GCTGTGTATGGTGGTGCTACAAACAAGCTCATCTT TGGAACTGGCACTCTGCTTGCTGTCCAGCCAAATA TCCAGAACCCTGACCCTGCCGTGTACCAGCTGAGA GACTCTAAATCCAGTGACAAGTCTGTCTGCCTATT CACCGATTTTGATTCTCAAACAAATGTGTCACAAA GTAAGGATTCTGATGTGTATATCACAGACAAAACT GTGCTAGACATGAGGTCTATGGACTTCAAGAGCAA CAGTGCTGTGGCCTGGAGCAACAAATCTGACTTTG CATGTGCAAACGCCTTCAACAACAGCATTATTCCA GAAGACACCTTCTTCCCCAGCCCAGAAAGTTCCTG TGATGTCAAGCTGGTCGAGAAAAGCTTTGAAACAG ATACGAACCTAAACTTTCAAAACCTGTCAGTGATT |

TABLE 3C-continued

| SEQ ID NO: | TCR Chain | Sequence |
|---|---|---|
| | | MART1 Alpha Chain and Beta Chain TCR Sequences |
| | | GGGTTCCGAATCCTCCTCCTGAAAGTGGCCGGGTT TAATCTGCTCATGACGCTGCGGCTGTGGTCCAGCT GA |
| 22 | Beta Chain (amino acid) | MDTRVLCCAVICLLGAGLSNAGVMQNPRHLVRRRG QEARLRCSPMKGHSHVYWYRQLPEEGLKFMVYLQK ENIIDESGMPKERFSAEFPKEGPSILRIQQVVRGD SAAYFCASSPHAGGVDEKLFFGSGTQLSVLEDLNK VFPPEVAVFEPSEAEISHTQKATLVCLATGFFPDH VELSWWVNGKEVHSGVSTDPQPLKEQPALNDSRYC LSSRLRVSATFWQNPRNHFRCQVQFYGLSENDEWT QDRAKPVTQIVSAEAWGRADCGFTSVSYQQGVLSA TILYEILLGKATLYAVLVSALVLMAMVKRKDFZ |
| 24 | Beta Chain (nucle- otide) | ATGGACACCAGAGTACTCTGCTGTGCGGTCATCTG TCTTCTGGGGGGCAGGTCTCTCAAATGCCGGCGTCA TGCAGAACCCAAGACACCTGGTCAGGAGGAGGGGA CAGGAGGCAAGACTGAGATGCAGCCCAATGAAAGG ACACAGTCATGTTTACTGGTATCGGCAGCTCCCAG AGGAAGGTCTGAAATTCATGGTTTATCTCCAGAAA GAAAATATCATAGATGAGTCAGGAATGCCAAAGGA ACGATTTTCTGCTGAATTTCCCAAAGAGGGCCCCA GCATCCTGAGGATCCAGCAGGTAGTGCGAGGAGAT TCGGCAGCTTATTCTGTGCCAGCTCACCACACGC GGGGGGGAGTTGATGAAAAACTGTTTTTTGGCAGTG GAACCCAGCTCTCTGTCTTGGAGGACCTGAACAAG GTGTTCCCACCCGAGGTCGCTGTGTTTGAGCCATC AGAAGCAGAGATCTCCCACACCCAAAAGGCCACAC TGGTGTGCCTGGCCACAGGCTTCTTCCCTGACCAC GTGGAGCTGAGCTGGTGGGTGAATGGGAAGGAGGT GCACAGTGGGGTCAGCACGGACCCGCAGCCCCTCA AGGAGCAGCCCGCCCTCAATGACTCCAGATACTGC CTGAGCAGCCGCCTGAGGGTCTCGGCCACCTTCTG GCAGAACCCCGCAACCACTTCCGCTGTCAAGTCC AGTTCTACGGGCTCTCGGAGAATGACGAGTGGACC CAGGATAGGGCCAAACCCGTCACCCAGATCGTCAG CGCCGAGGCCTGGGGTAGAGCAGACTGTGGCTTTA CCTCGGTGTCCTACCAGCAAGGGGTCCTGTCTGCC TACCACCTCTATGAGATCCTGCTAGGGAAGGCCAC CCTGTATGCTGTGCTGGTCAGCGCCCTTGTGTTGA TGGCCATGGTCAAGAGAAAGGATTTCTGA |

TABLE 3D

| SEQ ID NO: | TCR Chain | Sequence |
|---|---|---|
| | | MAGE-A3 Alpha Chain and Beta Chain TCR Sequences |
| 31 | Alpha Chain (amino acid) | MLTASLLRAVIASICVVSSMAQKVTQAQTEISVVE KEDVTLDCVYETRDTTYYLFWYKQPPSGELVFLIR RNSFDEQNEISGRYSWNFQKSTSSFNFTITASQVV DSAVYFCALEVRSSASKIIFGSGTRLSIRPNIQNP DPAVYQLRDSKSSDKSVCLFTDFDSQTNVSQSKDS DVYITDKTVLDMRSMDFKSNSAVAWSNKSDFACAN AFNNSIIPEDTFFPSPESSCDVKLVEKSFETDTNL NFQNLSVIGFRILLLKVAGFNLLMTLRLWSSZ |
| 33 | Alpha Chain (nucle- otide) | ATGCTGACTGCCAGCCTGTTGAGGGCAGTCATAGC CTCCATCTGTGTTGTATCCAGCATGGCTCAGAAGG TAACTCAAGCGCAGACTGAAATTTCTGTGGTGGAG AAGGAGGATGTGACCTTGGACTGTGTGTATGAAAC CCGTGATACTACTTATTACTTATTCTGGTACAAGC AACCACCAAGTGGAGAATTGGTTTTCCTTATTCGT CGGAACTCTTTTGATGAGCAAAATGAAATAAGTGG TCGGTATTCTTGGAACTTCCAGAAATCCACCAGTT CCTTCAACTTCACCATCACAGCCTCACAAGTCGTG GACTCAGCAGTATACTTCTGTGCTCTGGAAGTGAG |

TABLE 3D-continued

MAGE-A3 Alpha Chain and Beta Chain TCR Sequences

| SEQ ID NO: | TCR Chain | Sequence |
|---|---|---|
| | | AAGCAGTGCTTCCAAGATAATCTTTGGATCAGGGA<br>CCAGACTCAGCATCCGGCCAAATATCCAGAACCCT<br>GACCCTGCCGTGTACCAGCTGAGAGACTCTAAATC<br>CAGTGACAAGTCTGTCTGCCTATTCACCGATTTTG<br>ATTCTCAAACAAATGTGTCACAAAGTAAGGATTCT<br>GATGTGTATATCACAGACAAAACTGTGCTAGACAT<br>GAGGTCTATGGACTTCAAGAGCAACAGTGCTGTGG<br>CCTGGAGCAACAAATCTGACTTTGCATGTGCAAAC<br>GCCTTCAACAACAGCATTATTCCAGAAGCACACTT<br>CTTCCCCAGCCCAGAAAGTTCCTGTGATGTCAAGC<br>TGGTCGAGAAAAGCTTTGAAACAGATACGAACCTA<br>AACTTTCAAAACCTGTCAGTGATTGGGTTCCGAAT<br>CCTCCTCCTGAAAGTGGCCGGGTTTAATCTGCTCA<br>TGACGCTGCGGCTGTGGTCCAGCTGA |
| 32 | Beta Chain (amino acid) | MLLLLLLLGPGSGLGAVVSQHPSWVICKSGTSVKI<br>ECRSLDFQATTMFWYRQFPKQSLMLMATSNEGSKA<br>TYEQGVEKDKFLINHASLTLSTLTVTSAHPEDSSF<br>YICSANPRTTLYEQYFGPGTRLTVTEDLKNVFPPE<br>VAVFEPSEAEISHTQKATLVCLATGFYPDHVELSW<br>WVNGKEVHSGVSTDPQPLKEQPALNDSRYCLSSRL<br>RVSATFWQNPRNHFRCQVQFYGLSENDEWTQDRAK<br>PVTQIVSAEAWGRADCGFTSESYQQGVLSATILYE<br>ILLGKATLYAVLVSALVLMAMVKRKDSRGZ |
| 34 | Beta Chain (nucleotide) | ATGCTGCTGCTTCTGCTGCTTCTGGGGCCAGGCTC<br>CGGGCTTGGTGCTGTCGTCTCTCAACATCCGAGCT<br>GGGTTATCTGTAAGAGTGGAACCTCTGTGAAGATC<br>GAGTGCCGTTCCCTGGACTTTCAGGCCACAACTAT<br>GTTTTGGTATCGTCAGTTCCCGAAACAGAGTCTCA<br>TGCTGATGGCAACTTCCAATGAGGGCTCCAAGGCC<br>ACATACGAGCAAGGCGTCGAGAAGGACAAGTTTCT<br>CATCAACCATGCAAGCCTGACCTTGTCCACTCTGA<br>CAGTGACCAGTGCCCATCCTGAAGACAGCAGCTTC<br>TACATCTGCAGTGCAAACCCCGGACTACCCTCTA<br>CGAGCAGTACTTCGGGCCGGGCACCAGGCTCACGG<br>TCACAGAGGACCTGAAAAACGTGTTCCCACCCGAG<br>GTCGCTGTGTTTGAGCCATCAGAAGCAGAGATCTC<br>CCACACCCAAAAGGCCACACTGGTGTGCCTGGCCA<br>CAGGCTTCTACCCCGACCACGTGGAGCTGAGCTGG<br>TGGGTGAATGGGAAGGAGGTGCACAGTGGGGTCAG<br>CACAGACCCGCAGCCCTCAAGGAGCAGCCCGCCC<br>TCAATGACTCCAGATACTGCCTGAGCAGCCGCCTG<br>AGGGTCTCGGCCACCTTCTGGCAGAACCCCCGCAA<br>CCACTTCCGCTGTCAAGTCCAGTTCTACGGGCTCT<br>CGGAGAATGACGAGTGGACCCAGGATAGGGCCAAA<br>CCTGTCACCCAGATCGTCAGCGCCGAGGCCTGGGG<br>TAGAGCAGACTGTGGCTTCACCTCCGAGTCTTACC<br>AGCAAGGGGTCCTGTCTGCCACCATCCTCTATGAG<br>ATCTTGCTAGGGAAGGCCACCTTGTATGCCGTGCT<br>GGTCAGTGCCCTTGTGCTGATGGCCATGGTCAAGA<br>GAAAGGATTCCAGAGGCTAG |

TABLE 3E

SSX2 Alpha Chain and Beta Chain TCR Sequences

| SEQ ID NO: | TCR Chain | Sequence |
|---|---|---|
| 41 | Alpha Chain (amino acid) | METLLGLLILWLQLQWVSSKQEVTQIPAALSVPEG<br>ENLVLNCSFTDSAIYNLQWFRQDPGKGLTSLLLIQ<br>SSQREQTSGRLNASLDKSSGRSTLYIAASQPGDSA<br>TYLCAVEPMEYGNKLVFGAGTILRVKSYIQNPDPA<br>VYQLRDSKSSDKSVCLFTDFDSQTNVSQSKDSDVY<br>ITDKTVLDMRSMDFKSNSAVAWSNKSDFACANAFN<br>NSIIPEDTFFPSPESSCDVKLVEKSFETDTNLNFQ<br>NLSVIGFRILLLKVAGFNLLMTLRLWSSZ |

TABLE 3E-continued

SSX2 Alpha Chain and Beta Chain TCR Sequences

| SEQ ID NO: | TCR Chain | Sequence |
|---|---|---|
| 43 | Alpha Chain (nucleotide) | ATGGAGACCCTCTTGGGCCTGCTTATCCTTTGGCT<br>GCAGCTGCAATGGGTGAGCAGCAAACAGGAGGTGA<br>CACAGATTCCTGCAGCTCTGAGTGTCCCAGAAGGA<br>GAAAACTTGGTTCTCAACTGCAGTTTCACTGATAG<br>CGCTATTTACAACCTCCAGTGGTTTAGGCAGGACC<br>CTGGGAAAGGTCTCACATCTCTGTTGCTTATTCAG<br>TCAAGTCAGAGAGAGCAAACAAGTGGAAGACTTAA<br>TGCCTCGCTGGATAAATCATCAGGACGTAGTACTT<br>TATACATTGCAGCTTCTCAGCCTGGTGACTCAGCC<br>ACCTACCTCTGTGCTGTGGAACCCATGGAATATGG<br>AAACAAACTGGTCTTTGGCGCAGGAACCATTCTGA<br>GAGTCAAGTCCTATATCCAGAACCCTGACCCTGCC<br>GTGTACCAGCTGAGAGACTCTAAATCCAGTGACAA<br>GTCTGTCTGCCTATTCACCGATTTTGATTCTCAAA<br>CAAATGTGTCACAAAGTAAGGATTCTGATGTGTAT<br>ATCACAGACAAAACTGTGCTAGACATGAGGTCTAT<br>GGACTTCAAGAGCAACAGTGCTGTGGCCTGGAGCA<br>ACAAATCTGACTTTGCATGTGCAAACGCCTTCAAC<br>AACAGCATTATTCCAGAAGACACCTTCTTCCCCAG<br>CCCAGAAAGTTCCTGTGATGTCAAGCTGGTCGAGA<br>AAGCTTTGAAACAGATACGAACCTAAACTTTCAA<br>AACCTGTCAGTGATTGGGTTCCGAATCCTCCTCCT<br>GAAAGTGGCCGGGTTTAATCTGCTCATGACGCTGC<br>GGCTGTGGTCCAGCTGA |
| 42 | Beta Chain (amino acid) | MSNQVLCCVVLCLLGANTVDGGITQSPKYLFRKEG<br>QNVTLSCEQNLNHDAMYWYRQDPGQGLRLIYYSQI<br>VNDFQKGDIAEGYSVSREKKESFPLTVTSAQKNPT<br>AFYLCASSALFSGANVLTFGAGSRLTVLEDLKNVF<br>PPEVAVFEPSEAEISHTQKATLVCLATGFYPDHVE<br>LSWWVNGKEVHSGVSTDPQPLKEQPALNDSRYCLS<br>SRLRVSATFWQNPRNHFRCQVQFYGLSENDEWTQD<br>RAKPVTQIVSAEAWGRADCGFTSESYQQGVLSATI<br>LYEILLGKATLYAVLVSALVLMAMVKRKDSRGZ |
| 44 | Beta Chain (nucleotide) | ATGAGCAACCAGGTGCTCTGCTGTGTGGTCCTTTG<br>TCTCCTGGGAGCAAACACCGTGGATGGTGGAATCA<br>CTCAGTCCCCAAAGTACCTGTTCAGAAAGGAAGGA<br>CAGAATGTGACCCTGAGTTGTGAACAGAATTTGAA<br>CCACGATGCCATGTACTGGTACCGACAGGACCCAG<br>GGCAAGGGCTGAGATTGATCTACTACTCACAGATA<br>GTAAATGACTTTCAGAAAGGAGATATAGCTGAAGG<br>GTACAGCGTCTCTCGGGAAGAAGGAATCCTTTC<br>CTCTCACTGTGACATCGGCCCAAAAGAACCCGACA<br>GCTTTCTATCTCTGTGCCAGTAGTGCGTTATTCTC<br>TGGGGCCAACGTCCTGACTTTCGGGGCCGGCAGCA<br>GGCTGACCGTGCTGGAGGACCTGAAAAACGTGTTC<br>CCACCCGAGGTCGCTGTGTTTGAGCCATCAGAAGC<br>AGAGATCTCCCACACCCAAAAGGCCACACTGGTGT<br>GCCTGGCCACAGGCTTCTACCCCGACCACGTGGAG<br>CTGAGCTGGTGGGTGAATGGGAAGGAGGTGCACAG<br>TGGGGTCAGCACAGACCCGCAGCCCTCAAGGAGC<br>AGCCCGCCCTCAATGACTCCAGATACTGCCTGAGC<br>AGCCGCCTGAGGGTCTCGGCCACCTTCTGGCAGAA<br>CCCCCGCAACCACTTCCGCTGTCAAGTCCAGTTCT<br>ACGGGCTCTCGGAGAATGACGAGTGGACCCAGGAT<br>AGGGCCAAACCTGTCACCCAGATCGTCAGCGCCGA<br>GGCCTGGGGTAGAGCAGACTGTGGCTTCACCTCCG<br>AGTCTTACCAGCAAGGGGTCCTGTCTGCCACCATC<br>CTCTATGAGATCTTGCTAGGGAAGGCCACCTTGTA<br>TGCCGTGCTGGTCAGTGCCCTCGTGCTGATGGCCA<br>TGGTCAAGAGAAAGGATTCCAGAGGCTGA |

II.A.1. Epitope-Specific TCRs

Certain aspects of the present disclosure are directed to an epitope-specific TCR. In some embodiments, the epitope-specific TCR is encoded by a first nucleotide sequence described herein. In some embodiments, the epitope-specific TCR, e.g., encoded by the first nucleotide sequence, specifically binds an epitope of a target human protein selected from the group consisting of tyrosinase, MAGE-A1, MART1, MAGE-A3, and SSX2. In some embodiments, the epitope-specific TCR, e.g., encoded by the first nucleotide sequence, comprises an alpha chain and a beta chain, wherein the alpha chain comprises a variable domain comprising an alpha chain CDR1, an alpha chain CDR2, and an alpha chain CDR3; and wherein the beta chain comprises a variable domain comprising a beta chain CDR1, a beta chain CDR2, and a beta chain CDR3.

II.A.1.a. Anti-Tyrosinase TCRs

In some embodiments, the epitope-specific TCR, e.g., the epitope-specific TCR encoded by the first nucleotide sequence, specifically binds an epitope on human tyrosinase ("anti-tyrosinase TCR"), and the anti-tyrosinase TCR comprises an alpha chain CDR3 comprising an amino acid sequence as set forth in SEQ ID NO: 7 (CLVGDVEG-SQGNLIF). In some embodiments, the anti-tyrosinase TCR comprises a beta chain CDR3 comprising an amino acid sequence as set forth in SEQ ID NO: 10 (CASSHHSGGIY-NEQFF). In some embodiments, the anti-tyrosinase TCR, e.g., encoded by the first nucleotide sequence, comprises an alpha chain CDR1, wherein the alpha chain CDR1 of the anti-tyrosinase TCR comprises an amino acid sequence as set forth in SEQ ID NO: 5 (NIATNDY). In some embodiments, the anti-tyrosinase TCR, e.g., the epitope-specific TCR encoded by the first nucleotide sequence, comprises a beta chain CDR1, wherein the beta chain CDR1 of the anti-tyrosinase TCR comprises an amino acid sequence as set forth in SEQ ID NO: 8 (MNHEY).

In some embodiments, the anti-tyrosinase TCR, e.g., encoded by the first nucleotide sequence, comprises an alpha chain CDR2, wherein the alpha chain CDR2 of the anti-tyrosinase TCR comprises an amino acid sequence as set forth in SEQ ID NO: 6 (GYKTK). In some embodiments, the anti-tyrosinase TCR, e.g., encoded by the first nucleotide sequence, comprises a beta chain CDR2, wherein the beta chain CDR2 of the anti-tyrosinase TCR comprises an amino acid sequence as set forth in SEQ ID NO: 9 (SVGAGI).

In certain embodiments, the anti-tyrosinase TCR, e.g., encoded by the first nucleotide sequence, comprises an alpha chain CDR1 comprising the amino acid sequence set forth in SEQ ID NO: 5; an alpha chain CDR2 comprising the amino acid sequence set forth in SEQ ID NO: 6; an alpha chain CDR3 comprising the amino acid sequence set forth in SEQ ID NO: 7; a beta chain CDR1 comprising the amino acid sequence set forth in SEQ ID NO: 8; a beta chain CDR2 comprising the amino acid sequence set forth in SEQ ID NO: 9; and a beta chain CDR3 comprising the amino acid sequence set forth in SEQ ID NO: 10.

In some embodiments, the non-CDR regions in the alpha chain and/or the beta chain of the epitope-specific TCR, e.g., the anti-tyrosinase TCR, are further modified, e.g., substitution or mutation of one amino acid, two amino acids, three amino acids, four amino acids, five amino acids, or six amino acids, thereby the alpha chain and/or the beta chain are not naturally occurring. In some embodiments, the substitutions or mutations can improve the TCRs described herein in various ways, e.g., binding affinity, binding specificity, stability, viscosity, or any combination thereof.

In some embodiments, the anti-tyrosinase TCR, e.g., encoded by the first nucleotide sequence, comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 1. In some embodiments, the anti-tyrosinase TCR, e.g., encoded by the first nucleotide sequence, comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 1, wherein the anti-tyrosinase TCR comprises an alpha chain CDR3 comprising an amino acid sequence as set forth in SEQ ID NO: 7. In some embodiments, the anti-tyrosinase TCR, e.g., encoded by the first nucleotide sequence, comprises an alpha chain variable domain present in the alpha chain amino acid sequence set forth in SEQ ID NO: 1.

In some embodiments, the anti-tyrosinase TCR, e.g., encoded by the first nucleotide sequence, comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 2. In some embodiments, the anti-tyrosinase TCR, e.g., encoded by the first nucleotide sequence, comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 2, wherein the anti-tyrosinase TCR comprises a beta chain CDR3 comprising an amino acid sequence as set forth in SEQ ID NO: 10. In some embodiments, the anti-tyrosinase TCR, e.g., encoded by the first nucleotide sequence, comprises a beta chain variable domain present in the amino acid sequence set forth in SEQ ID NO: 2.

In some embodiments, the anti-tyrosinase TCR, e.g., encoded by the first nucleotide sequence, further comprises an alpha chain constant region, a beta chain constant region, or both an alpha chain constant region and a beta chain constant region. In some embodiments, the anti-tyrosinase TCR, e.g., encoded by the first nucleotide sequence, comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 1. In some embodiments, the anti-tyrosinase TCR, e.g., encoded by the first nucleotide sequence, comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 1, wherein the anti-tyrosinase TCR comprises an alpha chain CDR3 comprising an amino acid sequence as set forth in SEQ ID NO: 7. In some embodiments, the anti-tyrosinase TCR, e.g., encoded by the first nucleotide sequence, comprises an alpha chain constant region present in the alpha chain amino acid sequence set forth in SEQ ID NO: 1. In some embodiments, the anti-tyrosinase TCR, e.g., encoded by the first nucleotide sequence, further comprises an alpha constant region that is different from endogenous, e.g., naturally occurring, constant regions of the alpha chain. In some embodiments, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 1.

In some embodiments, the anti-tyrosinase TCR, e.g., encoded by the first nucleotide sequence, comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 2. In some embodiments, the anti-tyrosinase TCR, e.g., encoded by the first nucleotide sequence, comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 2, wherein the anti-tyrosinase TCR comprises a beta chain CDR3 comprising an amino acid sequence as set forth in SEQ ID NO: 10. In some embodiments, the anti-tyrosinase TCR, e.g., encoded by the first nucleotide sequence, comprises a beta chain constant region present in the amino acid sequence set forth in SEQ ID NO: 2. In some embodiments, the anti-tyrosinase TCR, e.g., encoded by the first nucleotide sequence, further comprises a beta constant region that is different from endogenous, e.g., naturally occurring, constant regions of the beta chain. In some embodiments, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 2.

In certain embodiments, the anti-tyrosinase TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1. In some embodiments, the anti-tyrosinase TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1, wherein the anti-tyrosinase TCR comprises an alpha chain CDR3 comprising an amino acid sequence as set forth in SEQ ID NO: 7. In some embodiments, the anti-tyrosinase TCR, e.g., encoded by the first nucleotide sequence, comprises an alpha chain comprising the amino acid sequence set forth in SEQ ID NO: 1.

In certain embodiments, the anti-tyrosinase TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2. In some embodiments, the anti-tyrosinase TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2, wherein the anti-tyrosinase TCR comprises a beta chain CDR3 comprising an amino acid sequence as set forth in SEQ ID NO: 10. In some embodiments, the anti-tyrosinase TCR, e.g., encoded by the first nucleotide sequence, comprises a beta chain comprising the amino acid sequence set forth in SEQ ID NO: 2.

In some embodiments, the anti-tyrosinase TCR, e.g., encoded by the first nucleotide sequence, comprises an alpha chain constant region, a beta chain constant region, or both; wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR. In some embodiments, the anti-tyrosinase TCR, e.g., encoded by the first nucleotide sequence, comprises an alpha chain and a beta chain, wherein the alpha chain comprises a constant region, and wherein the beta chain comprises a constant region; wherein (i) the alpha chain constant region comprises an amino acid sequence having at least 1, at least 2, at least 3, at least 4, or at least 5 amino acid substitutions relative to the constant region of an alpha chain comprising the amino acid sequence set forth in SEQ ID NO: 1; and (ii) the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 2.

In some embodiments, the anti-tyrosinase TCR, e.g., encoded by the first nucleotide sequence, cross competes for binding to human tyrosinase with a reference TCR. In some embodiments, the anti-tyrosinase TCR binds the same epitope or an overlapping epitope of human tyrosinase as a reference TCR. In some embodiments, the reference TCR comprises an alpha chain and a beta chain, and the alpha chain of the reference TCR comprises an amino acid sequence as set forth in SEQ ID NO: 1. In some embodiments, the beta chain of the reference TCR comprises an amino acid sequence as set forth in SEQ ID NO: 2.

II.A.1.b. Anti-MAGE-A1 TCRs

In some embodiments, the epitope-specific TCR, e.g., the epitope specific TCR encoded by the first nucleotide sequence, specifically binds an epitope on human MAGE-A1 ("anti-MAGE-A1 TCR"), and the anti-MAGE-A1 TCR comprises an alpha chain CDR3 comprising an amino acid sequence as set forth in SEQ ID NO: 17 (CALSESYS-GAGSYQLTF). In some embodiments, the anti-MAGE-A1 TCR comprises a beta chain CDR3 comprising an amino acid sequence as set forth in SEQ ID NO: 20 (CASSLASG-SNQPQHF).

In some embodiments, the anti-MAGE-A1 TCR, e.g., encoded by the first nucleotide sequence, comprises an alpha chain CDR1, wherein the alpha chain CDR1 of the anti-MAGE-A1 TCR comprises an amino acid sequence as set forth in SEQ ID NO: 15 (TRDTTYYL). In some embodiments, the anti-MAGE-A1 TCR, e.g., encoded by the first nucleotide sequence, comprises a beta chain CDR1, wherein the beta chain CDR1 of the anti-MAGE-A1 TCR comprises an amino acid sequence as set forth in SEQ ID NO: 18 (SEHNR).

In some embodiments, the anti-MAGE-A1 TCR, e.g., encoded by the first nucleotide sequence, comprises an alpha chain CDR2, wherein the alpha chain CDR2 of the anti-MAGE-A1 TCR comprises an amino acid sequence as set forth in SEQ ID NO: 16 (RNSFDEQN). In some embodiments, the anti-MAGE-A1 TCR, e.g., encoded by the first nucleotide sequence, comprises a beta chain CDR2, wherein the beta chain CDR2 of the anti-MAGE-A1 TCR comprises an amino acid sequence as set forth in SEQ ID NO: 19 (FQNEAQ).

In certain embodiments, the anti-MAGE-A1 TCR, e.g., encoded by the first nucleotide sequence, comprises an alpha chain CDR1 comprising the amino acid sequence set forth in SEQ ID NO: 15; an alpha chain CDR2 comprising the amino acid sequence set forth in SEQ ID NO: 16; an alpha chain CDR3 comprising the amino acid sequence set forth in SEQ ID NO: 17; a beta chain CDR1 comprising the amino acid sequence set forth in SEQ ID NO: 18; a beta chain CDR2 comprising the amino acid sequence set forth in SEQ ID NO: 19; and a beta chain CDR3 comprising the amino acid sequence set forth in SEQ ID NO: 20.

In some embodiments, the non-CDR regions in the alpha chain and/or the beta chain of the epitope-specific TCR, e.g., the anti-MAGE-A1 TCR, are further modified, e.g., substitution or mutation of one amino acid, two amino acids, three amino acids, four amino acids, five amino acids, or six amino acids, thereby the alpha chain and/or the beta chain are not naturally occurring. In some embodiments, the substitutions or mutations can improve the TCRs described herein in various ways, e.g., binding affinity, binding specificity, stability, viscosity, or any combination thereof.

In some embodiments, the anti-MAGE-A1 TCR, e.g., encoded by the first nucleotide sequence, comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 11. In some embodiments, the anti-MAGE-A1 TCR, e.g., encoded by the first nucleotide sequence, comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 11, wherein the anti-MAGE-A1 TCR comprises an alpha chain CDR3 comprising an amino acid sequence as set forth in SEQ ID NO: 17. In some embodiments, the anti-MAGE-A1 TCR, e.g., encoded by the first nucleotide sequence, comprises an alpha chain variable domain present in the alpha chain amino acid sequence set forth in SEQ ID NO: 11.

In some embodiments, the anti-MAGE-A1 TCR, e.g., encoded by the first nucleotide sequence, comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 12. In some embodiments, the anti-MAGE-A1 TCR, e.g., encoded by the first nucleotide sequence, comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 12, wherein the anti-MAGE-A1 TCR comprises a beta chain CDR3 comprising an amino acid sequence as set forth in SEQ ID NO: 20. In some embodiments, the anti-MAGE-A1 TCR, e.g., encoded by the first nucleotide sequence, comprises a beta chain variable domain present in the amino acid sequence set forth in SEQ ID NO: 12.

In some embodiments, the anti-MAGE-A1 TCR, e.g, encoded by the first nucleotide sequence, further comprises an alpha chain constant region, a beta chain constant region, or both an alpha chain constant region and a beta chain constant region. In some embodiments, the anti-MAGE-A1 TCR, e.g., encoded by the first nucleotide sequence, comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 11. In some embodiments, the anti-MAGE-A1 TCR, e.g., encoded by the first nucleotide sequence, comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 11, wherein the anti-MAGE-A1 TCR comprises an alpha chain CDR3 comprising an amino acid sequence as set forth in SEQ ID NO: 17. In some embodiments, the anti-MAGE-A1 TCR, e.g., encoded by the first nucleotide sequence, comprises an alpha chain constant region present in the alpha chain amino acid sequence set forth in SEQ ID NO: 11. In some embodiments, the anti-MAGE-A1 TCR, e.g, encoded by the first nucleotide sequence, further comprises an alpha constant region that is different from endogenous, e.g., naturally occurring, constant regions of the alpha chain. In some embodiments, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 11.

In some embodiments, the anti-MAGE-A1 TCR, e.g., encoded by the first nucleotide sequence, comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 12. In some embodiments, the anti-MAGE-A1 TCR, e.g., encoded by the first nucleotide sequence, comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 12, wherein the anti-MAGE-A1 TCR comprises a beta chain CDR3 comprising an amino acid sequence as set forth in SEQ ID NO: 20. In some embodiments, the anti-MAGE-A1 TCR, e.g., encoded by the first nucleotide sequence, comprises a beta chain constant region present in the amino acid sequence set forth in SEQ ID NO: 12. In some embodiments, the anti-MAGE-A1 TCR, e.g, encoded by the first nucleotide sequence, further comprises a beta constant region that is different from endogenous, e.g., naturally occurring, constant regions of the beta chain. In some embodiments, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 12.

In certain embodiments, the anti-MAGE-A1 TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 11. In some embodiments, the anti-MAGE-A1 TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 11, wherein the anti-MAGE-A1 TCR comprises an alpha chain CDR3 comprising an amino acid sequence as set forth in SEQ ID NO: 17. In some embodiments, the anti-MAGE-A1 TCR, e.g., encoded by the first nucleotide sequence, comprises an alpha chain comprising the amino acid sequence set forth in SEQ ID NO: 11.

In certain embodiments, the anti-MAGE-A1 TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 12. In some embodiments, the anti-MAGE-A1 TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 12, wherein the anti-MAGE-A1 TCR comprises a beta chain CDR3 comprising an amino acid sequence as set forth in SEQ ID NO: 10. In some embodiments, the anti-MAGE-A1 TCR, e.g., encoded by the first nucleotide sequence, comprises a beta chain comprising the amino acid sequence set forth in SEQ ID NO: 12.

In some embodiments, the anti-MAGE-A1 TCR, e.g., encoded by the first nucleotide sequence, comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR. In some embodiments, the anti-MAGE-A1 TCR, e.g., encoded by the first nucleotide sequence, comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 11; and (ii) the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 12.

In some embodiments, the anti-MAGE-A1 TCR cross competes for binding to human MAGE-A1 with a reference TCR. In some embodiments, the anti-MAGE-A1 TCR binds the same epitope or an overlapping epitope of human MAGE-A1 as a reference TCR. In some embodiments, the reference TCR comprises an alpha chain and a beta chain, and the alpha chain of the reference TCR comprises an amino acid sequence as set forth in SEQ ID NO: 11. In some embodiments, the beta chain of the reference TCR comprises an amino acid sequence as set forth in SEQ ID NO: 12.

II.A.1.c. Anti-MART1 TCRs

In some embodiments, the epitope-specific TCR, e.g., the epitope specific TCR encoded by the first nucleotide sequence, specifically binds an epitope on human MART1 ("anti-MART1 TCR"), and the anti-MART1 TCR comprises an alpha chain CDR3 comprising an amino acid sequence as set forth in SEQ ID NO: 27 (CAVYGGATNKLIF). In some embodiments, the anti-MART1 TCR comprises a beta chain CDR3 comprising an amino acid sequence as set forth in SEQ ID NO: 30 (CASSPHAGGVDEKLFF).

In some embodiments, the anti-MART1 TCR, e.g., encoded by the first nucleotide sequence, comprises an alpha chain CDR1, wherein the alpha chain CDR1 of the anti-anti-MART1 TCR comprises an amino acid sequence as set forth in SEQ ID NO: 25 (TSGFNG). In some embodiments, the anti-MART1 TCR, e.g., encoded by the first nucleotide sequence, comprises a beta chain CDR1, wherein the beta chain CDR1 of the anti-MART1 TCR comprises an amino acid sequence as set forth in SEQ ID NO: 28 (KGHSH).

In some embodiments, the anti-MART1 TCR, e.g., encoded by the first nucleotide sequence, comprises an alpha chain CDR2, wherein the alpha chain CDR2 of the anti-MART1 TCR comprises an amino acid sequence as set forth in SEQ ID NO: 26 (NVLDGL). In some embodiments, the anti-MART1 TCR, e.g., encoded by the first nucleotide sequence, comprises a beta chain CDR2, wherein the beta chain CDR2 of the anti-MART1 TCR comprises an amino acid sequence as set forth in SEQ ID NO: 29 (LQKENI).

In certain embodiments, the anti-MART1 TCR, e.g., encoded by the first nucleotide sequence, comprises an alpha chain CDR1 comprising the amino acid sequence set forth in SEQ ID NO: 25; an alpha chain CDR2 comprising the amino acid sequence set forth in SEQ ID NO: 26; an alpha chain CDR3 comprising the amino acid sequence set forth in SEQ ID NO: 27; a beta chain CDR1 comprising the amino acid sequence set forth in SEQ ID NO: 28; a beta chain CDR2 comprising the amino acid sequence set forth in SEQ ID NO: 29; and a beta chain CDR3 comprising the amino acid sequence set forth in SEQ ID NO: 30.

In some embodiments, the non-CDR regions in the alpha chain and/or the beta chain of the epitope-specific TCR, e.g., the anti-MART1 TCR, are further modified, e.g., substitution or mutation of one amino acid, two amino acids, three amino acids, four amino acids, five amino acids, or six amino acids, thereby the alpha chain and/or the beta chain are not naturally occurring. In some embodiments, the substitutions or mutations can improve the TCRs described herein in various ways, e.g., binding affinity, binding specificity, stability, viscosity, or any combination thereof.

In some embodiments, the anti-MART1 TCR, e.g., encoded by the first nucleotide sequence, comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 21. In some embodiments, the anti-MART1 TCR, e.g., encoded by the first nucleotide sequence, comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 21, wherein the anti-MART1 TCR comprises an alpha chain CDR3 comprising an amino acid sequence as set forth in SEQ ID NO: 27. In some embodiments, the anti-MART1 TCR, e.g., encoded by the first nucleotide sequence, comprises an alpha chain variable domain present in the alpha chain amino acid sequence set forth in SEQ ID NO: 21.

In some embodiments, the anti-MART1 TCR, e.g., encoded by the first nucleotide sequence, comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 22. In some embodiments, the anti-MART1 TCR, e.g., encoded by the first nucleotide sequence, comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 22, wherein the anti-MART1 TCR comprises a beta chain CDR3 comprising an amino acid sequence as set forth in SEQ ID NO: 30. In some embodiments, the anti-MART1 TCR, e.g., encoded by the first nucleotide sequence, comprises a beta chain variable domain present in the amino acid sequence set forth in SEQ ID NO: 22.

In some embodiments, the anti-MART1 TCR, e.g, encoded by the first nucleotide sequence, further comprises an alpha chain constant region, a beta chain constant region, or both an alpha chain constant region and a beta chain constant region. In some embodiments, the anti-MART1 TCR, e.g., encoded by the first nucleotide sequence, comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 21. In some embodiments, the anti-MART1 TCR, e.g., encoded by the first nucleotide sequence, comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 21, wherein the anti-MART1 TCR comprises an alpha chain CDR3 comprising an amino acid sequence as set forth in SEQ ID NO: 27. In some embodiments, the anti-MART1 TCR, e.g., encoded by the first nucleotide sequence, comprises an alpha chain constant region present in the alpha chain amino acid sequence set forth in SEQ ID NO: 21. In some embodiments, the anti-MART1 TCR, e.g, encoded by the first nucleotide sequence, further comprises an alpha constant region that is different from endogenous, e.g., naturally occurring, constant regions of the alpha chain. In some embodiments, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 21.

In some embodiments, the anti-MAGE-A1 TCR, e.g., encoded by the first nucleotide sequence, comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 22. In some embodiments, the anti-MART1 TCR, e.g., encoded by the first nucleotide sequence, comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 22, wherein the anti-MART1 TCR comprises a beta chain CDR3 comprising an amino acid sequence as set forth in SEQ ID NO: 30. In some embodiments, the anti-MART1 TCR, e.g., encoded by the first nucleotide sequence, comprises a beta chain constant region present in the amino acid sequence set forth in SEQ ID NO: 22. In some embodiments, the anti-MART1 TCR, e.g, encoded by the first nucleotide sequence, further comprises a beta constant region that is different from endogenous, e.g., naturally occurring, constant regions of the beta chain. In some embodiments, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 22.

In certain embodiments, the anti-MART1 TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 21. In some embodiments, the anti-MART1 TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 21, wherein the anti-MART1 TCR comprises an alpha chain CDR3 comprising an amino acid sequence as set forth in SEQ ID NO: 27. In some embodiments, the anti-MART1 TCR, e.g., encoded by the first nucleotide sequence, comprises an alpha chain comprising the amino acid sequence set forth in SEQ ID NO: 21.

In certain embodiments, the anti-MART1 TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 22. In some embodiments, the anti-MART1 TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 22, wherein the anti-MART1 TCR comprises a beta chain CDR3 comprising an amino acid sequence as set forth in SEQ ID NO: 30. In some embodiments, the anti-MART1 TCR, e.g., encoded by the first nucleotide sequence, comprises a beta chain comprising the amino acid sequence set forth in SEQ ID NO: 22.

In some embodiments, the anti-MART1 TCR, e.g., encoded by the first nucleotide sequence, comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR. In some embodiments, the anti-MART1 TCR, e.g., encoded by the first nucleotide sequence, comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 21; and (ii) the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 22.

In some embodiments, the anti-MART1 TCR, e.g., encoded by the first nucleotide sequence, cross competes for binding to human MART1 with a reference TCR. In some embodiments, the anti-MART1 TCR binds the same epitope or an overlapping epitope of human MART1 as a reference TCR. In some embodiments, the reference TCR comprises an alpha chain and a beta chain, and the alpha chain of the reference TCR comprises an amino acid sequence as set forth in SEQ ID NO: 21. In some embodiments, the beta chain of the reference TCR comprises an amino acid sequence as set forth in SEQ ID NO: 22.

II.A.1.d. Anti-MAGE-A3 TCRs

In some embodiments, the epitope-specific TCR, e.g., the epitope specific TCR encoded by the first nucleotide sequence, specifically binds an epitope on human MAGE-A3 ("anti-MAGE-A3 TCR"), and the anti-MAGE-A3 TCR comprises an alpha chain CDR3 comprising an amino acid sequence as set forth in SEQ ID NO: 37 (CALEVRSSAS-KIIF). In some embodiments, the anti-MAGE-A3 TCR comprises a beta chain CDR3 comprising an amino acid sequence as set forth in SEQ ID NO: 40 (CSANPRTTLY-EQYF).

In some embodiments, the anti-MAGE-A3 TCR, e.g., encoded by the first nucleotide sequence, comprises an alpha chain CDR1, wherein the alpha chain CDR1 of the anti-MAGE-A3 TCR comprises an amino acid sequence as set forth in SEQ ID NO: 35 (TRDTTYY). In some embodiments, the anti-MAGE-A3 TCR, e.g., encoded by the first nucleotide sequence, comprises a beta chain CDR1, wherein the beta chain CDR1 of the anti-MAGE-A3 TCR comprises an amino acid sequence as set forth in SEQ ID NO: 38 (DFQATT).

In some embodiments, the anti-MAGE-A3 TCR, e.g., encoded by the first nucleotide sequence, comprises an alpha chain CDR2, wherein the alpha chain CDR2 of the anti-MAGE-A3 TCR comprises an amino acid sequence as set forth in SEQ ID NO: 36 (RNSFDEQN). In some embodiments, the anti-MAGE-A3 TCR, e.g., encoded by the first nucleotide sequence, comprises a beta chain CDR2, wherein the beta chain CDR2 of the anti-MAGE-A3 TCR comprises an amino acid sequence as set forth in SEQ ID NO: 39 (SNEGSKA).

In certain embodiments, the anti-MAGE-A3 TCR, e.g., encoded by the first nucleotide sequence, comprises an alpha chain CDR1 comprising the amino acid sequence set forth in SEQ ID NO: 35; an alpha chain CDR2 comprising the amino acid sequence set forth in SEQ ID NO: 36; an alpha chain CDR3 comprising the amino acid sequence set forth in SEQ ID NO: 37; a beta chain CDR1 comprising the amino acid sequence set forth in SEQ ID NO: 38; a beta chain CDR2 comprising the amino acid sequence set forth in SEQ ID NO: 39; and a beta chain CDR3 comprising the amino acid sequence set forth in SEQ ID NO: 40

In some embodiments, the non-CDR regions in the alpha chain and/or the beta chain of the epitope-specific TCR, e.g., the anti-MAGE-A3 TCR, are further modified, e.g., substitution or mutation of one amino acid, two amino acids, three amino acids, four amino acids, five amino acids, or six amino acids, thereby the alpha chain and/or the beta chain are not naturally occurring. In some embodiments, the substitutions or mutations can improve the TCRs described herein in various ways, e.g., binding affinity, binding specificity, stability, viscosity, or any combination thereof.

In some embodiments, the anti-MAGE-A3 TCR, e.g., encoded by the first nucleotide sequence, comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 31. In some embodiments, the anti-MAGE-A3 TCR, e.g., encoded by the first nucleotide sequence, comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 31, wherein the anti-MAGE-A3 TCR comprises an alpha chain CDR3 comprising an amino acid sequence as set forth in SEQ ID NO: 37. In some embodiments, the anti-MAGE-A3 TCR, e.g., encoded by the first nucleotide sequence, comprises an alpha chain variable domain present in the alpha chain amino acid sequence set forth in SEQ ID NO: 31.

In some embodiments, the anti-MAGE-A3 TCR, e.g., encoded by the first nucleotide sequence, comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 32. In some embodiments, the anti-MAGE-A3 TCR, e.g., encoded by the first nucleotide sequence, comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 32, wherein the anti-MAGE-A3 TCR comprises a beta chain CDR3 comprising an amino acid sequence as set forth in SEQ ID NO: 40. In some embodiments, the anti-MAGE-A3 TCR, e.g., encoded by the first nucleotide sequence, comprises a beta chain variable domain present in the amino acid sequence set forth in SEQ ID NO: 32.

In some embodiments, the anti-MAGE-A3 TCR, e.g, encoded by the first nucleotide sequence, further comprises an alpha chain constant region, a beta chain constant region, or both an alpha chain constant region and a beta chain constant region. In some embodiments, the anti-MAGE-A3 TCR, e.g., encoded by the first nucleotide sequence, comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 31. In some embodiments, the anti-MAGE-A3 TCR, e.g., encoded by the first nucleotide sequence, comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 31, wherein the anti-MAGE-A3 TCR comprises an alpha chain CDR3 comprising an amino acid sequence as set forth in SEQ ID NO: 37. In some embodiments, the anti-MAGE-A3 TCR, e.g., encoded by the first nucleotide sequence, comprises an alpha chain constant region present in the alpha chain amino acid sequence set forth in SEQ ID NO: 31. In some embodiments, the anti-MAGE-A3 TCR, e.g., encoded by the first nucleotide sequence, further comprises an alpha constant region that is different from endogenous, e.g., naturally occurring, constant regions of the alpha chain. In some embodiments, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 31.

In some embodiments, the anti-MAGE-A3 TCR, e.g., encoded by the first nucleotide sequence, comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 32. In some embodiments, the anti-MAGE-A3 TCR, e.g., encoded by the first nucleotide sequence, comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 32, wherein the anti-MAGE-A3 TCR comprises a beta chain CDR3 comprising an amino acid sequence as set forth in SEQ ID NO: 40. In some embodiments, the anti-MAGE-A3 TCR, e.g., encoded by the first nucleotide sequence, comprises a beta chain constant region present in the amino acid sequence set forth in SEQ ID NO: 32. In some embodiments, the anti-MAGE-A3 TCR, e.g, encoded by the first nucleotide sequence, further comprises a beta constant region that is different from endogenous, e.g., naturally occurring, constant regions of the beta chain. In some embodiments, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 32.

In certain embodiments, the anti-MAGE-A3 TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 31. In some embodiments, the anti-MAGE-A3 TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 31, wherein the anti-MAGE-A3 TCR comprises an alpha chain CDR3 comprising an amino acid sequence as set forth in SEQ ID NO: 37. In some embodiments, the anti-MAGE-A3 TCR, e.g., encoded by the first nucleotide sequence, comprises an alpha chain comprising the amino acid sequence set forth in SEQ ID NO: 31.

In certain embodiments, the anti-MAGE-A3 TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 32. In some embodiments, the anti-MAGE-A3 TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 32, wherein the anti-MAGE-A3 TCR comprises a beta chain CDR3 comprising an amino acid sequence as set forth in SEQ ID NO: 40. In some embodiments, the anti-MAGE-A3 TCR, e.g., encoded by the first nucleotide sequence, comprises a beta chain comprising the amino acid sequence set forth in SEQ ID NO: 32.

In some embodiments, the anti-MAGE-A3 TCR, e.g., encoded by the first nucleotide sequence, comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

In some embodiments, the anti-MAGE-A3 TCR, e.g., encoded by the first nucleotide sequence, comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 31; and (ii) the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 32.

In some embodiments, the anti-MAGE-A3 TCR, e.g., encoded by the first nucleotide sequence, cross competes for binding to human MAGE-A3 with a reference TCR. In some embodiments, the anti-MAGE-A3 TCR binds the same epitope or an overlapping epitope of human MAGE-A3 as a reference TCR. In some embodiments, the reference TCR comprises an alpha chain and a beta chain, and the alpha chain of the reference TCR comprises an amino acid sequence as set forth in SEQ ID NO: 31. In some embodiments, the beta chain of the reference TCR comprises an amino acid sequence as set forth in SEQ ID NO: 32.

II.A.1.e. Anti-SSX2 TCRs

In some embodiments, the epitope-specific TCR, e.g., the epitope specific TCR encoded by the first nucleotide sequence, specifically binds an epitope on human SSX2 ("anti-SSX2 TCR"), and the anti-SSX2 TCR comprises an alpha chain CDR3 comprising an amino acid sequence as set forth in SEQ ID NO: 47 (CAVEPMEYGNKLVF). In some embodiments, the anti-SSX2 TCR comprises a beta chain CDR3 comprising an amino acid sequence as set forth in SEQ ID NO: 50 (CASSALFSGANVLTF).

In some embodiments, the anti-SSX2 TCR, e.g., encoded by the first nucleotide sequence, comprises an alpha chain CDR1, wherein the alpha chain CDR1 of the anti-SSX2 TCR comprises an amino acid sequence as set forth in SEQ ID NO: 45 (DSAIYN). In some embodiments, the anti-SSX2 TCR, e.g., encoded by the first nucleotide sequence, comprises a beta chain CDR1, wherein the beta chain CDR1 of the anti-SSX2 TCR comprises an amino acid sequence as set forth in SEQ ID NO: 48 (LNHDA).

In some embodiments, the anti-SSX2 TCR, e.g., encoded by the first nucleotide sequence, comprises an alpha chain CDR2, wherein the alpha chain CDR2 of the anti-SSX2

TCR comprises an amino acid sequence as set forth in SEQ ID NO: 46 (IQSSQRE). In some embodiments, the anti-SSX2 TCR, e.g., encoded by the first nucleotide sequence, comprises a beta chain CDR2, wherein the beta chain CDR2 of the anti-SSX2 TCR comprises an amino acid sequence as set forth in SEQ ID NO: 49 (SQIVND).

In certain embodiments, the anti-SSX2 TCR, e.g., encoded by the first nucleotide sequence, comprises an alpha chain CDR1 comprising the amino acid sequence set forth in SEQ ID NO: 45; an alpha chain CDR2 comprising the amino acid sequence set forth in SEQ ID NO: 46; an alpha chain CDR3 comprising the amino acid sequence set forth in SEQ ID NO: 47; a beta chain CDR1 comprising the amino acid sequence set forth in SEQ ID NO: 48; a beta chain CDR2 comprising the amino acid sequence set forth in SEQ ID NO: 49; and a beta chain CDR3 comprising the amino acid sequence set forth in SEQ ID NO: 50.

In some embodiments, the non-CDR regions in the alpha chain and/or the beta chain of the epitope-specific TCR, e.g., the anti-SSX2 TCR, are further modified, e.g., substitution or mutation of one amino acid, two amino acids, three amino acids, four amino acids, five amino acids, or six amino acids, thereby the alpha chain and/or the beta chain are not naturally occurring. In some embodiments, the substitutions or mutations can improve the TCRs described herein in various ways, e.g., binding affinity, binding specificity, stability, viscosity, or any combination thereof.

In some embodiments, the anti-SSX2 TCR, e.g., encoded by the first nucleotide sequence, comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 41. In some embodiments, the anti-SSX2 TCR, e.g., encoded by the first nucleotide sequence, comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 41, wherein the anti-SSX2 TCR comprises an alpha chain CDR3 comprising an amino acid sequence as set forth in SEQ ID NO: 47. In some embodiments, the anti-SSX2 TCR, e.g., encoded by the first nucleotide sequence, comprises an alpha chain variable domain present in the alpha chain amino acid sequence set forth in SEQ ID NO: 41.

In some embodiments, the anti-SSX2 TCR, e.g., encoded by the first nucleotide sequence, comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 42. In some embodiments, the anti-SSX2 TCR, e.g., encoded by the first nucleotide sequence, comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 42, wherein the anti-SSX2 TCR comprises a beta chain CDR3 comprising an amino acid sequence as set forth in SEQ ID NO: 50. In some embodiments, the anti-SSX2 TCR, e.g., encoded by the first nucleotide sequence, comprises a beta chain variable domain present in the amino acid sequence set forth in SEQ ID NO: 42.

In some embodiments, the anti-SSX2 TCR, e.g, encoded by the first nucleotide sequence, further comprises an alpha chain constant region, a beta chain constant region, or both an alpha chain constant region and a beta chain constant region. In some embodiments, the anti-SSX2 TCR, e.g., encoded by the first nucleotide sequence, comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 41. In some embodiments, the anti-SSX2 TCR, e.g., encoded by the first nucleotide sequence, comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 41, wherein the anti-SSX2 TCR comprises an alpha chain CDR3 comprising an amino acid sequence as set forth in SEQ ID NO: 7. In some embodiments, the anti-SSX2 TCR, e.g., encoded by the first nucleotide sequence, comprises an alpha chain constant region present in the alpha chain amino acid sequence set forth in SEQ ID NO: 41. In some embodiments, the anti-SSX2 TCR, e.g, encoded by the first nucleotide sequence, further comprises an alpha constant region that is different from endogenous, e.g., naturally occurring, constant regions of the alpha chain. In some embodiments, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 41.

In some embodiments, the anti-SSX2 TCR, e.g., encoded by the first nucleotide sequence, comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 42. In some embodiments, the anti-SSX2 TCR, e.g., encoded by the first nucleotide sequence, comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 42, wherein the anti-SSX2 TCR comprises a beta chain CDR3 comprising an amino acid sequence as set forth in SEQ ID NO: 50. In some embodiments, the anti-SSX2 TCR, e.g., encoded by the first nucleotide sequence, comprises a beta chain constant region present in the amino acid sequence set forth in SEQ ID NO: 42. In some embodiments, the anti-SSX2 TCR, e.g, encoded by the first nucleotide sequence, further comprises a beta constant region that is different from endogenous, e.g., naturally occurring, constant regions of the beta chain. In some embodiments, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 42.

In certain embodiments, the anti-SSX2 TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 41. In some embodiments, the anti-SSX2 TCR, e.g., encoded by the first nucleotide sequence, comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 41, wherein the anti-SSX2 TCR comprises an alpha chain CDR3 comprising an amino acid sequence as set forth in SEQ ID NO: 47. In some embodiments, the anti-SSX2 TCR, e.g., encoded by the first nucleotide sequence, comprises an alpha chain comprising the amino acid sequence set forth in SEQ ID NO: 41.

In certain embodiments, the anti-SSX2 TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 42. In some embodiments, the anti-SSX2 TCR, e.g., encoded by the first nucleotide sequence, comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 42, wherein the anti-SSX2 TCR comprises a beta chain CDR3 comprising an amino acid sequence as set forth in SEQ ID NO: 50. In some embodiments, the anti-SSX2 TCR, e.g., encoded by the first nucleotide sequence, comprises a beta chain comprising the amino acid sequence set forth in SEQ ID NO: 42.

In some embodiments, the anti-SSX2 TCR, e.g., encoded by the first nucleotide sequence, comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR. In some embodiments, the anti-SSX2 TCR, e.g., encoded by the first nucleotide sequence, comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 41; and (ii) the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 42.

In some embodiments, the anti-SSX2 TCR, e.g., encoded by the first nucleotide sequence, cross competes for binding to human SSX2 with a reference TCR. In some embodiments, the anti-SSX2 TCR binds the same epitope or an overlapping epitope of human SSX2 as a reference TCR. In some embodiments, the reference TCR comprises an alpha chain and a beta chain, and the alpha chain of the reference TCR comprises an amino acid sequence as set forth in SEQ ID NO: 41. In some embodiments, the beta chain of the reference TCR comprises an amino acid sequence as set forth in SEQ ID NO: 42.

II.A.2 The Second Nucleotide Sequence

The second nucleotide sequence of the nucleic acid molecule disclosed herein can be any sequence or can encode for any polypeptide that is capable of inhibiting the expression of an endogenous TCR. In some embodiments, the second nucleotide sequence is one or more siRNAs. In some embodiments, the one or more siRNAs are complementary to a target sequence within a nucleotide sequence encoding a constant region of an endogenous TCR. In certain embodiments, the one or more siRNAs are complementary to a target sequence within a nucleotide sequence encoding a constant region of wild-type, human TCR. In some embodiments, the one or more siRNAs are complementary to a target sequence within a nucleotide sequence encoding a constant region of the alpha chain of wild-type TCR. In some embodiments, the one or more siRNAs are complementary to a target sequence within a nucleotide sequence encoding a constant region of the beta chain of wild-type TCR. In some embodiments, the one or more siRNAs comprise (i) one or more siRNA's that are complementary to a target sequence within a nucleotide sequence encoding a constant region of the alpha chain of wild-type TCR and (ii) one or more siRNA's that are complementary to a target sequence within a nucleotide sequence encoding a constant region of the beta chain of wild-type TCR.

In some embodiments, the one or more siRNAs comprise a nucleotide sequence selected from the group consisting of SEQ ID NOs: 57-60 (Table 4). In some embodiments, the second nucleotide sequence of the nucleic acid molecule encodes one or more siRNAs, wherein the one or more siRNAs are complementary to a target sequence within a nucleotide sequence encoding a constant region of the alpha chain of wild-type TCR, and wherein the one or more siRNAs comprise the nucleic acid sequences set forth in SEQ ID NOs: 57 and 58.

TABLE 4

| siRNA Sequences | | |
| --- | --- | --- |
| SEQ ID NO: | siRNA | Sequence (Nucleotides 1-19 are ribonucleotides; nucleotides 20-21 are deoxy-ribonucleotides) |
| 57 | siRNA-TCRa-1 | GUAAGGAUUCUGAUGUGUAUU |
| 58 | siRNA-TCRa-2 | UACACAUCAGAAUCCUUACUU |
| 59 | siRNA-TCRb-1 | CCACCAUCCUCUAUGAGAUUU |
| 60 | siRNA-TCRb-2 | AUCUCAUAGAGGAUGGUGGUU |

In some embodiments, the second nucleotide sequence of the nucleic acid molecule encodes one or more siRNAs, wherein the one or more siRNAs are complementary to a target sequence within a nucleotide sequence encoding a constant region of the beta chain of wild-type TCR, and wherein the one or more siRNAs comprise the nucleic acid sequences set forth in SEQ ID NOs: 59 and 60. In some embodiments, the second nucleotide sequence of the nucleic acid molecule encodes one or more siRNAs, wherein the one or more siRNAs comprise (i) one or more siRNAs that are complementary to a target sequence within a nucleotide sequence encoding a constant region of the alpha chain of wild-type TCR, wherein the one or more siRNAs comprise the nucleic acid sequences set forth in SEQ ID NOs: 57 and 58; and (ii) one or more siRNAs that are complementary to a target sequence within a nucleotide sequence encoding a constant region of the beta chain of wild-type TCR, wherein the one or more siRNAs comprise the nucleic acid sequences set forth in SEQ ID NOs: 59 and 60.

In some embodiments, the second nucleotide sequence of the nucleic acid molecule comprises SEQ ID NOs: 57-60. In some embodiments, the second nucleotide sequence comprises SEQ ID NOs: 57-60, wherein one or more of SEQ ID NOs: 57-60 is separated by one or more nucleic acids that do not encode an siRNA. In certain embodiments, the one or more siRNAs are selected from the siRNAs disclosed in U.S. Publication No. 2010/0273213 A1, which is incorporated by reference herein in its entirety.

In some embodiments, the second nucleotide sequence of the nucleic acid molecule encodes a protein, wherein the protein is capable of inhibiting the expression of an endogenous, e.g., wild-type, TCR. In some embodiments, the second nucleotide sequence encodes Cas9.

II.A.3 Vectors

Certain aspects of the present disclosure are directed to vectors comprising a nucleic acid molecule disclosed herein. In some embodiments, the vector is a viral vector. In some embodiments, the vector is a viral particle or a virus. In some embodiments, the vector is a mammalian vector. In some embodiments, the vector is a bacterial vector.

In certain embodiments, the vector is a retroviral vector. In some embodiments, the vector is selected from the group consisting of an adenoviral vector, a lentivirus, a Sendai virus, a baculoviral vector, an Epstein Barr viral vector, a papovaviral vector, a vaccinia viral vector, a herpes simplex viral vector, and an adeno associated virus (AAV) vector. In particular embodiments, the vector is an AAV vector. In some embodiments, the vector is a lentivirus. In particular embodiments, the vector is an AAV vector. In some embodiments, the vector is a Sendai virus. In some embodiments, the vector is a hybrid vector. Examples of hybrid vectors that can be used in the present disclosure can be found in Huang and Kamihira, Biotechnol. Adv. 31(2):208-23 (2103), which is incorporated by reference herein in its entirety.

II.B. Recombinant T Cell Receptors (TCRs)

Certain aspects of the present disclosure are directed to recombinant T cell receptors (TCRs) or an antigen binding portion thereof that specifically bind a target human protein selected from the group consisting of tyrosinase, MAGE-A1, MART1, MAGE-A3, and SSX2. In some embodiments, the antigen-specific TCR is encoded by a nucleic acid molecule disclosed herein.

The epitope-specific TCR can be selected from (i) any epitope-specific TCR disclosed herein, e.g., a TCR disclosed in sections IIA.1.a. to II.A.1.e., above, and (ii) any TCR that cross-competes for binding to the target human protein with a reference antibody, wherein the reference antibody is selected from any epitope-specific TCR disclosed herein, e.g., a TCR disclosed in sections IIA.1.a. to II.A.1.e., above.

In certain embodiments, the epitope-specific TCR is an anti-tyrosinase TCR disclosed herein. In certain embodiments, the anti-tyrosinase TCR comprises an alpha chain CDR1 comprising the amino acid sequence set forth in SEQ ID NO: 5; an alpha chain CDR2 comprising the amino acid sequence set forth in SEQ ID NO: 6; an alpha chain CDR3 comprising the amino acid sequence set forth in SEQ ID NO: 7; a beta chain CDR1 comprising the amino acid sequence set forth in SEQ ID NO: 8; a beta chain CDR2 comprising the amino acid sequence set forth in SEQ ID NO: 9; and a beta chain CDR3 comprising the amino acid sequence set forth in SEQ ID NO: 10.

In certain embodiments, the epitope-specific TCR is an anti-MAGE-A1 TCR disclosed herein. In certain embodiments, the anti-MAGE-A1 TCR comprises an alpha chain CDR1 comprising the amino acid sequence set forth in SEQ ID NO: 15; an alpha chain CDR2 comprising the amino acid sequence set forth in SEQ ID NO: 16; an alpha chain CDR3 comprising the amino acid sequence set forth in SEQ ID NO: 17; a beta chain CDR1 comprising the amino acid sequence set forth in SEQ ID NO: 18; a beta chain CDR2 comprising the amino acid sequence set forth in SEQ ID NO: 19; and a beta chain CDR3 comprising the amino acid sequence set forth in SEQ ID NO: 20.

In certain embodiments, the epitope-specific TCR is an anti-MART1 TCR disclosed herein. In certain embodiments, the anti-MART1 TCR comprises an alpha chain CDR1 comprising the amino acid sequence set forth in SEQ ID NO: 25; an alpha chain CDR2 comprising the amino acid sequence set forth in SEQ ID NO: 26; an alpha chain CDR3 comprising the amino acid sequence set forth in SEQ ID NO: 27; a beta chain CDR1 comprising the amino acid sequence set forth in SEQ ID NO: 28; a beta chain CDR2 comprising the amino acid sequence set forth in SEQ ID NO: 29; and a beta chain CDR3 comprising the amino acid sequence set forth in SEQ ID NO: 30.

In certain embodiments, the epitope-specific TCR is an anti-MAGE-A3 TCR disclosed herein. In certain embodiments, the anti-MAGE-A3 TCR comprises an alpha chain CDR1 comprising the amino acid sequence set forth in SEQ ID NO: 35; an alpha chain CDR2 comprising the amino acid sequence set forth in SEQ ID NO: 36; an alpha chain CDR3 comprising the amino acid sequence set forth in SEQ ID NO: 37; a beta chain CDR1 comprising the amino acid sequence set forth in SEQ ID NO: 38; a beta chain CDR2 comprising the amino acid sequence set forth in SEQ ID NO: 39; and a beta chain CDR3 comprising the amino acid sequence set forth in SEQ ID NO: 40.

In certain embodiments, the epitope-specific TCR is an anti-SSX2 TCR disclosed herein. In certain embodiments, the anti-SSX2 TCR comprises an alpha chain CDR1 comprising the amino acid sequence set forth in SEQ ID NO: 45; an alpha chain CDR2 comprising the amino acid sequence set forth in SEQ ID NO: 46; an alpha chain CDR3 comprising the amino acid sequence set forth in SEQ ID NO: 47; a beta chain CDR1 comprising the amino acid sequence set forth in SEQ ID NO: 48; a beta chain CDR2 comprising the amino acid sequence set forth in SEQ ID NO: 49; and a beta chain CDR3 comprising the amino acid sequence set forth in SEQ ID NO: 50.

II.B.3. Bispecific T Cell Receptors (TCRs)

Certain aspects of the present disclosure are directed to a bispecific TCR comprising a first antigen-binding domain and a second antigen-binding domain, wherein the first antigen-binding domain comprises a TCR or an antigen-binding portion thereof disclosed herein. In some embodiments, the bispecific TCR comprises a first antigen-binding domain and a second antigen-binding domain, wherein the first antigen binding domain comprises an anti-tyrosinase TCR disclosed herein or an antigen-binding portion thereof. In some embodiments, the bispecific TCR comprises a first antigen-binding domain and a second antigen-binding domain, wherein the first antigen binding domain comprises an anti-MAGE-A1 TCR disclosed herein or an antigen-binding portion thereof. In some embodiments, the bispecific TCR comprises a first antigen-binding domain and a second antigen-binding domain, wherein the first antigen binding domain comprises an anti-MART1 TCR disclosed herein or an antigen-binding portion thereof. In some embodiments, the bispecific TCR comprises a first antigen-binding domain and a second antigen-binding domain, wherein the first antigen binding domain comprises an anti-MAGE-A3 TCR disclosed herein or an antigen-binding portion thereof. In some embodiments, the bispecific TCR comprises a first antigen-binding domain and a second antigen-binding domain, wherein the first antigen binding domain comprises an anti-SSX2 TCR disclosed herein or an antigen-binding portion thereof. In some embodiments, the first antigen-binding domain comprises a single chain variable fragment ("scFv").

In some embodiments, the second antigen-binding domain binds specifically to a protein expressed on the surface of a T cell. Any protein expressed on the surface of a T cell can be targeted by the bispecific antibody disclosed herein. In certain embodiments, the protein expressed on the surface of a T cell is not expressed by other cells. In some embodiments, the protein expressed on the surface of a T cell is expressed on the surface of one or more other human immune cells. In some embodiments, the protein expressed on the surface of a T cell is expressed on the surface of one or more other human immune cells, but it is not expressed on the surface of a human non-immune cell. In some embodiments, the second antigen-binding domain binds specifically to a protein expressed on the surface of a T cell selected from CD3, CD2, CD5, CD6, CD8, CD11a (LFA-1α), CD43, CD45, and CD53. In certain embodiments, the second antigen-binding domain binds specifically to CD3. In some embodiments, the second antigen-binding domain comprises an scFv.

In some embodiments, the first antigen-binding domain and the second antigen-binding domain are linked or associated by a covalent bond. In some embodiments, the first antigen-binding domain and the second antigen-binding domain are linked by a peptide bond.

II.C. Epitopes

In some embodiments, the antigen-specific TCR binds the same epitope as a reference TCR. In some embodiments, the antigen-specific TCR specifically binds to human tyrosinase ("anti-tyrosinase TCR"), wherein the anti-tyrosinase TCR binds to an epitope of tyrosinase comprising the amino acid sequence set forth in SEQ ID NO: 51 (FQDYIKSYL). In some embodiments, the anti-tyrosinase TCR binds to an epitope of tyrosinase consisting of an amino acid sequence as set forth in SEQ ID NO: 51. In some embodiments, the epitope comprises amino acid residues 460-468 of tyrosinase (SEQ ID NO: 89), e.g., "tyrosinase$_{460-468}$." In some embodiments, the epitope consists of amino acid residues 460-468 of tyrosinase (SEQ ID NO: 89), e.g., "tyrosinase$_{460-468}$."

In some embodiments, the antigen-specific TCR specifically binds to human MAGE-A1 ("anti-MAGE-A1 TCR"), wherein the anti-MAGE-A1 TCR binds to an epitope of MAGE-A1 comprising the amino acid sequence set forth in SEQ ID NO: 52 (RVRFFFPSL). In some embodiments, the anti-MAGE-A1 TCR binds to an epitope of MAGE-A1 consisting of an amino acid sequence as set forth in SEQ ID NO: 52. In some embodiments, the epitope comprises amino acid residues 289-297 of MAGE-A1 (SEQ ID NO: 90), e.g., "MAGE-A1$_{289-297}$." In some embodiments, the epitope consists of amino acid residues 289-297 of MAGE-A1 (SEQ ID NO: 90), e.g., "MAGE-A1$_{289-297}$."

In some embodiments, the antigen-specific TCR specifically binds to human MART1 ("anti-MART1 TCR"), wherein the anti-MART1 TCR binds to an epitope of MART1 comprising the amino acid sequence set forth in SEQ ID NO: 53 (EEAAGIGIL). In some embodiments, the anti-MART1 TCR binds to an epitope of MART1 consisting of an amino acid sequence as set forth in SEQ ID NO: 53.

In some embodiments, the epitope comprises amino acid residues 25-33 of MART1 (SEQ ID NO: 91), e.g., "MART1$_{25-33}$." In some embodiments, the epitope consists of amino acid residues 25-33 of MART1 (SEQ ID NO: 91), e.g., "MART1$_{25-33}$."

In some embodiments, the antigen-specific TCR specifically binds to human MAGE-A3 ("anti-MAGE-A3 TCR"), wherein the anti-MAGE-A3 TCR binds to an epitope of MAGE-A3 comprising the amino acid sequence set forth in SEQ ID NO: 54 (MEVDPIGHLY). In some embodiments, the anti-MAGE-A3 TCR binds to an epitope of MAGE-A3 consisting of an amino acid sequence as set forth in SEQ ID NO: 54. In some embodiments, the epitope comprises amino acid residues 167-176 of MAGE-A3 (SEQ ID NO: 92), e.g., "MAGE-A3$_{167-176}$." In some embodiments, the epitope consists of amino acid residues 167-176 of MAGE-A3 (SEQ ID NO: 92), e.g., "MAGE-A3$_{167-176}$."

In some embodiments, the antigen-specific TCR specifically binds to human SSX2 ("anti-SSX2 TCR"), wherein the anti-SSX2 TCR binds to an epitope of SSX2 comprising the amino acid sequence set forth in SEQ ID NO: 55 (KASEKIFYV). In some embodiments, the anti-SSX2 TCR binds to an epitope of SSX2 consisting of an amino acid sequence as set forth in SEQ ID NO: 55. In some embodiments, the epitope comprises amino acid residues 41-49 of SSX2 (SEQ ID NO: 93), e.g., "SSX2$_{41-49}$." In some embodiments, the epitope consists of amino acid residues 41-49 of SSX2 (SEQ ID NO: 93), e.g., "SSX2$_{41-49}$."

II.D. HLA Class I Molecules

Certain aspects of the present disclosure are directed to a complex comprising an HLA class I molecule and an epitope disclosed herein. The HLA class I molecule can be any HLA class I molecule known in the art. In some embodiments, the HLA class I molecule is selected from an HLA-A, HLA-B, and HLA-C allele. In some embodiments, the HLA class I molecule is selected from an HLA-E, HLA-F, and HLA-G allele. In certain embodiments, the HLA class I molecule is an HLA-A allele. In certain embodiments, the HLA class I molecule is an HLA-B allele. In certain embodiments, the HLA class I molecule is an HLA-C allele.

Many HLA-A, HLA-B, and HLA-C alleles are known in the art, and any of the known alleles can be used in the present disclosure. An updated list of HLA alleles is available at hla.alleles.org/(last visited on Feb. 27, 2019).

II.D.1. HLA-A Alleles and Complexes Thereof

Certain aspects of the present disclosure are directed to a complex comprising an HLA class I molecule and an epitope, wherein the HLA class I molecule is an HLA-A allele, and wherein the epitope is an SSX2 epitope disclosed herein. In certain embodiments, the SSX2 epitope comprises, consists of, or consists essentially of SEQ ID NO: 55.

In some embodiments, the HLA-A allele is selected from an HLA-A*01, an HLA-A*02, an HLA-A*03, an HLA-A*11, an HLA-A*23, an HLA-A*24, an HLA-A*25, an HLA-A*26, an HLA-A*29, an HLA-A*30, an HLA-A*31, an HLA-A*32, an HLA-A*33, an HLA-A*34, an HLA-A*36, an HLA-A*43, an HLA-A*66, an HLA-A*68, an HLA-A*69, an HLA-A*74, and an HLA-A*80. In certain embodiments, the HLA-A allele is an HLA-A*02 allele.

In certain embodiments, the complex comprises an HLA-A*02 allele and an SSX2 epitope disclosed herein, e.g., an epitope compromising, consisting of, or consisting essentially of SEQ ID NO: 55. In certain embodiments, the HLA-A allele is an HLA-A*02:01 allele. In particular embodiments, the complex comprises an HLA-A*02:01 allele and an SSX2 epitope compromising, consisting of, or consisting essentially of SEQ ID NO: 55.

In certain embodiments, the HLA-A allele is selected from the group consisting of HLA-A*02:01:01:01, HLA-A*02:01:01:02L, HLA-A*02:01:01:03, HLA-A*02:01:01:04, HLA-A*02:01:01:05, HLA-A*02:01:01:06, HLA-A*02:01:01:07, HLA-A*02:01:01:08, HLA-A*02:01:01:09, HLA-A*02:01:01:10, HLA-A*02:01:01:11, HLA-A*02:01:01:12, HLA-A*02:01:01:13, HLA-A*02:01:01:14, HLA-A*02:01:01:15, HLA-A*02:01:01:16, HLA-A*02:01:01:17, HLA-A*02:01:01:18, HLA-A*02:01:01:19, HLA-A*02:01:01:20, HLA-A*02:01:01:21, HLA-A*02:01:01:22, HLA-A*02:01:01:23, HLA-A*02:01:01:24, HLA-A*02:01:01:25, HLA-A*02:01:01:26, HLA-A*02:01:01:27, HLA-A*02:01:01:28, HLA-A*02:01:01:29, HLA-A*02:01:01:30, HLA-A*02:01:01:31, HLA-A*02:01:01:32, HLA-A*02:01:01:33, HLA-A*02:01:01:34, HLA-A*02:01:01:35, HLA-A*02:01:01:36, HLA-A*02:01:01:37, HLA-A*02:01:01:38, HLA-A*02:01:01:39, HLA-A*02:01:01:40, HLA-A*02:01:01:41, HLA-A*02:01:01:42, HLA-A*02:01:01:43, HLA-A*02:01:01:44, HLA-A*02:01:01:45, HLA-A*02:01:01:46, HLA-A*02:01:01:47, HLA-A*02:01:01:48, HLA-A*02:01:01:49, HLA-A*02:01:01:50, HLA-A*02:01:01:51, HLA-A*02:01:01:52, HLA-A*02:01:01:53, HLA-A*02:01:01:54, HLA-A*02:01:01:55, HLA-A*02:01:02, HLA-A*02:01:03, HLA-A*02:01:04, HLA-A*02:01:05, HLA-A*02:01:06, HLA-A*02:01:07, HLA-A*02:01:08, HLA-A*02:01:09, HLA-A*02:01:10, HLA-A*02:01:100, HLA-A*02:01:101, HLA-A*02:01:102, HLA-A*02:01:103, HLA-A*02:01:104, HLA-A*02:01:105, HLA-A*02:01:106, HLA-A*02:01:107, HLA-A*02:01:108, HLA-A*02:01:109, HLA-A*02:01:11, HLA-A*02:01:110, HLA-A*02:01:111, HLA-A*02:01:112, HLA-A*02:01:113, HLA-A*02:01:114, HLA-A*02:01:115, HLA-A*02:01:116, HLA-A*02:01:117, HLA-A*02:01:118, HLA-A*02:01:119, HLA-A*02:01:12, HLA-A*02:01:120, HLA-A*02:01:121, HLA-A*02:01:122, HLA-A*02:01:123, HLA-A*02:01:124, HLA-A*02:01:125, HLA-A*02:01:126, HLA-A*02:01:127, HLA-A*02:01:128, HLA-A*02:01:129, HLA-A*02:01:13, HLA-A*02:01:130, HLA-A*02:01:131, HLA-A*02:01:132, HLA-A*02:01:133, HLA-A*02:01:134, HLA-A*02:01:135, HLA-A*02:01:136, HLA-A*02:01:137, HLA-A*02:01:138, HLA-A*02:01:139, HLA-A*02:01:140, HLA-A*02:01:141, HLA-A*02:01:142, HLA-A*02:01:143, HLA-A*02:01:144, HLA-A*02:01:145, HLA-A*02:01:146, HLA-A*02:01:147, HLA-A*02:01:148, HLA-A*02:01:149, HLA-A*02:01:14Q, HLA-A*02:01:15, HLA-A*02:01:150, HLA-A*02:01:151, HLA-A*02:01:152, HLA-A*02:01:153, HLA-A*02:01:154, HLA-A*02:01:155, HLA-A*02:01:156, HLA-A*02:01:157, HLA-A*02:01:158, HLA-A*02:01:159, HLA-A*02:01:160, HLA-A*02:01:161, HLA-A*02:01:17, HLA-A*02:01:18, HLA-A*02:01:19, HLA-A*02:01:21, HLA-A*02:01:22, HLA-A*02:01:23, HLA-A*02:01:24, HLA-A*02:01:25, HLA-A*02:01:26, HLA-A*02:01:27, HLA-A*02:01:28, HLA-A*02:01:29, HLA-A*02:01:30, HLA-A*02:01:31, HLA-A*02:01:32, HLA-A*02:01:33, HLA-A*02:01:34, HLA-A*02:01:35, HLA-A*02:01:36, HLA-A*02:01:37, HLA-A*02:01:38, HLA-A*02:01:39, HLA-A*02:01:40, HLA-A*02:01:41, HLA-A*02:01:42, HLA-A*02:01:43, HLA-A*02:01:44, HLA-A*02:01:45, HLA-A*02:01:46, HLA-A*02:01:47, HLA-A*02:01:48, HLA-A*02:01:49, HLA-A*02:01:50, HLA-A*02:01:51, HLA-A*02:01:52, HLA-A*02:01:53, HLA-A*02:01:54, HLA-A*02:01:55, HLA-A*02:01:56, HLA-A*02:01:57, HLA-A*02:01:58, HLA-A*02:01:59, HLA-A*02:01:60, HLA-A*02:01:61, HLA-A*02:01:62, HLA-A*02:01:63, HLA-A*02:01:64, HLA-A*02:01:65, HLA-A*02:01:66, HLA-A*02:01:

67, HLA-A*02:01:68, HLA-A*02:01:69, HLA-A*02:01:70, HLA-A*02:01:71, HLA-A*02:01:72, HLA-A*02:01:73, HLA-A*02:01:74, HLA-A*02:01:75, HLA-A*02:01:76, HLA-A*02:01:77, HLA-A*02:01:78, HLA-A*02:01:79, HLA-A*02:01:80, HLA-A*02:01:81, HLA-A*02:01:83, HLA-A*02:01:84, HLA-A*02:01:85, HLA-A*02:01:86, HLA-A*02:01:87, HLA-A*02:01:88, HLA-A*02:01:89, HLA-A*02:01:90, HLA-A*02:01:91, HLA-A*02:01:92, HLA-A*02:01:93, HLA-A*02:01:94, HLA-A*02:01:95, HLA-A*02:01:96, HLA-A*02:01:97, HLA-A*02:01:98, HLA-A*02:01:99, HLA-A*02:02:01:01, HLA-A*02:02:01:02, HLA-A*02:02:01:03, HLA-A*02:02:01:04, HLA-A*02:02:02, HLA-A*02:02:03, HLA-A*02:02:04, HLA-A*02:03:01, HLA-A*02:03:02, HLA-A*02:03:03, HLA-A*02:03:04, HLA-A*02:03:05, HLA-A*02:03:06, HLA-A*02:03:07, HLA-A*02:03:08, HLA-A*02:04, HLA-A*02:05:01:01, HLA-A*02:05:01:02, HLA-A*02:05:02, HLA-A*02:05:03, HLA-A*02:05:04, HLA-A*02:05:05, HLA-A*02:05:06, HLA-A*02:05:07, HLA-A*02:05:08, HLA-A*02:05:09, HLA-A*02:06:01:01, HLA-A*02:06:01:02, HLA-A*02:06:01:03, HLA-A*02:06:01:04, HLA-A*02:06:01:05, HLA-A*02:06:01:06, HLA-A*02:06:02, HLA-A*02:06:03, HLA-A*02:06:04, HLA-A*02:06:05, HLA-A*02:06:06, HLA-A*02:06:07, HLA-A*02:06:08, HLA-A*02:06:09, HLA-A*02:06:10, HLA-A*02:06:11, HLA-A*02:06:12, HLA-A*02:06:13, HLA-A*02:06:14, HLA-A*02:06:15, HLA-A*02:06:16, HLA-A*02:06:17, HLA-A*02:06:18, HLA-A*02:06:19, HLA-A*02:06:20, HLA-A*02:06:21, HLA-A*02:06:22, HLA-A*02:06:23, HLA-A*02:06:24, HLA-A*02:06:25, HLA-A*02:06:26, HLA-A*02:06:27, HLA-A*02:07:01, HLA-A*02:07:02, HLA-A*02:07:03, HLA-A*02:07:04, HLA-A*02:07:05, HLA-A*02:07:06, HLA-A*02:07:07, HLA-A*02:07:08, HLA-A*02:07:09, HLA-A*02:07:10, HLA-A*02:07:11, HLA-A*02:07:12, HLA-A*02:08, HLA-A*02:09:01:01, HLA-A*02:09:01:02, HLA-A*02:10, HLA-A*02:101:01, HLA-A*02:101:02, HLA-A*02:102, HLA-A*02:103, HLA-A*02:104, HLA-A*02:105, HLA-A*02:106, HLA-A*02:107, HLA-A*02:108, HLA-A*02:109, HLA-A*02:110, HLA-A*02:111, HLA-A*02:112, HLA-A*02:113:01N, HLA-A*02:113:02N, HLA-A*02:114, HLA-A*02:115, HLA-A*02:116, HLA-A*02:117, HLA-A*02:118, HLA-A*02:119, HLA-A*02:11:01:01, HLA-A*02:11:01:02, HLA-A*02:11:02, HLA-A*02:11:03, HLA-A*02:11:04, HLA-A*02:11:05, HLA-A*02:11:06, HLA-A*02:11:07, HLA-A*02:11:08, HLA-A*02:11:09, HLA-A*02:12, HLA-A*02:120, HLA-A*02:121, HLA-A*02:122, HLA-A*02:123, HLA-A*02:124, HLA-A*02:125N, HLA-A*02:126, HLA-A*02:127, HLA-A*02:128, HLA-A*02:129, HLA-A*02:13, HLA-A*02:130, HLA-A*02:131:01, HLA-A*02:131:02, HLA-A*02:132, HLA-A*02:133, HLA-A*02:134, HLA-A*02:135, HLA-A*02:136, HLA-A*02:137, HLA-A*02:138, HLA-A*02:139, HLA-A*02:14, HLA-A*02:140, HLA-A*02:141, HLA-A*02:142, HLA-A*02:143, HLA-A*02:144, HLA-A*02:145, HLA-A*02:146, HLA-A*02:147, HLA-A*02:148, HLA-A*02:149, HLA-A*02:150:01, HLA-A*02:150:02, HLA-A*02:151, HLA-A*02:152, HLA-A*02:153:01, HLA-A*02:153:02, HLA-A*02:154, HLA-A*02:155, HLA-A*02:156, HLA-A*02:157:01, HLA-A*02:157:02, HLA-A*02:158, HLA-A*02:159, HLA-A*02:15N, HLA-A*02:16, HLA-A*02:160, HLA-A*02:161, HLA-A*02:162, HLA-A*02:163, HLA-A*02:164:01, HLA-A*02:164:02, HLA-A*02:165, HLA-A*02:166, HLA-A*02:167, HLA-A*02:168, HLA-A*02:169, HLA-A*02:170, HLA-A*02:171:01, HLA-A*02:171:02, HLA-A*02:172, HLA-A*02:173, HLA-A*02:174, HLA-A*02:175, HLA-A*02:176, HLA-A*02:177, HLA-A*02:

178, HLA-A*02:179, HLA-A*02:17:02, HLA-A*02:17:03, HLA-A*02:17:04, HLA-A*02:18, HLA-A*02:180, HLA-A*02:181, HLA-A*02:182, HLA-A*02:183, HLA-A*02:184, HLA-A*02:185, HLA-A*02:186, HLA-A*02:187, HLA-A*02:188, HLA-A*02:189, HLA-A*02:19, HLA-A*02:190, HLA-A*02:191, HLA-A*02:192, HLA-A*02:193, HLA-A*02:194, HLA-A*02:195, HLA-A*02:196, HLA-A*02:197:01, HLA-A*02:197:02, HLA-A*02:198, HLA-A*02:199, HLA-A*02:200, HLA-A*02:201, HLA-A*02:202, HLA-A*02:203, HLA-A*02:204, HLA-A*02:205, HLA-A*02:206, HLA-A*02:207, HLA-A*02:208, HLA-A*02:209, HLA-A*02:20:01, HLA-A*02:20:02, HLA-A*02:21, HLA-A*02:210, HLA-A*02:211:01, HLA-A*02:211:02, HLA-A*02:212, HLA-A*02:213, HLA-A*02:214, HLA-A*02:215, HLA-A*02:216, HLA-A*02:217:01, HLA-A*02:217:02, HLA-A*02:218, HLA-A*02:219, HLA-A*02:220, HLA-A*02:221, HLA-A*02:222N, HLA-A*02:223N, HLA-A*02:224, HLA-A*02:225N, HLA-A*02:226N, HLA-A*02:227N, HLA-A*02:228, HLA-A*02:229, HLA-A*02:22:01:01, HLA-A*02:22:01:02, HLA-A*02:22:02, HLA-A*02:230, HLA-A*02:231, HLA-A*02:232, HLA-A*02:233, HLA-A*02:234, HLA-A*02:235, HLA-A*02:236, HLA-A*02:237, HLA-A*02:238, HLA-A*02:239, HLA-A*02:240, HLA-A*02:241, HLA-A*02:242, HLA-A*02:243:01, HLA-A*02:243:02, HLA-A*02:243:03, HLA-A*02:244, HLA-A*02:245, HLA-A*02:246, HLA-A*02:247, HLA-A*02:248, HLA-A*02:249, HLA-A*02:24:01, HLA-A*02:24:02, HLA-A*02:25, HLA-A*02:250N, HLA-A*02:251, HLA-A*02:252, HLA-A*02:253, HLA-A*02:254, HLA-A*02:255, HLA-A*02:256, HLA-A*02:257, HLA-A*02:258, HLA-A*02:259, HLA-A*02:26, HLA-A*02:260, HLA-A*02:261, HLA-A*02:262, HLA-A*02:263, HLA-A*02:264, HLA-A*02:265, HLA-A*02:266, HLA-A*02:267, HLA-A*02:268, HLA-A*02:269, HLA-A*02:27, HLA-A*02:270, HLA-A*02:271, HLA-A*02:272, HLA-A*02:273, HLA-A*02:274, HLA-A*02:275, HLA-A*02:276, HLA-A*02:277, HLA-A*02:278, HLA-A*02:279, HLA-A*02:28, HLA-A*02:280, HLA-A*02:281, HLA-A*02:282, HLA-A*02:283, HLA-A*02:284N, HLA-A*02:285, HLA-A*02:286, HLA-A*02:287, HLA-A*02:288, HLA-A*02:289:01, HLA-A*02:289:02, HLA-A*02:29, HLA-A*02:290, HLA-A*02:291, HLA-A*02:292, HLA-A*02:293Q, HLA-A*02:294, HLA-A*02:295, HLA-A*02:296, HLA-A*02:297, HLA-A*02:298, HLA-A*02:299, HLA-A*02:300, HLA-A*02:301N, HLA-A*02:302, HLA-A*02:303, HLA-A*02:304, HLA-A*02:305N, HLA-A*02:306, HLA-A*02:307, HLA-A*02:308, HLA-A*02:309, HLA-A*02:30:01, HLA-A*02:30:02, HLA-A*02:31, HLA-A*02:310, HLA-A*02:311, HLA-A*02:312, HLA-A*02:313, HLA-A*02:314N, HLA-A*02:315, HLA-A*02:316, HLA-A*02:317, HLA-A*02:318, HLA-A*02:319, HLA-A*02:320, HLA-A*02:321N, HLA-A*02:322, HLA-A*02:323, HLA-A*02:324, HLA-A*02:325, HLA-A*02:326, HLA-A*02:327, HLA-A*02:328, HLA-A*02:329, HLA-A*02:32N, HLA-A*02:33, HLA-A*02:330, HLA-A*02:331, HLA-A*02:332, HLA-A*02:333, HLA-A*02:334, HLA-A*02:335, HLA-A*02:336, HLA-A*02:337, HLA-A*02:338, HLA-A*02:339, HLA-A*02:34, HLA-A*02:340, HLA-A*02:341, HLA-A*02:342, HLA-A*02:343, HLA-A*02:344, HLA-A*02:345, HLA-A*02:346, HLA-A*02:347, HLA-A*02:348, HLA-A*02:349, HLA-A*02:350N, HLA-A*02:351, HLA-A*02:352, HLA-A*02:353, HLA-A*02:354, HLA-A*02:355, HLA-A*02:356N, HLA-A*02:357, HLA-A*02:358, HLA-A*02:359, HLA-A*02:35:01, HLA-A*02:35:02, HLA-A*02:35:03, HLA-A*02:36, HLA-A*02:360, HLA-A*02:361, HLA-A*02:362, HLA-A*02:

363, HLA-A*02:364, HLA-A*02:365, HLA-A*02:366N, HLA-A*02:367, HLA-A*02:368, HLA-A*02:369, HLA-A*02:37, HLA-A*02:370, HLA-A*02:371, HLA-A*02:372, HLA-A*02:373N, HLA-A*02:374, HLA-A*02:375, HLA-A*02:376, HLA-A*02:377, HLA-A*02:378, HLA-A*02:379, HLA-A*02:38, HLA-A*02:380, HLA-A*02:381, HLA-A*02:382, HLA-A*02:383, HLA-A*02:384, HLA-A*02:385, HLA-A*02:386, HLA-A*02:387, HLA-A*02:388, HLA-A*02:389, HLA-A*02:39, HLA-A*02:390, HLA-A*02:391, HLA-A*02:392, HLA-A*02:393, HLA-A*02:394, HLA-A*02:395N, HLA-A*02:396, HLA-A*02:397, HLA-A*02:398, HLA-A*02:399, HLA-A*02:400, HLA-A*02:401, HLA-A*02:402, HLA-A*02:403, HLA-A*02:404, HLA-A*02:405, HLA-A*02:406, HLA-A*02:407, HLA-A*02:408, HLA-A*02:409, HLA-A*02:40:01, HLA-A*02:40:02, HLA-A*02:41, HLA-A*02:410, HLA-A*02:411, HLA-A*02:412, HLA-A*02:413, HLA-A*02:414, HLA-A*02:415, HLA-A*02:416, HLA-A*02:417, HLA-A*02:418, HLA-A*02:419:01, HLA-A*02:419:02, HLA-A*02:42, HLA-A*02:420, HLA-A*02:421, HLA-A*02:422, HLA-A*02:423, HLA-A*02:424, HLA-A*02:425, HLA-A*02:426, HLA-A*02:427, HLA-A*02:428, HLA-A*02:429, HLA-A*02:430, HLA-A*02:431, HLA-A*02:432, HLA-A*02:433, HLA-A*02:434, HLA-A*02:435, HLA-A*02:436, HLA-A*02:437, HLA-A*02:438, HLA-A*02:439N, HLA-A*02:43N, HLA-A*02:44, HLA-A*02:440Q, HLA-A*02:441, HLA-A*02:442, HLA-A*02:443, HLA-A*02:444, HLA-A*02:445, HLA-A*02:446, HLA-A*02:447, HLA-A*02:448, HLA-A*02:449, HLA-A*02:45, HLA-A*02:450, HLA-A*02:451, HLA-A*02:452, HLA-A*02:453, HLA-A*02:454, HLA-A*02:455, HLA-A*02:456, HLA-A*02:457, HLA-A*02:458, HLA-A*02:459, HLA-A*02:46, HLA-A*02:460, HLA-A*02:461, HLA-A*02:462, HLA-A*02:463, HLA-A*02:464, HLA-A*02:465, HLA-A*02:466, HLA-A*02:467, HLA-A*02:468:01N, HLA-A*02:468:02N, HLA-A*02:469, HLA-A*02:47, HLA-A*02:470, HLA-A*02:471, HLA-A*02:472, HLA-A*02:473, HLA-A*02:474, HLA-A*02:475, HLA-A*02:476N, HLA-A*02:477, HLA-A*02:478, HLA-A*02:479, HLA-A*02:48, HLA-A*02:480, HLA-A*02:481, HLA-A*02:482, HLA-A*02:483, HLA-A*02:484, HLA-A*02:485, HLA-A*02:486, HLA-A*02:487, HLA-A*02:488, HLA-A*02:489, HLA-A*02:49, HLA-A*02:490N, HLA-A*02:491, HLA-A*02:492, HLA-A*02:493, HLA-A*02:494, HLA-A*02:495, HLA-A*02:496, HLA-A*02:497, HLA-A*02:498, HLA-A*02:499, HLA-A*02:50, HLA-A*02:500Q, HLA-A*02:501N, HLA-A*02:502, HLA-A*02:503, HLA-A*02:504, HLA-A*02:505, HLA-A*02:506N, HLA-A*02:507, HLA-A*02:508, HLA-A*02:509, HLA-A*02:51, HLA-A*02:510, HLA-A*02:511, HLA-A*02:512, HLA-A*02:513, HLA-A*02:514N, HLA-A*02:515, HLA-A*02:516N, HLA-A*02:517, HLA-A*02:518, HLA-A*02:519, HLA-A*02:52, HLA-A*02:520, HLA-A*02:521, HLA-A*02:522, HLA-A*02:523, HLA-A*02:524:01, HLA-A*02:524:02, HLA-A*02:525N, HLA-A*02:526, HLA-A*02:527, HLA-A*02:528:01, HLA-A*02:528:02, HLA-A*02:529, HLA-A*02:530, HLA-A*02:531, HLA-A*02:532, HLA-A*02:533, HLA-A*02:534, HLA-A*02:535, HLA-A*02:536, HLA-A*02:537, HLA-A*02:538, HLA-A*02:539, HLA-A*02:53N, HLA-A*02:54, HLA-A*02:540N, HLA-A*02:541, HLA-A*02:542, HLA-A*02:543, HLA-A*02:544, HLA-A*02:545, HLA-A*02:546, HLA-A*02:547, HLA-A*02:548, HLA-A*02:549, HLA-A*02:55, HLA-A*02:550, HLA-A*02:551, HLA-A*02:552, HLA-A*02:553, HLA-A*02:554, HLA-A*02:555, HLA-A*02:556, HLA-A*02:557, HLA-A*02:558, HLA-A*02:559, HLA-A*02:560, HLA-

A*02:561, HLA-A*02:562, HLA-A*02:563, HLA-A*02:564, HLA-A*02:565, HLA-A*02:566, HLA-A*02:567, HLA-A*02:568, HLA-A*02:569, HLA-A*02:56:01, HLA-A*02:56:02, HLA-A*02:57, HLA-A*02:570:01, HLA-A*02:570:02, HLA-A*02:571, HLA-A*02:572, HLA-A*02:573, HLA-A*02:574, HLA-A*02:575, HLA-A*02:576, HLA-A*02:577, HLA-A*02:578, HLA-A*02:579, HLA-A*02:58, HLA-A*02:580, HLA-A*02:581, HLA-A*02:582, HLA-A*02:583, HLA-A*02:584, HLA-A*02:585, HLA-A*02:586, HLA-A*02:587, HLA-A*02:588, HLA-A*02:589, HLA-A*02:59, HLA-A*02:590, HLA-A*02:591:01, HLA-A*02:591:02, HLA-A*02:592, HLA-A*02:593, HLA-A*02:594, HLA-A*02:595, HLA-A*02:596, HLA-A*02:597, HLA-A*02:598, HLA-A*02:599, HLA-A*02:600, HLA-A*02:601, HLA-A*02:602, HLA-A*02:603, HLA-A*02:604, HLA-A*02:605Q, HLA-A*02:606, HLA-A*02:607, HLA-A*02:608N, HLA-A*02:609, HLA-A*02:60:01, HLA-A*02:60:02, HLA-A*02:61, HLA-A*02:610:01, HLA-A*02:610:02, HLA-A*02:611, HLA-A*02:612, HLA-A*02:613, HLA-A*02:614, HLA-A*02:615, HLA-A*02:616, HLA-A*02:617, HLA-A*02:618Q, HLA-A*02:619, HLA-A*02:62, HLA-A*02:620, HLA-A*02:621, HLA-A*02:622N, HLA-A*02:623, HLA-A*02:624, HLA-A*02:625, HLA-A*02:626, HLA-A*02:627, HLA-A*02:628, HLA-A*02:629, HLA-A*02:63, HLA-A*02:630, HLA-A*02:631, HLA-A*02:632, HLA-A*02:633, HLA-A*02:634, HLA-A*02:635, HLA-A*02:636, HLA-A*02:637, HLA-A*02:638, HLA-A*02:639, HLA-A*02:640, HLA-A*02:641, HLA-A*02:642, HLA-A*02:643N, HLA-A*02:644, HLA-A*02:645, HLA-A*02:646, HLA-A*02:647, HLA-A*02:648, HLA-A*02:649, HLA-A*02:64:01, HLA-A*02:64:02, HLA-A*02:65, HLA-A*02:650, HLA-A*02:651, HLA-A*02:652, HLA-A*02:653, HLA-A*02:654, HLA-A*02:655, HLA-A*02:656, HLA-A*02:657, HLA-A*02:658, HLA-A*02:659, HLA-A*02:66, HLA-A*02:660, HLA-A*02:661, HLA-A*02:662, HLA-A*02:663, HLA-A*02:664, HLA-A*02:665, HLA-A*02:666, HLA-A*02:667, HLA-A*02:668, HLA-A*02:669, HLA-A*02:67, HLA-A*02:670, HLA-A*02:671, HLA-A*02:672Q, HLA-A*02:673, HLA-A*02:674, HLA-A*02:675N, HLA-A*02:676, HLA-A*02:677, HLA-A*02:678, HLA-A*02:679, HLA-A*02:68, HLA-A*02:680, HLA-A*02:681, HLA-A*02:682, HLA-A*02:683, HLA-A*02:684, HLA-A*02:685, HLA-A*02:686, HLA-A*02:687, HLA-A*02:688, HLA-A*02:689, HLA-A*02:69, HLA-A*02:690, HLA-A*02:691N, HLA-A*02:692, HLA-A*02:693, HLA-A*02:694, HLA-A*02:695, HLA-A*02:696N, HLA-A*02:697, HLA-A*02:698, HLA-A*02:699, HLA-A*02:70, HLA-A*02:700, HLA-A*02:701, HLA-A*02:702, HLA-A*02:703, HLA-A*02:704, HLA-A*02:705, HLA-A*02:706, HLA-A*02:707, HLA-A*02:708, HLA-A*02:709, HLA-A*02:71, HLA-A*02:710N, HLA-A*02:711, HLA-A*02:712, HLA-A*02:713, HLA-A*02:714, HLA-A*02:715N, HLA-A*02:716, HLA-A*02:717, HLA-A*02:718, HLA-A*02:719, HLA-A*02:72, HLA-A*02:720, HLA-A*02:721, HLA-A*02:722, HLA-A*02:723, HLA-A*02:724, HLA-A*02:725, HLA-A*02:726, HLA-A*02:727, HLA-A*02:728, HLA-A*02:729, HLA-A*02:73, HLA-A*02:730, HLA-A*02:731, HLA-A*02:732, HLA-A*02:733, HLA-A*02:734, HLA-A*02:735, HLA-A*02:736, HLA-A*02:737, HLA-A*02:738, HLA-A*02:739, HLA-A*02:740, HLA-A*02:741, HLA-A*02:742, HLA-A*02:743, HLA-A*02:744, HLA-A*02:745, HLA-A*02:746, HLA-A*02:747, HLA-A*02:748N, HLA-A*02:749, HLA-A*02:74:01, HLA-A*02:74:02, HLA-A*02:75, HLA-A*02:750, HLA-A*02:751, HLA-A*02:752, HLA-A*02:753, HLA-A*02:754, HLA-A*02:

755, HLA-A*02:756, HLA-A*02:757, HLA-A*02:758, HLA-A*02:759, HLA-A*02:760N, HLA-A*02:761, HLA-A*02:762, HLA-A*02:763, HLA-A*02:764, HLA-A*02:765, HLA-A*02:766, HLA-A*02:767, HLA-A*02:768, HLA-A*02:769, HLA-A*02:76:01, HLA-A*02:76:02, HLA-A*02:77, HLA-A*02:770, HLA-A*02:771, HLA-A*02:772, HLA-A*02:773N, HLA-A*02:774, HLA-A*02:775N, HLA-A*02:776, HLA-A*02:777, HLA-A*02:778, HLA-A*02:779, HLA-A*02:78, HLA-A*02:780, HLA-A*02:781, HLA-A*02:782, HLA-A*02:783, HLA-A*02:784, HLA-A*02:785, HLA-A*02:786, HLA-A*02:787, HLA-A*02:788N, HLA-A*02:789N, HLA-A*02:790, HLA-A*02:791N, HLA-A*02:792N, HLA-A*02:793N, HLA-A*02:794, HLA-A*02:795, HLA-A*02:796N, HLA-A*02:797N, HLA-A*02:798, HLA-A*02:799, HLA-A*02:79:01, HLA-A*02:79:02, HLA-A*02:80, HLA-A*02:800, HLA-A*02:801, HLA-A*02:802, HLA-A*02:803N, HLA-A*02:804, HLA-A*02:805Q, HLA-A*02:806N, HLA-A*02:807N, HLA-A*02:808, HLA-A*02:809, HLA-A*02:81, HLA-A*02:810, HLA-A*02:811, HLA-A*02:812, HLA-A*02:813, HLA-A*02:814, HLA-A*02:815, HLA-A*02:816, HLA-A*02:817, HLA-A*02:818, HLA-A*02:819, HLA-A*02:820, HLA-A*02:821, HLA-A*02:822, HLA-A*02:823, HLA-A*02:824, HLA-A*02:825, HLA-A*02:82N, HLA-A*02:83N, HLA-A*02:84, HLA-A*02:85, HLA-A*02:86:01, HLA-A*02:86:02, HLA-A*02:87, HLA-A*02:88N, HLA-A*02:89:01, HLA-A*02:89:02, HLA-A*02:90, HLA-A*02:91, HLA-A*02:92, HLA-A*02:93:01, HLA-A*02:93:02, HLA-A*02:94N, HLA-A*02:95, HLA-A*02:96, HLA-A*02:97:01, HLA-A*02:97:02, and HLA-A*02:99.

II.D.2. HLA-B Alleles and Complexes Thereof

Certain aspects of the present disclosure are directed to a complex comprising an HLA class I molecule and an epitope, wherein the HLA class I molecule is an HLA-B allele, and wherein the epitope is a MAGE-A1 epitope disclosed herein. In certain embodiments, the MAGE-A1 epitope comprises, consists of, or consists essentially of SEQ ID NO: 52.

Other aspects of the present disclosure are directed to a complex comprising an HLA class I molecule and an epitope, wherein the HLA class I molecule is an HLA-B allele, and wherein the epitope is a MART1 epitope disclosed herein. In certain embodiments, the MART1 epitope comprises, consists of, or consists essentially of SEQ ID NO: 53.

Other aspects of the present disclosure are directed to a complex comprising an HLA class I molecule and an epitope, wherein the HLA class I molecule is an HLA-B allele, and wherein the epitope is a MAGE-A3 epitope disclosed herein. In certain embodiments, the MAGE-A3 epitope comprises, consists of, or consists essentially of SEQ ID NO: 54.

In some embodiments, the HLA-B allele is selected from selected from an HLA-B*07, an HLA-B*08, an HLA-B*13, an HLA-B*14, an HLA-B*15, an HLA-B*18, an HLA-B*27, an HLA-B*35, an HLA-B*37, an HLA-B*38, an HLA-B*39, an HLA-B*40, an HLA-B*41, an HLA-B*42, an HLA-B*44, an HLA-B*45, an HLA-B*46, an HLA-B*47, an HLA-B*48, an HLA-B*49, an HLA-B*50, an HLA-B*51, an HLA-B*52, an HLA-B*53, an HLA-B*54, an HLA-B*55, an HLA-B*56, an HLA-B*57, an HLA-B*58, an HLA-B*59, an HLA-B*67, an HLA-B*73, an HLA-B*78, an HLA-B*79, an HLA-B*81, an HLA-B*82, and an HLA-B*83.

II.D.2.a. HLA-B*07 Alleles and Complexes Thereof

In some embodiments, the HLA-B allele is an HLA-B*07 allele. In certain embodiments, the complex comprises an HLA-B*07 allele and a MAGE-A1 epitope disclosed herein, e.g., an epitope compromising, consisting of, or consisting essentially of SEQ ID NO: 52. In certain embodiments, the HLA-B allele is an HLA-B*07:02 allele. In certain embodiments, the HLA-B allele is an HLA-B*07:03 allele. In certain embodiments, the HLA-B allele is an HLA-B*07:04 allele. In certain embodiments, the HLA-B allele is an HLA-B*07:05 allele. In certain embodiments, the HLA-B allele is an HLA-B*07:06 allele. In particular embodiments, the complex comprises an HLA-B*07:02 allele and a MAGE-A1 epitope compromising, consisting of, or consisting essentially of SEQ ID NO: 52.

In certain embodiments, the HLA-B allele is selected from the group consisting of HLA-B*07:02:01:01, HLA-B*07:02:01:02, HLA-B*07:02:01:03, HLA-B*07:02:01:04, HLA-B*07:02:01:05, HLA-B*07:02:01:06, HLA-B*07:02:01:07, HLA-B*07:02:01:08, HLA-B*07:02:01:09, HLA-B*07:02:01:10, HLA-B*07:02:01:11, HLA-B*07:02:01:12, HLA-B*07:02:01:13, HLA-B*07:02:01:14, HLA-B*07:02:02, HLA-B*07:02:03, HLA-B*07:02:04, HLA-B*07:02:05, HLA-B*07:02:06, HLA-B*07:02:07, HLA-B*07:02:08, HLA-B*07:02:09, HLA-B*07:02:10, HLA-B*07:02:11, HLA-B*07:02:12, HLA-B*07:02:13, HLA-B*07:02:14, HLA-B*07:02:15, HLA-B*07:02:16, HLA-B*07:02:17, HLA-B*07:02:18, HLA-B*07:02:19, HLA-B*07:02:20, HLA-B*07:02:21, HLA-B*07:02:22, HLA-B*07:02:23, HLA-B*07:02:24, HLA-B*07:02:25, HLA-B*07:02:26, HLA-B*07:02:27, HLA-B*07:02:28, HLA-B*07:02:29, HLA-B*07:02:30, HLA-B*07:02:31, HLA-B*07:02:32, HLA-B*07:02:33, HLA-B*07:02:34, HLA-B*07:02:35, HLA-B*07:02:36, HLA-B*07:02:37, HLA-B*07:02:38, HLA-B*07:02:39, HLA-B*07:02:40, HLA-B*07:02:41, HLA-B*07:02:42, HLA-B*07:02:43, HLA-B*07:02:44, HLA-B*07:02:45, HLA-B*07:02:46, HLA-B*07:02:47, HLA-B*07:02:48, HLA-B*07:02:49, HLA-B*07:02:50, HLA-B*07:02:51, HLA-B*07:02:52, HLA-B*07:02:53, HLA-B*07:02:54, HLA-B*07:02:55, HLA-B*07:02:56, HLA-B*07:02:57, HLA-B*07:02:58, HLA-B*07:02:59, HLA-B*07:02:60, HLA-B*07:02:61, HLA-B*07:02:62, HLA-B*07:02:63, HLA-B*07:02:64, HLA-B*07:02:65, HLA-B*07:02:66, HLA-B*07:02:67, HLA-B*07:02:68, HLA-B*07:02:69, HLA-B*07:02:70, HLA-B*07:02:71, HLA-B*07:02:72, HLA-B*07:02:73, HLA-B*07:03, HLA-B*07:04:01, HLA-B*07:04:02, HLA-B*07:05:01:01, HLA-B*07:05:01:02, HLA-B*07:05:01:03, HLA-B*07:05:01:04, HLA-B*07:05:02, HLA-B*07:05:03, HLA-B*07:05:04, HLA-B*07:05:05, HLA-B*07:05:06, HLA-B*07:05:07, HLA-B*07:05:08, HLA-B*07:05:09, HLA-B*07:06:01, HLA-B*07:06:02, HLA-B*07:06:03, HLA-B*07:07:01, HLA-B*07:07:02, HLA-B*07:08:01, HLA-B*07:08:02, HLA-B*07:09:01, HLA-B*07:09:02, HLA-B*07:10, HLA-B*07:100, HLA-B*07:101, HLA-B*07:102, HLA-B*07:103, HLA-B*07:104, HLA-B*07:105, HLA-B*07:106, HLA-B*07:107, HLA-B*07:108, HLA-B*07:109, HLA-B*07:11, HLA-B*07:110, HLA-B*07:111, HLA-B*07:112, HLA-B*07:113, HLA-B*07:114, HLA-B*07:115, HLA-B*07:116, HLA-B*07:117, HLA-B*07:118, HLA-B*07:119, HLA-B*07:12, HLA-B*07:120, HLA-B*07:121, HLA-B*07:122, HLA-B*07:123, HLA-B*07:124, HLA-B*07:125, HLA-B*07:126, HLA-B*07:127, HLA-B*07:128, HLA-B*07:129, HLA-B*07:13, HLA-B*07:130, HLA-B*07:131, HLA-B*07:132, HLA-B*07:133, HLA-B*07:134, HLA-B*07:135, HLA-B*07:136:01, HLA-B*07:136:02, HLA-B*07:137, HLA-B*07:138, HLA- B*07:139:01, HLA-B*07:139:02, HLA-B*07:14, HLA-B*07:140, HLA-B*07:141, HLA-B*07:142, HLA-B*07:143, HLA-B*07:144, HLA-B*07:145, HLA-B*07:146, HLA-B*07:147, HLA-B*07:148, HLA-B*07:149, HLA-B*07:15, HLA-B*07:150, HLA-B*07:151:01, HLA-B*07:151:02, HLA-B*07:152, HLA-B*07:153, HLA-B*07:154, HLA-B*07:155, HLA-B*07:156, HLA-B*07:157, HLA-B*07:158, HLA-B*07:159, HLA-B*07:16, HLA-B*07:160, HLA-B*07:161, HLA-B*07:162, HLA-B*07:163, HLA-B*07:164, HLA-B*07:165, HLA-B*07:166, HLA-B*07:167, HLA-B*07:168, HLA-B*07:169, HLA-B*07:17, HLA-B*07:170, HLA-B*07:171, HLA-B*07:172, HLA-B*07:173, HLA-B*07:174, HLA-B*07:175, HLA-B*07:176, HLA-B*07:177, HLA-B*07:178, HLA-B*07:179, HLA-B*07:180, HLA-B*07:181, HLA-B*07:182, HLA-B*07:183, HLA-B*07:184, HLA-B*07:185, HLA-B*07:186, HLA-B*07:187, HLA-B*07:188, HLA-B*07:189, HLA-B*07:18:01, HLA-B*07:18:02, HLA-B*07:19, HLA-B*07:190, HLA-B*07:191, HLA-B*07:192, HLA-B*07:193, HLA-B*07:194, HLA-B*07:195, HLA-B*07:196, HLA-B*07:197, HLA-B*07:198, HLA-B*07:199, HLA-B*07:20, HLA-B*07:200, HLA-B*07:201, HLA-B*07:202, HLA-B*07:203, HLA-B*07:204, HLA-B*07:205, HLA-B*07:206, HLA-B*07:207, HLA-B*07:208, HLA-B*07:209, HLA-B*07:21, HLA-B*07:210, HLA-B*07:211, HLA-B*07:212, HLA-B*07:213, HLA-B*07:214, HLA-B*07:215, HLA-B*07:216, HLA-B*07:217, HLA-B*07:218, HLA-B*07:219, HLA-B*07:220, HLA-B*07:221, HLA-B*07:222, HLA-B*07:223, HLA-B*07:224, HLA-B*07:225, HLA-B*07:226, HLA-B*07:227, HLA-B*07:228:01, HLA-B*07:228:02, HLA-B*07:229, HLA-B*07:22:01, HLA-B*07:22:02, HLA-B*07:23, HLA-B*07:230, HLA-B*07:231, HLA-B*07:232, HLA-B*07:233, HLA-B*07:234, HLA-B*07:235, HLA-B*07:236, HLA-B*07:237, HLA-B*07:238, HLA-B*07:239, HLA-B*07:24, HLA-B*07:240, HLA-B*07:241, HLA-B*07:242, HLA-B*07:243, HLA-B*07:244, HLA-B*07:245, HLA-B*07:246, HLA-B*07:247, HLA-B*07:248, HLA-B*07:249, HLA-B*07:25, HLA-B*07:250, HLA-B*07:251, HLA-B*07:252, HLA-B*07:253, HLA-B*07:254, HLA-B*07:255, HLA-B*07:256, HLA-B*07:257, HLA-B*07:258, HLA-B*07:259, HLA-B*07:26, HLA-B*07:260, HLA-B*07:261, HLA-B*07:262, HLA-B*07:263, HLA-B*07:264, HLA-B*07:265, HLA-B*07:266, HLA-B*07:267, HLA-B*07:268, HLA-B*07:269, HLA-B*07:27, HLA-B*07:270, HLA-B*07:271, HLA-B*07:272, HLA-B*07:273, HLA-B*07:274, HLA-B*07:275, HLA-B*07:276:01, HLA-B*07:276:02, HLA-B*07:277, HLA-B*07:278, HLA-B*07:279, HLA-B*07:28, HLA-B*07:280, HLA-B*07:281, HLA-B*07:282, HLA-B*07:283, HLA-B*07:284, HLA-B*07:285, HLA-B*07:286, HLA-B*07:287, HLA-B*07:288, HLA-B*07:289, HLA-B*07:29, HLA-B*07:290, HLA-B*07:291, HLA-B*07:292, HLA-B*07:293, HLA-B*07:294, HLA-B*07:295, HLA-B*07:296, HLA-B*07:297, HLA-B*07:298, HLA-B*07:299, HLA-B*07:30, HLA-B*07:300, HLA-B*07:301, HLA-B*07:302, HLA-B*07:303:01, HLA-B*07:303:02, HLA-B*07:304, HLA-B*07:305, HLA-B*07:306, HLA-B*07:307, HLA-B*07:308, HLA-B*07:309, HLA-B*07:31, HLA-B*07:310, HLA-B*07:311, HLA-B*07:312, HLA-B*07:313, HLA-B*07:314, HLA-B*07:315, HLA-B*07:316, HLA-B*07:317, HLA-B*07:318, HLA-B*07:319, HLA-B*07:32, HLA-B*07:320, HLA-B*07:321, HLA-B*07:322, HLA-B*07:323, HLA-B*07:324, HLA-B*07:325, HLA-B*07:326, HLA-B*07:327, HLA-B*07:328, HLA-B*07:329, HLA-B*07:330, HLA-B*07:331, HLA-B*07:332, HLA-B*07:333, HLA-B*07:334, HLA- B*07:335, HLA-B*07:336, HLA-B*07:337, HLA-B*07: 338, HLA-B*07:339, HLA-B*07:33:01, HLA-B*07:33:02, HLA-B*07:33:03, HLA-B*07:34, HLA-B*07:340, HLA-B*07:341, HLA-B*07:342, HLA-B*07:343, HLA-B*07: 344, HLA-B*07:345, HLA-B*07:346, HLA-B*07:347, HLA-B*07:348, HLA-B*07:349, HLA-B*07:35, HLA-B*07:350, HLA-B*07:351, HLA-B*07:352, HLA-B*07: 353, HLA-B*07:354, HLA-B*07:355, HLA-B*07:356, HLA-B*07:357, HLA-B*07:358, HLA-B*07:36, HLA-B*07:37:01, HLA-B*07:37:02, HLA-B*07:38, HLA-B*07: 39, HLA-B*07:40, HLA-B*07:41, HLA-B*07:42, HLA-B*07:43, HLA-B*07:44, HLA-B*07:45, HLA-B*07:46, HLA-B*07:47, HLA-B*07:48, HLA-B*07:49, HLA-B*07: 50, HLA-B*07:51, HLA-B*07:52, HLA-B*07:53, HLA-B*07:54, HLA-B*07:55, HLA-B*07:56:01, HLA-B*07:56: 02, HLA-B*07:57, HLA-B*07:58, HLA-B*07:59, HLA-B*07:60, HLA-B*07:61, HLA-B*07:62, HLA-B*07:63, HLA-B*07:64, HLA-B*07:65, HLA-B*07:66, HLA-B*07: 67, HLA-B*07:68:01, HLA-B*07:68:02, HLA-B*07:68:03, HLA-B*07:69, HLA-B*07:70, HLA-B*07:71, HLA-B*07: 72, HLA-B*07:73, HLA-B*07:74, HLA-B*07:75:01:01, HLA-B*07:75:01:02, HLA-B*07:76, HLA-B*07:77, HLA-B*07:78, HLA-B*07:79, HLA-B*07:80, HLA-B*07:81, HLA-B*07:82, HLA-B*07:83, HLA-B*07:84, HLA-B*07: 85:01, HLA-B*07:85:02, HLA-B*07:86, HLA-B*07:87, HLA-B*07:88, HLA-B*07:89, HLA-B*07:90, HLA-B*07: 91, HLA-B*07:92, HLA-B*07:93, HLA-B*07:94, HLA-B*07:95, HLA-B*07:96:01, HLA-B*07:96:02, HLA-B*07: 97, HLA-B*07:98, and HLA-B*07:99.

II.D.2.b. HLA-B*18 Alleles and Complexes Thereof

In some embodiments, the HLA-B allele is an HLA-B*18 allele. In certain embodiments, the complex comprises an HLA-B*18 allele and a MART1 epitope disclosed herein, e.g., an epitope compromising, consisting of, or consisting essentially of SEQ ID NO: 53. In certain embodiments, the HLA-B allele is an HLA-B*18:01 allele. In particular embodiments, the complex comprises an HLA-B*18:01 allele and a MART1 epitope compromising, consisting of, or consisting essentially of SEQ ID NO: 53.

In some embodiments, the HLA-B allele is an HLA-B*18 allele. In certain embodiments, the complex comprises an HLA-B*18 allele and a MAGE-A3 epitope disclosed herein, e.g., an epitope compromising, consisting of, or consisting essentially of SEQ ID NO: 54. In certain embodiments, the HLA-B allele is an HLA-B*18:01 allele. In particular embodiments, the complex comprises an HLA-B*18:01 allele and a MAGE-A3 epitope compromising, consisting of, or consisting essentially of SEQ ID NO: 54.

In certain embodiments, the HLA-B allele is selected from the group consisting of HLA-B*18:01:01:01, HLA-B*18:01:01:02, HLA-B*18:01:01:03, HLA-B*18:01:01:04, HLA-B*18:01:01:05, HLA-B*18:01:01:06, HLA-B*18:01: 01:07, HLA-B*18:01:01:08, HLA-B*18:01:01:09, HLA-B*18:01:01:10, HLA-B*18:01:01:11, HLA-B*18:01:01:12, HLA-B*18:01:01:13, HLA-B*18:01:01:14, HLA-B*18:01: 01:15, HLA-B*18:01:01:16, HLA-B*18:01:01:17, HLA-B*18:01:01:18, HLA-B*18:01:01:19, HLA-B*18:01:02, HLA-B*18:01:03, HLA-B*18:01:04, HLA-B*18:01:05, HLA-B*18:01:06, HLA-B*18:01:07, HLA-B*18:01:08, HLA-B*18:01:09, HLA-B*18:01:10, HLA-B*18:01:11, HLA-B*18:01:12, HLA-B*18:01:13, HLA-B*18:01:14, HLA-B*18:01:15, HLA-B*18:01:16, HLA-B*18:01:17, HLA-B*18:01:18, HLA-B*18:01:19, HLA-B*18:01:20, HLA-B*18:01:21, HLA-B*18:01:22, HLA-B*18:01:23, HLA-B*18:01:24, HLA-B*18:01:25, HLA-B*18:01:26, HLA-B*18:01:27, HLA-B*18:01:28, HLA-B*18:01:29, HLA-B*18:01:30, HLA-B*18:01:31, and HLA-B*18:01: 32.

In certain embodiments, the HLA-B allele is selected from the group consisting of HLA-B*18:02, HLA-B*18:03: 01, HLA-B*18:03:02, HLA-B*18:04:01, HLA-B*18:04:02, HLA-B*18:05:01:01, HLA-B*18:05:01:02, HLA-B*18:06, HLA-B*18:07:01, HLA-B*18:07:02, HLA-B*18:08, HLA-B*18:09, HLA-B*18:10, HLA-B*18:100, HLA-B*18:101, HLA-B*18:102, HLA-B*18:103, HLA-B*18:104, HLA-B*18:105, HLA-B*18:106, HLA-B*18:107, HLA-B*18: 108, HLA-B*18:109, HLA-B*18:11, HLA-B*18:110, HLA-B*18:111, HLA-B*18:112, HLA-B*18:113, HLA-B*18:114, HLA-B*18:115, HLA-B*18:116, HLA-B*18: 117, HLA-B*18:118, HLA-B*18:119, HLA-B*18:120, HLA-B*18:121, HLA-B*18:122, HLA-B*18:123, HLA-B*18:124, HLA-B*18:125, HLA-B*18:126, HLA-B*18: 127, HLA-B*18:128, HLA-B*18:129, HLA-B*18:12:01, HLA-B*18:12:02, HLA-B*18:13, HLA-B*18:130, HLA-B*18:131:01:01, HLA-B*18:131:01:02, HLA-B*18:132, HLA-B*18:133, HLA-B*18:134, HLA-B*18:135, HLA-B*18:136, HLA-B*18:137, HLA-B*18:138N, HLA-B*18: 139, HLA-B*18:14, HLA-B*18:140, HLA-B*18:141, HLA-B*18:142, HLA-B*18:143, HLA-B*18:144, HLA-B*18:145, HLA-B*18:146, HLA-B*18:147, HLA-B*18: 148, HLA-B*18:149, HLA-B*18:15, HLA-B*18:150, HLA-B*18:151, HLA-B*18:152, HLA-B*18:153, HLA-B*18:154N, HLA-B*18:155, HLA-B*18:156:01:01, HLA-B*18:156:01:02, HLA-B*18:157:01:01, HLA-B*18:157: 01:02, HLA-B*18:158, HLA-B*18:159, HLA-B*18:160, HLA-B*18:161, HLA-B*18:17N, HLA-B*18:18:01:01, HLA-B*18:18:01:02, HLA-B*18:19, HLA-B*18:20, HLA-B*18:21, HLA-B*18:22, HLA-B*18:23N, HLA-B*18:24, HLA-B*18:25, HLA-B*18:26, HLA-B*18:27, HLA-B*18: 28, HLA-B*18:29, HLA-B*18:30, HLA-B*18:31, HLA-B*18:32, HLA-B*18:33, HLA-B*18:34, HLA-B*18:35, HLA-B*18:36, HLA-B*18:37:01, HLA-B*18:37:02, HLA-B*18:38, HLA-B*18:39, HLA-B*18:40, HLA-B*18:41, HLA-B*18:42, HLA-B*18:43, HLA-B*18:44:01, HLA-B*18:44:02, HLA-B*18:45, HLA-B*18:46, HLA-B*18:47, HLA-B*18:48, HLA-B*18:49, HLA-B*18:50, HLA-B*18: 51, HLA-B*18:52, HLA-B*18:53, HLA-B*18:54, HLA-B*18:55, HLA-B*18:56, HLA-B*18:57:01, HLA-B*18:57: 02, HLA-B*18:58, HLA-B*18:59, HLA-B*18:60, HLA-B*18:61, HLA-B*18:62, HLA-B*18:63, HLA-B*18:64, HLA-B*18:65, HLA-B*18:66, HLA-B*18:67, HLA-B*18: 68, HLA-B*18:69, HLA-B*18:70, HLA-B*18:71, HLA-B*18:72:01, HLA-B*18:72:02, HLA-B*18:72:03, HLA-B*18:73, HLA-B*18:74N, HLA-B*18:75, HLA-B*18:76, HLA-B*18:77, HLA-B*18:78, HLA-B*18:79, HLA-B*18: 80, HLA-B*18:81, HLA-B*18:82, HLA-B*18:83, HLA-B*18:84, HLA-B*18:85, HLA-B*18:86, HLA-B*18:87, HLA-B*18:88, HLA-B*18:89, HLA-B*18:90, HLA-B*18: 91, HLA-B*18:92, HLA-B*18:93, HLA-B*18:94N, HLA-B*18:95, HLA-B*18:96, HLA-B*18:97, HLA-B*18:98, and HLA-B*18:99.

II.D.3. HLA-C Alleles and Complexes Thereof

Certain aspects of the present disclosure are directed to a complex comprising an HLA class I molecule and an epitope, wherein the HLA class I molecule is an HLA-C allele, and wherein the epitope is a tyrosinase epitope disclosed herein. In certain embodiments, the tyrosinase epitope comprises, consists, or consists essentially of SEQ ID NO: 51.

In some embodiments, the HLA-C allele selected from an HLA-C*05:01 allele, an HLA-C*05:03 allele, an HLA-C*05:04 allele, an HLA-C*05:05 allele, and an HLA-C*05:

06 allele. In certain embodiments, the HLA-C allele is an HLA-C*05:01 allele. In certain embodiments, the HLA-C allele is an HLA-C*05:03 allele. In certain embodiments, the HLA-C allele is an HLA-C*05:04 allele. In certain embodiments, the HLA-C allele is an HLA-C*05:05 allele. In certain embodiments, the HLA-C allele is an HLA-C*05:06 allele.

In certain embodiments, the complex comprises an HLA-C*05 allele and a tyrosinase epitope disclosed herein, e.g., an epitope compromising, consisting of, or consisting essentially of SEQ ID NO: 51. In certain embodiments, the HLA-C allele is an HLA-C*05:01 allele. In particular embodiments, the complex comprises an HLA-C*05:01 allele and a tyrosinase epitope compromising, consisting of, or consisting essentially of SEQ ID NO: 51.

In certain embodiments, the HLA-C allele is selected from the group consisting of HLA-C*05:01:01:01, HLA-C*05:01:01:02, HLA-C*05:01:01:03, HLA-C*05:01:01:04, HLA-C*05:01:01:05, HLA-C*05:01:01:06, HLA-C*05:01:01:07, HLA-C*05:01:01:08, HLA-C*05:01:01:09, HLA-C*05:01:01:10, HLA-C*05:01:01:11, HLA-C*05:01:01:12, HLA-C*05:01:01:13, HLA-C*05:01:01:14, HLA-C*05:01:01:15, HLA-C*05:01:01:16, HLA-C*05:01:02, HLA-C*05:01:03, HLA-C*05:01:04, HLA-C*05:01:05, HLA-C*05:01:06, HLA-C*05:01:07, HLA-C*05:01:08, HLA-C*05:01:09, HLA-C*05:01:10, HLA-C*05:01:11, HLA-C*05:01:12, HLA-C*05:01:13, HLA-C*05:01:14, HLA-C*05:01:15, HLA-C*05:01:16, HLA-C*05:01:17, HLA-C*05:01:18, HLA-C*05:01:19, HLA-C*05:01:20, HLA-C*05:01:21, HLA-C*05:01:22, HLA-C*05:01:23, HLA-C*05:01:24, HLA-C*05:01:25, HLA-C*05:01:26, HLA-C*05:01:27, HLA-C*05:01:28, HLA-C*05:01:29, HLA-C*05:01:30, HLA-C*05:01:31, HLA-C*05:01:32, HLA-C*05:01:33, HLA-C*05:01:34, HLA-C*05:01:35, HLA-C*05:01:36, HLA-C*05:01:37, HLA-C*05:01:38, HLA-C*05:01:39, HLA-C*05:01:40, HLA-C*05:01:41, HLA-C*05:01:42, HLA-C*05:01:43, HLA-C*05:01:44, HLA-C*05:01:45, HLA-C*05:03, HLA-C*05:04:01, HLA-C*05:04:02, HLA-C*05:05:01, HLA-C*05:05:02, HLA-C*05:06, HLA-C*05:07N, HLA-C*05:08, HLA-C*05:09:01, HLA-C*05:09:02, HLA-C*05:09:03, HLA-C*05:10, HLA-C*05:100, HLA-C*05:101, HLA-C*05:102, HLA-C*05:103:01, HLA-C*05:103:02, HLA-C*05:104, HLA-C*05:105, HLA-C*05:106:01, HLA-C*05:106:02, HLA-C*05:107, HLA-C*05:108, HLA-C*05:109, HLA-C*05:11, HLA-C*05:110, HLA-C*05:111, HLA-C*05:112, HLA-C*05:113N, HLA-C*05:114, HLA-C*05:115, HLA-C*05:116, HLA-C*05:117, HLA-C*05:118, HLA-C*05:119, HLA-C*05:12, HLA-C*05:120, HLA-C*05:121, HLA-C*05:122, HLA-C*05:123, HLA-C*05:124, HLA-C*05:125, HLA-C*05:126, HLA-C*05:127, HLA-C*05:128N, HLA-C*05:129, HLA-C*05:13, HLA-C*05:130, HLA-C*05:131, HLA-C*05:132, HLA-C*05:133, HLA-C*05:134, HLA-C*05:135, HLA-C*05:136, HLA-C*05:137, HLA-C*05:138, HLA-C*05:139, HLA-C*05:14, HLA-C*05:140, HLA-C*05:141, HLA-C*05:142, HLA-C*05:143, HLA-C*05:144, HLA-C*05:145, HLA-C*05:146, HLA-C*05:147, HLA-C*05:148, HLA-C*05:149, HLA-C*05:15, HLA-C*05:150, HLA-C*05:151, HLA-C*05:152, HLA-C*05:153N, HLA-C*05:154N, HLA-C*05:155, HLA-C*05:156, HLA-C*05:157, HLA-C*05:158, HLA-C*05:159, HLA-C*05:16, HLA-C*05:160, HLA-C*05:161, HLA-C*05:162, HLA-C*05:163, HLA-C*05:164, HLA-C*05:165, HLA-C*05:166, HLA-C*05:167, HLA-C*05:168, HLA-C*05:169N, HLA-C*05:17, HLA-C*05:170, HLA-C*05:171:01:01, HLA-C*05:171:01:02, HLA-C*05:172, HLA-C*05:173, HLA-C*05:174, HLA-C*05:175N, HLA-C*05:

176, HLA-C*05:177, HLA-C*05:178, HLA-C*05:179, HLA-C*05:180N, HLA-C*05:181, HLA-C*05:182, HLA-C*05:183, HLA-C*05:184, HLA-C*05:185, HLA-C*05:186, HLA-C*05:187, HLA-C*05:188, HLA-C*05:189, HLA-C*05:18:01, HLA-C*05:18:02, HLA-C*05:18:03, HLA-C*05:18:04, HLA-C*05:18:05, HLA-C*05:19, HLA-C*05:190, HLA-C*05:191, HLA-C*05:192, HLA-C*05:193, HLA-C*05:194, HLA-C*05:195, HLA-C*05:196, HLA-C*05:197, HLA-C*05:198, HLA-C*05:199, HLA-C*05:20, HLA-C*05:200, HLA-C*05:201, HLA-C*05:202Q, HLA-C*05:203, HLA-C*05:21, HLA-C*05:22:01, HLA-C*05:22:02, HLA-C*05:23, HLA-C*05:24, HLA-C*05:25, HLA-C*05:26, HLA-C*05:27, HLA-C*05:28, HLA-C*05:29:01, HLA-C*05:29:02, HLA-C*05:30, HLA-C*05:31, HLA-C*05:32, HLA-C*05:33, HLA-C*05:34, HLA-C*05:35, HLA-C*05:36, HLA-C*05:37, HLA-C*05:38, HLA-C*05:39, HLA-C*05:40, HLA-C*05:41, HLA-C*05:42, HLA-C*05:43, HLA-C*05:44:01, HLA-C*05:44:02, HLA-C*05:45, HLA-C*05:46, HLA-C*05:47, HLA-C*05:48N, HLA-C*05:49, HLA-C*05:50, HLA-C*05:51Q, HLA-C*05:52, HLA-C*05:53, HLA-C*05:54, HLA-C*05:55, HLA-C*05:56, HLA-C*05:57, HLA-C*05:58:01, HLA-C*05:58:02, HLA-C*05:58:03, HLA-C*05:58:04, HLA-C*05:59, HLA-C*05:60, HLA-C*05:61, HLA-C*05:62, HLA-C*05:63, HLA-C*05:64:01, HLA-C*05:64:02, HLA-C*05:65, HLA-C*05:66, HLA-C*05:67, HLA-C*05:68, HLA-C*05:69, HLA-C*05:70, HLA-C*05:71, HLA-C*05:72, HLA-C*05:73, HLA-C*05:74, HLA-C*05:75, HLA-C*05:76, HLA-C*05:77, HLA-C*05:78:01, HLA-C*05:78:02, HLA-C*05:79, HLA-C*05:80, HLA-C*05:81, HLA-C*05:82, HLA-C*05:83, HLA-C*05:84, HLA-C*05:85, HLA-C*05:86, HLA-C*05:87, HLA-C*05:88, HLA-C*05:89, HLA-C*05:90, HLA-C*05:91N, HLA-C*05:92N, HLA-C*05:93, HLA-C*05:94, HLA-C*05:95, HLA-C*05:96, HLA-C*05:97, HLA-C*05:98, and HLA-C*05:99N.

II.E. Cells Expressing TCRs

Certain aspects of the present disclosure are directed to cells comprising a nucleic acid molecule disclosed herein, a vector disclosed herein, a recombinant TCR disclosed herein, a bispecific TCR disclosed herein, or any combination thereof. Any cell can be used in the present disclosure.

In certain embodiments, the cell expresses CD3. CD3 expression can be naturally occurring, e.g., the CD3 is expressed from a nucleic acid sequence that is endogenously expressed by the cell. For example, T cells and natural killer (NK) cells naturally express CD3. Thus, in some embodiments, the cell is a T cell or a natural killer cell. In certain embodiments, the cell is a T cell selected from a natural killer T (NKT) cell and an innate lymphoid cell (ILC).

In some embodiments, the T cell is isolated from a human subject. In some embodiments, the human subject is the same subject that will ultimately receive the T cell therapy. In other embodiments, the subject is a donor subject, wherein the donor subject is not the same subject that will receive the T cell therapy.

In some embodiments, the cell is a cell that does not naturally express CD3, wherein the cell has been modified to express CD3. In some embodiments, the cell comprises a transgene encoding CD3, wherein the transgene is expressed by the cell. In some embodiments, the cell comprises a transgene encoding a protein that activates expression of endogenous CD3 by the cell. In some embodiments, the cell comprises a transgene encoding a protein or siRNA that inhibits an inhibitor of CD3 expression in the cell. In some embodiments, the transgene is incorporated into the genome of the cell. In some embodiments, the transgene is not incorporated into the genome of the cell.

In some embodiments, the cell that is modified to express CD3 is isolated from a human subject. In some embodiments, the human subject is the same subject that will ultimately receive the cell therapy. In other embodiments, the subject is a donor subject, wherein the donor subject is not the same subject that will receive the cell therapy.

II.F. Vaccines

Certain aspects of the present disclosure a cancer vaccine comprising a peptide comprising an amino acid sequence as set forth in SEQ ID NO: 13. In some embodiments, the cancer vaccine comprises a peptide that consists of the amino acid sequence set forth in SEQ ID NO: 13. In some embodiments, the vaccine further comprises one or more excipient. In some embodiments, the vaccine further comprises one or more additional peptides. In some embodiments, the one or more additional peptides comprise one or more additional epitopes.

III. Methods of the Disclosure

Certain aspects of the present disclosure are directed to methods of treating a cancer in a subject in need thereof. Other aspects of the present disclosure are directed to methods of engineering an antigen-targeting cell. Other aspects of the present disclosure are directed to methods of enriching a target population of T cells obtained from a human subject.

III.A. Methods of Treating Cancer

Certain aspects of the present disclosure are directed to methods of treating a cancer in a subject in need thereof, comprising administering to the subject a nucleic acid molecule disclosed herein, a recombinant TCR disclosed herein, a bispecific TCR disclosed herein, an epitope disclosed herein, or an HLA class I molecule disclosed herein, or a vector or cell comprising any of the above.

In some embodiments, the cancer is selected from melanoma, bone cancer, renal cancer, prostate cancer, breast cancer, colon cancer, lung cancer, cutaneous or intraocular malignant melanoma, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In some embodiments, the cancer melanoma.

In some embodiments, the cancer is relapsed. In some embodiments, the cancer is refractory. In some embodiments, the cancer is advanced. In some embodiments, the cancer is metastatic.

In some embodiments, the methods disclosed herein treat a cancer in a subject. In some embodiments, the methods disclosed herein reduce the severity of one or more symptom of the cancer. In some embodiments, the methods disclosed herein reduce the size or number of a tumor derived from the cancer. In some embodiments, the methods disclosed herein increase the overall survival of the subject, relative to a subject not provided the methods disclosed herein. In some embodiments, the methods disclosed herein increase the progressive-free survival of the subject, relative to a subject not provided the methods disclosed herein. In some embodiments, the methods disclosed herein lead to a partial response in the subject. In some embodiments, the methods disclosed herein lead to a complete response in the subject.

In some embodiments, the methods disclosed herein comprise treating a cancer in a subject in need thereof, comprising administering to the subject a cell described herein, wherein the cell comprises a nucleic acid molecule disclosed herein, a vector disclosed herein, a recombinant TCR disclosed herein, and/or a bispecific antibody disclosed herein. In some embodiments, the cell is a T cell. In some embodiments, the cell is a cell that is modified to express CD3.

In some embodiments, the cell, e.g., a T cell, is obtained from the subject. In some embodiments, the cell, e.g., a T cell, is obtained from a donor other than the subject.

In some embodiments, the subject is preconditioned prior to administering the cells. The preconditioning can comprise any substance that promotes T cell function and/or survival. In some embodiments, the preconditioning comprises administering to the subject a chemotherapy, a cytokine, a protein, a small molecule, or any combination thereof. In some embodiments, the preconditioning comprises administering an interleukin. In some embodiments, the preconditioning comprises administering IL-2, IL-4, IL-7, IL-9, IL-15, IL-21, or any combination thereof. In some embodiments, the preconditioning comprises administering cyclophosphamide, fludarabine, or both. In some embodiments, the preconditioning comprises administering vitamin C, an AKT inhibitor, ATRA (vesanoid, tretinoin), rapamycin, or any combination thereof.

III.B. Methods of Engineering an Antigen-Targeting Cell

Certain aspects of the present disclosure are directed to methods of engineering an antigen-targeting cell. In some embodiments, the antigen is selected from the group consisting of a tyrosinase antigen, a MAGE-A1 antigen, a MART1 antigen, a MAGE-A3 antigen, an SSX antigen, and any combination thereof. In some embodiments, the method comprises transducing a cell with a nucleic acid molecule disclosed herein or a vector disclosed herein. The cell can be any cell described herein. In some embodiments, the cell is a T cell described herein. In some embodiments, the cell is a cell that is modified to express CD3, as described herein. In some embodiments, the cell, e.g., the T cell, is obtained from a subject in need of a T cell therapy. In some embodiments, the cell is obtained from a donor other than the subject in need of the T cell therapy. In some embodiments, the cell is a T cell or a natural killer cell.

III.C. Methods of Enriching a Target Population of T Cells

Certain aspects of the present disclosure are directed to methods of enriching a target population of T cells obtained from a human subject. In some embodiments, the method comprises contacting the T cells with an HLA class I molecule disclosed herein. In some embodiments, the method comprises contacting the T cells with an APC disclosed herein. In some embodiments, following the contacting, the enriched population of T cells comprises a higher number of T cells capable of binding the HLA class I molecule relative to the number of T cells capable of binding the HLA class I molecule prior to the contacting.

In some embodiments, the method comprises contacting the T cells in vitro with a peptide, wherein the peptide comprises an amino acid sequence selected from the group consisting of SEQ ID NOs: 51, 52, 53, 54, 55, and any combination thereof. In some embodiments, the method comprises contacting the T cells in vitro with a peptide, wherein the peptide consists of an amino acid sequence selected from the group consisting of SEQ ID NOs: 51, 52, 53, 54, 55, and any combination thereof. In some embodiments, following the contacting, the enriched population of T cells comprises a higher number of T cells capable of binding the HLA class I molecule relative to the number of T cells capable of binding the HLA class I molecule prior to the contacting.

Some aspects of the present disclosure are directed to a method of selecting a T cell capable of targeting a tumor cell. In some embodiments, the method comprises contacting a population of isolated T cells in vitro with a peptide, wherein the peptide consists of an amino acid sequence selected from the group consisting of SEQ ID NOs: 51, 52, 53, 54, 55, and any combination thereof. In some embodiments, the T cells are obtained from a human subject.

The T cells obtained from the human subject can be any T cells disclosed herein. In some embodiments, the T cells obtained from the human subject are tumor infiltrating lymphocytes (TIL).

In some embodiments, the method further comprises administering to the human subject the enriched T cells. In some embodiments, the subject is preconditioned prior to receiving the T cells, as described herein.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this disclosure, a further understanding can be obtained by reference to the examples provided herein. These examples are for purposes of illustration only and are not intended to be limiting.

EXAMPLES

Example 1—Methods

Cell Samples

Peripheral blood samples were obtained from healthy donors. Mononuclear cells were obtained via density gradient centrifugation (Ficoll-Paque PLUS; GE Healthcare). K562 is an erythroleukemic cell line with defective HLA expression. T2 is an HLA-A*02:01$^+$ T cell leukemia/B-LCL hybrid cell line. Jurkat 76 is a T cell leukemic cell line lacking TCR and CD8 expression. The K562, T2, and Jurkat 76 cell lines were cultured in RPMI 1640 supplemented with 10% FBS and 50 μg/ml gentamicin (Invitrogen). TILs isolated from a metastatic melanoma patient were grown in vitro.

Tyrosinase: Me275 and MCF7 cell lines were grown in DMEM supplemented with 10% FBS and 50 μg/ml gentamicin (Invitrogen). Melme-3M cell line was grown in IMDM supplemented with 20% FBS and 50 μg/ml gentamicin (Invitrogen).

MAGE-A1: Me275, SK-MEL-37, and SK-MEL-21 cell lines were grown in DMEM supplemented with 10% FBS and 50 μg/ml gentamicin (Invitrogen).

MART1: A375 and SK-MEL-28 cell lines were grown in DMEM supplemented with 10% FBS and 50 μg/ml gentamicin (Invitrogen). Malme-3M cell line was grown in IMDM supplemented with 20% FBS and 50 μg/ml gentamicin.

MAGE-A3: SK-MEL-28 and HEK293T cell lines were grown in DMEM supplemented with 10% FBS and 50 μg/ml gentamicin (Invitrogen).

SSX2: SK-MEL-21, SK-MEL-37, and SK-MEL-28 cell lines were grown in DMEM supplemented with 10% FBS and 50 μg/ml gentamicin (Invitrogen).

Peptides

Synthetic peptides were dissolved to 50 μg/ml in DMSO.

Tyrosinase: Peptides used were C*05:01-restricted tyrosinase$_{460-468}$ (FQDYIKSYL; SEQ ID NO: 51) and HIV rev$_{67-75}$ (SAEPVPLQL; SEQ ID NO: 82) peptides. The HIV rev$_{67-75}$ peptide was utilized as a negative control.

MAGE-A1: Peptides used were B*07:02-restricted MAGE-A1$_{289-297}$ (RVRFFFPSL; SEQ ID NO: 52), NY-ESO-1$_{60-72}$ (APRGPHGGAASGL; SEQ ID NO: 83), EBV EBNA3A379-387 (RPPIFIRRL; SEQ ID NO: 84), and HIV nef$_{128}$-137 (TPGPGVRYPL; SEQ ID NO: 85) peptides. The NY-ESO-1$_{60-72}$, EBV EBNA3A379-387, and HIV nef$_{128-137}$ peptides were utilized as negative controls.

MART1: Peptides used were 20-mer overlapping peptides to cover the whole protein of MART1 and B*18:01-restricted MART1$_{25-33}$ (EEAAGIGIL; SEQ ID NO: 53), MAGE-A3$_{167-176}$ (MEVDPIGHLY; SEQ ID NO: 54), and HIV gag$_{161-170}$ (FRDYVDRFYK; SEQ ID NO: 86) peptides. The MAGE-A3$_{167-176}$ and HIV gag$_{161-170}$ peptides were utilized as negative controls.

MAGE-A3: Peptides used were B*18:01-restricted MAGE-A3$_{167-176}$ (MEVDPIGHLY; SEQ ID NO: 54), MART1$_{25-33}$ (EEAAGIGIL; SEQ ID NO: 53) and HIV gag$_{161-170}$ (FRDYVDRFYK; SEQ ID NO: 86) peptides. The MART1$_{25-33}$ and HIV gag$_{161-170}$ peptide was utilized as negative controls.

SSX2: Peptides used were A*02:01-restricted SSX2$_{41-49}$ (KASEKIFYV; SEQ ID NO: 55), NY-ESO-1$_{157-165}$ (SLLMWITQV; SEQ ID NO: 87), and HTLV-1 tax$_{11-19}$ (LLFGYPVYV; SEQ ID NO: 88) peptides. The NY-ESO-1$_{157-165}$ and HTLV-1 tax$_{11-19}$ peptides were utilized as negative controls.

Genes

Each of the HLA C*05:01, B*07:02, and B*18:01 genes, as applicable, was fused with a truncated version of the human nerve growth factor receptor (ΔNGFR) via the internal ribosome entry site. ΔNGFR-transduced cells were isolated using anti-NGFR mAb. The full-length tyrosinase gene was cloned from SK-MEL-28 cells via RT-PCR according to the published sequence. The full-length MART1 gene was cloned from Malme-3M cells via RT-PCR according to the published sequence. The full-length SSX2 gene was cloned from SK-MEL-37 cells via RT-PCR according to the published sequence. TCR genes were cloned by 5'-rapid amplification of cDNA ends (RACE) PCR using a SMARTer RACE cDNA amplification kit (Takara Bio). The 5'-RACE PCR products were cloned into a retrovirus vector and sequenced. All genes were cloned into the pMX retrovirus vector and transduced using the 293GPG cell-based retrovirus system.

Transfectants

Jurkat 76/CD8 cells were transduced with individual TCRα and TCRβ genes. The Jurkat 76/CD8-derived TCR transfectants were purified (>95% purity) using CD3 Microbeads (Miltenyi Biotec). The K562-based artificial APCs individually expressing various HLA class I genes as a single HLA allele in conjunction with CD80 and CD83 have been reported previously (Butler and Hirano, *Immunol. Rev.* 257:191-209 (2014); Hirano et al., *Clin. Cancer Res.* 12:2967-75 (2006)). PG13-derived retrovirus supernatants were used to transduce TCR genes into human primary T cells. TransIT293 (Minis Bio) was used to transfect TCR genes into the 293GPG cell line.

Tyrosinase⁻ MCF7 cells were retrovirally transduced with the full-length tyrosinase gene to generate MCF7/tyrosinase cells. The expression of transduced tyrosinase was evaluated by flow cytometry after staining with an anti-tyrosinase monoclonal antibody (mAb) (clone ERP10141; Abcam). HLA-C*05:01⁻ Malme-3M and Me275 cells were retrovirally transduced with HLA-C*05:01 to generate Malme-3M/C*05:01 and Me275/C*05:01 cells. HLA-C*05:01 gene were tagged with the ΔNGFR gene as described above, and the ΔNGFR⁺ cells were purified (>95% purity) and used in subsequent experiments. The ΔNGFR gene alone was retrovirally transduced as a control.

MAGE-A1⁻ SK-MEL-21 cells were retrovirally transduced with the full-length MAGE-A1 gene to generate SK-MEK-21/MAGE-A1 cells. The expression of transduced MAGE-A1 was evaluated by flow cytometry after staining with an anti-MAGE-A1 mAb (clone MA454; LifeSpan Biosciences). HLA-B*07:02⁻ Me275 and SK-MEL-37 cells were retrovirally transduced with HLA-B*07:02 to generate Me275/B*07:02 and SK-MEL-37/B*07:02 cells. HLA-B*07:02 gene were tagged with the ΔNGFR gene as described above, and the Δ NGFR⁺ cells were purified (>95% purity) and used in subsequent experiments. The ΔNGFR gene alone was retrovirally transduced as a control.

MART1⁻ A375 cells were retrovirally transduced with the full-length MART1 gene to generate A375/MART1 cells. The expression of transduced MART1 was evaluated by flow cytometry after staining with an anti-MART1 mAb (clone A103; Santa Cruz Biotechnology). HLA-B*18:01⁻ Malme-3M, SK-MEL-28, and A375 cells were retrovirally transduced with HLA-B*18:01 to generate Malme-3M/B*18:01, SK-MEL-28B*18:01, and A375/B*18:01 cells. HLA-B*18:01 gene were tagged with the ΔNGFR gene as described above, and the Δ NGFR⁺ cells were purified (>95% purity) and used in subsequent experiments. The ΔNGFR gene alone was retrovirally transduced as a control.

MAGE-A3⁻ HEK293T cells were retrovirally transduced with the full-length MAGE-A3 gene to generate HEK293T/MAGE-A3 cells. The expression of MAGE-A3 in the transduced cells was evaluated by Western blot analysis with an anti-MAGE-A3 polyclonal antibody (pAb) (LifeSpan Biosciences). HLA-B*18:01⁻ SK-MEL-28 and HEK293T cells were retrovirally transduced with HLA-B*18:01 to generate SK-MEL-28/B*18:01 and HEK293T/B*18:01 cells. HLA-B*18:01 gene were tagged with the Δ NGFR gene as described above, and the ΔNGFR⁺ cells were purified (>95% purity) and used in subsequent experiments. The ΔNGFR gene alone was retrovirally transduced as a control.

SSX2⁻ SK-MEL-21 and SK-MEL-28 cells were retrovirally transduced with the full-length SSX2 gene to generate SK-MEK-21/SSX2 and SK-MEL-28/SSX2 cells. The expression of SSX2 in the transduced cells was evaluated by Western blot analysis with an anti-SSX2 pAb (Thermo Fisher Scientific). HLA-A*02:01⁻ SK-MEL-28 cells were retrovirally transduced with HLA-A*02:01 to generate SK-MEL-28/A*02:01 cells.

Flow Cytometry and Cell Sorting

Cell surface molecules were stained with a PC5-conjugated anti-CD8 mAb (clone B9.11; Beckman Coulter), FITC-conjugated anti-NGFR (clone ME20.4; Biolegend), and APC/Cy7-conjugated anti-CD3 (clone UCHT1; Biolegend). Dead cells were discriminated with the LIVE/DEAD Fixable Aqua Dead Cell Stain kit (Life Technologies). For intracellular staining, cells were fixed and permeabilized by using a Cytofix/Cytoperm kit (BD Biosciences). Stained cells were analyzed with flow cytometry (BD Biosciences), and data analysis was performed using FlowJo (Tree Star). Cell sorting was conducted using a FACS Aria II (BD Bioscience).

Cytokine ELISPOT Analysis

IFN-γ ELISPOT assays were conducted as described previously (see, e.g., Kagoya et al., *Nat. Commun.* 9:1915 (2018); Anczurowski et al., *Sci. Rep.* 8:4804 (2018); and Yamashita et al., *Nat Commun.* 8:15244 (2017)). PVDF plates (Millipore, Bedford, MA) were coated with the capture mAb (1-D1K; MABTECH, Mariemont, OH), and T cells were incubated with $2 \times 10^4$ target cells per well in the presence or absence of a peptide for 20-24 hours at 37° C. The plates were subsequently washed and incubated with a biotin-conjugated detection mAb (7-B6-1; MABTECH). HRP-conjugated SA (Jackson ImmunoResearch) was then added, and IFN-γ spots were developed. The reaction was stopped by rinsing thoroughly with cold tap water. ELISPOT plates were scanned and counted using an ImmunoSpot plate reader and ImmunoSpot version 5.0 software (Cellular Technology Limited, Shaker Heights, OH).

Expansion of CD8⁺ TILs in an HLA-Restricted Peptide-Specific Manner

When applicable, e.g., for the MAGE-A3 TCRs, CD8⁺ TILs were purified through negative magnetic selection using a CD8⁺ T Cell Isolation Kit (Miltenyi Biotec). B*18:01-artificial APCs were pulsed with 10 μg/mL class I-restricted peptides of interest for 6 hours. The artificial APCs were then irradiated at 200 Gy, washed, and added to the TILs at an effector to target (E:T) ratio of 20:1. Starting on the next day, 10 IU/ml IL-2 (Novartis), 10 ng/ml IL-15 (Peprotech), and 30 ng/ml IL-21 (Peprotech) were added to the cultures every three days.

Expansion of Primary CD8⁺ T Cells Transduced with the Cloned TCR

CD3⁺ T cells were purified through negative magnetic selection using a Pan T Cell Isolation Kit (Miltenyi Biotec). Purified T cells were stimulated with artificial APC/mOKT3 irradiated with 200 Gy at an E:T ratio of 20:1. Starting on the next day, activated T cells were retrovirally transduced with the cloned TCR genes via centrifugation for 1 hour at 1,000 g at 32° C. for 3 consecutive days. On the following day, 100 IU/ml IL-2 and 10 ng/ml IL-15 were added to the TCR-transduced T cells. The culture medium was replenished every 2-3 days.

Production of Mammalian Cell-Based pHLA Multimers

The affinity-matured HLA class I gene was engineered to carry a Glu (E) residue in lieu of the Gln (Q) residue at position 115 of the α2 domain and a mouse $K^b$ gene-derived α3 domain instead of the HLA class I α3 domain. By fusing the extracellular domain of the affinity-matured HLA class I gene with a Gly-Ser (GS) flexible linker followed by a 6×His tag, we generated the soluble HLA class $I^{Q115E}-K^b$ gene. HEK293T cells were individually transduced with various soluble HLA class $I^{Q115E}-K^b$ genes along with the β2m gene using the 293GPG cell-based retrovirus system. Stable HEK293T cells ectopically expressing soluble affinity-matured class $I^{Q115E}$-$K^b$ were grown until confluent, and the medium was then changed. Forty-eight hours later, the conditioned medium was harvested and immediately used or frozen until use. The soluble HLA class $I^{Q115E}$-$K^b$-containing supernatant produced by the HEK293T transfectants was incubated with 100-1000 μg/ml of class I-restricted peptide of interest overnight at 37° C. for in vitro peptide exchange. Soluble monomeric class $I^{Q115E}$-$K^b$ loaded with the peptide was dimerized using an anti-His mAb (clone AD1.1.10; Abcam) conjugated to a fluorochrome such as phycoerythrin (PE) at a 2:1 molar ratio for 2 hours at room temperature or overnight at 4° C. The concentration of functional soluble HLA class $I^{Q115E}$E-$K^b$ molecules was measured by specific ELISA using an anti-pan class I mAb (clone W6/32, in-house) and an anti-His tag biotinylated mAb (clone AD1.1.10, R&D systems) as capture and detection Abs, respectively.

pHLA Multimer Staining

T cells ($1 \times 10^5$) were incubated for 30 minutes at 37° C. in the presence of 50 nM dasatinib (LC laboratories). The cells were then washed and incubated with 5-10 μg/ml of multimer for 30 minutes at room temperature, and R-phycoerythrin-conjugated AffiniPure Fab fragment goat anti-mouse IgG1 (Jackson ImmunoResearch Laboratories) was added for 15 minutes at 4° C. Next, the cells were washed three times and co-stained with an anti-CD8 mAb for 15 minutes at 4° C. Dead cells were finally discriminated using the LIVE/DEAD Fixable Dead Cell Stain kit.

Statistical Analysis

Statistical analysis was performed using GraphPad Prism 5.0e. A Welch's t test (two-sided) analysis was conducted to determine whether two groups were significantly different for a given variable. P values <0.05 were considered significant.

Example 2—Tyrosinase-Specific TCR

Figure 2:
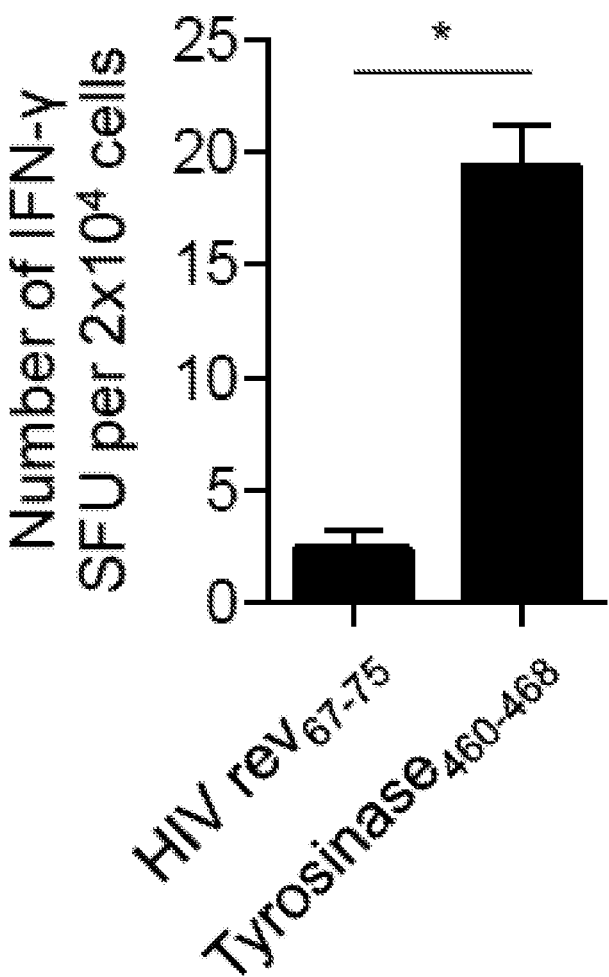
FIG. 2 is a bar graph illustrating the functional assessment of C*05:01/tyrosinase$_{460-468}$ multimer-positive melanoma TILs. IFN-γ production by C*05:01-positive TILs in an HLA-C*05:01-restricted peptide-specific manner. The TILs were employed as responder cells in IFN-γ ELISPOT analysis. C*05:01-artificial APCs pulsed with the indicated peptides were used as stimulator cells. The HIV rev$_{67-75}$ peptide was employed as a control. Experiments were carried out in triplicate, and error bars depict standard deviation (SD). *P<0.05.

Tumor infiltrating lymphocytes (TILs) were isolated from a metastatic melanoma patient, then polyclonally expanded in vitro, and their tyrosinase antigen specificity for HLA-C*05:01 allele was examined. The combination of structure-based analysis using peptide/HLA (pHLA) multimers and functional analysis has been used to measure antigen-specific T cell responses. The T cells were stained using pHLA multimer with tyrosinase$_{460-468}$ peptide (FIG. 1). The TILs showed positivity for C*05:01/tyrosinase$_{460-468}$ multimer. The multimer-positive T cells secreted detectable IFN-γ in an HLA-restricted peptide-specific manner according to ELISPOT analysis (FIG. 2).

Figure 3:
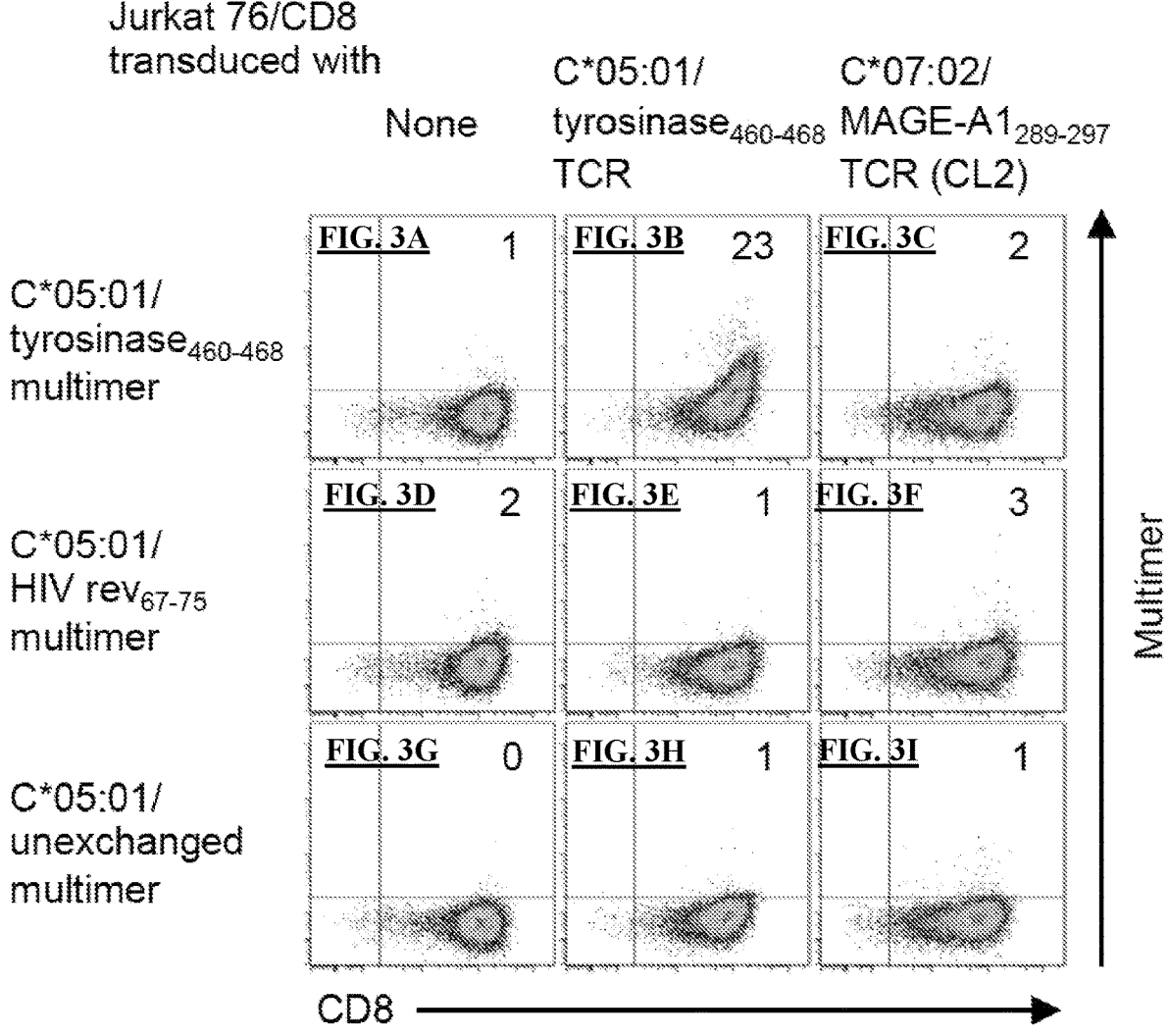
FIGS. 3A-3I are graphical representations of positive staining of Jurkat 76/CD8 cells transduced with C*05:01/tyrosinase$_{460-468}$ TCR genes with a cognate multimer. Jurkat 76/CD8 cells transduced with the C*05:01/tyrosinase$_{460-468}$ TCR (FIGS. 3B, 3E, and 3H) were stained with the C*05:01/tyrosinase$_{460-468}$ multimer (FIG. 3B). The C*05:01/HIV rev$_{67-75}$ multimer (FIGS. 3D, 3E, and 3F), C*05:01/unexchanged multimer (FIGS. 3G, 3H, and 3I), and C*07:02/MAGE-A1$_{289-297}$ TCR (clone CL2.
Figure 4:
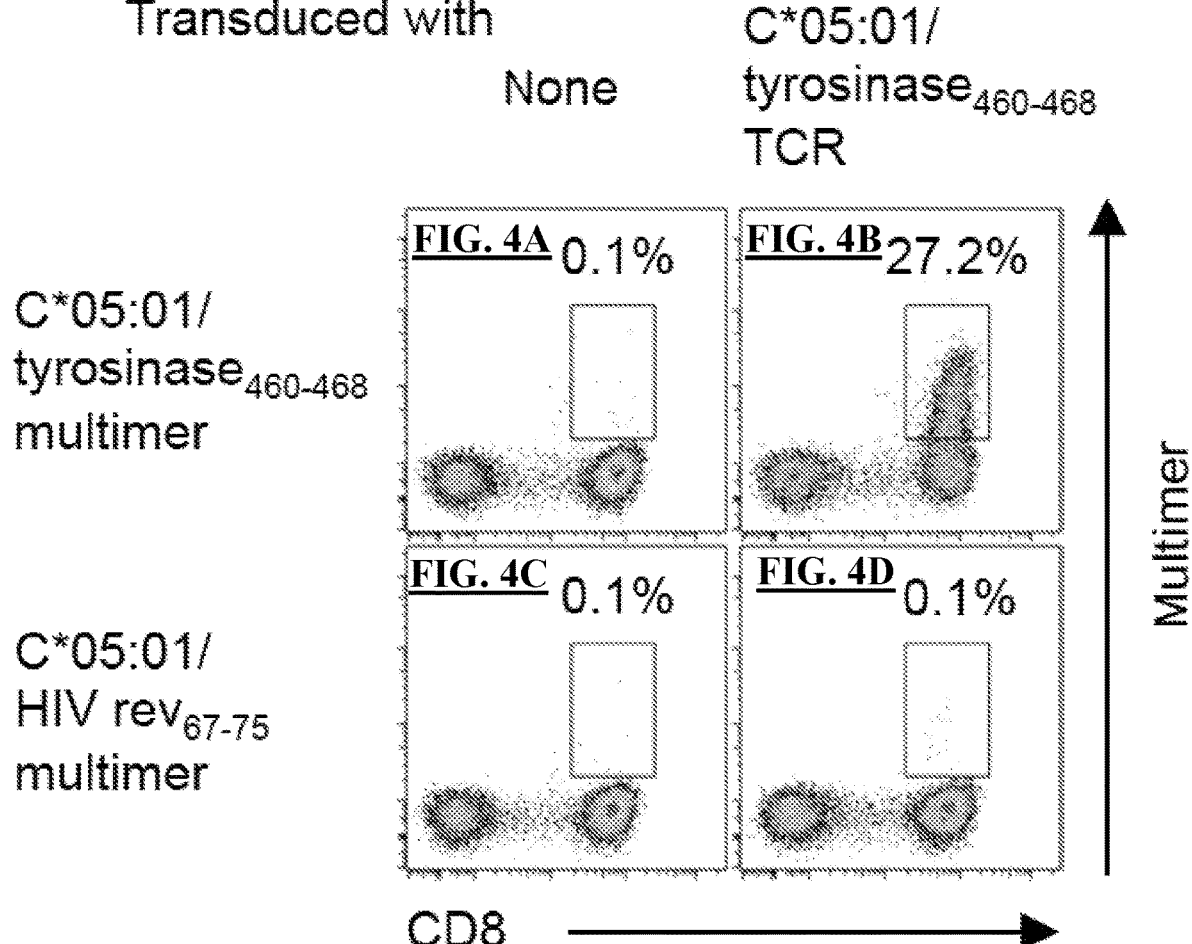
FIGS. 4A-4D are graphical representations of positive staining of human primary T cells transduced with C*05:01/tyrosinase$_{460-468}$ TCR genes (FIGS. 4B and 4D) with a cognate multimer. Primary T cells transduced with the C*05:01/tyrosinase$_{460-468}$ TCR were stained with the C*05:01/tyrosinase$_{460-468}$ (FIG. 4B) or C*05:01/HIV rev$_{67-75}$ control multimer (FIG. 4D). Untransduced primary T cells were employed as negative controls (FIGS. 4A and 4C). The percentage of multimer$^{+}$ CD8$^{+}$ T cells is shown.
Figure 5:
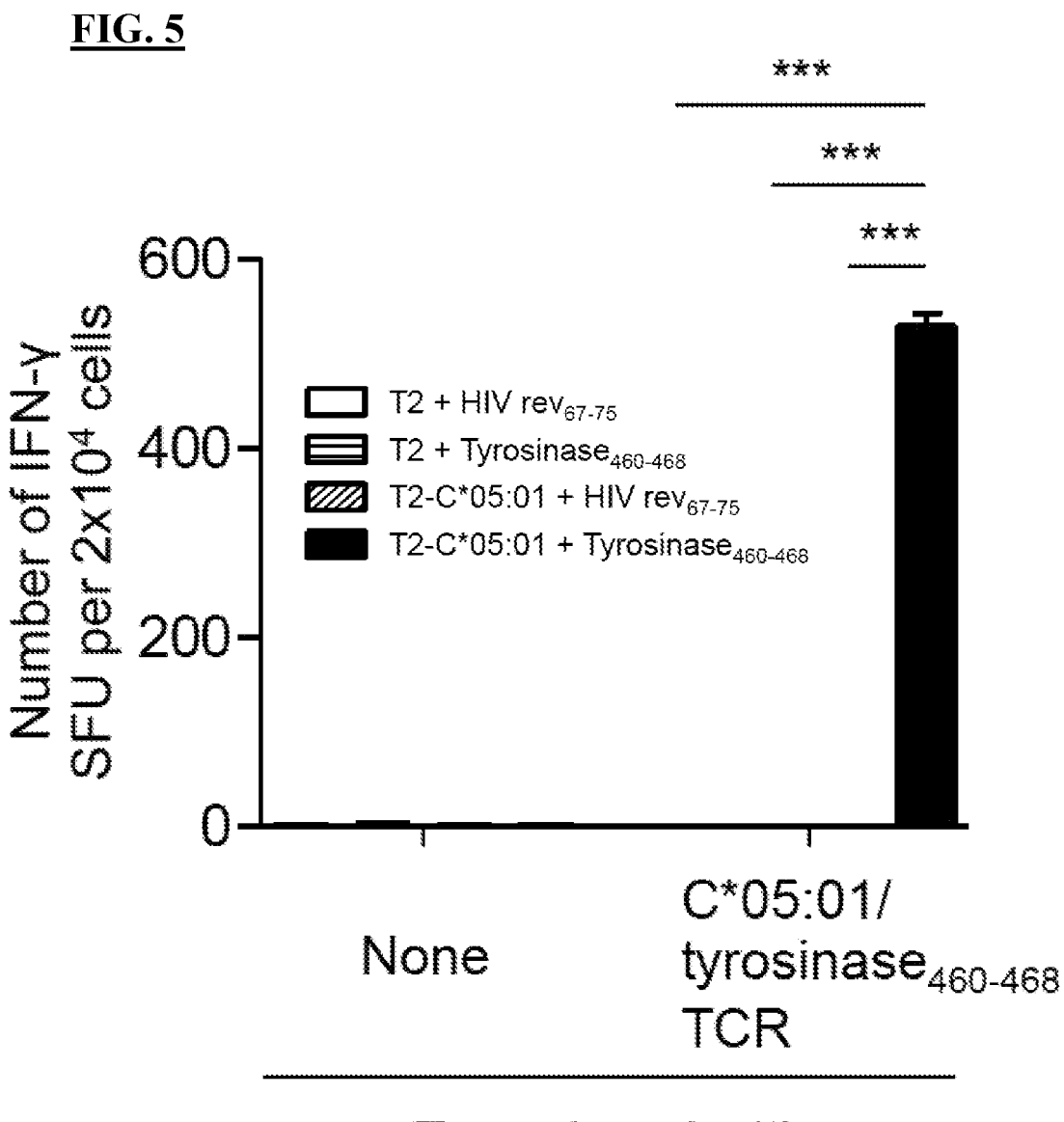
FIG. 5 is a bar graph illustrating that human primary T cells transduced with C*05:01/tyrosinase$_{460-468}$ TCR genes react strongly with the cognate peptide presented by the target class I molecule. Primary T cells transduced with C*05:01/tyrosinase$_{460-468}$ TCR genes or untransduced primary T cells (x-axis) were used as responder cells in IFN-γ ELISPOT analysis. HLA-C*05:01-transduced T2 cells (T2-C*05:01) were generated. T2 or T2-005:01 cells pulsed with the tyrosinase$_{460-468}$ or HIV rev$_{67-75}$ peptide (control) were used as stimulator cells. Experiments were carried out in triplicate, and error bars depict SD. ***P<0.001.
Figures 6A, 6B:
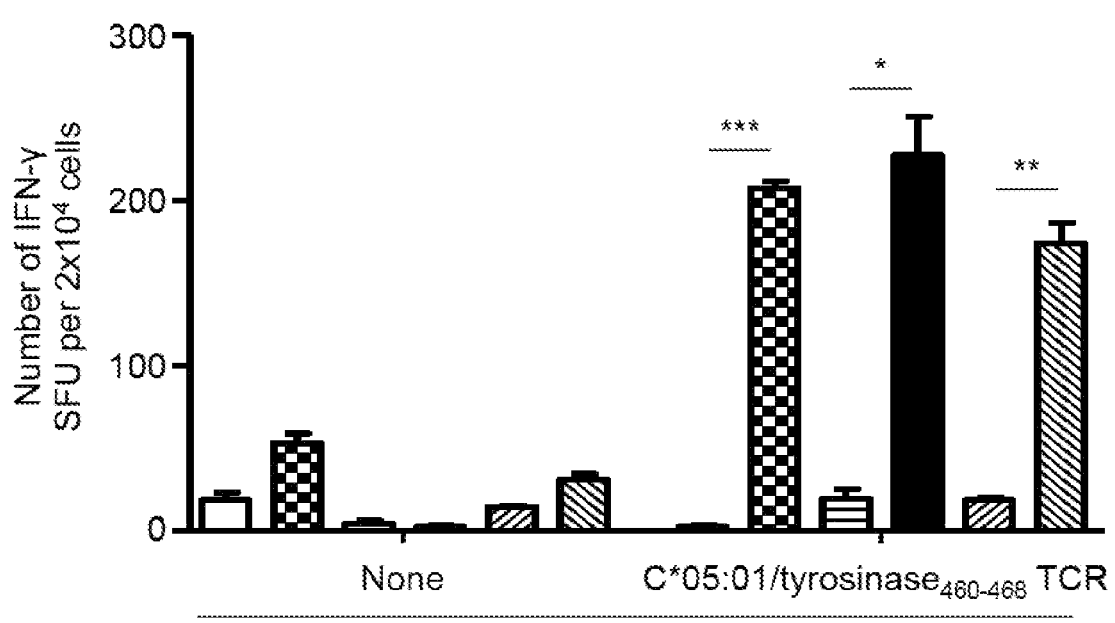
FIG. 6A is a graphical representation illustrating that primary T cells transduced with C*05:01/tyrosinase$_{460-468}$ TCR genes recognize tumor cells. Primary T cells transduced with C*05:01/tyrosinase$_{460-468}$ TCR genes or untransduced primary T cells were employed as responder cells in IFN-γ ELISPOT analysis. Malme-3M, Me275, and MCF7 cells that were either untransduced or transduced with HLA-C*05:01 or tyrosinase, as indicated (FIG. 6B), were employed as stimulator cells following treatment with 100 ng/ml IFNγ for 48 hours. Experiments were carried out in triplicate, and error bars depict SD. *P<0.05, P<0.01, *P<0.001.
Figures 7A, 7B, 7C, 7D:
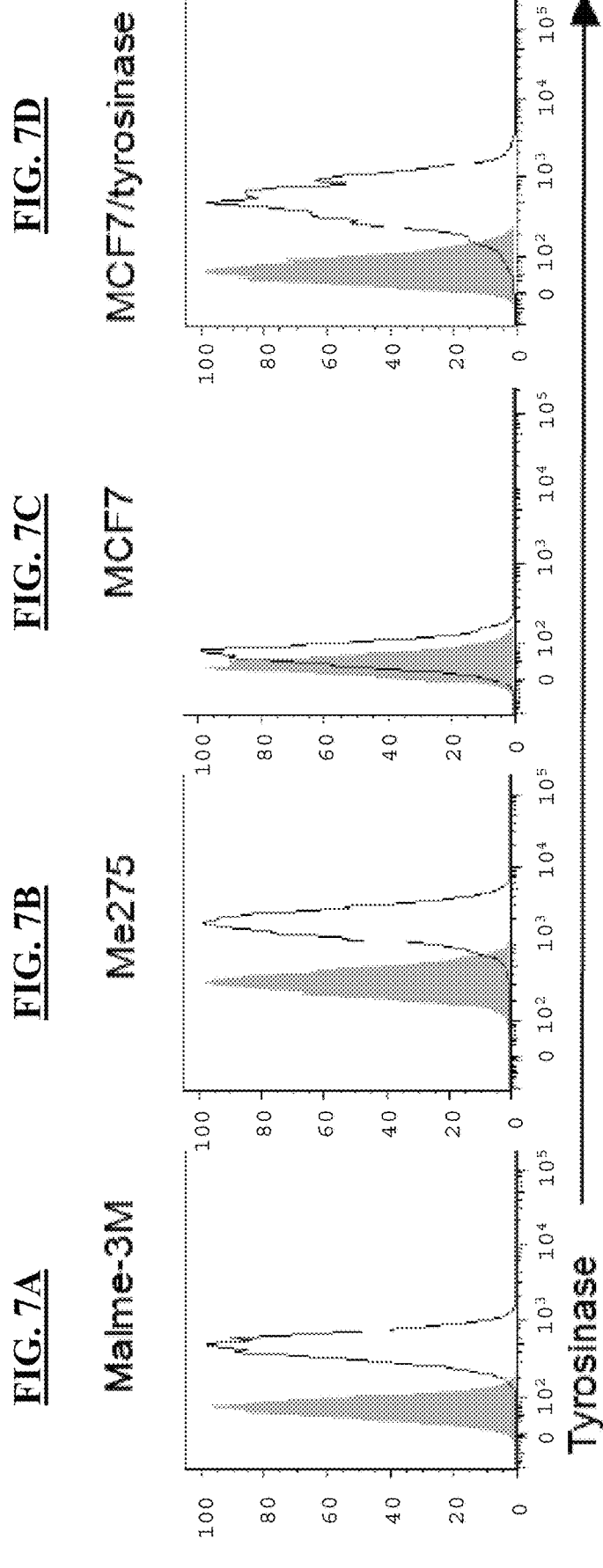
FIGS. 7A-7D are graphical representations of the expression of endogenous or transduced tyrosinase gene. The expression of endogenous or transduced tyrosinase gene in target cells was analyzed via intracellular flow cytometry following staining with anti-tyrosinase mAb (open curve) and an isotype control (filled curve).
Figures 8A, 8B, 8C, 8D:
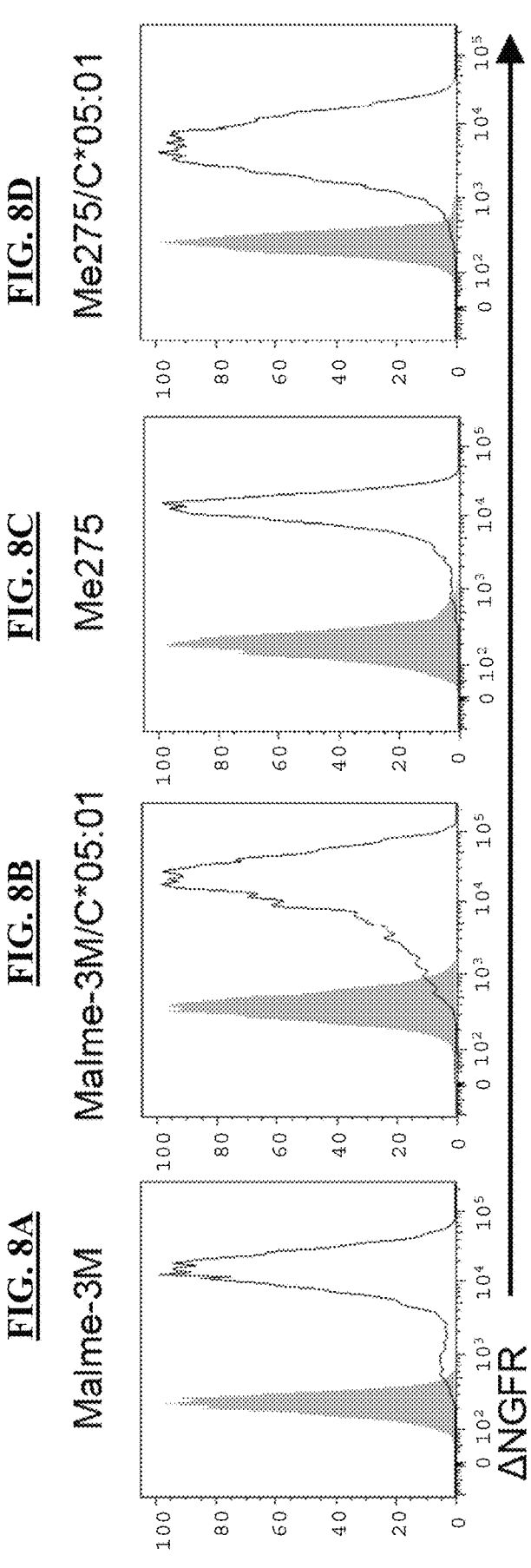
FIGS. 8A-8D are graphical representations of the expression of ΔNGFR in target cells transduced with the full-length HLA-C*05:01 gene tagged with ΔNGFR (FIGS. 8B and 8D). Surface expression of ΔNGFR in target cells transduced with the full-length HLA-C*05:01 gene tagged with ΔNGFR was analyzed by flow cytometry following staining with an anti-NGFR mAb (open curve) and an isotype control (filled curve). ΔNGFR alone was used as a control (FIGS. 8A and 8C).

The multimer-positive antitumor T cells were collected and their TCR genes were molecularly cloned (FIG. 3). The antigen specificity and functional reactivity of the cloned TCR were verified by multimer staining and ELISPOT assay of TCR-reconstituted T cells. When reconstituted on primary T cells, C*05:01/tyrosinase$_{460-468}$ TCR-transduced T cells were successfully stained with the cognate multimer (FIG. 4) and strongly reacted with the tyrosinase$_{460-468}$ peptide presented by surface C*05:01 molecules (FIG. 5). Importantly, these cells were able to recognize C*05:01-matched and peptide-unpulsed tumor cells naturally expressing the tyrosinase gene. Although Malme-3M and Me275 melanoma cell lines are negative for C*05:01, they express the tyrosinase gene endogenously. When C*05:01 molecules were ectopically expressed, both melanoma cell lines were successfully recognized by C*05:01/tyrosinase$_{460-468}$ TCR-transduced T cells. Moreover, MCF7 breast cancer cells, which lack endogenous expression of tyrosinase, became reactive to C*05:01/tyrosinase$_{460-468}$ TCR-transduced T cells when the full-length tyrosinase gene was transduced (FIGS. 6-8). These results clearly demonstrate that the C*05:01/tyrosinase$_{460-468}$ TCR-transduced T cells were sufficiently avid to recognize tumor cells and that the cloned C*05:01/tyrosinase$_{460-468}$ TCR was tumor-reactive.

Example 3—MAGE-A1-Specific TCR

Figures 9A, 9B:
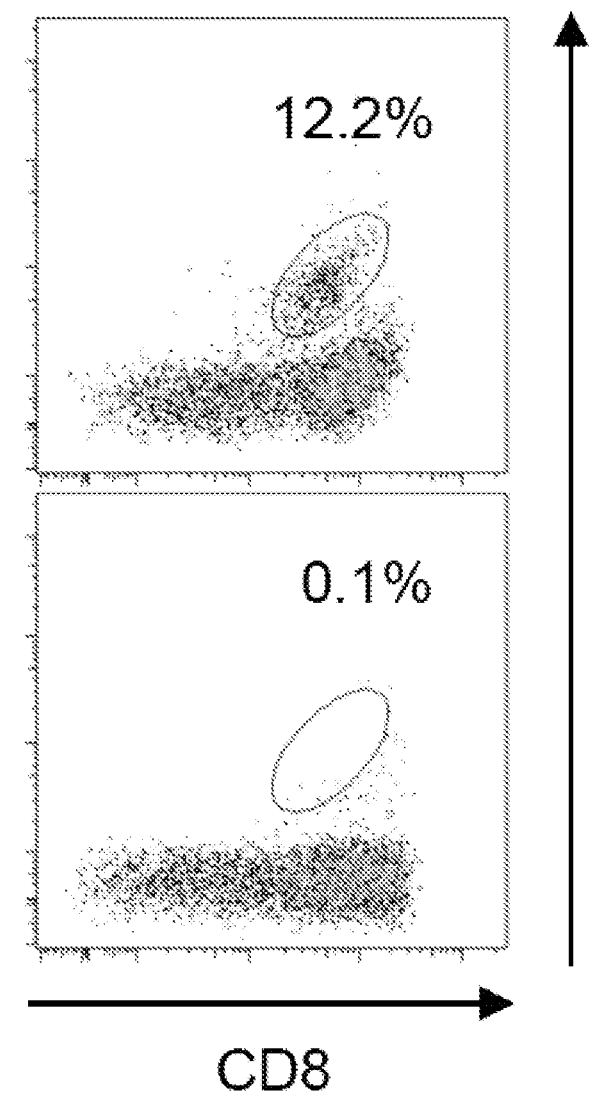
FIGS. 9A-9B are graphical representations of B*07:02/MAGE-A1$_{289-297}$ multimer staining of melanoma TILs.
Figure 10:
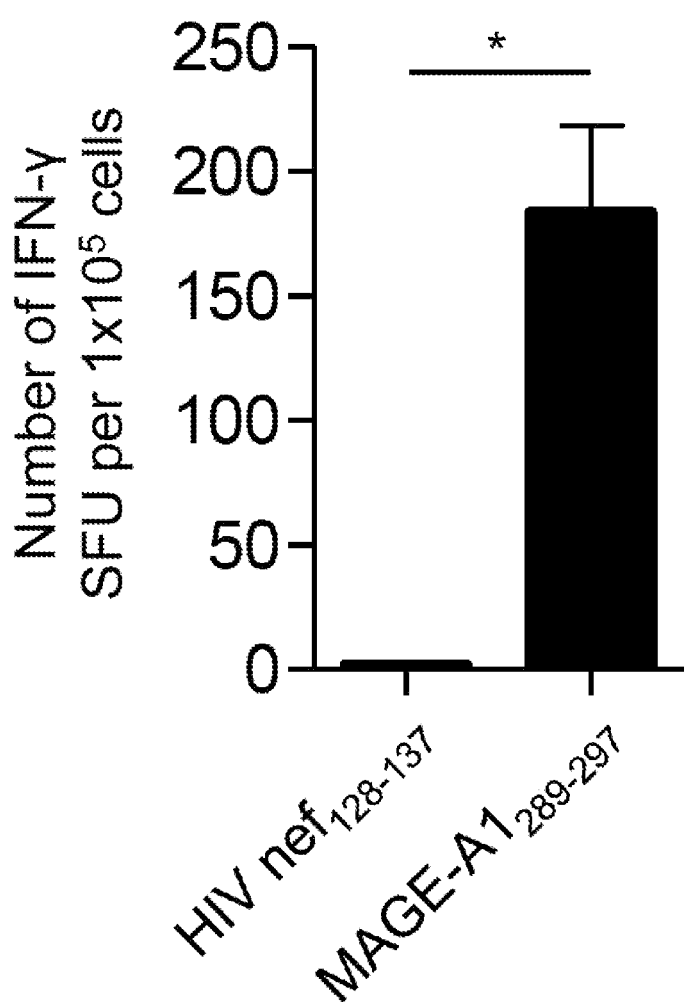
FIG. 10 is a bar graph illustrating the functional assessment of B*07:02/MAGE-A1$_{289-297}$ multimer-positive melanoma TILs. IFN-γ production by the TILs in a B*07:02/MAGE-A1$_{289-297}$-specific manner. The TILs were employed as responder cells in IFN-γ ELISPOT analysis. B*07:02-artificial APCs pulsed with the indicated peptides were used as stimulator cells. The HIV nef$_{128-137}$ peptide was employed as a control. Experiments were carried out in triplicate, and error bars depict standard deviation (SD). *P<0.05.

TILs were isolated from a metastatic melanoma patient, then polyclonally expanded in vitro, and their MAGE-A1 antigen specificity for HLA-B*07:02 allele was examined. The T cells were stained using pHLA multimer with MAGE-A1$_{289-297}$ peptide (FIG. 9). The TILs showed positivity for B*07:02/MAGE-A1$_{289-297}$ multimer. The multimer-positive T cells secreted detectable IFN-γ in an HLA-restricted peptide-specific manner according to ELISPOT analysis (FIG. 10).

Figures 12A, 12B, 12C, 12D:
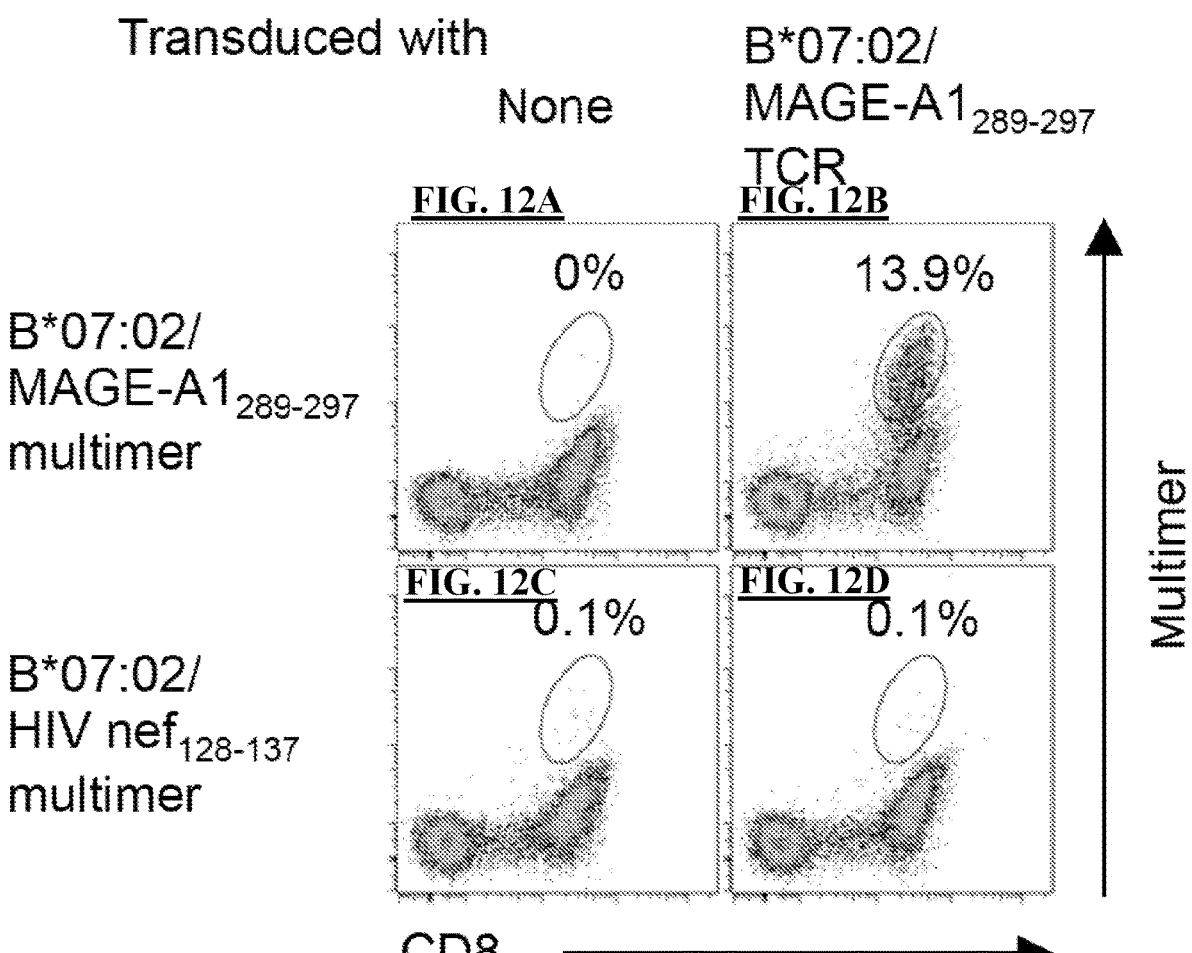
FIGS. 12A-12D are graphical representations of positive staining of human primary T cells transduced with B*07:02/MAGE-A1$_{289-297}$ TCR genes (FIGS. 12B and 12D) with a cognate multimer. Primary T cells transduced with the B*07:02/MAGE-A1$_{289-297}$ TCR were stained with the B*07:02/MAGE-A1$_{289-297}$ (FIG. 12B) or B*07:02/HIV nef$_{128-137}$ control multimer (FIG. 12D). Untransduced primary T cells were employed as negative controls (FIGS. 12A and 12C). The percentage of multimer$^+$ CD8$^+$ T cells is shown.
Figure 13:
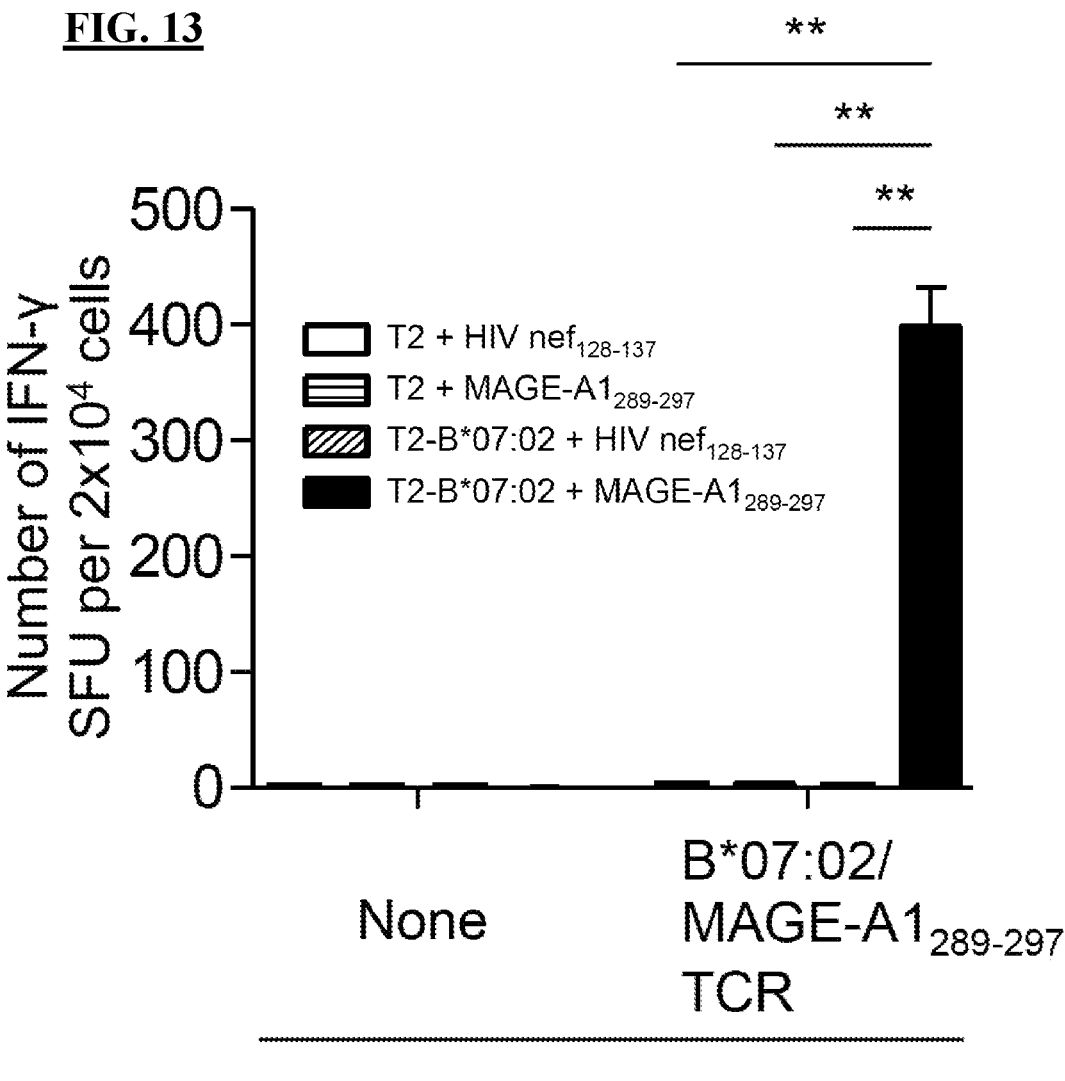
FIG. 13 is a bar graph illustrating that human primary T cells transduced with B*07:02/MAGE-A1$_{289-297}$ TCR genes react strongly with the cognate peptide presented by the target class I molecule. Primary T cells transduced with B*07:02/MAGE-A1$_{289-297}$ TCR genes or untransduced primary T cells (x-axis) were used as responder cells in IFN-γ ELISPOT analysis. HLA-B*07:02-transduced T2 cells (T2-B*07:02) were generated. T2 or T2-B*07:02 cells pulsed with the MAGE-A1$_{289-297}$ or HIV nef$_{128-137}$ peptide (control) were used as stimulator cells. Experiments were carried out in triplicate, and error bars depict SD. **P<0.01.
Figures 14A, 14B:
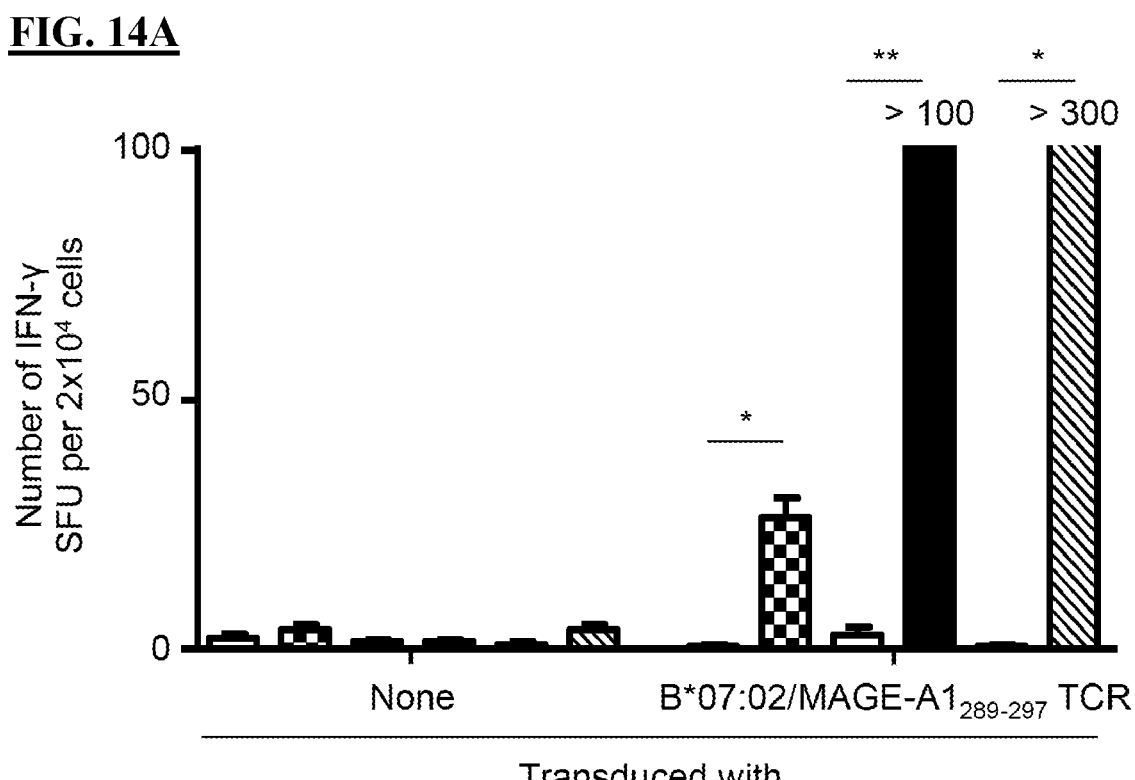
FIG. 14A is a graphical representation illustrating that primary T cells transduced with B*07:02/MAGE-A1$_{289-297}$ TCR genes recognize tumor cells. Primary T cells transduced with B*07:02/MAGE-A1$_{289-297}$ TCR genes or untransduced primary T cells were employed as responder cells in IFN-γ ELISPOT analysis. Me275, SL-MEL-37, and SK-MEL-21 cells that were either untransduced or transduced with HLA-B*07:02 or MAGE-A1, as indicated (FIG. 14B), were employed as stimulator cells. Experiments were carried out in triplicate, and error bars depict SD. *P<0.05, **P<0.01.
Figures 15A, 15B, 15C, 15D:
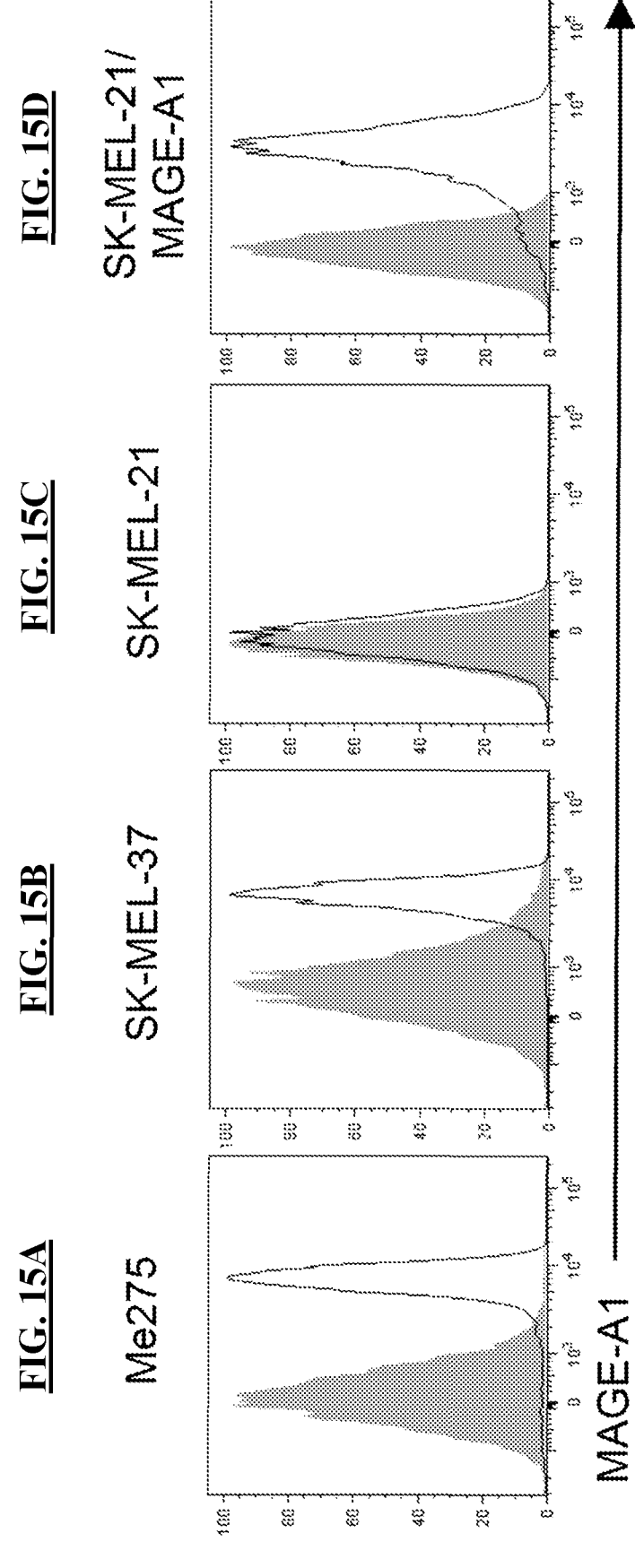
FIGS. 15A-15D are graphical representations of the expression of MAGE-A1 derived from endogenous or transduced full-length gene. The expression of MAGE-A1 derived from endogenous or transduced full-length gene in target cells was analyzed via intracellular flow cytometry following staining with anti-MAGE-A1 mAb (open curve) and an isotype control (filled curve).
Figures 16A, 16B, 16C, 16D:
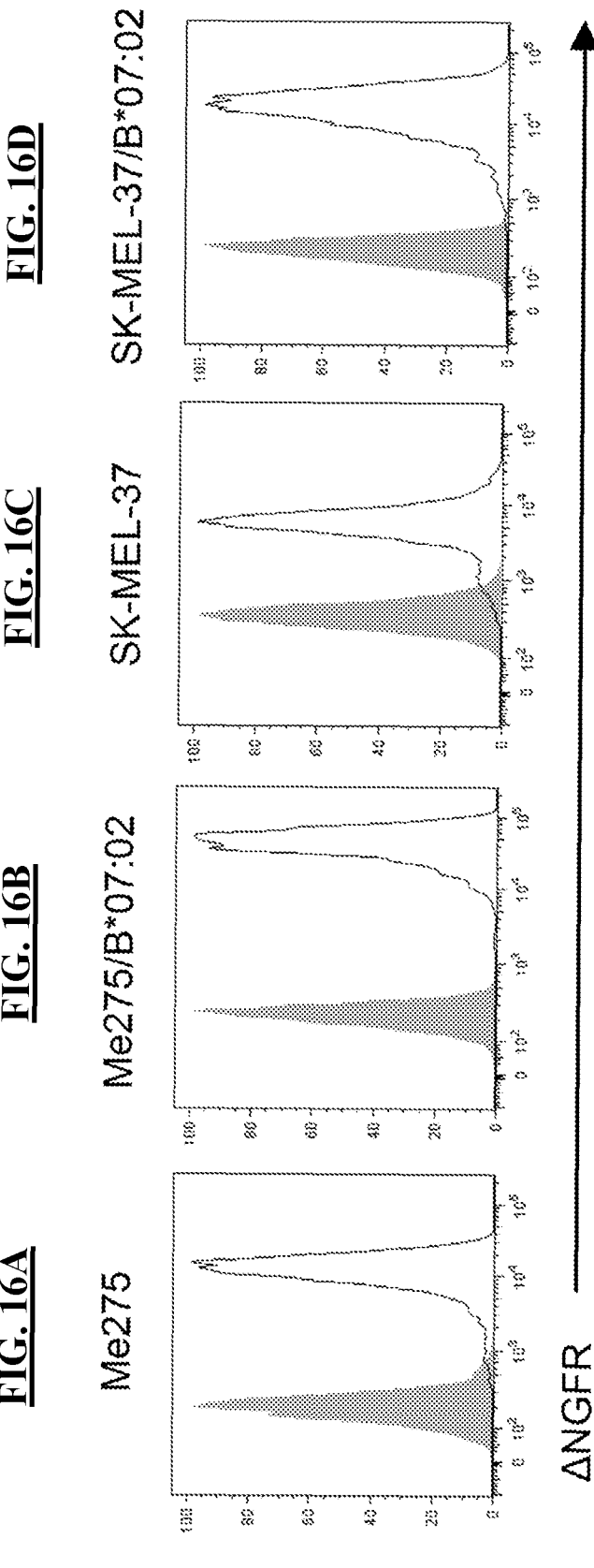
FIGS. 16A-16D are graphical representations of the expression of ΔNGFR in target cells transduced with the full-length HLA-B*07:02 gene tagged with ΔNGFR (FIGS. 16B and 16D). Surface expression of ΔNGFR in target cells transduced with the full-length HLA-B*07:02 gene tagged with ΔNGFR was analyzed by flow cytometry following staining with an anti-NGFR mAb (open curve) and an isotype control (filled curve). ΔNGFR alone was used as a control (FIGS. 16A and 16C).

The multimer-positive antitumor T cells were collected and their TCR genes were molecularly cloned (FIG. 11). The antigen specificity and functional reactivity of the cloned TCR were verified by multimer staining and ELISPOT assay of TCR-reconstituted T cells. When reconstituted on primary T cells, B*07:02/MAGE-A1$_{289-297}$ TCR-transduced T cells were successfully stained with the cognate multimer (FIG. 12) and strongly reacted with the MAGE-A1$_{289-297}$ peptide presented by surface B*07:02 molecules (FIG. 13). Importantly, these cells were able to recognize B*07:02-matched and peptide-unpulsed tumor cells naturally expressing the MAGE-A1 gene. Although both the Me275 and SK-MEL-37 melanoma cell lines are negative for B*07:02, they express the MAGE-A1 gene endogenously. When B*07:02 molecules were ectopically expressed, both melanoma cell lines were successfully recognized by B*07:02/MAGE-A1$_{289-297}$ TCR-transduced T cells. Moreover, SK-MEL-21 melanoma cells, which lack endogenous expression of MAGE-A1, became reactive to B*07:02/MAGE-A1$_{289-297}$ TCR-transduced T cells when the full-length MAGE-A1 gene was transduced (FIGS. 14-16). These results clearly demonstrate that the B*07:02/MAGE-A1$_{289-297}$ TCR-transduced T cells were sufficiently avid to recognize tumor cells and that the cloned B*07:02/MAGE-A1$_{289-297}$ TCR was tumor-reactive.

The use of the newly cloned tumor-reactive B*07:02-restricted MAGE-A1 TCR genes may widen the applicability of anti-MAGE-A1 TCR gene therapy.

Example 4—MART1-Specific TCR

Figure 17:
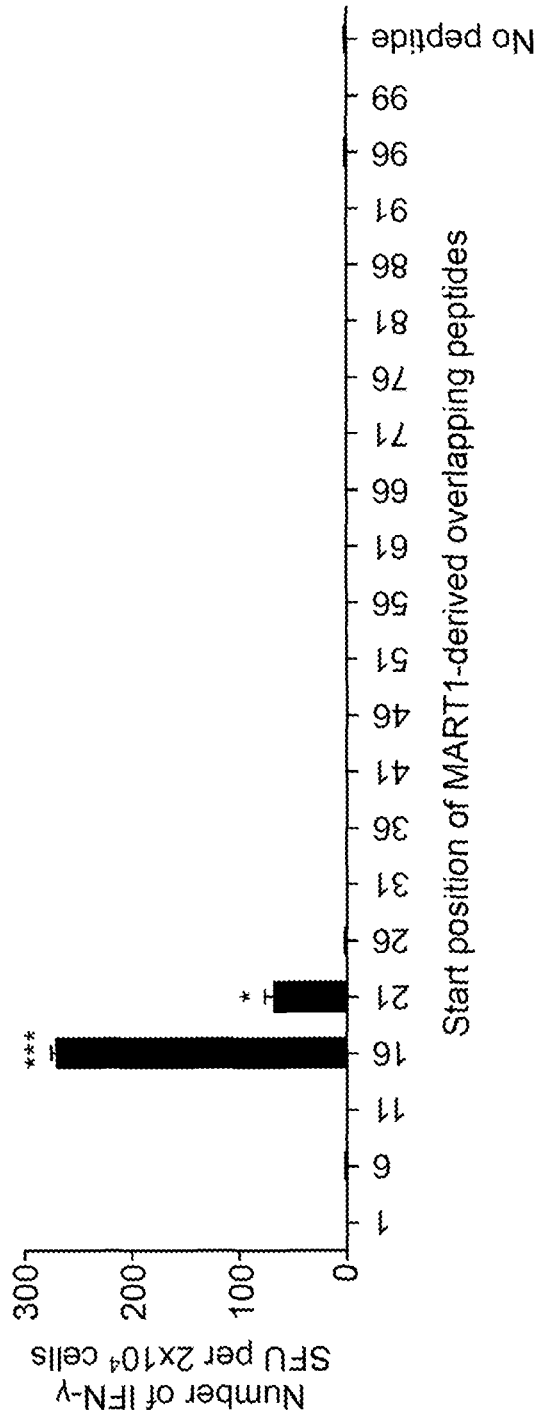
FIG. 17 is a bar graph illustrating the number of B*18:01/MART1 T cells in melanoma TILs. The TILs were used as responder cells in IFN-γ ELISPOT analysis. B*18:01-artificial APCs pulsed with overlapping peptides to cover the whole protein of MART1 were employed as stimulator cells. When stimulated with B*18:01-artificial APCs pulsed with MART1-derived overlapping peptides, the TILs showed positive responses to two adjacent peptides with the shared sequence 21YTTAEEAAGIGILTV35 (see also Table 5). Experiments were carried out in triplicate, and error bars depict SD. *P<0.05, ***P<0.001.
Figure 18:
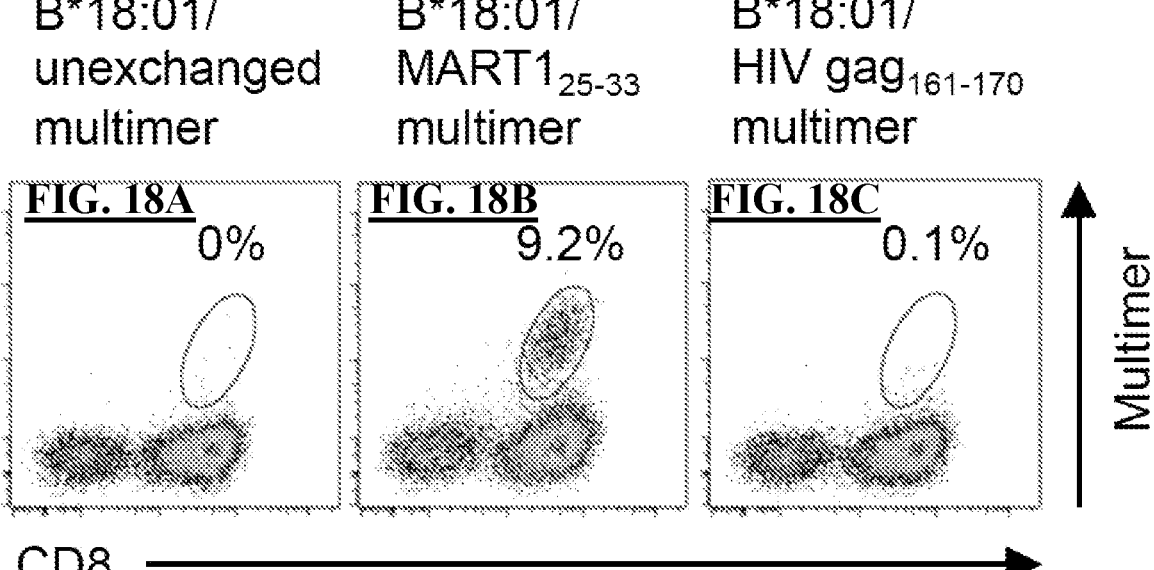
FIGS. 18A-18C are graphical representations of B*18:01/MART1$_{25-33}$ multimer staining of melanoma TILs.
Figure 19:
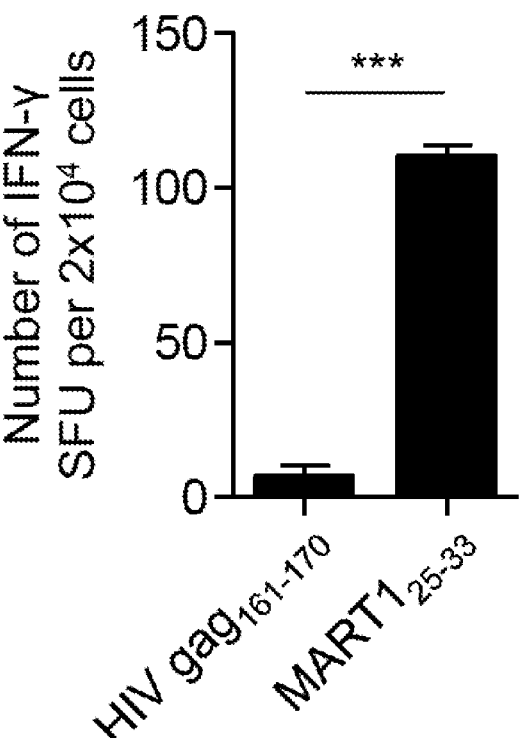
FIG. 19 is a bar graph illustrating the functional assessment of B*18:01/MART1$_{25-33}$ multimer-positive melanoma TILs. IFN-γ production by the TILs in a B*18:01/MART1$_{25-33}$-specific manner. The TILs were employed as responder cells in IFN-γ ELISPOT analysis. B*18:01-artificial APCs pulsed with the indicated peptides were used as stimulator cells. The HIV gag$_{161-170}$ peptide was employed as a control. Experiments were carried out in triplicate, and error bars depict standard deviation (SD). ***P<0.001.

TILs were isolated from a metastatic melanoma patient, then polyclonally expanded in vitro, and their MART1 antigen specificity for HLA-B*18:01 allele was examined. Since pHLA multimer production requires the use of a peptide with a known exact sequence, it is not straightforward or practical to conduct high-throughput screening for new epitope peptides using a pHLA multimer-based strategy. In addition to structure-based analysis using pHLA multimers, functional analysis can be applied to determine the antigen specificity of T cells. We conducted functional assays using artificial antigen-presenting cells (APCs), which can take up and process longer peptides and present epitope peptides via class I molecules, as stimulator cells. HLA-B*18:01-artificial APCs were pulsed with overlapping peptides to cover the whole protein of MART1 (Table 5) and used as stimulators in cytokine ELISPOT assays. When stimulated with B*18:01-artificial APCs pulsed with MART1-derived overlapping peptides, B*18:01⁺ melanoma TILs showed positive responses to two adjacent peptides with the shared sequence $_{21}$YTTAEEAAGIGILTV$_{35}$ in the IFN-γ ELISPOT analysis (FIG. 17). Using a series of mutant deletion peptides, we determined the minimally required peptide epitope, $_{25}$EEAAGIGIL$_{33}$ presented by B*18:01 molecules. Importantly, the B*18:01/MART1$_{25-33}$ multimer successfully stained up to 9.2% of the polyclonally expanded TILs, suggesting that the B*18:01/MART1$_{25-33}$ T cells were a dominant population of the TILs (FIG. 18). The multimer-positive T cells secreted detectable IFN-γ in an HLA-restricted peptide-specific manner according to ELIS-POT analysis (FIG. 19).

TABLE 5

MART1-derived overlapping peptides.

| Position | Peptide Sequence | SEQ ID NO |
|---|---|---|
| 1 | MPREDAHFIYGYPKKGHGHS | 61 |
| 6 | AHFIYGYPKKGHGHSYTTAE | 62 |
| 11 | GYPKKGHGHSYTTAEEAAGI | 63 |
| 16 | GHGHSYTTAEEAAGIGILTV | 64 |
| 21 | YTTAEEAAGIGILTVILGVL | 65 |
| 26 | EAAGIGILTVILGVLLLIGC | 66 |
| 31 | GILTVILGVLLLIGCWYCRR | 67 |
| 36 | ILGVLLLIGCWYCRRRNGYR | 68 |
| 41 | LLIGCWYCRRRNGYRALMDK | 69 |
| 46 | WYCRRRNGYRALMDKSLHVG | 70 |
| 51 | RNGYRALMDKSLHVGTQCAL | 71 |
| 56 | ALMDKSLHVGTQCALTRRCP | 72 |
| 61 | SLHVGTQCALTRRCPQEGFD | 73 |
| 66 | TQCALTRRCPQEGFDHRDSK | 74 |
| 71 | TRRCPQEGFDHRDSKVSLQE | 75 |
| 76 | QEGFDHRDSKVSLQEKNCEP | 76 |
| 81 | HRDSKVSLQEKNCEPVVPNA | 77 |
| 86 | VSLQEKNCEPVVPNAPPAYE | 78 |
| 91 | KNCEPVVPNAPPAYEKLSAE | 79 |
| 96 | VVPNAPPAYEKLSAEQSPPP | 80 |
| 99 | NAPPAYEKLSAEQSPPPYSP | 81 |

Figure 20:
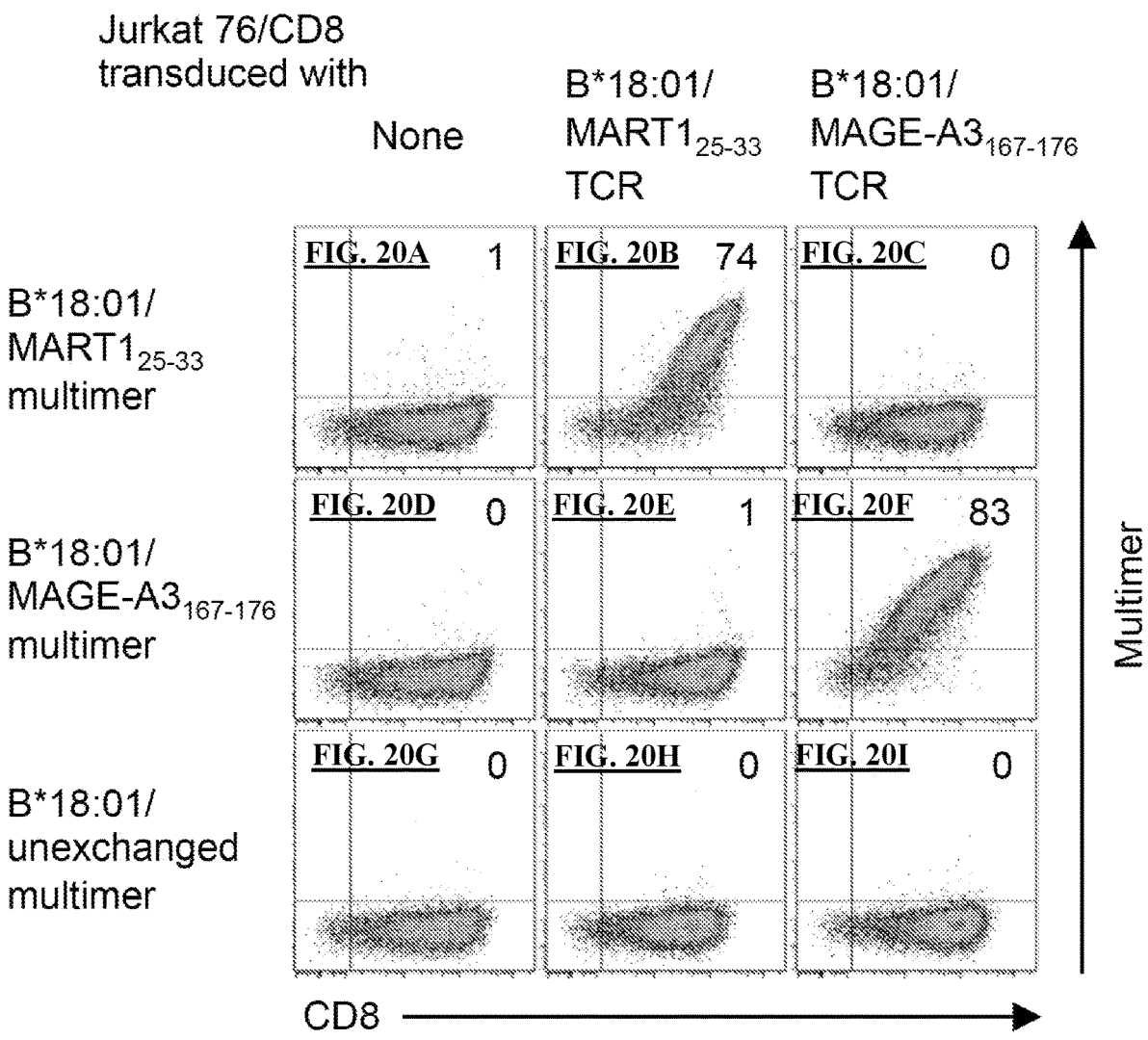
FIGS. 20A-20I are graphical representations of positive staining of Jurkat 76/CD8 cells transduced with B*18:01/MART1$_{25-33}$ TCR genes with a cognate multimer. Jurkat 76/CD8 cells transduced with the B*18:01/MART1$_{25-33}$ TCR (FIGS. 20B, 20E, and 20H) were stained with the B*18:01/MART1$_{25-33}$ multimer (FIG. 20B). The B*18:01/MAGE-A3$_{167-176}$ multimer (FIGS. 20D, 20E, and 20F), B*18:01/MAGE-A3$_{167-176}$ TCR (FIGS. 20C, 20F, and 20I), and B*18:01/unexchanged multimer (FIGS. 20G, 20H, and 20I) were employed as controls, as well as Jurkat 76/CD8 not transduced with a TCR (FIGS. 20A, 20D, and 20G). The percentage of multimer$^+$ CD8$^+$ cells is shown.
Figure 21:
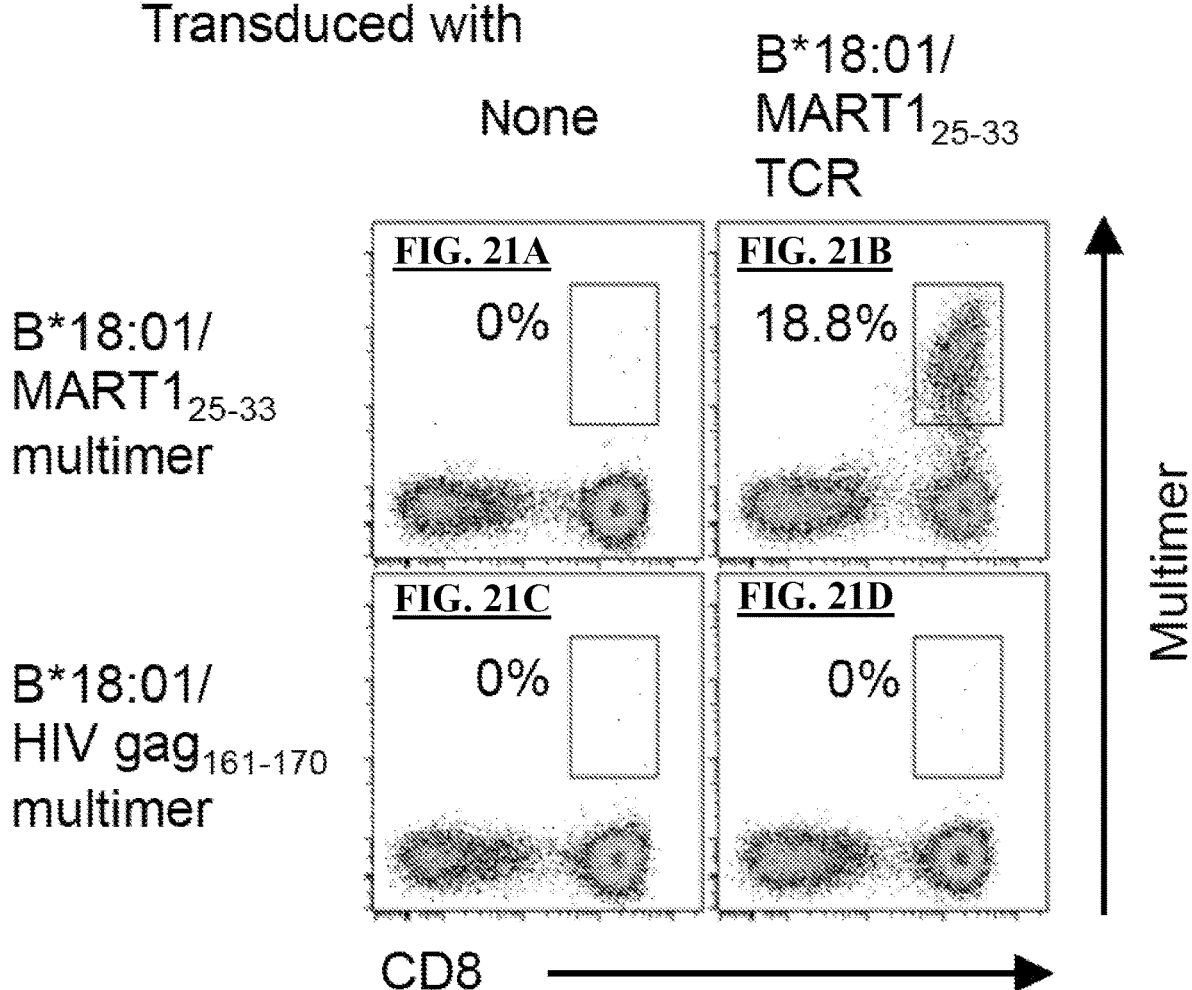
FIGS. 21A-21D are graphical representations of positive staining of human primary T cells transduced with B*18:01/MART1$_{25-33}$ TCR genes (FIGS. 21B and 21D) with a cognate multimer. Primary T cells transduced with the B*18:01/MART1$_{25-33}$ TCR were stained with the B*18:01/MART1$_{25-33}$ (FIG. 21B) or B*18:01/HIV gag$_{161-170}$ control multimer (FIG. 21D). Untransduced primary T cells were employed as negative controls (FIGS. 21A and 21C). The percentage of multimer$^+$ CD8$^+$ T cells is shown.
Figure 22:
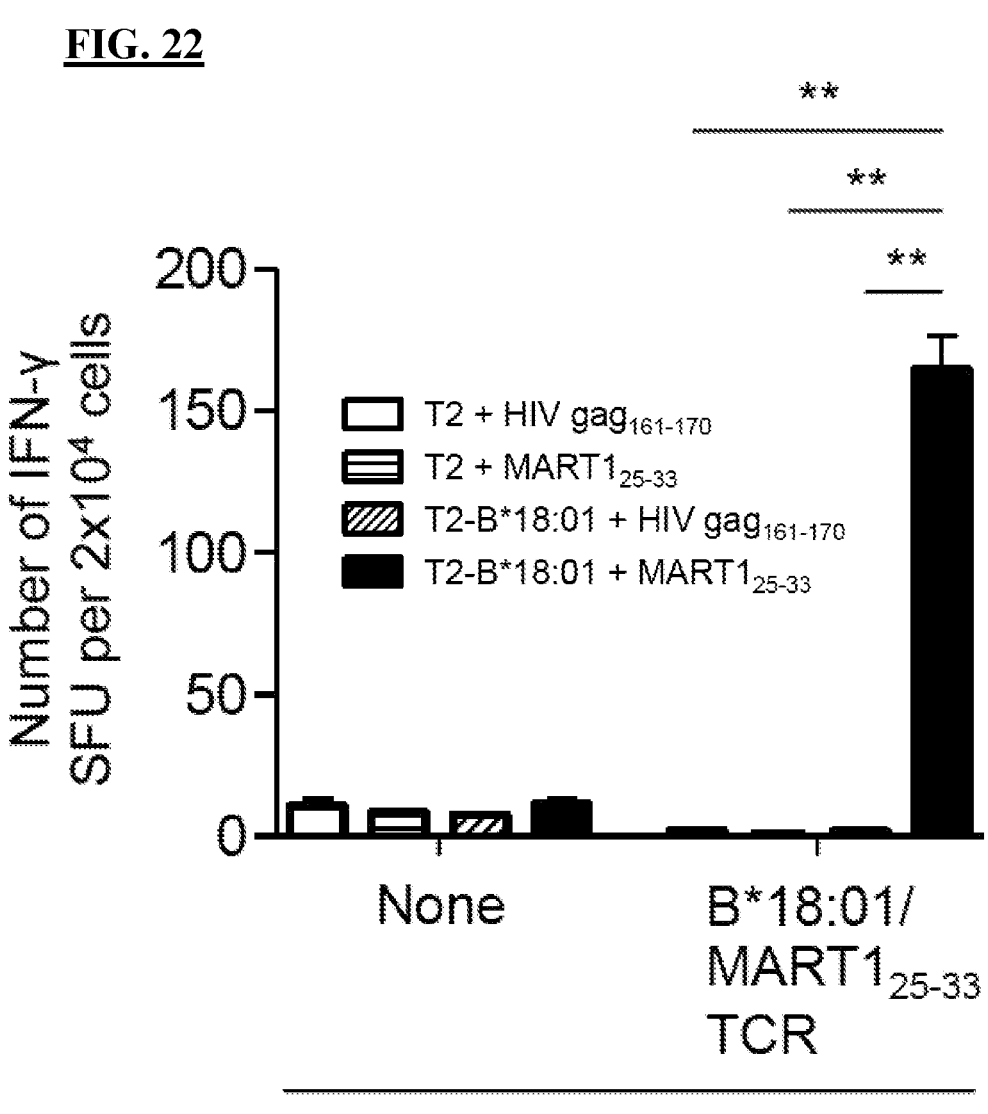
FIG. 22 is a bar graph illustrating that human primary T cells transduced with B*18:01/MART1$_{25-33}$ TCR genes react strongly with the cognate peptide presented by the target class I molecule. Primary T cells transduced with B*18:01/MART1$_{25-33}$ TCR genes or untransduced primary T cells (x-axis) were used as responder cells in IFN-γ ELISPOT analysis. HLA-B*18:01-transduced T2 cells (T2-B*18:01) were generated. T2 or T2-B*18:01 cells pulsed with the MART1$_{25-33}$ or HIV gag$_{161-170}$ peptide (control) were used as stimulator cells. Experiments were carried out in triplicate, and error bars depict SD. **P<0.01.
Figures 23A, 23B:
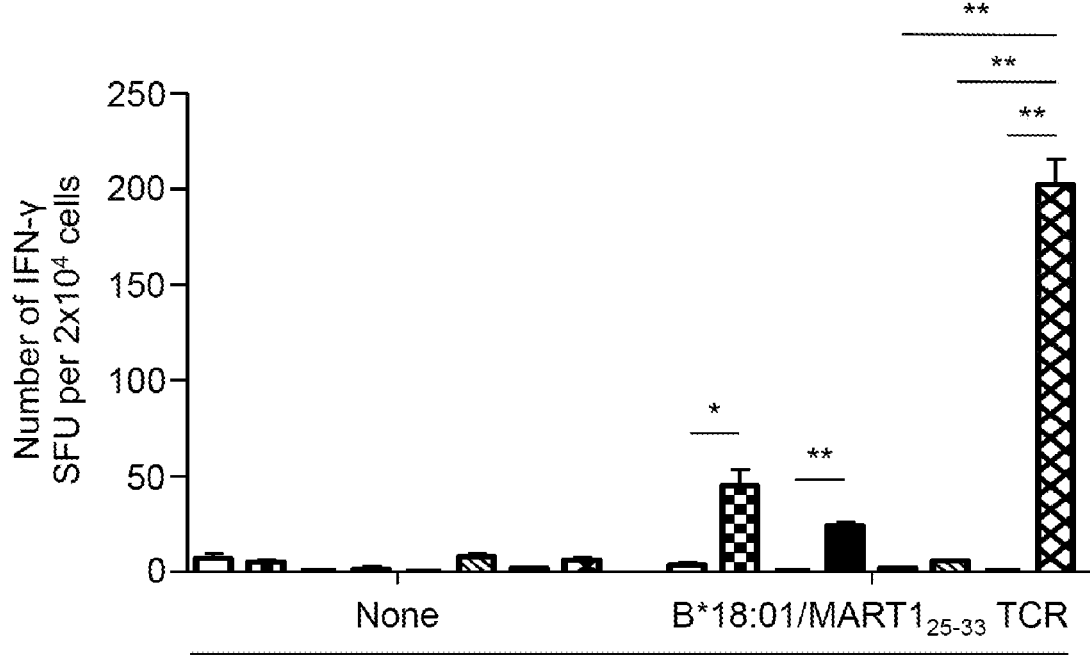
FIG. 23A is a graphical representation of illustrating that primary T cells transduced with B*18:01/MART1$_{25-33}$ TCR genes recognize tumor cells. Primary T cells transduced with B*18:01/MART1$_{25-33}$ TCR genes or untransduced primary T cells were employed as responder cells in IFN-γ ELISPOT analysis. Malme-3M, SL-MEL-28, and A375 cells that were either untransduced or transduced with HLA-B*18:01 or MART1, as indicated (FIG. 23B), were employed as stimulator cells. Experiments were carried out in triplicate, and error bars depict SD. *P<0.05, **P<0.01.

The multimer-positive antitumor T cells were collected and their TCR genes were molecularly cloned (FIG. 20). The antigen specificity and functional reactivity of the cloned TCR were verified by multimer staining and ELISPOT assay of TCR-reconstituted T cells. When reconstituted on primary T cells, B*18:01/MART1$_{25-33}$ TCR-transduced T cells were successfully stained with the cognate multimer (FIG. 21) and strongly reacted with the MART1$_{25-33}$ peptide presented by surface B*18:01 molecules (FIG. 22). Importantly, these cells were able to recognize B*18:01-matched and peptide-unpulsed tumor cells naturally expressing the MART1 gene. Although both the Malme-3M and SK-MEL-28 melanoma cell lines are negative for B*18:01, they express the MART1 gene endogenously. When B*18:01 molecules were ectopically expressed, both melanoma cell lines were successfully recognized by B*18:01/MART1$_{25-33}$ TCR-transduced T cells. Moreover, A375 melanoma cells, which lack endogenous expression of both B*18:01 and MART1, became reactive to B*18:01/MART1$_{25-33}$ TCR-transduced T cells only when both the B*18:01 and full-length MART1 genes (but not either of the single genes) were transduced (FIGS. 23-25). These results clearly demonstrate that the B*18:01/MART1$_{25-33}$ TCR-transduced T cells were sufficiently avid to recognize tumor cells and that the cloned B*18:01/MART1$_{25-33}$ TCR was tumor-reactive.

The use of the newly cloned tumor-reactive B*18:01-restricted MART1 TCR genes may widen the applicability of anti-MART1 TCR gene therapy beyond HLA-A*02:01-positive cancer patients.

Example 5—MAGE-A3-Specific TCR

Figure 27:
FIG. 27 is a bar graph illustrating the functional assessment of B*18:01/MAGE-A3$_{167-176}$ multimer-positive melanoma TILs. IFN-γ production by B*18:01-positive TILs in an HLA-B*18:01-restricted peptide-specific manner. The TILs stimulated with B*18:01-artificial APCs pulsed with the MAGE-A3$_{167-176}$ peptide were employed as responder cells in IFN-γ ELISPOT analysis. HLA-B*18:01 transduced T2 cells (T2-B*18:01) were generated. T2 or T2-B*18:01 cells pulsed with the indicated peptide were used as stimulator cells. The HIV gag$_{161-170}$ peptide was employed as a control. Experiments were carried out in triplicate, and error bars depict standard deviation (SD). P<0.01, *P<0.001.

TILs were isolated from a metastatic melanoma patient, then polyclonally expanded in vitro, and their MAGE-A3 antigen specificity for HLA-B*18:01 allele was examined. The T cells were stained using pHLA multimer with MAGE-A3$_{167-176}$ peptide. The B*18:01/MAGE-A3$_{167-176}$ multimer positivity of polyclonally expanded TILs was only 0.04% prior to peptide-specific stimulation. However, when the TILs were weakly stimulated once with B*18:01-artificial APCs pulsed with the MAGE-A3$_{167-176}$ peptide, 5.5% of the TILs were stained with the cognate multimer and secreted IFN-γ in a B*18:01/MAGE-A3$_{167-176}$-specific manner (FIGS. 26-27).

Figures 29A, 29B, 29C, 29D:
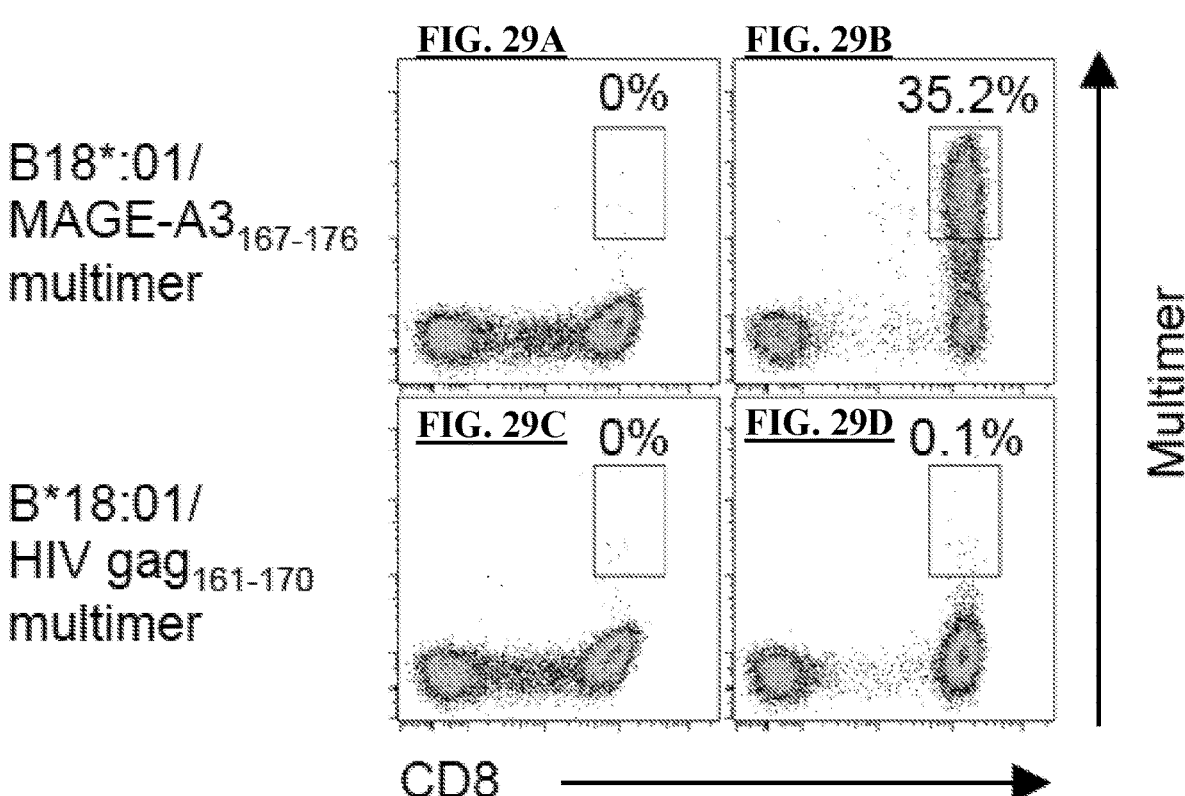
FIGS. 29A-29D are graphical representations of positive staining of human primary T cells transduced with B*18:01/MAGE-A3167176 TCR genes (FIGS. 29B and 29D) with a cognate multimer. Primary T cells transduced with the B*18:01/MAGE-A3167-176 TCR were stained with the B*18:01/MAGE-A3$_{167-176}$ (FIG. 29B) or B18:01/HIV 170 control multimer (FIG. 29D). Untransduced primary T cells were employed as negative controls (FIGS. 29A and 29C). The percentage of multimer$^+$ CD8$^+$ T cells is shown.
Figure 30:
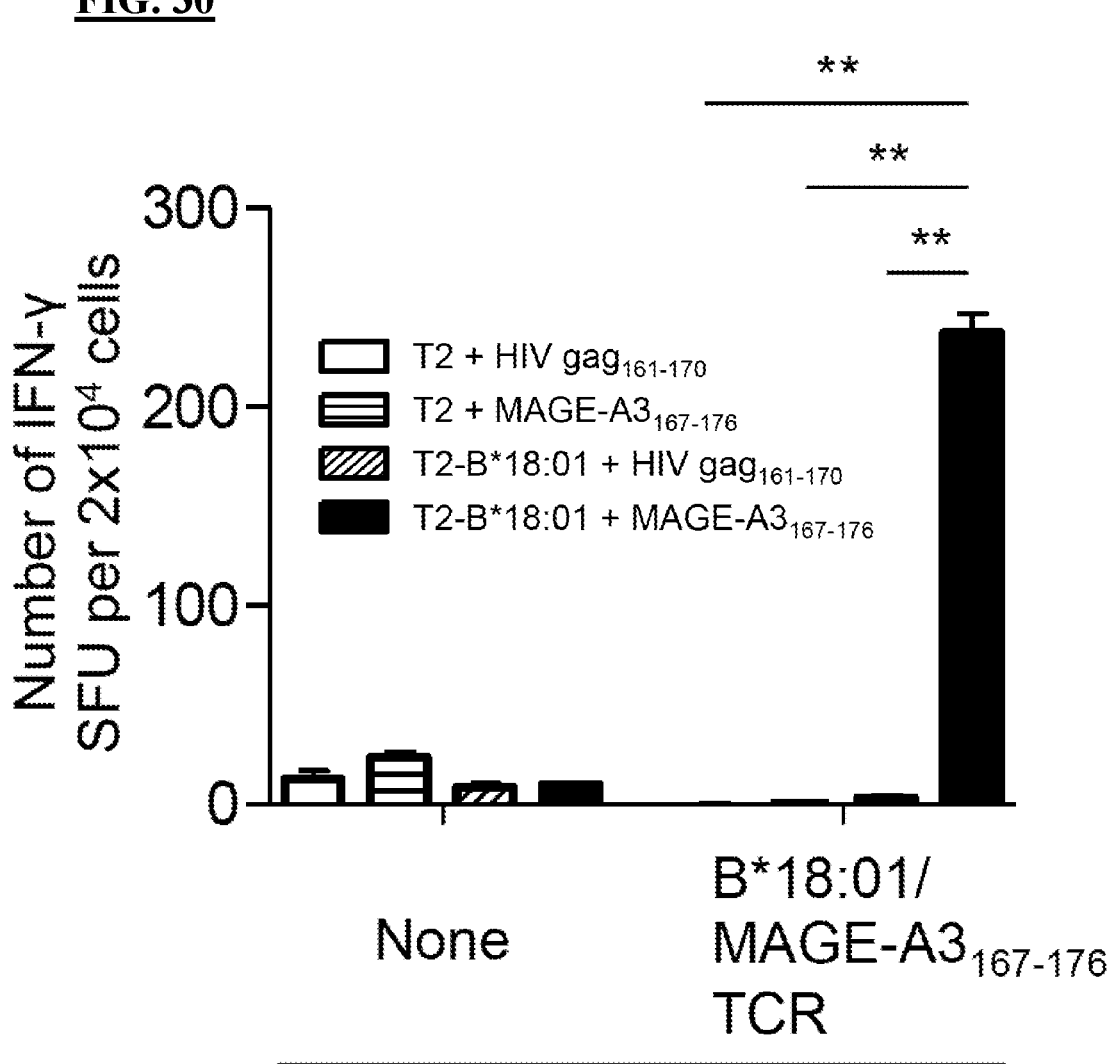
FIG. 30 is a bar graph illustrating that human primary T cells transduced with B*18:01/MAGE-A3$_{167-176}$ TCR genes react strongly with the cognate peptide presented by the target class I molecule. Primary T cells transduced with B*18:01/MAGE-A3$_{167-176}$ TCR genes or untransduced primary T cells (x-axis) were used as responder cells in IFN-γ ELISPOT analysis. T2 cells pulsed with the MAGE-A3$_{167-176}$ or HIV gag$_{161-170}$ peptide (control) were used as stimulator cells. Experiments were carried out in triplicate, and error bars depict SD. **P<0.01.
Figures 31A, 31B:
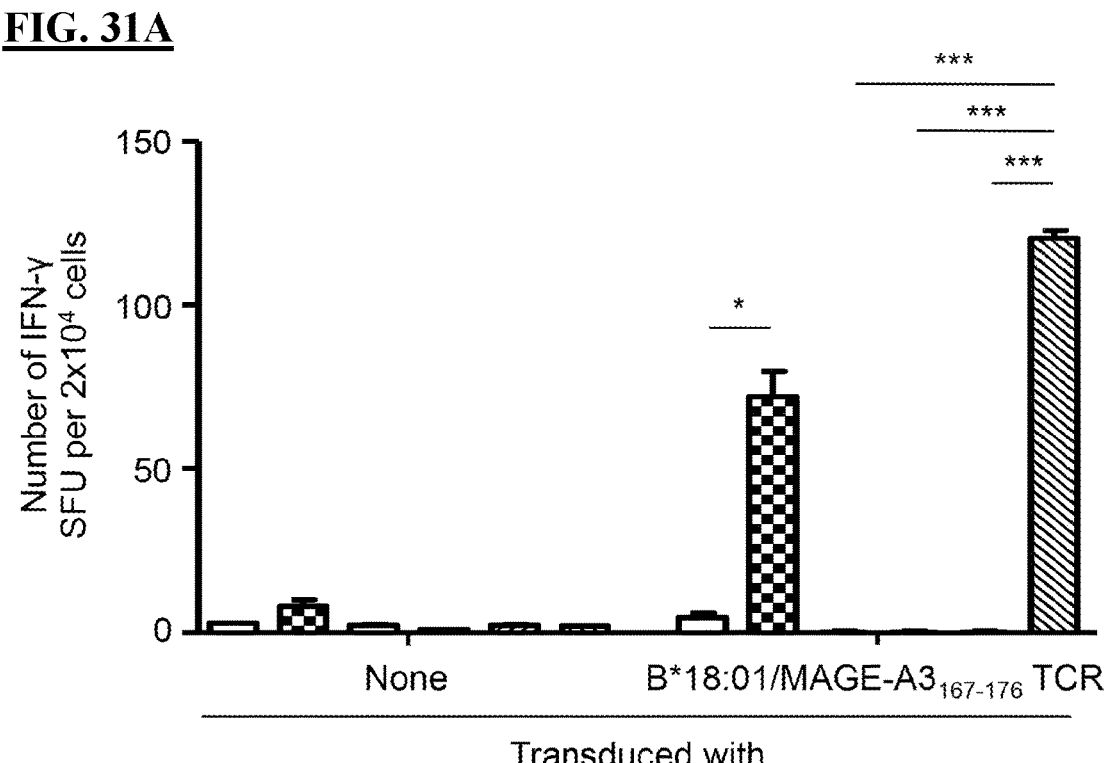
FIG. 31A is a graphical representation illustrating that primary T cells transduced with B*18:01/MAGE-A3$_{167-176}$ TCR genes recognize tumor cells. Primary T cells transduced with B*18:01/MAGE-A3$_{167-176}$ TCR genes or untransduced primary T cells were employed as responder cells in IFN-γ ELISPOT analysis. SK-MEL-28 and HEK293T cells that were either untransduced or transduced with HLA-B*07:02 and/or MAGE-A1, as indicated (FIG. 31B), were employed as stimulator cells. Experiments were carried out in triplicate, and error bars depict SD. *P<0.05, ***P<0.001.
Figure 32:
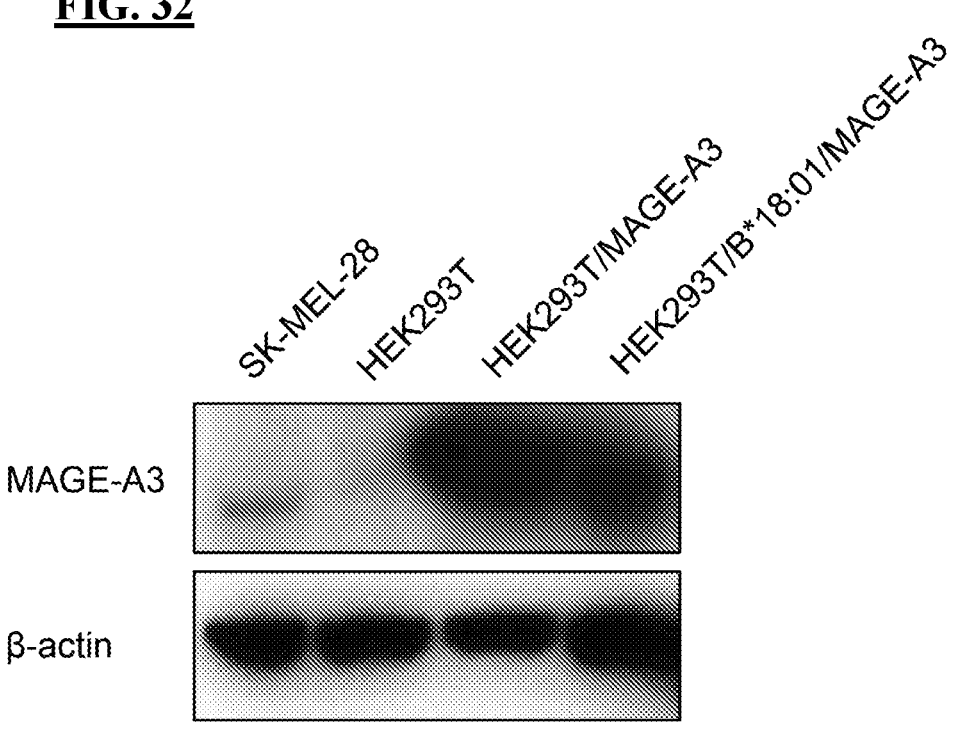
FIG. 32 is a graphical representation of the expression of MAGE-A3 derived from endogenous or transduced full-length gene. The expression of MAGE-A3 derived from endogenous or transduced full-length gene in target cells was evaluated by Western blot analysis with an anti-MAGE-A3 pAb. (3-actin expression was employed as a positive control.
Figures 33A, 33B, 33C, 33D:
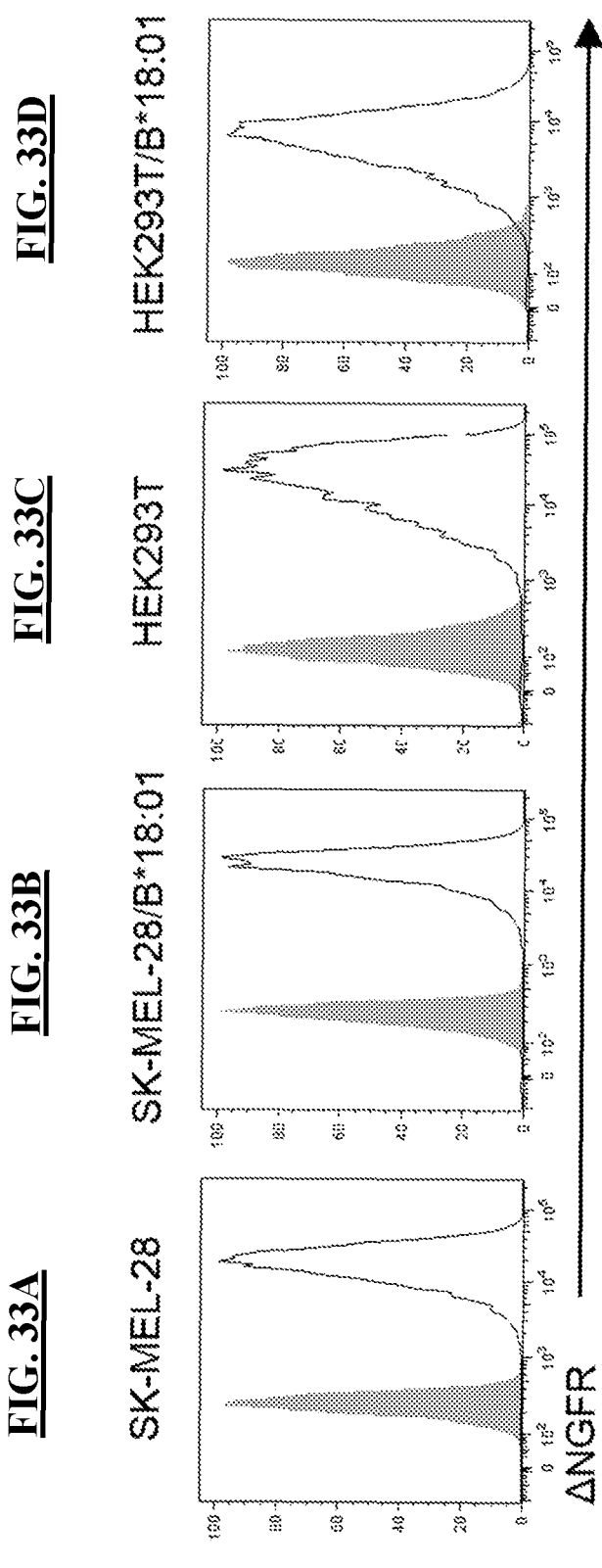
FIGS. 33A-33D are graphical representations of the expression of ΔNGFR in target cells transduced with the full-length HLA-B*18:01 gene tagged with ΔNGFR (FIGS. 33B and 33D). Surface expression of ΔNGFR in target cells transduced with the full-length HLA-B*18:01 gene tagged with ΔNGFR was analyzed by flow cytometry following staining with an anti-NGFR mAb (open curve) and an isotype control (filled curve). ΔNGFR alone was used as a control (FIGS. 33A and 33C).

The multimer-positive antitumor T cells were collected and their TCR genes were molecularly cloned (FIG. 28). The antigen specificity and functional reactivity of the cloned TCR were verified by multimer staining and ELISPOT assay of TCR-reconstituted T cells. When reconstituted on primary T cells, B*18:01/MAGE-A3$_{167-176}$ TCR-transduced T cells were successfully stained with the cognate multimer (FIG. 29) and strongly reacted with the MAGE-A3$_{167-176}$ peptide presented by surface B*18:01 molecules (FIG. 30). Importantly, these cells were able to recognize B*18:01-matched and peptide-unpulsed tumor cells naturally expressing the MAGE-A3 gene. Although the SK-MEL-28 melanoma cells are negative for B*18:01, they express the MAGE-A3 gene endogenously. When B*18:01 molecules were ectopically expressed, the melanoma cells were successfully recognized by B*18:01/MAGE-A3$_{167-176}$ TCR-transduced T cells. Moreover, HEK293T melanoma cells, which lack endogenous expression of both B*18:01 and MAGE-A3, became reactive to B*18:01/MAGE-A3$_{167-176}$ TCR-transduced T cells only when both the B*18:01 and full-length MAGE-A3 genes (but not either of the single genes) were transduced (FIGS. 31-33). These results clearly demonstrate that the B*18:01/MAGE-A3$_{167-176}$ TCR-transduced T cells were sufficiently avid to recognize tumor cells and that the cloned B*18:01/MAGE-A3$_{167-176}$ TCR was tumor-reactive.

The use of the newly cloned tumor-reactive B*18:01/MAGE-A3 TCR genes may widen the applicability of anti-MAGE-A3 TCR gene therapy beyond HLA-A*02:01-positive cancer patients.

Example 6—SSX2-Specific TCR

Figures 34A, 34B:
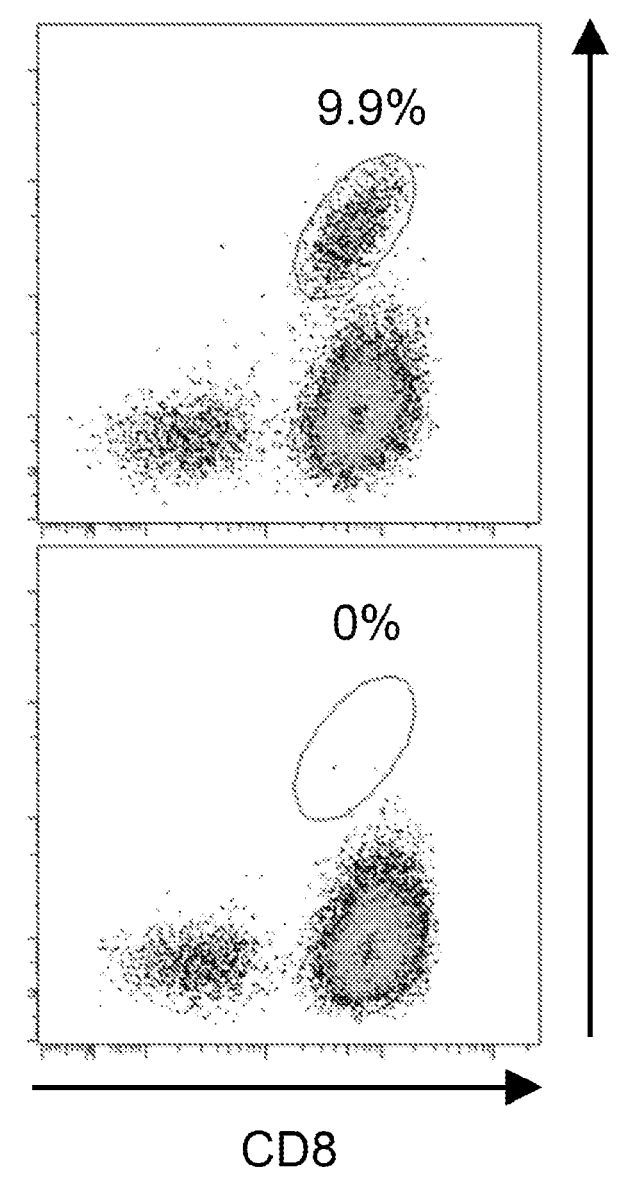
FIGS. 34A-34B are graphical representations of A*02:01/SSX2$_{41-49}$ multimer staining of melanoma TILs.
Figure 35:
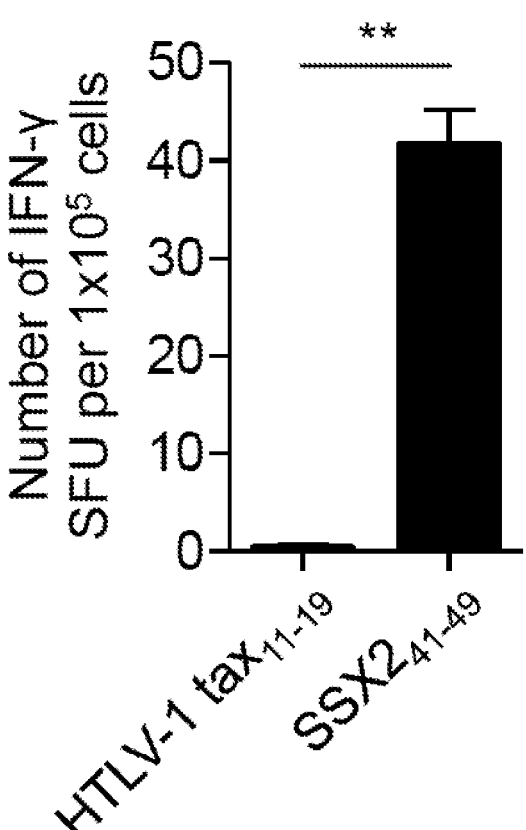
FIG. 35 is a bar graph illustrating the functional assessment of A*02:01/SSX2$_{41-49}$ multimer-positive melanoma TILs. IFN-γ production by the TILs in an A*02:01/SSX2$_{41-49}$-specific manner. The TILs were employed as responder cells in IFN-γ ELISPOT analysis. T2 cells pulsed with the indicated peptides were used as stimulator cells. The HTLV-1 tax$_{11-19}$ peptide was employed as a control. Experiments were carried out in triplicate, and error bars depict standard deviation (SD). **P<0.01.

TILs were isolated from a metastatic melanoma patient, then polyclonally expanded in vitro, and their SSX2 antigen specificity for HLA-A*02:01 allele was examined. The T cells were stained using pHLA multimer with SSX2$_{41-49}$ peptide (FIG. 34). The TILs showed positivity for A*02:01/ SSX2$_{41-49}$ multimer. The multimer-positive T cells secreted detectable IFN-γ in an HLA-restricted peptide-specific manner according to ELISPOT analysis (FIG. 35).

Figure 36:
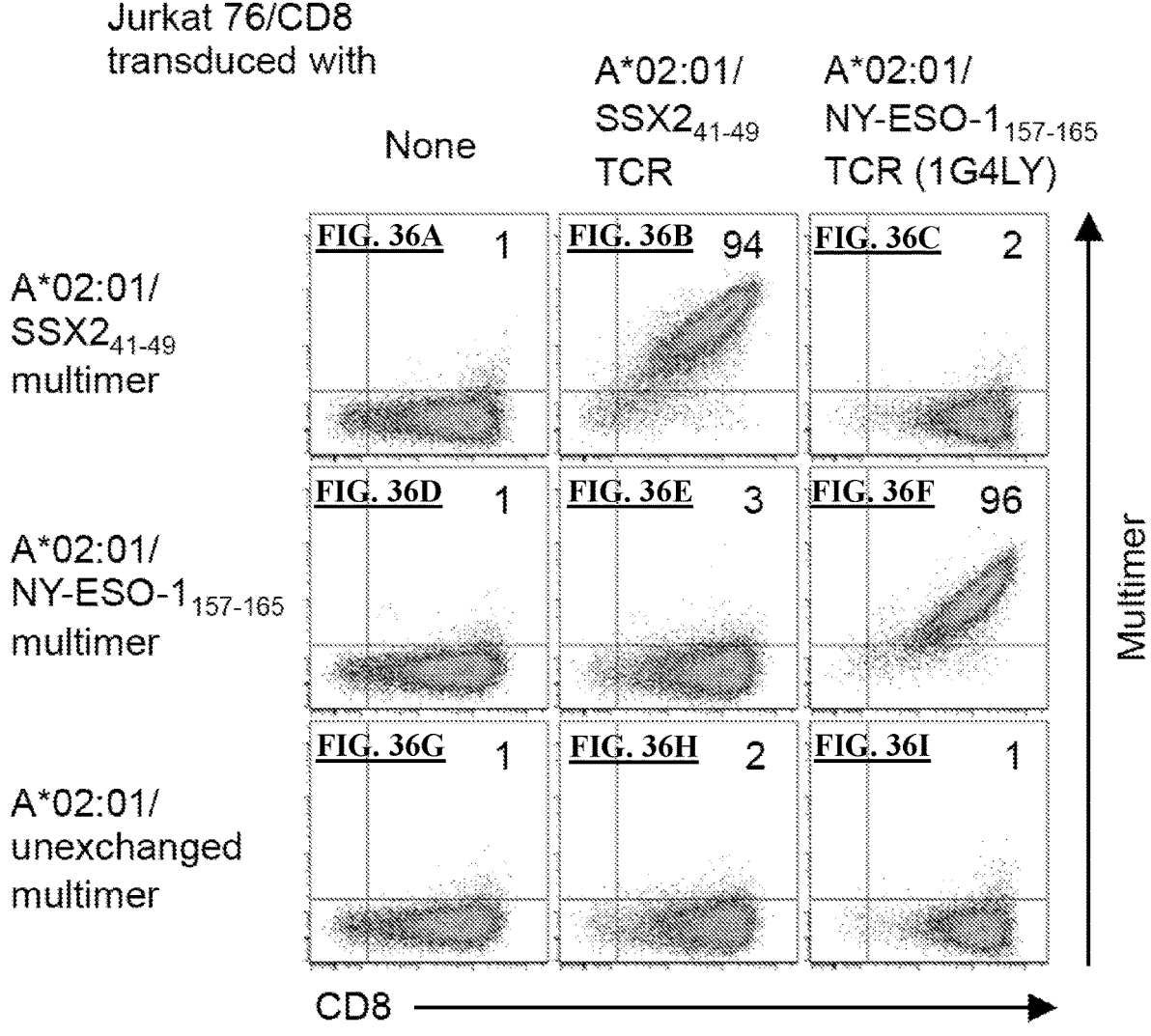
FIGS. 36A-36I are graphical representations of positive staining of Jurkat 76/CD8 cells transduced with A*02:01/SSX2$_{41-49}$ TCR genes with a cognate multimer. Jurkat 76/CD8 cells transduced with the A*02:01/SSX2$_{41-49}$ TCR (FIGS. 36B, 36E, and 36H) were stained with the A*02:01/SSX2$_{41-49}$ multimer (FIG. 36B). The A*02:01/NY-ESO-1$_{157-165}$ multimer (FIGS. 36D, 36E, and 36F), A*02:01/unexchanged multimer (FIGS. 36G, 36H, and 36I), and A*02:01/NY-ESO-1$_{157-165}$ TCR (clone 1G4LY.
Figure 37:
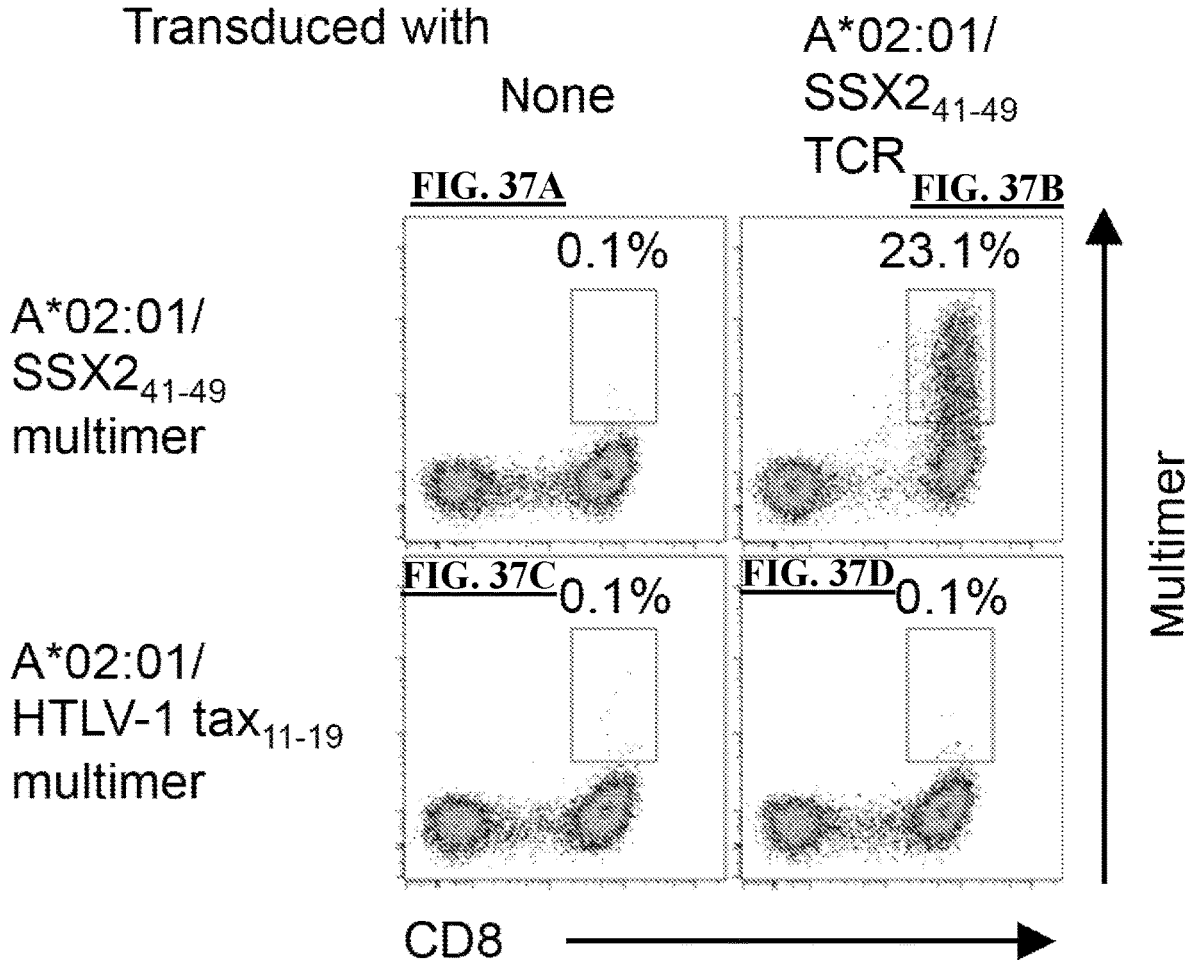
FIGS. 37A-37D are graphical representations of positive staining of human primary T cells transduced with A*02:01/SSX2$_{41-49}$ TCR genes with a cognate multimer. Primary T cells transduced with the A*02:01/SSX2$_{41-49}$ TCR (FIGS. 37B and 37D) were stained with the A*02:01/SSX2$_{41-49}$ (FIG. 37B) or A*02:01/HTLV-1 tax$_{11-19}$ control multimer (FIG. 37D). Untransduced primary T cells were employed as negative controls (FIGS. 37A and 37C). The percentage of multimer$^+$ CD8$^+$ T cells is shown.
Figure 38:
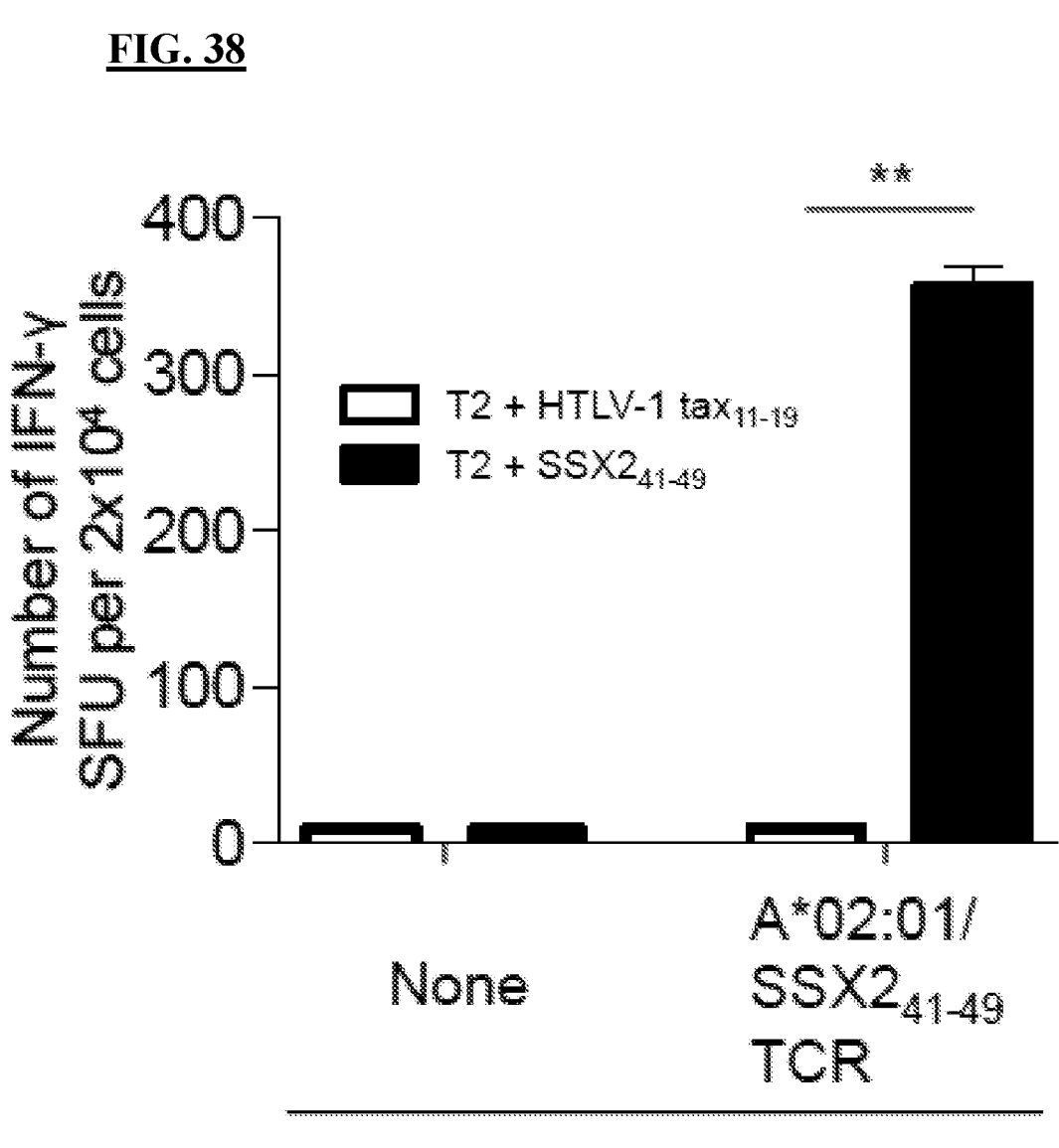
FIG. 38 is a bar graph illustrating that human primary T cells transduced with A*02:01/SSX2$_{41-49}$ TCR genes react strongly with the cognate peptide presented by the target class I molecule. Primary T cells transduced with A*02:01/SSX2$_{41-49}$ TCR genes or untransduced primary T cells (x-axis) were used as responder cells in IFN-γ ELISPOT analysis. T2 cells pulsed with the SSX2$_{41-49}$ or HTLV-1 tax$_{11-19}$ peptide (control) were used as stimulator cells. Experiments were carried out in triplicate, and error bars depict SD. **P<0.01.
Figures 39A, 39B:
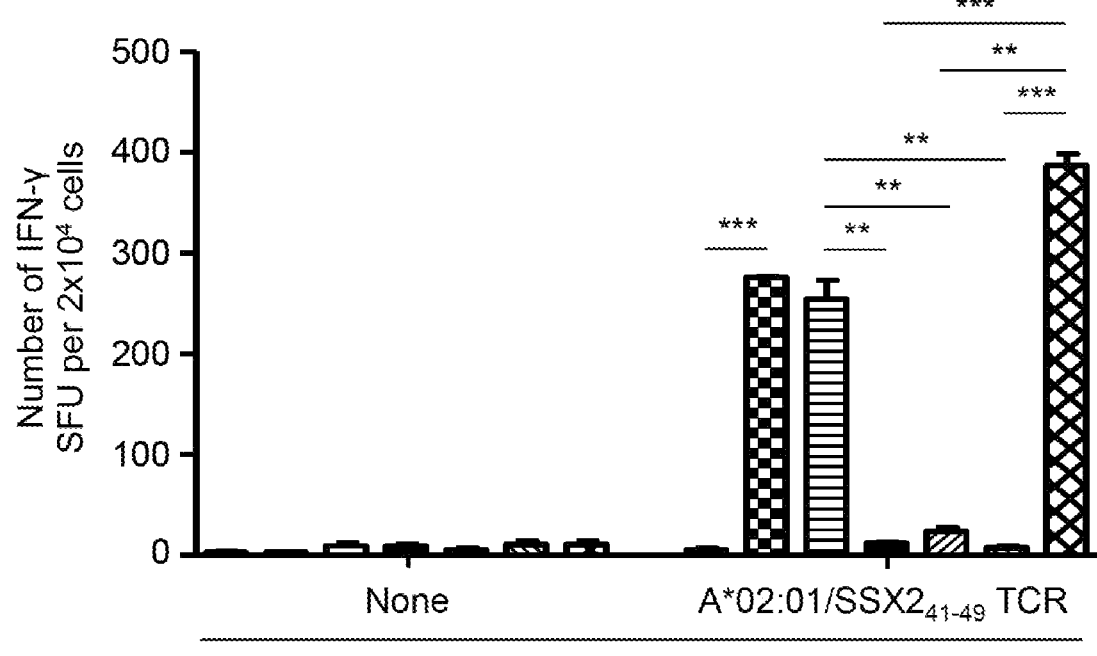
FIG. 39A is a graphical representation illustrating that primary T cells transduced with A*02:01/SSX2$_{41-49}$ TCR genes recognize tumor cells. Primary T cells transduced with A*02:01/SSX2$_{41-49}$ TCR genes or untransduced primary T cells were employed as responder cells in IFN-γ ELISPOT analysis. SK-MEL-21, SL-MEL-37, and SK-MEL-28 cells that were either untransduced or transduced with HLA-A*02:01 and/or SSX2, as indicated (FIG. 39B), were employed as stimulator cells. Experiments were carried out in triplicate, and error bars depict SD. P<0.01, *P<0.001.
Figure 40:
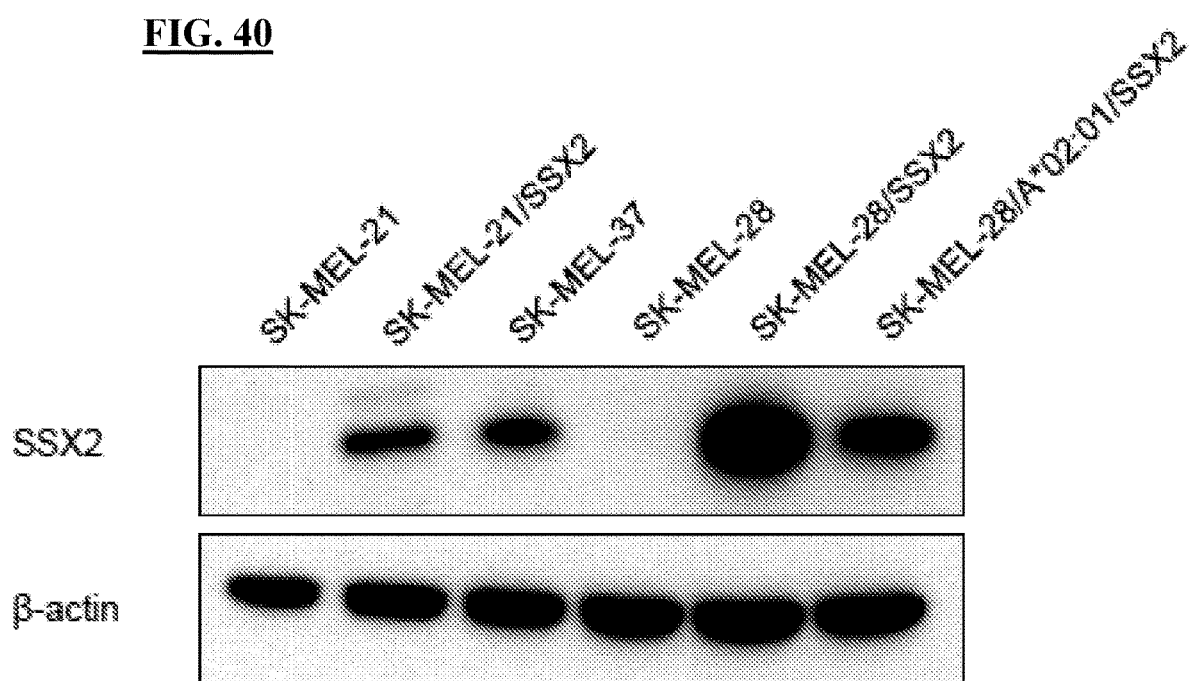
FIG. 40 is a graphical representation of the expression of SSX2 derived from endogenous or transduced full-length gene. The expression of SSX2 derived from endogenous or transduced full-length gene in target cells was evaluated by Western blot analysis with an anti-SSX2 pAb. (β-actin expression was employed as a positive control.
Figures 41A, 41B, 41C, 41D:
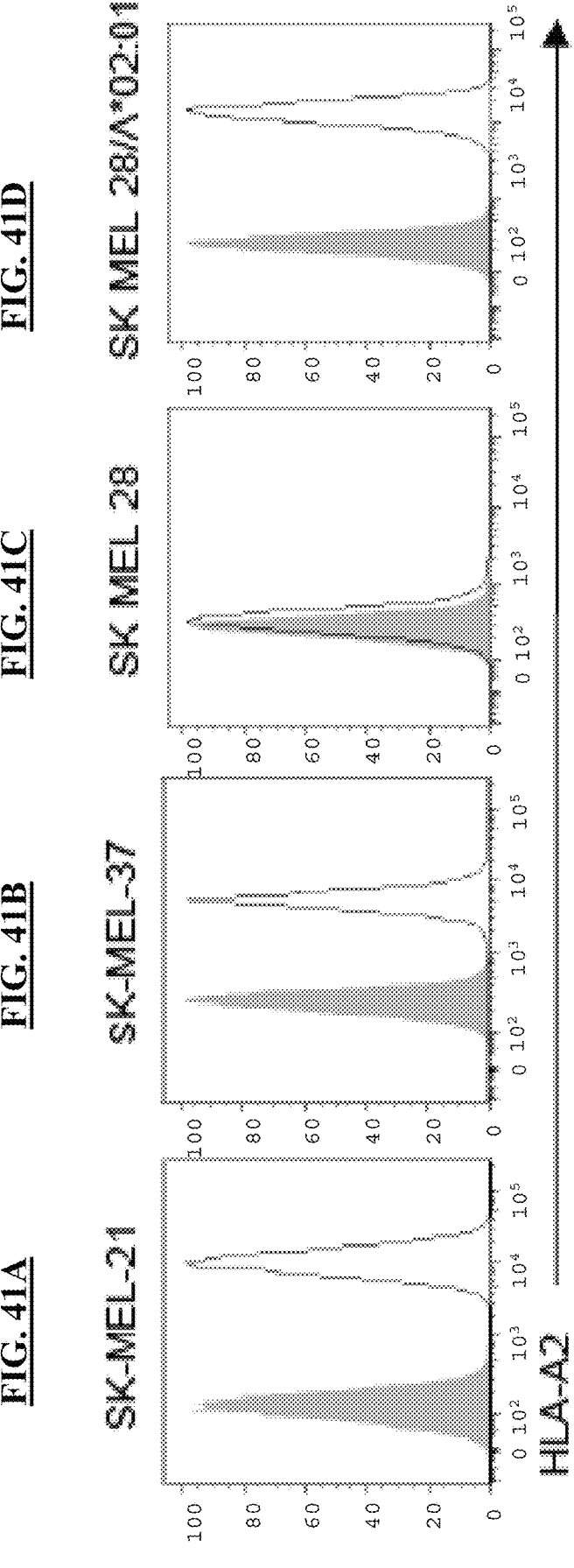
FIGS. 41A-41D are graphical representations of the expression of HLA-A2 derived from endogenous or transduced full-length HLA-A*02:01 gene in target cells. Surface expression of HLA-A2 derived from endogenous or transduced full-length HLA-A*02:01 in target cells was analyzed via flow cytometry following staining with an anti-HLA-A2 mAb (open curve) and an isotype control (filled curve).

The multimer-positive antitumor T cells were collected and their TCR genes were molecularly cloned (FIG. 36). The antigen specificity and functional reactivity of the cloned TCR were verified by multimer staining and ELISPOT assay of TCR-reconstituted T cells. When reconstituted on primary T cells, A*02:01/SSX2$_{41-49}$ TCR-transduced T cells were successfully stained with the cognate multimer (FIG. 37) and strongly reacted with the SSX2$_{41-49}$ peptide presented by surface A*02:01 molecules (FIG. 38). Importantly, these cells were able to recognize A*02:01-matched and peptide-unpulsed tumor cells naturally expressing the SSX2 gene. Although the SK-MEL-21 melanoma cells are positive for A*02:01, they do not express the SSX2 gene endogenously. When the SSX2 gene was ectopically expressed, the melanoma cells were successfully recognized by A*02:01/SSX2$_{41-49}$ TCR-transduced T cells. Moreover, SK-MEL-28 melanoma cells, which lack endogenous expression of both A*02:01 and SSX2, became reactive to A*02:01/SSX2$_{41-49}$ TCR-transduced T cells only when both the A*02:01 and full-length SSX2 genes (but not either of the single genes) were transduced (FIG. 39-41). These results clearly demonstrate that the A*02:01/SSX2$_{41-49}$ TCR-transduced T cells were sufficiently avid to recognize tumor cells and that the cloned A*02:01/SSX2$_{41-49}$ TCR was tumor-reactive.

The use of the newly cloned tumor-reactive A*02:01-restricted SSX2 TCR genes may widen the applicability of anti-SSX2 TCR gene therapy.

---

The invention claimed is:

1. A nucleic acid molecule comprising:

(i) a first nucleotide sequence encoding a recombinant T cell receptor (TCR) or an antigen binding portion thereof that specifically binds to tyrosinase ("anti-tyrosinase TCR"); wherein the anti-tyrosinase TCR comprises an alpha chain variable domain comprising an alpha chain CDR1, an alpha chain CDR2, and an alpha chain CDR3; and a beta chain variable domain comprising a beta chain CDR1, a beta chain CDR2, and a beta chain CDR3; and wherein:

(i) the beta chain CDR3 of the anti-tyrosinase TCR comprises the amino acid sequence set forth in SEQ ID NO: 10;

(ii) the beta chain CDR2 of the anti-tyrosinase TCR comprises the amino acid sequence set forth in SEQ ID NO: 9;

(iii) the beta chain CDR1 of the anti-tyrosinase TCR comprises the amino acid sequence set forth in SEQ ID NO: 8;

(iv) the alpha chain CDR3 of the anti-tyrosinase TCR comprises the amino acid sequence set forth in SEQ ID NO: 7;

(v) the alpha chain CDR2 of the anti-tyrosinase TCR comprises the amino acid sequence set forth in SEQ ID NO: 6; and (vi) the alpha chain CDR1 of the anti-tyrosinase TCR comprises the amino acid sequence set forth in SEQ ID NO: 5; and (ii) a second nucleotide sequence, wherein the second nucleotide sequence or the polypeptide encoded by the second nucleotide sequence inhibits the expression of an endogenous TCR.

2. The nucleic acid molecule of claim 1, wherein:

(i) the alpha chain variable domain comprises the amino acid sequence of a variable domain present in the amino acid sequence set forth in SEQ ID NO: 1;

(ii) the beta chain variable domain comprises the amino acid sequence of a variable domain present in the amino acid sequence set forth in SEQ ID NO: 2; or (iii) both (i) and (ii).

3. The nucleic acid molecule of claim 1, wherein:

(a) the anti-tyrosinase TCR further comprises an alpha chain constant region, wherein the alpha chain constant region is different from a constant region of an endogenous alpha chain, and wherein:

(i) the alpha chain constant region comprises an amino acid sequence having at least about 85% sequence identity to a constant region present in the amino acid sequence set forth in SEQ ID NO: 1;

or (ii) the alpha chain constant region comprises an amino acid sequence comprising at least 1 amino acid substitutions relative to a constant region present in the amino acid sequence set forth in SEQ ID NO: 1;

(b) the anti-tyrosinase TCR further comprises a beta chain constant region, wherein the beta chain constant region is different from a constant region of an endogenous beta chain, and wherein the beta chain constant region comprises an amino acid sequence having at least about 85% sequence identity to a constant region present in the amino acid sequence set forth in SEQ ID NO: 2;

or (ii) the beta chain constant region comprises an amino acid sequence comprising at least 1 amino acid substitution relative to a constant region present in the amino acid sequence set forth in SEQ ID NO: 2 or (c) both (a) and (b).

4. The nucleic acid molecule of claim 1, wherein the second nucleotide sequence (i) is one or more siRNAs that reduce the expression of endogenous TCRs, wherein the one or more siRNAs are complementary to a target sequence within a nucleotide sequence encoding a constant region of the endogenous TCRs;

(ii) encodes Cas9; or (iii) both (i) and (ii).

5. The nucleic acid molecule of claim 1, wherein the anti-tyrosinase TCR comprises an alpha chain comprising the amino acid sequence set forth in SEQ ID NO: 1 and a beta chain comprising the amino acid sequence set forth in SEQ ID NO: 2.

6. A cell comprising the nucleic acid molecule of claim 5.

7. The cell of claim 6, which further expresses CD3.

8. The cell of claim 6, which is a T cell.

9. The cell of claim 6, which is an NK cell, a natural killer T (NKT) cell, or an ILC.

10. A vector comprising the nucleic acid molecule of claim 1.

11. A cell comprising the nucleic acid molecule of claim 1.

12. The cell of claim 11, which further expresses CD3.

13. The cell of claim 11, which is a T cell.

14. The cell of claim 11, which is a natural killer (NK) cell, a natural killer T (NKT) cell, or an ILC.

15. A method of treating a cancer in a subject in need thereof, comprising administering to the subject the cell of claim 11, wherein the cell is a T cell or an NK cell.

16. The method of claim 15, wherein the cancer comprises melanoma, bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, or a combination of one or more of said cancers.

17. The method of claim 15, wherein the cancer is locally advanced, advanced, or metastatic.

18. The method of claim 15, wherein the cancer is relapsed or refractory.

19. The method of claim 15, wherein the cells are obtained from the subject.

\* \* \* \* \*